United States Patent
Aicher et al.

(10) Patent No.: US 7,598,423 B2
(45) Date of Patent: Oct. 6, 2009

(54) POTENTIATORS OF GLUTAMATE RECEPTORS

(75) Inventors: Thomas Daniel Aicher, Superior, CO (US); Guillermo S. Cortez, Indianapolis, IN (US); Todd Michael Groendyke, Ann Arbor, MI (US); Albert Khilevich, Westfield, IN (US); James Allen Knobelsdorf, Fishers, IN (US); Fredrik Pehr Marmsater, Longmont, CO (US); Jeffrey Michael Schkeryantz, Fishers, IN (US); Tony Pisal Tang, Longmont, CO (US); Nicholas Andrew Magnus, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 92 days.

(21) Appl. No.: 11/718,753

(22) PCT Filed: Nov. 15, 2005

(86) PCT No.: PCT/US2005/041441

§ 371 (c)(1),
(2), (4) Date: May 7, 2007

(87) PCT Pub. No.: WO2006/057870

PCT Pub. Date: Jun. 1, 2006

(65) Prior Publication Data

US 2008/0139505 A1 Jun. 12, 2008

Related U.S. Application Data

(60) Provisional application No. 60/630,060, filed on Nov. 22, 2004.

(51) Int. Cl.
*C07D 239/26* (2006.01)
*C07D 239/28* (2006.01)
*C07D 241/10* (2006.01)
*C07D 401/10* (2006.01)
*C07D 213/02* (2006.01)
*C07D 291/04* (2006.01)
*C07D 271/06* (2006.01)
*C07D 277/20* (2006.01)
*C07D 417/10* (2006.01)
*C07D 333/06* (2006.01)
*C07D 319/06* (2006.01)
*C07C 49/76* (2006.01)

(52) U.S. Cl. .......................... 568/331; 549/75; 549/78; 549/274; 549/495; 549/502; 548/122; 548/132; 548/182; 548/194; 548/206; 548/236; 548/243; 548/247; 548/253; 548/263.2; 548/316.4; 548/544; 546/268.1; 546/340; 544/297; 544/298; 544/335; 544/336

(58) Field of Classification Search .................. 568/331
See application file for complete search history.

(56) References Cited

U.S. PATENT DOCUMENTS

| | | | |
|---|---|---|---|
| 4,853,398 | A | 8/1989 | Carr et al. |
| 5,977,177 | A | 11/1999 | Englert et al. |
| 6,194,432 | B1 | 2/2001 | Sheftell et al. |

FOREIGN PATENT DOCUMENTS

| | | |
|---|---|---|
| EP | 0028063 | 6/1984 |
| EP | 0174770 | 3/1988 |
| EP | 0288189 | 10/1988 |
| EP | 0516069 | 5/1991 |
| JP | 61-130271 | 6/1986 |
| WO | WO0156990 | 8/2001 |
| WO | WO2004018386 | 3/2004 |
| WO | WO2006014918 | 2/2006 |
| WO | WO2006015158 | 2/2006 |
| WO | WO2006049968 | 5/2006 |
| WO | WO2006057860 | 6/2006 |
| WO | WO2006057869 | 6/2006 |

OTHER PUBLICATIONS

Brown et al., Hydroxyacetophenone-Derived Antagonists of the Peptidoleukotrienes, *J. Med. Chem.*, 1989, 807-826, 32.
Pinkerton et al., Allosteric potentiators of the metabotropic glutamate receptor 2 (mGlu2). Part 1: Identification and synthesis of phenyl-tetrazolyl acetophenones, *Bioorganic & Medicinal Chemistry Letters*, 2004, 5329-5332, 14.
Pinkerton et al., Allosteric potentiators of the mteabotropic glutamate receptor 2 (mGlu2). Part 2: 4-Thiopyridyl acetophenones as non-tetrazole containing mGlu2 receptor potentiators, *Bioorganic & Medicinal Chemistry Letters*, 2004, 5867-5872, 14.
Sola, et al., A Superior, Readily Available Enantiopure Ligand for the Catalytic Enantioselective Addition of Diethylzinc to α-Substituted Aldehydes, *J. Org. Chem.* 1998, pp. 7078-7082, 63.

(Continued)

*Primary Examiner*—Rebecca L Anderson
*Assistant Examiner*—Shawquia Young
(74) *Attorney, Agent, or Firm*—Mark A. Winter

(57) ABSTRACT

This application relates to a substituted hydroxyphenyl ketone compound of formula I, or a pharmaceutically acceptable salt thereof, a pharmaceutical composition thereof and its use in treating migraine.

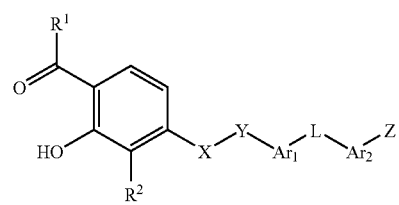

formula I

This application also relates to processes for preparing a compound of formula I, and intermediate compounds useful therein.

23 Claims, No Drawings

OTHER PUBLICATIONS

Bolm, et al., Catalyzed Asymmetric Aryl Transfer Reactions to Aldehydes with Boronic Acids as Aryl Source, *J. Am. Chem. Soc.*, 2002, pp. 14850-14851, 124.

Fontes et al., 2-Piperidino-1,1,2-triphenylethanol: A Highly Effective Catalyst for the Enantioselective Arylation of Aldehydes, *J. Org. Chem.*, 2004, pp. 2532-2543, 69.

Castellnou, et al., Polystyrene-Supported (R)-2-Piperazino-1,1,2-triphenylethanol: A Readily Available Supported Ligand with Unparalleled Catalytic Activity and Enantioselectivity, *J. Org. Chem.*, 2005, pp. 433-438, 70.

Ji et al., Highly Enantioselective Phenyl Transfer to Aryl Aldehydes Catalyzed by Easily Accessible Chiral Tertiary Aminonaphthol, *J. Org. Chem.*, 2005, pp. 1093-1095, 70.

POTENTIATORS OF GLUTAMATE RECEPTORS

This application claims the benefit of U.S. provisional application Ser. No. 60/630,060 filed Nov. 22, 2004.

The present invention provides a compound of formula I, pharmaceutical compositions thereof, and methods of using the same, as well as processes for preparing the same, and intermediates thereof.

BACKGROUND OF THE INVENTION

The excitatory amino acid L-glutamate (at times referred to herein simply as glutamate) through its many receptors mediates most of the excitatory neurotransmission within the mammalian central nervous system (CNS) and has been implicated in numerous peripheral nervous system (PNS) pathways. The excitatory amino acids, including glutamate, are of great physiological importance, playing a role in a variety of neurological, physiological and psychiatric processes, such as synaptic plasticity, motor control, respiration, cardiovascular regulation, sensory perception, and emotional responses.

Glutamate acts via at least two distinct classes of receptors. One class is composed of the ionotropic glutamate (iGlu) receptors that act as ligand-gated ion channels. Via activation of the iGlu receptors, glutamate is thought to regulate fast neuronal transmission within the synapse of two connecting neurons in the CNS. The second general type of receptor is the G-protein or second messenger-linked "metabotropic" glutamate (mGlu) receptor. Both types of receptors appear not only to mediate normal synaptic transmission along excitatory pathways, but also participate in the modification of synaptic connections during development and throughout life. Schoepp, Bockaert, and Sladeczek, Trends in Pharmacol. Sci., 11, 508 (1990); McDonald and Johnson, Brain Research Reviews, 15, 41 (1990).

The mGlu receptors belong to the Class C G-protein coupled receptor (GPCR) family. This family of GPCR's, including the calcium-sensing receptors, $GABA_B$ receptors and sensory receptors, are unique in that effectors bind to the amino-terminus portion of the receptor protein translating a signal via the transmembrane segments to the intracellular matrix through receptor/G-protein interactions. Ozawa, Kamiya and Tsuzuski, Prog. Neurobio., 54, 581 (1998). It has been demonstrated that the receptors are localized either pre- and/or post-synapticly where they can regulate neurotransmitter release, either glutamate or other neurotransmitters, or modulate the post-synaptic response of neurotransmitters, respectively.

At present, there are eight mGlu receptors that have been positively identified, cloned, and their sequences reported. These are further subdivided based on their amino acid sequence homology, their ability to effect certain signal transduction mechanisms, and their known pharmacological properties. Ozawa, Kamiya and Tsuzuski, Prog. Neurobio., 54, 581 (1998). For instance, the Group I mGlu receptors, which include the mGlu1 and mGlu5, are known to activate phospholipase C (PLC) via $G\alpha q$-proteins thereby resulting in the increased hydrolysis of phosphoinositides and intracellular calcium mobilization. There are several compounds that are reported to activate the Group I mGlu receptors including DHPG, (+/−)-3,5-dihydroxyphenylglycine. Schoepp, Goldworthy, Johnson, Salhoff and Baker, J. Neurochem., 63, 769 (1994); Ito, et al., Neurorep., 3, 1013 (1992). The Group II mGlu receptors consist of the two distinct receptors, mGlu2 and mGlu3 receptors. Both receptors are negatively coupled to adenylate cyclase via activation of $G\alpha i$-protein. These receptors can be activated by a group-selective compound such as (1S,2S,5R,6S)-2-aminobicyclo[3.1.0]hexane-2,6-dicarboxylate. Monn, et al., J. Med. Chem., 40, 528 (1997); Schoepp, et al., Neuropharmacol., 36, 1 (1997). Similarly, the Group III mGlu receptors, including mGlu4, mGlu6, mGlu7 and mGlu8, are negatively coupled to adenylate cyclase via $G\alpha i$ and are potently activated by L-AP4 (L-(+)-2-amino-4-phosphonobutyric acid). Schoepp, Neurochem. Int., 24, 439 (1994).

It should be noted that many of the available pharmacological tools are not ideal in that they cross react not only on the receptors within a group of mGlu receptors but also often have some activity between groups of mGlu receptors. For instance, compounds such as 1S,3R-ACPD, (1S,3R)-1-aminocyclopentane-trans-1,3-dicarboxylic acid, are believed to activate all of the Group I, II and III mGlu receptors depending upon the dose utilized while others, such as 1S,3S-ACPD, (1S,3S)-1-aminocyclopentane-trans-1,3-dicarboxylic acid, are more selective for the Group II receptors (mGlu2/3) than the Group I (mGlu1/5) or Group III (mGlu4/6/7/8). Schoepp, Neurochem. Int., 24, 439 (1994). To date, there are very few examples of selective agents for the mGlu receptors. Schoepp, Jane, and Monn, Neuropharmacol., 38, 1431 (1999).

It has become increasingly clear that there is a link between modulation of excitatory amino acid receptors, including the glutamatergic system, through changes in glutamate release or alteration in postsynaptic receptor activation, and a variety of neurological, psychiatric and neuroinflammatory disorders. e.g. Monaghan, Bridges and Cotman, Ann. Rev. Pharmacol. Toxicol., 29, 365-402 (1989); Schoepp and Sacann, Neurobio. Aging, 15, 261-263 (1994); Meldrum and Garthwaite, Tr. Pharmacol. Sci., 11, 379-387 (1990). The medical consequences of such glutamate dysfunction make the abatement of these neurological processes an important therapeutic goal.

Leukotrienes are potent local mediators, playing a major role in inflammatory and allergic responses including arthritis, asthma, psoriasis, and thrombotic disease. Leukotrienes are straight chain eicosanoids produced by the oxidation of arachidonic acid by lipoxygenases in several cell types including: eosinophils, neutrophils, mast cells, leukocytes, and macrophages. At the present time, there are two established Class A GPCR receptors for the cysteinyl-leukotrienes (CysLT1 and CysLT2) which the leukotrienes LTC4, LTD4 and LTE4 activate, mediating their proinflammatory effects. Each of the CysLT receptors has distinct tissue distributions and associations with physiological responses. Also, the leukotriene LTD4 has a higher affinity for the CysLT1 receptor than the other leukotrienes. Back, M. Life Sciences 71, 611-622, (2002). The leukotrienes, especially LTD4 and its receptor CysLT1, have been implicated in the pathogenesis of airway and allergic diseases such as asthma by contributing to bronchoconstriction, mucus secretion, and eosinophil migration. Thus, leukotrienes have been shown to play an important role in the pathology of asthma. Rigorous proof for the role of leukotrienes in asthma has been provided by several pivotal clinical trials in which orally administered LTD4 receptor antagonists produce clear therapeutic benefit in asthma patients. These benefits include reduction in the use of classic asthma therapies such as corticosteroids. Kemp, J. P., Amer. J. Resp. Medi. 2, 139-156, (2003).

Numerous investigations confirm the importance of the leukotrienes in allergic disorders as well. Thus, after allergen provocation, a marked increase in the LT concentration in the nasal lavage fluid of patients with allergic rhinitis was detected both in the early phase and in the late phase. Creticos, P. S., S. P. Peters, N. F. Adkinson, R. M. Naclerio, E. C. Hayes, P. S. Norman, L. M. Lichtenstein, N. Eng. J. Med. 310:1626 (1984). In addition, treatment with clinically efficacious antihistamines, such as azelastine, has shown a reduction in the formation of the cysteinyl-leukotrines, establishing a correlative relationship of allergic reaction symptoms to the degree of leukotriene formation and, thus, CysLT receptor activation. Achterrath-Tuckermann, U., Th. Simmet, W. Luck, I. Szelenyi, B. A. Peskar, Agents and Actions 24:217, 1988; Shin, M. H., F. M. Baroody, D. Proud, A. Kagey-Sobotka, L. M. Lichtenstein, M. Naclerio, Clin. Exp. Allergy 22:289, 1992.

U.S. Pat. No. 6,194,432 B1 discloses a method for using leukotriene antagonist drugs to prevent and treat recurrent primary headaches including migraine headaches.

U.S. Pat. No. 5,977,177 discloses certain substituted phenyl derivative compounds are modulators of endothelin and, as such, are useful in treating many different conditions including asthma.

U.S. Pat. No. 4,853,398 discloses certain benzene derivative compounds are selective antagonists of leukotrienes and, as such, are useful in treating allergic disorders such as asthma.

European Patent Application No. EP 28063 A1 and UK Patent Application No. GB 2058785 disclose certain phenol derivative compounds are antagonists of slow reacting substance of anaphylaxis and, as such, are useful in treating asthma, hay fever and skin afflictions.

Brown, F. J. et al *J. Med. Chem.* 32, p. 807-826 (1989) discloses certain hydroxyacetophenone derivative compounds are antagonists of leukotrienes and, as such, play a role in treating asthma.

International Patent Application Publication No. WO 2001056990 A2 and U.S. Pat. No. 6,800,651 B2 disclose certain pyridine derivative compounds are potentiators of metabotropic glutamate receptor function, specifically; potentiators of mGlu2 receptor function and, as such, are useful in the treatment of many different conditions including anxiety and migraine headache.

International Patent Application Publication No. WO 2004018386 and Pinkerton, A. B. et al *Bioorg. Med. Chem. Lett.*, 14, p. 5329-5332 (2004) disclose certain acetophenone derivative compounds are potentiators of glutamate receptor function, specifically; potentiators of mGlu2 receptor function and, as such, are useful in the treatment of many different conditions including anxiety, schizophrenia and migraine headache.

Recently, Pinkerton, A. B. et al *Bioorg. Med. Chem. Lett.*, 14, p. 5867-5872 (2004) disclose certain 4-thiopyridyl acetophenone derivative compounds are potentiators of glutamate receptor function, specifically; potentiators of mGlu2 receptor function and, as such, may be useful in the treatment of CNS disorders including anxiety, schizophrenia and epilepsy.

The present invention provides compounds of formula I that are potentiators of the mGlu2 receptor and antagonists of the CysLT1 receptor. As such, compounds of formula I would provide a means to treat disorders associated with glutamate or leukotrienes. In addition, it is anticipated that in disorders with a glutamate and leukotriene component to the onset, propagation and/or symptoms, the compounds of formula I will provide an effective treatment for the patient. The medical consequences of such glutamate dysfunction make the abatement of these neurological processes an important therapeutic goal.

SUMMARY OF THE INVENTION

The present invention provides a compound of formula I:

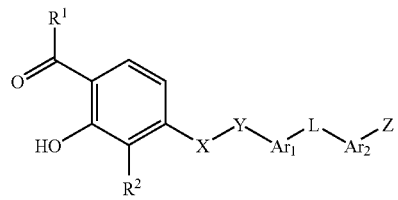

wherein $R^1$ is selected from the group consisting of C1-C5 alkyl, C3-C7 cycloalkyl, C4-C8 cycloalkylalkyl, phenyl and substituted phenyl;

$R^2$ is selected from the group consisting of hydrogen, C1-C5 alkyl, substituted C1-C5 alkyl, halo, phenyl, substituted phenyl, C1-C3 fluoroalkyl, CN, $CO_2R^3$, thiophenyl, substituted thiophenyl, thiazolyl, substituted thiazoyl, furanyl, substituted furanyl, pyridinyl, substituted pyridinyl, oxazolyl, substituted oxazolyl, isothiazolyl, substituted isothiazoyl, isoxazolyl, substituted isoxazolyl, 1,2,4-oxadiazolyl, substituted 1,2,4-oxadiazolyl, pyrimidinyl, substituted pyrimidinyl, pyridazinyl and substituted pyridazinyl;

X is selected from the group consisting of O, $S(O)_m$, and $NR^3$;

Y is selected from the group consisting of C1-C3 alkanediyl and substituted C1-C3 alkanediyl;

$Ar_1$ and $Ar_2$ are independently selected from the group consisting of phenylene, substituted phenylene, thiophenediyl, substituted thiophenediyl, thiazolediyl, substituted thiazolediyl, furanediyl, substituted furanediyl, pyridinediyl, substituted pyridinediyl, oxazolediyl, substituted oxazolediyl, isothiazolediyl, substituted isothiazolediyl, isoxazolediyl, substituted isoxazolediyl, pyrimidinediyl, substituted pyrimidinediyl, pyridazinediyl, substituted pyridazinediyl and 1,2,4-oxadiazole-3,5-diyl;

L is selected from the group consisting of C1-C5 alkanediyl, substituted C1-C5 alkanediyl, and —G—C(=W)—J—;

W is $CR^3R^3$, O or $NR^3$;

G and J are independently selected from the group consisting of a bond and C1-C3 alkanediyl;

$R^3$ is independently hydrogen or C1-C5 alkyl;

Z is selected from the group consisting of $(CH_2)_n COOH$,

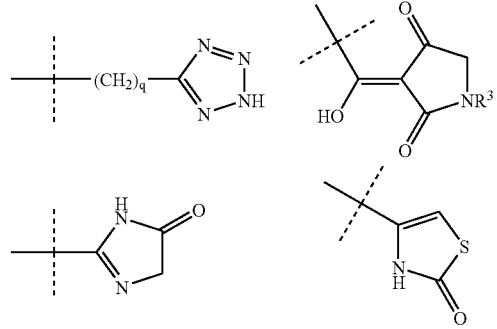

-continued

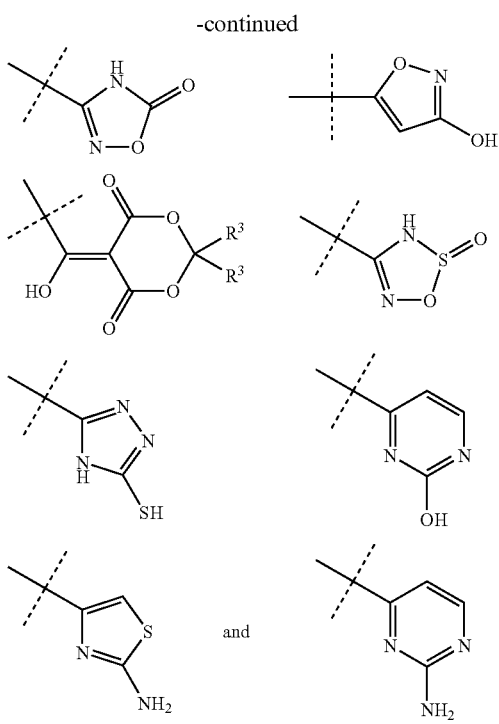

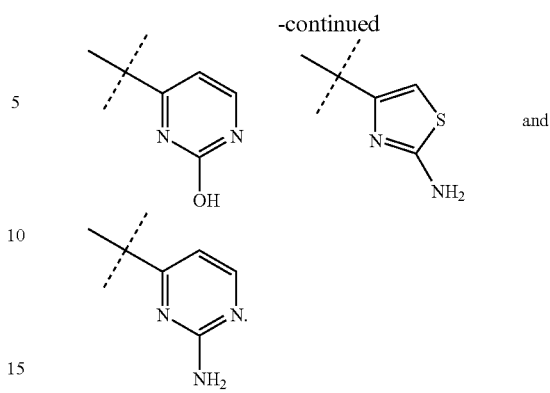

m is 0, 1, or 2;

n and q are independently 0, 1, 2 or 3;

and pharmaceutically acceptable salts thereof.

In another embodiment, the present invention provides a compound of formula I wherein Z is selected from the group consisting of $(CH_2)_nCOOH$,

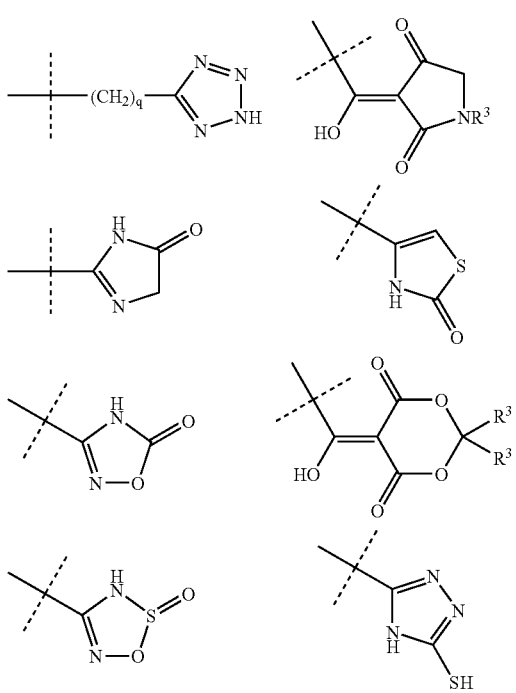

The present invention also provides for novel pharmaceutical compositions, comprising a compound of the formula I and a pharmaceutically acceptable diluent.

Because the compounds of formula I are potentiators of the mGlu2 receptor, the compounds of formula I are useful for the treatment of a variety of neurological and psychiatric disorders associated with glutamate dysfunction, including: acute neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, multiple sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, substance withdrawal (including, substances such as opiates, nicotine, tobacco products, alcohol, benzodiazepines, cocaine, sedatives, hypnotics, etc.), psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic pain states, severe pain, intractable pain, neuropathic pain, and post-traumatic pain), tardive dyskinesia, sleep disorders (including narcolepsy), attention deficit/hyperactivity disorder, and conduct disorder.

In another embodiment the present invention provides methods of treating neurological and psychiatric disorders associated with glutamate dysfunction, comprising administering to a patient in need thereof an effective amount of a compound of formula I. That is, the present invention provides for the use of a compound of formula I or pharmaceutical composition thereof for the treatment neurological and psychiatric disorders associated with glutamate dysfunction.

Of the disorders above, the treatment of migraine, anxiety, schizophrenia, and epilepsy are of particular importance.

In a preferred embodiment the present invention provides a method of treating migraine, comprising administering to a patient in need thereof an effective amount of a compound of formula I.

In another preferred embodiment the present invention provides a method of treating anxiety, comprising administering to a patient in need thereof an effective amount of a compound of formula I. Particularly preferred anxiety disorders are generalized anxiety disorder, panic disorder, and obsessive compulsive disorder.

In another preferred embodiment the present invention provides a method of treating schizophrenia, comprising administering to a patient in need thereof an effective amount of a compound of formula I.

In yet another preferred embodiment the present invention provides the use of a compound of formula I for the manufacture of a medicament for the treatment of neurological and psychiatric disorders associated with glutamate dysfunction.

In yet another preferred embodiment the present invention provides a compound of formula I for use as a medicament.

In yet another preferred embodiment the present invention provides the use of a compound of formula I for the manufacture of a medicament for the treatment of migraine.

In yet another preferred embodiment the present invention provides a pharmaceutical composition for the treatment of neurological and psychiatric disorders associated with glutamate dysfunction containing as an active ingredient a compound of formula I.

In yet another preferred embodiment the present invention provides a method of treating epilepsy, comprising administering to a patient in need thereof an effective amount of a compound of formula I.

Because such potentiators, including the compounds of formula I, positively modulate metabotropic glutamate receptor response to glutamate, it is an advantage that the present methods utilize endogenous glutamate.

Because such potentiators positively modulate metabotropic glutamate receptor response to glutamate agonists it is understood that the present invention extends to the treatment of neurological and psychiatric disorders associated with glutamate dysfunction by administering an effective amount of a metabotropic glutamate potentiator, including the compounds of formula I, in combination with a potentiated amount of a metabotropic glutamate receptor agonist. Such a combination may be advantageous in that it may augment the activity and selectivity of an agonist of metabotropic glutamate receptors, in particular a potentiator of mGlu2 receptors.

Because many the compounds of formula I are antagonists of the CysLT1 receptor, many of the compounds of formula I are useful for the treatment of a variety of disorders mediated by one or more leukotrienes such as inflammatory and allergic disorders associated with leukotriene mediation including inflammatory bowel syndrome, inflammatory bowel disease, arthritis, asthma, psoriasis, and thrombotic disease.

In another embodiment the present invention provides methods of treating a variety of disorders mediated by one or more leukotrienes, comprising administering to a patient in need thereof an effective amount of a compound of formula I. That is, the present invention provides for the use of a compound of formula I or pharmaceutical composition thereof for the treatment inflammatory and allergic disorders associated with leukotriene mediation.

In a preferred embodiment the present invention provides a method of treating asthma, comprising administering to a patient in need thereof an effective amount of a compound of formula I.

In another embodiment the present invention provides a process for preparing a compound of formula I or a pharmaceutically acceptable salt thereof.

DETAILED DESCRIPTION OF THE INVENTION

This invention provides methods of potentiating metabotropic glutamate receptors, in particular mGlu2 receptors. In the present methods an effective amount of a potentiator of metabotropic glutamate 2 receptors, including a compound of formula I, is administered which positively modulates the effect of glutamate or glutamate agonists on the subject receptor.

Before describing the present invention in greater detail, it is understood that the invention in its broadest sense is not limited to particular embodiments described herein, as variations of the particular embodiments described herein are within the scope of the claimed invention.

Thus, compounds useful in the present invention are those which are potentiators of metabotropic glutamate receptors, particularly, those that potentiate the effects of glutamate and glutamate agonists at mGlu2 metabotropic glutamate receptors, and even more particularly, those that potentiate the effects of glutamate and glutamate agonists at mGlu2 receptors. Useful compounds are varied in structure, and so long as they embrace the above properties, they are suitable for use in the present invention. Preferred compounds include, but are not limited to, those described herein.

The compounds of formula I potentiate the function of glutamate receptors. Specifically, the compounds of formula I are potentiators of the mGlu2 receptor.

Compounds of in the present invention also include those which are modulators of leukotriene receptors, particularly, those that antagonize the CysLT1 receptor.

As used herein, the following terms have the meanings indicated:

The term "C1-C5 alkyl" refers to a straight or branched alkyl chain having from one to five carbon atoms, and includes methyl, ethyl, propyl, iso-propyl, butyl, iso-butyl, sec-butyl, t-butyl, pentyl and the like. Particular values of "C1-C5 alkyl" are methyl, ethyl, n-propyl and iso-propyl.

The term "alkyl" refers to a monovalent aliphatic hydrocarbon. Within the meaning of "alkyl" is the term "C1-C3 alkyl".

The term "C1-C3 alkyl" refers to a straight or branched alkyl chain having from one to three carbon atoms, and includes methyl, ethyl, propyl, iso-propyl, and the like.

The term "substituted C1-C5 alkyl" refers to a straight or branched alkyl chain having from one to five carbon atoms, and includes methyl, ethyl, propyl, iso-propyl, butyl, iso-butyl, sec-butyl, t-butyl and pentyl having from 1 to 3 substituents selected from the group consisting of hydroxy, halogen, azido, alkoxy, acyloxy, carboxy, alkoxycarbonyl, amido, substituted amido, amino, acylamino, sulfonylamido, sulfonamide, phenyl, substituted phenyl, phenoxy, substituted phenoxy, benzyloxy, substituted benzyloxy, pyridyl, substituted pyridyl, thienyl, and substituted thienyl.

The term "C1-C5 alkanediyl" refers to a straight or branched divalent alkyl chain having from one to five carbon atoms, and includes methylene and ethane-1,1-diyl.

The term "substituted C1-C5 alkanediyl" refers to a straight or branched divalent alkyl chain having from one to five carbon atoms, and includes methylene having a substituent selected from the group consisting of hydroxyl, fluoro, azido, methoxy, amino, acetylamino and methylsulfonamide. Particular values of "substituted C1-C5 alkanediyl" are CH(OH), CH(F), CHN$_3$, CH(OCH$_3$), CHNH$_2$, CHNH(C=O)CH$_3$, CHNH(SO$_2$)CH$_3$.

The term "C1-C3 alkanediyl" refers to a straight or branched divalent alkyl chain having from one to three carbon atoms, and includes methylene.

The term "substituted C1-C3 alkanediyl" refers to a straight or branched alkyl chain having from one to three carbon atoms, and includes methylene, having from 1 or 2 substituents selected from the group consisting of hydroxy, halogen, azido, alkoxy, acyloxy, carboxy, alkoxycarbonyl, amido, substituted amido, amino, acylamino, sulfonylamido, sulfonamide, phenyl, substituted phenyl, pyridyl, substituted pyridyl, thienyl, and substituted thienyl The term "halogen or halo" refers to chloro, fluoro, bromo or iodo.

The term "C1-C3 fluoro alkyl" refers to an alkyl chain having from one to three carbon atoms substituted with one or more fluorine atoms, and includes fluoromethyl, difluoromethyl, trifluoromethyl, 2,2,2-trifluoroethyl, 3,3,3-trifluoropropyl and the like. A particular value of "C1-C3 fluoro alkyl" is trifluoromethyl.

The term "alkoxy" refers to a straight or branched alkyl chain attached to an oxygen atom. Within the meaning of "alkoxy" is the term "C1-C4 alkoxy".

The term "C1-C4 alkoxy" refers to straight or branched alkyl chain having from one to four carbon atoms attached to an oxygen atom, and includes methoxy, ethoxy, propoxy, iso-propoxy, butoxy, iso-butoxy, sec-butoxy, t-butoxy, and the like.

The term "substituted alkoxy" refers to a straight or branched alkyl chain attached to an oxygen atom having from 1 to 3 substituents. Within the meaning of "substituted alkoxy" is the term "substituted C1-C4 alkoxy".

The term "substituted C1-C4 alkoxy" refers to straight or branched alkyl chain having from one to four carbon atoms attached to an oxygen atom, and includes methoxy, ethoxy, propoxy, iso-propoxy, butoxy, iso-butoxy, sec-butoxy, t-butoxy, and the like, having from 1 to 3 substituents selected from the group consisting of hydroxy, halogen, alkoxy, carboxy, amido, substituted amido, amino, acylamino, sulfonylamido, sulfonamide, phenyl, and substituted phenyl; and when one or more of the substituents is hydroxy, halogen, alkoxy, amino, acylamino, and sulfonamide, then those substituents are not attached to the same carbon as the alkoxy oxygen atom.

The term "C3-C7 cycloalkyl" refers to saturated cyclic alkyl group having from three to seven carbon atoms and includes cyclopropyl, cyclobutyl, cyclopentyl, cyclohexyl, and cycloheptyl.

The term "C4-C8 cycloalkylalkyl" refers to saturated cyclic alkyl group having from three to seven carbon atoms linked to the point of substitution by a divalent unsubstituted saturated straight-chain or branched-chain hydrocarbon radical having at least 1 carbon atom and includes, cyclopropylmethyl, cyclopropyl-2-propyl, cyclobutylethyl, cyclopentylmethyl, cyclohexylmethyl, cycloheptylmethyl and the like.

The terms "phenyl and substituted phenyl" or "phenylene and substituted phenylene" refer to a monovalent or divalent radical, respectively, of the formula

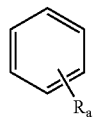

wherein $R_a$ is from 1 to 3 groups independently selected from the group consisting of hydrogen, hydroxy, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. Particular values of $R_a$ are hydrogen, methoxy and fluoro. Particular values of $R_a$ are hydrogen, methoxy and fluoro.

The terms "thiophenyl and substituted thiophenyl" or "thiophenediyl and substituted thiophenediyl" refer to a monovalent or divalent radical, respectively, of the formula

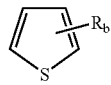

wherein $R_b$ is 1 or 2 groups independently selected from the group consisting of hydrogen, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. A particular value of $R_b$ is hydrogen.

The terms "pyridinyl and substituted pyridinyl" or "pyridinediyl and substituted pyridinediyl" refer to a monovalent or divalent radical, respectively, of the formula

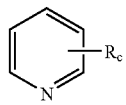

wherein $R_c$ is from 1 to 3 groups independently selected from the group consisting of hydrogen, hydroxy, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. A particular value of $R_c$ is hydrogen.

The terms "thiazolyl and substituted thiazolyl" or "thiazolediyl and substituted thiazolediyl" refer to a monovalent or divalent radical, respectively, of the formula

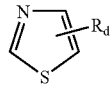

wherein $R_d$ is 1 or 2 groups independently selected from the group consisting of hydrogen, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. A particular value of $R_d$ is hydrogen.

The terms "furanyl and substituted furanyl" or "furanediyl and substituted furanediyl" refer to a monovalent or divalent radical, respectively, of the formula

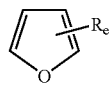

wherein $R_e$ is 1 or 2 groups independently selected from the group consisting of hydrogen, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. A particular value of $R_e$ is hydrogen.

The terms "isothiazolyl and substituted isothiazoyl" or "isothiazolediyl and substituted isothiazolediyl" refer to a monovalent or divalent radical, respectively, of the formula

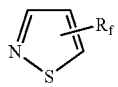

wherein $R_f$ is 1 or 2 groups independently selected from the group consisting of hydrogen, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. A particular value of $R_f$ is hydrogen.

The terms "isoxazolyl and substituted isoxazolyl" or "isoxazolediyl and substituted isoxazolediyl" refer to a monovalent or divalent radical, respectively, of the formula

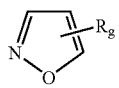

wherein $R_g$ is 1 or 2 groups independently selected from the group consisting of hydrogen, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. A particular value of $R_g$ is hydrogen.

The terms "1,2,4-oxadiazolyl and substituted 1,2,4-oxadiazolyl" or "1,2,4-oxadiazole-3,5-diyl" refer to a monovalent radical or divalent radical lacking $R_h$, respectively, of the formula

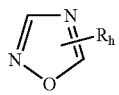

wherein $R_h$ is independently selected from the group consisting of hydrogen, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. A particular value of $R_h$ is hydrogen.

The terms "pyrimidinyl and substituted pyrimidinyl" or "pyrimidinediyl and substituted pyrimidinediyl" refer to a monovalent or divalent radical, respectively, of the formula

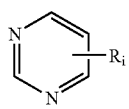

wherein $R_i$ is from 1 to 3 groups independently selected from the group consisting of hydrogen, hydroxy, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. A particular value of $R_i$ is hydrogen.

The terms "pyridazinyl and substituted pyridazinyl" or "pyridazinediyl and substituted pyridazinediyl" refer to a monovalent or divalent radical, respectively, of the formula

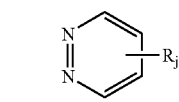

wherein $R_j$ is from 1 to 3 groups independently selected from the group consisting of hydrogen, hydroxy, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. A particular value of $R_j$ is hydrogen.

The terms "oxazolyl and substituted oxazolyl" or "oxazolediyl and substituted oxazolediyl" refer to a monovalent or divalent radical, respectively, of the formula

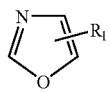

wherein $R_l$ is 1 or 2 groups independently selected from the group consisting of hydrogen, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. A particular value of $R_l$ is hydrogen.

The term "carboxy" refers to a radical of the formula

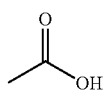

The term "alkoxycarbonyl" refers to a radical of the formula

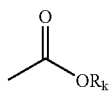

wherein $R_k$ is selected from the group consisting of alkyl, substituted alkyl, phenyl and substituted phenyl. Particular values of $R_k$ are methyl and ethyl.

The term "amido" refers to a radical of the formula

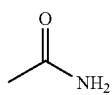

The term "substituted amido" refers to a radical of the formula

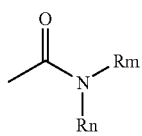

wherein $R_m$ is selected from the group consisting of alkyl and $R_n$ is selected from the group consisting of hydrogen, alkyl, phenyl and substituted phenyl. A particular value for $R_m$ is methyl. Particular values for $R_n$ are hydrogen and methyl.

The term "acylamino" refers to a radical of the formula

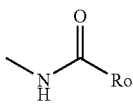

wherein $R_o$ is selected from the group consisting of alkyl, phenyl, and substituted phenyl. A particular value of $R_o$ is methyl.

The term "sulfonylamido" refers to a radical of the formula

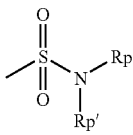

wherein $R_p$ is selected from the group consisting of alkyl, phenyl, and substituted phenyl; and $R_{p'}$ is selected from the group consisting of hydrogen and alkyl. A particular value for $R_p$ is methyl. Particular values for $R_{p'}$ are hydrogen and methyl.

The term "sulfonamide" refers to a radical of the formula

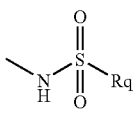

wherein $R_q$ is selected from the group consisting of alkyl, phenyl, and substituted phenyl. A particular value of $R_q$ is methyl.

As is readily apparent to those skilled in the art, the compounds of formula I may exist as tautomers. Where tautomers exist, each tautomeric form and mixtures thereof, are contemplated as included in the present invention. When any reference in this application to one of the specific tautomers of the compounds of formula I is given, it is understood to encompass every tautomeric form and mixtures thereof. For example, where the group Z is tetrazolyl, a compound of formula I exists as tautomer I and tautomer II. As such, it is understood any reference to a compound of formula I where the group Z is tetrazolyl as tautomer I encompasses tautomer II as well as mixtures of tautomer I and tautomer II.

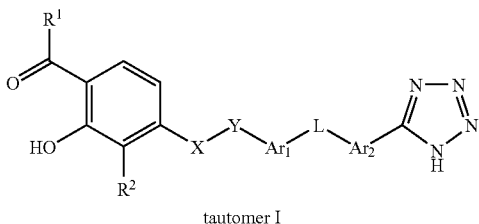

tautomer I

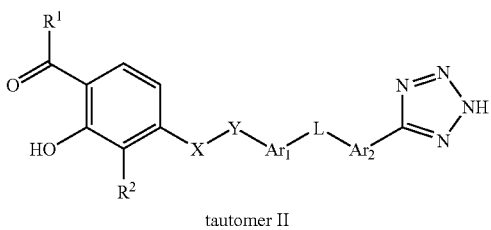

tautomer II

It is understood that compounds of the present invention may exist as stereoisomers. All enantiomers, diastereomers, and mixtures thereof, are contemplated within the present invention. Where specific stereochemistries are identified in this application, the Cahn-Ingold-Prelog designations of (R)- and (S)- and the cis- and trans-designation of relative stereochemistry are used to refer to specific isomers and relative stereochemistry. Known optical rotations are designated by (+) and (−) for dextrorotatary and levorotatary, respectively. Where a chiral compound is resolved into its enantiomers, but absolute configurations are not determined, the isomers are designated as isomer 1, isomer 2, etc.

Specific stereoisomers can be prepared by stereospecific synthesis using enantiomerically pure or enriched starting materials. The specific stereoisomers of either starting materials or compounds of formula I can be resolved by techniques well known in the art, such as those found in *Stereochemistry of Organic Compounds*, E. I. Eliel and S. H. Wilen (Wiley 1994) and *Enantiomers, Racemates, and Resolutions*, J. Jacques, A. Collet, and S. H. Wilen (Wiley 1991), including chromatography on chiral stationary phases, enzymatic resolutions, or fractional crystallization or chromatography of diastereomers formed for that purpose, such as diastereomeric salts.

While all enantiomers, diastereomers, and mixtures thereof, are contemplated within the present invention, preferred embodiments are single enantiomers and single diastereomers.

The terms "$Ar_1$ and $Ar_2$" refer to five or six member aryl or heterocyclic rings independently selected from the group consisting of phenylene, substituted phenylene, thiophenediyl, substituted thiophenediyl, thiazolediyl, substituted thiazolediyl, furanediyl, substituted furanediyl, pyridinediyl, substituted pyridinediyl, oxazolediyl, substituted oxazolediyl, isothiazolediyl, substituted isothiazolediyl, isoxazolediyl, substituted isoxazolediyl, pyrimidinediyl, substituted pyrimidinediyl, pyridazinediyl, substituted pyridazinediyl and 1,2,4-oxadiazole-3,5-diyl. It is understood that $Ar_1$ and $Ar_2$ being at least bi-radical may be attached in a 1-2, 1-3 or 1-4 regioisomeric position depending on the nature of the ring and the number and location of substituents. It is further understood that the present invention encompasses all possible regioisomeric combinations of attachment to $Ar_1$ and $Ar_2$. For example, where $Ar_1$ is phenylene there exists three possible regioisomers, designated as 1-2 (ortho or o-), 1-3 (meta or m-) and 1-4 (para or p-), all of which are encompassed in the present invention for a compound of formula I where $Ar_1$ is phenylene.

formula I

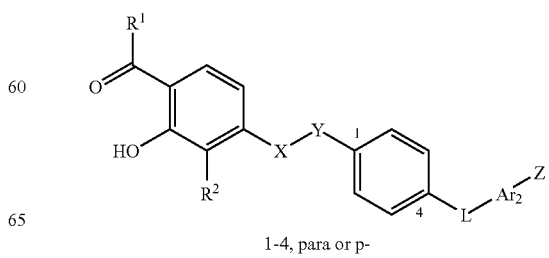

1-4, para or p-

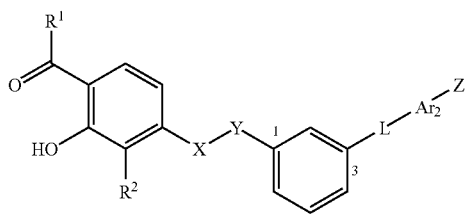

1-3, meta or m- formula I

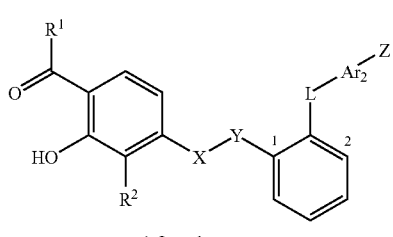

1-2, ortho or o-

The term "pharmaceutically acceptable salt" refers to an addition salt that exists in conjunction with the acidic and/or basic portion of a compound of formula I. Such salts include the pharmaceutically acceptable salts listed in *Handbook of Pharmaceutical Salts: Properties, Selection and Use*, P. H. Stahl and C. G. Wermuth (Eds.), Wiley-VCH, New York, 2002 which are known to the skilled artisan. Pharmaceutically acceptable salts that are acid addition are formed when a compound of formula I and the intermediates described herein containing a basic functionality are reacted with a pharmaceutically acceptable acid. Pharmaceutically acceptable acids commonly employed to form such acid addition salts include inorganic acids, such as hydrochloric, hydrobromic, nitric, sulphuric or phosphoric acids, and organic acids such as acetic, citric, esylic, fumaric, glycolic, glucuronic, glutaric, lactic, maleic, malic, mandelic, mesylic, napadisylic, oxalic, succinic, tartaric, salicyclic, o-acetoxybenzoic, or p-toluene-sulphonic. Pharmaceutically acceptable salts that are base addition are formed when a compound of formula I and the intermediates described herein containing a acidic functionality are reacted with a pharmaceutically acceptable base. Pharmaceutically acceptable bases commonly employed to form base addition salts include organic bases such as ammonia, arginine, benethamine, benzathine, benzylamine, betaine, butylamine, choline, dicyclohexylamine, diethanolamine, diethylamine, ethylenediamine, glucosamine, imidazole, lysine, piperazine, procaine, and inorganic bases such as calcium, potassium, sodium and zinc salts of hydroxide, carbonate or bicarbonate and the like.

In addition to pharmaceutically acceptable salts, other salts are included in the invention. They may serve as intermediates in the purification of compounds or in the preparation of other, for example pharmaceutically-acceptable, acid addition salts, or are useful for identification, characterization or purification.

The term "protecting group or Pg," as used herein, refers to those groups intended to protect or block functional groups against undesirable reactions during synthetic procedures. In the case of an amino or hydroxyl functional group, the suitable protecting group used will depend upon the conditions that will be employed in subsequent reaction steps wherein protection is required. For example, it may be desirable to employ the protection of multiple functional groups, such as amino and hydroxyl, and control their protection and deprotection independently. Commonly used amino and hydroxyl protecting groups are disclosed in *Protective Groups In Organic Synthesis*, T. W. Greene and P. G. M. Wuts 3rd Ed. (John Wiley & Sons, New York (1999)). Suitable amino protecting groups include acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, alpha-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like, carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, alpha,alpha-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred suitable amino protecting groups are acetyl, methyloxycarbonyl, benzoyl, pivaloyl, allyloxycarbonyl, t-butylacetyl, benzyl, t-butyloxycarbonyl (Boc) and benzyloxycarbonyl (Cbz). Suitable hydroxyl protecting groups include ethers such as methoxymethyl, 1-ethoxyethyl, tert-butyl, allyl, benzyl, tetrahydropyranyl and the like; silyl ethers such as trimethylsilyl, triethylsilyl, triisopropylsilyl, tert-butyldimethylsilyl and the like; esters such as formate, acetate, pivaloate, benzoate and the like; and sulfonates such as mesylate, benzylsulfonate, tosylate and the like. Preferred suitable hydroxyl protecting groups are acetyl, trimethylsilyl, triisopropylsilyl, tert-butyldimethylsilyl and benzyl.

As with any group of pharmaceutically active compounds, some groups are preferred in their end use application. Preferred embodiments for a compound of formula I of the present invention are given below.

Compounds in which $R^1$ is C3-C7 cycloalkyl or C4-C8 cycloalkylalkyl are preferred. Compounds in which $R^1$ is C1-C5 alkyl are more preferred. Compounds in which $R^1$ is methyl are even more preferred.

Compounds in which $R^2$ is phenyl, substituted phenyl, thiophenyl, substituted thiophenyl, thiazolyl, substituted thiazolyl, pyridinyl, or substituted pyridinyl are preferred. Compounds in which $R^2$ is C1-C5 alkyl, halo or C1-C3 fluoroalkyl are more preferred. Compounds in which $R^2$ is methyl, propyl, trifluoromethyl, or chloro are even more preferred.

Compounds in which X is $S(O)_m$ where m is 0, 1 or 2 are preferred. Compounds in which X is O are more preferred.

Compounds in which Y is C1-C3 alkanediyl are preferred. Compounds in which Y is methylene are more preferred.

Compounds in which $Ar_1$ is phenylene are preferred.

Compounds in which $Ar_1$ and $Ar_2$ are independently phenylene or pyridinediyl are preferred.

Compounds in which $Ar_1$ is substituted phenylene, 1,2,4-oxadiazol-3,5-diyl or substituted pyridinediyl are preferred. Compounds in which $Ar_1$ is phenylene or pyridinediyl, either attached in the 1-3 position, are more preferred. Compounds in which $Ar_1$ is phenylene or pyridinediyl, either ring attached in the 1-4 position, are even more preferred.

Compounds in which $Ar_2$ is phenylene are preferred.

Compounds in which Ar$_2$ is substituted phenylene or substituted pyridinediyl are preferred. Compounds in which Ar$_2$ is phenylene or pyridinediyl are more preferred. Compounds in which Ar$_2$ is pyridinediyl attached in the 1-4 or 1-3 position are even more preferred.

Compounds in which Ar$_1$ and Ar$_2$ are independently phenylene or pyridinediyl are preferred.

Compounds in which Ar$_1$ is phenylene are preferred.

Compounds in which Ar$_2$ is pyridinediyl are preferred.

Compounds in which Ar$_2$ is attached at the 1-4 position are preferred.

Compounds in which Ar$_2$ is attached at the 1-3 position are preferred.

Compounds in which Ar$_1$ is attached at the 1-3 position or 1-4 position are preferred.

Compounds in which L is C1-C5 alkanediyl, substituted C1-C5 alkanediyl or C(=W) where W is CH$_2$ or O are preferred. Compounds in which L is —CH(OH)—, —CH(F)— or —CH$_2$— are more preferred.

Compounds in which Z is

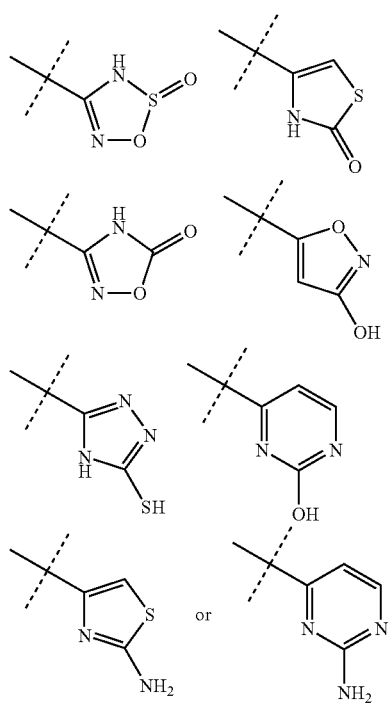

are preferred. Compounds in which Z is

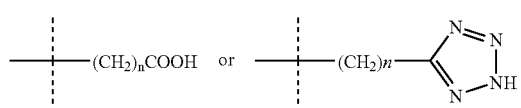

are more preferred. Compounds in which Z is

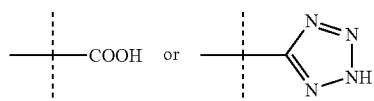

are even more preferred.

A compound of formula I as described above wherein

R$^1$ is methyl or ethyl;

R$^2$ is selected from the group consisting of methyl, ethyl, n-propyl, iso-propyl, fluoro, chloro, iodo, phenyl, 4-fluorophenyl, trifluoromethyl, CN, 2-thiophenyl, 3-thiophenyl, 2-thiazolyl, 2-pyridinyl, 3-pyridinyl, and 4-pyridinyl;

X is selected from the group consisting of O, S, SO$_2$, NH and NCH$_3$;

Y is methylene;

Ar$_1$ is phenylene or 1,2,4-oxadiazole-3,5-diyl;

Ar$_2$ is selected from the group consisting of phenylene, fluorophenylene, methoxyphenylene and pyridinediyl;

L is selected from the group consisting of CH$_2$, CHCH$_3$, CH(OH), CH(F), CHN$_3$, CH(OCH$_3$), CHNH$_2$, CHNH(C=O)CH$_3$, CHNH(SO$_2$)CH$_3$, C=O, and CH=CH$_2$;

Z is selected from the group consisting of (CH$_2$)$_n$COOH,

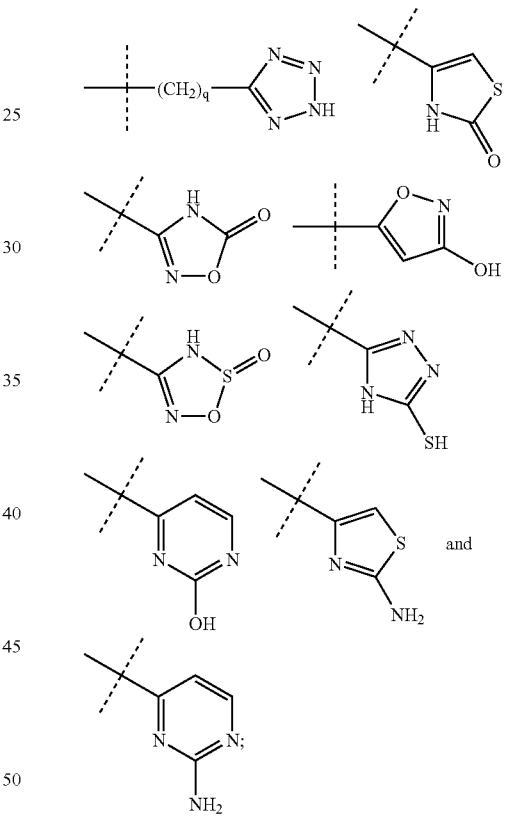

n is 0; and q is 0 is preferred.

A compound of formula I selected from the group consisting of (+)-3-{[4-(4-acetyl-3-hydroxy-2-propyl-phenoxymethyl)-phenyl]-hydroxy-methyl}-benzoic acid (isomer 1) and (−)-3-{[4-(4-acetyl-3-hydroxy-2-propyl-phenoxymethyl)-phenyl]-hydroxy-methyl}-benzoic acid (isomer 2) is preferred. A compound of formula I which is 3-{[4-(4-acetyl-3-hydroxy-2-propyl-phenoxymethyl)-phenyl]-(S)-hydroxymethyl}-benzoic acid is more preferred.

Further embodiments of the invention include a process for preparing the compound of formula I, or a pharmaceutically acceptable salt thereof, comprising (A) for a compound of formula I where Z is tetrazolyl,

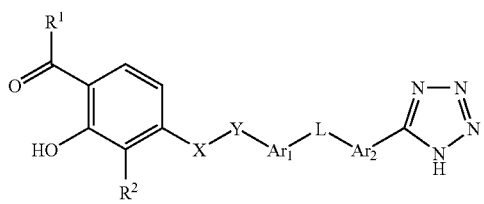

I, Z is tetrazolyl cycloaddition of a compound of formula II where $R^{10}$ is cyano with an azide reagent;

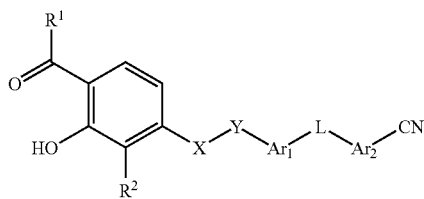

II, $R^{10}$ is cyano (B) for a compound of formula I where Z is COOH,

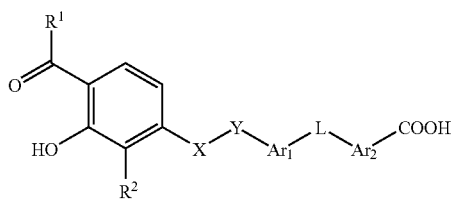

I, Z is COOH hydrolysis of a compound of formula II wherein $R^{10}$ is $COOR^{14}$ and $R^{14}$ is selected from the group consisting of C1-C5 alkyl, phenyl and benzyl;

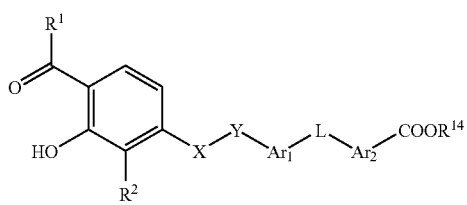

II, $R^{10}$ is $COOR^{14}$ (C) for a compound of formula I where Z is COOH,

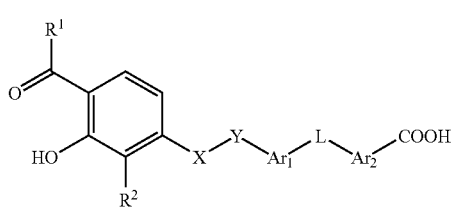

I, Z is COOH hydrolysis of a compound of formula II where $R^{10}$ is cyano; and

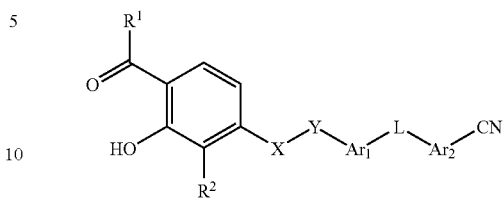

II, $R^{10}$ is cyano (D) for a compound of formula I

I where Z is

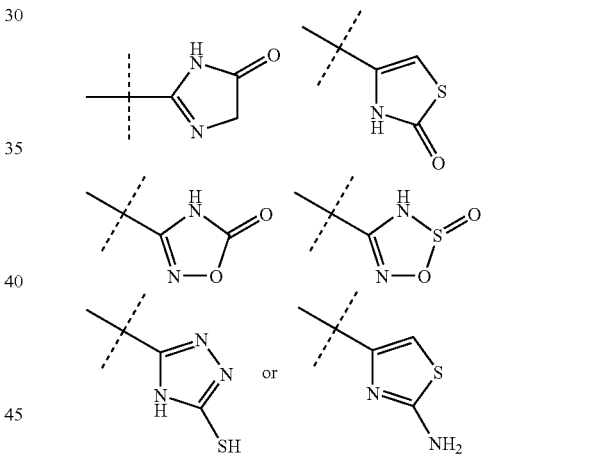

cyclocondensating a compound of formula II where $R^{10}$ is an acyl chloride

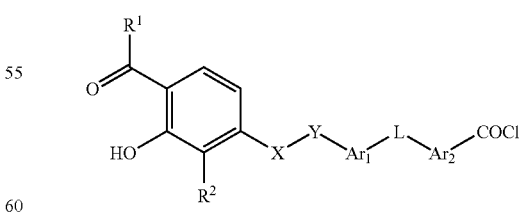

II, $R^{10}$ is acid chloride.

whereafter, when a pharmaceutically acceptable salt of the compound of formula I is required, it is obtained by reacting the acid of formula I with a physiologically acceptable base or by reacting a basic compound of formula I with a physiologically acceptable acid or by any other conventional procedure.

A further embodiment of the present invention provides intermediate compounds useful for the preparation of a compound of formula I. More specifically, the present invention provides a compound of formula II

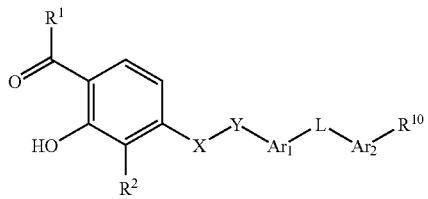

wherein
$R^1$, $R^2$, X, Y, $Ar_1$, $Ar_2$ and L are defined as above; and
$R^{10}$ is CN or $COOR^{14}$ in which $R^{14}$ is selected from the group consisting of C1-C5 alkyl, phenyl and benzyl. A particular value of $R^{14}$ is methyl.

A further embodiment of the present invention provides a process for preparing 3-{[4-(4-acetyl-3-hydroxy-2-propyl-phenoxymethyl)-phenyl]-(S)-hydroxymethyl}-benzoic acid or a pharmaceutically acceptable salt thereof, comprising
(i) alkylating 2,4-dihydroxy-3-propyl-acetophenone with 3-[4-(methanesulfonyloxymethylphenyl)-(S)-acetoxymethyl]-benzonitrile in the presence of potassium carbonate to afford 3-{[4-(4-acetyl-3-hydroxy-2-propylphenoxymethyl)-phenyl]-(S)-acetoxymethyl}-benzonitrile;
(ii) hydrolyzing 3-{[4-(4-acetyl-3-hydroxy-2-propylphenoxymethyl)-phenyl]-(S)-acetoxymethyl}-benzonitrile in the presence of potassium hydroxide wherein the hydrolysis reaction is followed by acidification with hydrochloric acid to afford 3-{[4-(4-acetyl-3-hydroxy-2-propyl-phenoxymethyl)-phenyl]-(S)-hydroxymethyl}-benzoic acid; whereafter, when a pharmaceutically acceptable salt of 3-{[4-(4-acetyl-3-hydroxy-2-propyl-phenoxymethyl)-phenyl]-(S)-hydroxymethyl}benzoic acid is required, it is obtained by reacting 3-{[4-(4-acetyl-3-hydroxy-2-propyl-phenoxymethyl)-phenyl]-(S)-hydroxymethyl}-benzoic acid with a physiologically acceptable base or by any other conventional procedure.

A further embodiment of the present invention provides the above mentioned starting 3-[4-(methanesulfonyloxymethylphenyl)-(S)-acetoxymethyl]-benzonitrile is prepared using a process comprising
(i) arylating enantioselectively 3-cyanobenzaldehyde with 2,4,6-tris-[4-(tert-butyl-dimethyl-silanyloxymethyl)-phenyl]-cyclotriboroxane in the presence of a dialkyl zinc and chiral catalyst wherein the dialkyl zinc is diethyl zinc; and the chiral catalyst is (R)-(−)-2-piperidino-1,1,2-triphenyl ethanol to afford 3-{[4-(tert-butyldimethylsilanyloxymethyl)phenyl]-(S)-hydroxymethyl}-benzonitrile;
(ii) acylating 3-{[4-(tert-butyldimethylsilanyloxymethyl)phenyl]-(S)-hydroxymethyl}-benzonitrile with acetic anhydride whereafter hydrolyzing the 4-(tert-butyl-dimethyl-silanyl group with hydrochloric acid to afford 3-[4-(hydroxymethylphenyl)-(S)-acetoxymethyl]-benzonitrile;
(iii) sulfonating 3-[4-(hydroxymethylphenyl)-(S)-acetoxymethyl]-benzonitrile with methane sulfonyl chloride to afford 3-[4-(methanesulfonyloxymethylphenyl)-(S)-acetoxymethyl]-benzonitrile.

A further embodiment of the present invention provides intermediate compounds useful for the preparation of a compound of formula I. More specifically, the present invention provides a compound which is 3-[4-(hydroxymethylphenyl)-(S)-acetoxymethyl]-benzonitrile.

Compounds of the present invention may be made by a process which is analogous to one known in the chemical art for the production of structurally analogous compounds or by a novel process described herein. Such processes useful for the manufacture of a compound of formula I as defined above are provided as further features of the invention and are illustrated by the following procedures in which, unless otherwise specified, the meanings of the generic radicals are as defined above and all reagents are well known and appreciated in the art.

Generally, a compound of formula I may be prepared from a compound of formula II where $R^{10}$ represents a precursor to Z (Reaction Scheme A, step a). More specifically, a compound of formula II where $R^{10}$ is carboxylic acid ester or nitrile is reacted with a suitable base such as potassium hydroxide in a suitable solvent such as water to provide a compound of formula I where Z is carboxylic acid. Additionally, a compound of formula II where $R^{10}$ is cyano is reacted with an azide reagent to provide a compound of formula I where Z is tetrazolyl. Azide reagents include $HN_3$ wherein $HN_3$ is provided from the reaction of sodium azide and a protic acid such as triethylamine hydrochloride or ammonium chloride. The reaction is conveniently in a solvent such solutions of water and an organic co-solvent wherein the organic cosolvent is an alcohol such as isopropyl alcohol or a tertiary amide such as N-methylpyrrolidinone. Other examples of azide reagents include transition metal azide complexes such as provided from the reaction of zinc bromide and sodium azide, as well as the trialkylsilylazides such as trimethylsilylazide. A compound of formula II where $R^{10}$ is an acid halide is reacted in one or more steps with cyclocondensating agents to provide a compound of formula I where Z is

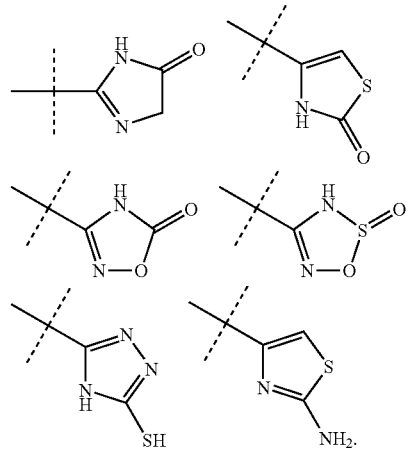

A compound of formula of II may be prepared from a compound of formula III (Reaction Scheme A, step b) or, alternatively, from a compound of formula V (Reaction Scheme A, step c). More specifically in step b, a compound of formula III where X is O is reacted under Mitsunobu conditions with a compound of formula IV where $R^{11}$ is OH in the presence of an organophosphine such as tributylphosphine and an appropriate azodicarbonyl reagent such as 1,1'-(azodicarbonyl)dipiperidine to provide a compound of formula II. Suitable solvents include toluene and dichloromethane. In step b, a compound of formula II may also be prepared by reacting a compound of formula III where X is O, S, NH with a compound of formula IV where $R^{11}$ is a leaving group in the presence of a suitable base such as cesium carbonate and a suitable solvent such as acetone. Suitable leaving groups include halides such as iodide, and sulfonate esters such as methanesulfonate ester.

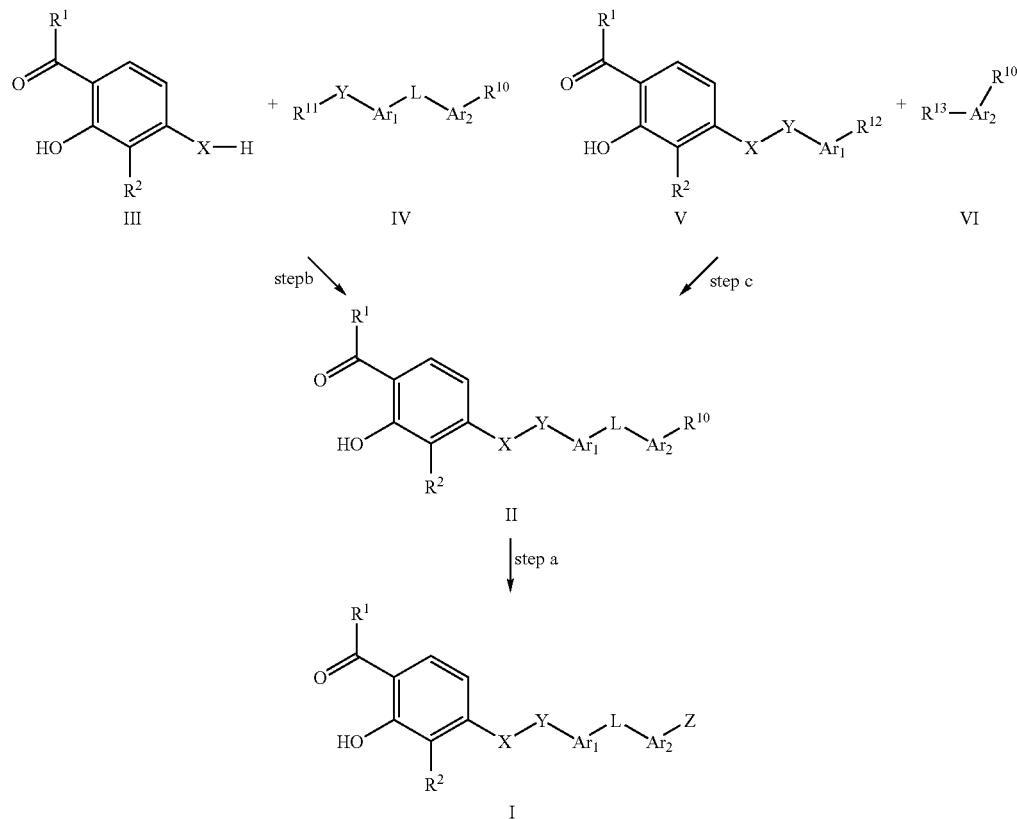

Reaction Scheme A

Alternatively, a compound of formula of II may be prepared from a compound of formula V (Reaction Scheme A, step c) where $R^{12}$ is an appropriate precursor to the group L.

A compound of formula III where $R^2$ is halo, phenyl, substituted phenyl, thiophenyl, substituted thiophenyl and the like may be prepared from a compound of formula VII (Reaction Scheme B). More specifically, a compound of formula VII where X is O is reacted under the appropriate halogenation conditions to provide a compound of formula III where X is O and $R^2$ is a halogen such as chloro, bromo or iodo. A compound of formula III where X is O and $R^2$ is a halogen such as chloro, bromo or iodo is reacted with a boronic acid of phenyl, substituted phenyl, thiophenyl, substituted thiophenyl and the like in the presence of a transition metal catalyst such as $Pd(dppf)_2Cl_2$ and a base such as cesium hydroxide to provide a compound of formula III where $R^2$ is the corresponding phenyl, substituted phenyl, thiophenyl, substituted thiophenyl and the like. The reaction is conveniently carried out in a solvent such as solutions of tetrahydrofuran and water.

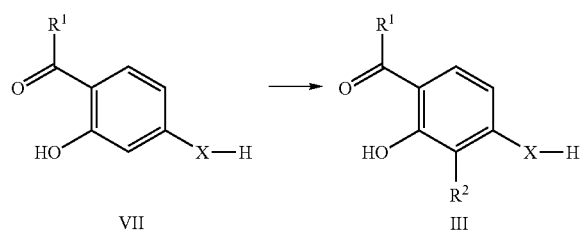

Reaction Scheme B

A compound of formula III where X is S may be prepared from a compound of formula III where X is O. More specifically, a compound of formula III where X is O is reacted with dimethylthiocarbamoyl chloride in a suitable solvent such as dichloromethane. The resulting thiocarbamate is heated in a suitable solvent such as dodecane and treated with sodium hydroxide to provide a compound of formula III where X is S.

A compound of formula III may also be prepared from a compound of formula IX where the group Pg represents a suitable protecting group (Reaction Scheme C). More specifically in step a, a compound of formula IX where $R^2$ is a halogen such iodo or bromo and Pg is methyl, is reacted with a boronic acid of phenyl, substituted phenyl, thiophenyl, substituted thiophenyl and the like in the presence of a transition metal catalyst such as $Pd(dppf)_2Cl_2$ and a base such as cesium hydroxide to provide a compound of formula IX where $R^2$ is phenyl, substituted phenyl, thiophenyl, substituted thiophenyl and the like, and Pg is methyl. The reaction is conveniently carried out in a solvent such as a solution of tetrahydrofuran and water. Further in step a, a compound of formula IX where $R^2$ is phenyl, substituted phenyl, thiophenyl, substituted thiophenyl and the like is reacted with an $R^1$ acyl halide such as acetyl chloride and a Lewis acid such as aluminum chloride in a suitable solvent to provide a compound of formula VIII where $R^1$ is methyl and $R^2$ is phenyl, substituted phenyl, thiophenyl, substituted thiophenyl and the like. Suitable solvents include dichloromethane. In step b, a compound of formula VIII where the group Pg is methyl is reacted with deprotection agents such as pyridine hydrochloride in the presence of microwave radiation to provide a compound of formula III where $R^2$ is phenyl, substituted phenyl, thiophenyl, substituted thiophenyl and the like.

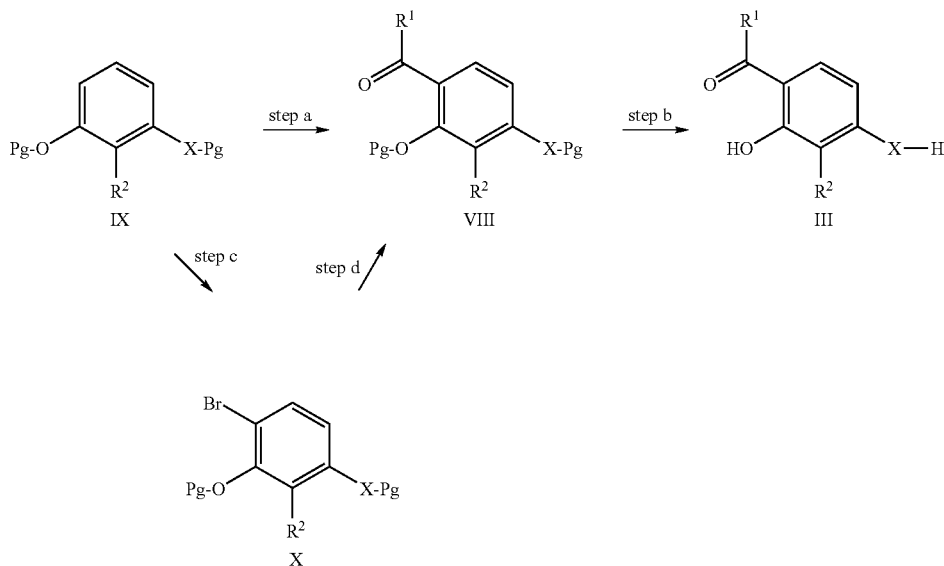

Additionally in Reaction Scheme C, a compound of formula III where $R^2$ is C1-C3 fluoroalkyl may be prepared from a compound of formula IX where $R^2$ is a halogen. More specifically, a compound of formula IX where $R^2$ is iodo, X is O and Pg is a suitable protecting group such as benzyl is reacted with an alkyl ester of difluoro-fluorosulfonyl-acetic acid in the presence of hexamethylphosphoramide and a transition metal catalyst such as copper iodide in a suitable solvent to provide a compound of formula IX where $R^2$ is trifluoromethyl, X is O, and Pg is benzyl. Suitable solvents include dimethylformamide. In step c, a compound of formula IX where $R^2$ is trifluoromethyl, X is O, and Pg is benzyl is reacted N-bromosuccinimide in a suitable solvent such as dimethylformamide to provide a compound of formula X. In step d, a compound of formula X is reacted with tributyl-(1-ethoxy-vinyl)-stannane and a transition metal catalyst such as tetrakis(triphenylphosphine)palladium in a solvent such as dioxane followed by acid hydrolysis to provide a compound of formula VIII where $R^1$ is methyl, $R^2$ is trifluoromethyl, X is O, and Pg is benzyl. In step b, a compound of formula VIII where $R^1$ is methyl, $R^2$ is trifluoromethyl, X is O, and Pg is benzyl is reacted with a transition metal catalyst such as palladium hydroxide in the presence of an effective hydrogen source such as cyclohexene to provide a compound of formula III where $R^1$ is methyl, $R^2$ is trifluoromethyl, and X is O, Suitable solvents include ethanol.

In Reaction Scheme D, a compound of formula IIa where $Pg^1$ is a suitable hydroxyl protecting group may be prepared from a compound of formula IVf where $Pg^1$ is the same. More specifically in step a, a compound of formula XVII where Pg is a trialkylsilyl such as tert-butyldimethylsilyl is reacted with magnesium in a suitable solvent such as tetrahydrofuran. The resulting Grignard reagent of XVII is reacted with a compound of formula XVIII in a suitable solvent such as tetrahydrofuran to provide a compound of formula XIX where Pg is tert-butyldimethylsilyl and $R^{10}$ is a suitable precursor to Z such as cyano.

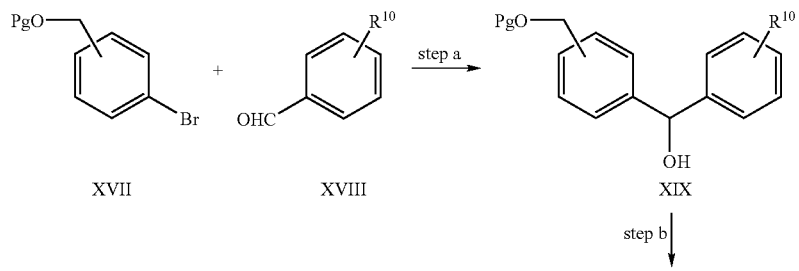

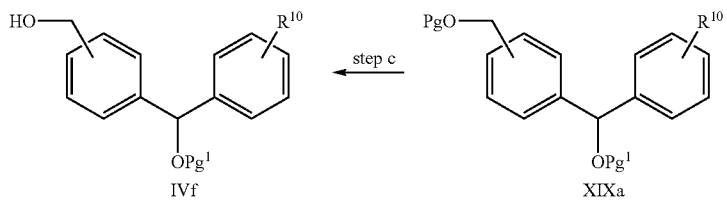

In step b, a compound of formula XIX where Pg is tert-butyldimethylsilyl is reacted with a second protecting agent such as 3,4-dihydro-2H-pyran and a suitable catalyst such as pyridinium-para-toluenesulfonate to provide a compound of formula XIXa where Pg is tert-butyldimethylsilyl and $Pg^1$ is tetrahydro-2H-pyran. The reaction is conveniently carried out in a solvent such as dichloromethane. Additional second protecting agents such as acetic acid anhydride in the presence of a base such as triethylamine may be used to provide a compound of formula XIXa where Pg is tert-butyldimethylsilyl and $Pg^1$ is acetyl. In step c, a compound of formula XIXa is reacted with an agent that removes protecting group Pg without removing protecting group $Pg^1$. More specifically in step c, a compound of formula XIXa where Pg is tert-butyldimethylsilyl and $Pg^1$ is tetrahydro-2H-pyran is reacted with tetrabutylammonium fluoride in a suitable solvent such as tetrahydrofuran to provide a compound of formula IVf where $Pg^1$ is tetrahydro-2H-pyran. Alternatively, a compound of formula XIXa where Pg is tert-butyldimethylsilyl and $Pg^1$ is acetyl is reacted with an acid such as hydrochloric acid at about room temperature to provide a compound of formula IVf where $Pg^1$ is acetyl.

In Reaction Scheme E, compounds of formula Ia and Ib may be prepared from a compound of formula Ia where $Pg^1$ represents a suitable protecting group. More specifically in step a, a compound of formula Ia where $R^{10}$ is a suitable precursor to Z such as nitrile is reacted with an azide source such as sodium azide in the presence of a suitable Lewis acid such as zinc bromide to provide a compound of formula Ia where Z is tetrazolyl. The reaction is conveniently carried out in a solvent such as water and isopropyl alcohol. In step b, a compound of formula Ia is reacted with reducing agents such as triethylsilane in the presence of a suitable Lewis acid such as boron trifluoride diethyl etherate to provide a compound of formula Ib where Z is tetrazolyl. The reaction is conveniently carried out in a solvent such as dichloromethane.

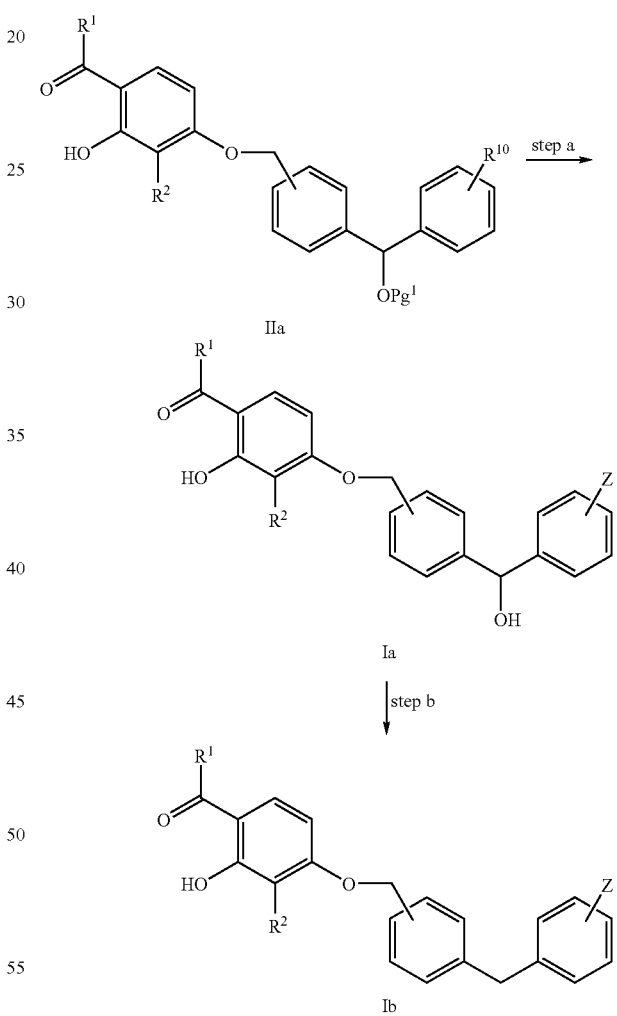

In Reaction Scheme F, compounds of IIc and IId may be prepared from a compound of formula IIa where $Pg^1$ is a suitable protecting group. More specifically in step a, a compound of formula IIa is reacted with a suitable acid such as p-toluenesulfonic acid to provide a compound of formula IIb. The reaction is conveniently carried out in a solvent such as methanol. In step b, a compound of formula IIb is reacted with a halogenating agent such as diethylaminosulfur trifluoride Reaction Scheme F

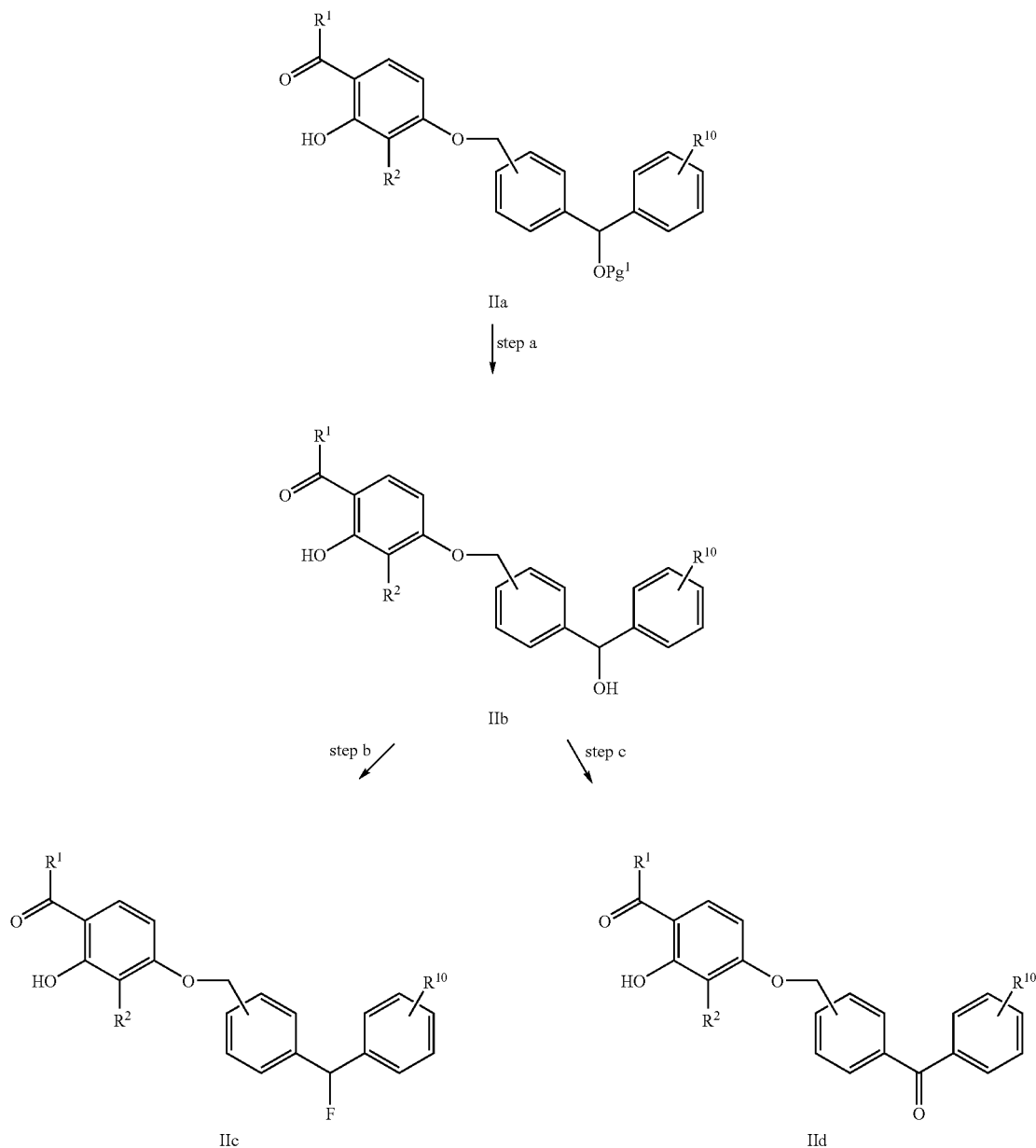

in a solvent such as dichloromethane to provide a compound of formula IIc. In step c, a compound of formula IIb is reacted with an oxidizing agent such as Dess-Martin periodinane (1,1,1-triacetoxy-1,1-dihydro-1,2-benziodoxol-3 (1)-one) in a suitable solvent such as dichloromethane to provide a compound of formula IId.

In Reaction Scheme G, a compound of IIf where $R^2$ is phenyl, substituted phenyl, thiophenyl, substituted thiophenyl, thiazolyl, substituted thiazolyl, furanyl, substituted furanyl, pyridinyl, substituted pyridinyl, oxazolyl, substituted oxazolyl, isothiazolyl, substituted isothiazolyl, isoxazolyl, substituted isoxazolyl, 1,2,4-oxadiazolyl, pyrimidinyl, substituted pyrimidinyl or substituted 1,2,4-oxadiazolyl may be prepared from a compound where $R^2$ is a suitable coupling group such as the halogen iodo. More specifically in step a, a compound of formula XXI where $R^{14}$ is a suitable coupling group such as the halogen bromo is reacted with a compound of formula XX in the presence of a suitable transition metal catalyst such as tetrakistriphenylphosphine palladium(0) and a suitable base such as aqueous sodium carbonate to provide a compound of formula Ivg where $R^{11}$ is hydroxyl. The reaction is conveniently carried out in a solvent such as toluene. In step b, a compound of formula IVg where $R^{11}$ is a suitable coupling group such as hydroxyl or the halogen iodo is reacted with a compound of formula IIIa, as described in Scheme A for a compound of formula II, to provide a compound of formula IIe.

Reaction Scheme G

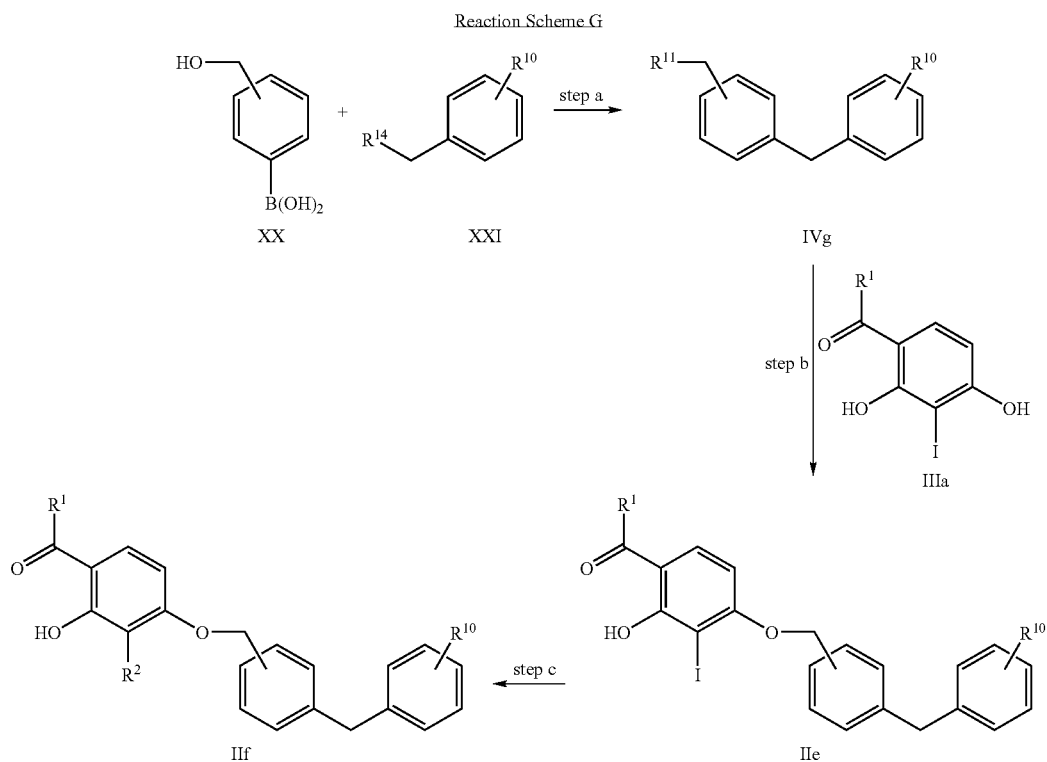

In step c, a compound of formula IIe is reacted with a trialkylstannanyl derivative of phenyl, substituted phenyl, thiophenyl, substituted thiophenyl, thiazolyl, substituted thiazolyl, furanyl, substituted furanyl, pyridinyl, substituted pyridinyl, oxazolyl, substituted oxazolyl, isothiazolyl, substituted isothiazolyl, isoxazolyl, substituted isoxazolyl, 1,2,4-oxadiazolyl, pyrimidinyl, substituted pyrimidinyl or substituted 1,2,4-oxadiazolyl in the presence of a suitable transition metal catalyst such as tetrakistriphenylphosphine palladium (0) to provide a compound of formula IIf where $R^2$ is phenyl, substituted phenyl, thiophenyl, substituted thiophenyl, thiazolyl, substituted thiazolyl, furanyl, substituted furanyl, pyridinyl, substituted pyridinyl, oxazolyl, substituted oxazolyl, isothiazolyl, substituted isothiazolyl, isoxazolyl, substituted isoxazolyl, 1,2,4-oxadiazolyl, pyrimidinyl, substituted pyrimidinyl or substituted 1,2,4-oxadiazolyl. The reaction is conveniently carried out in a solvent such as toluene.

In Reaction Scheme H, a compound of formula IVh where $Ar_1$ is a heterocyclic ring such as 1,2,4-oxadiazol-3,5-diyl may be prepared by condensing two heterocyclic precursors. More specifically in step a, a chloroacetic anhydride of formula XXII is reacted with an N-hydroxyphenylacetamide of formula XXIII under conditions of water removal to provide a compound of formula IVh where $Ar_1$ is 1,2,4-oxadiazol-3,5-diyl. The reaction is conveniently carried out in a solvent such as toluene. Compound IVh may then be coupled to a compound of formula III as described in step b of Scheme A to provide a compound of formula IIg where $Ar_1$ is a heterocyclic ring such as 1,2,4-oxadiazol-3,5-diyl and $R^{10}$ is a halogen such as an iodide. A compound of formula IIg where $Ar_1$ is a heterocyclic ring such as 1,2,4-oxadiazol-3,5-diyl and $R^{10}$ is iodide may then be transformed into a compound of formula I where $Ar_1$ is a heterocyclic ring such as 1,2,4-oxadiazol-3,5-diyl and Z is a carboxylic acid through carbonylation with an appropriate transition metal catalyst such as $(CH_3CN)_2PdCl_2$ in the presence of carbon monoxide. An appropriate solvent for this transformation is water.

Reaction Scheme H

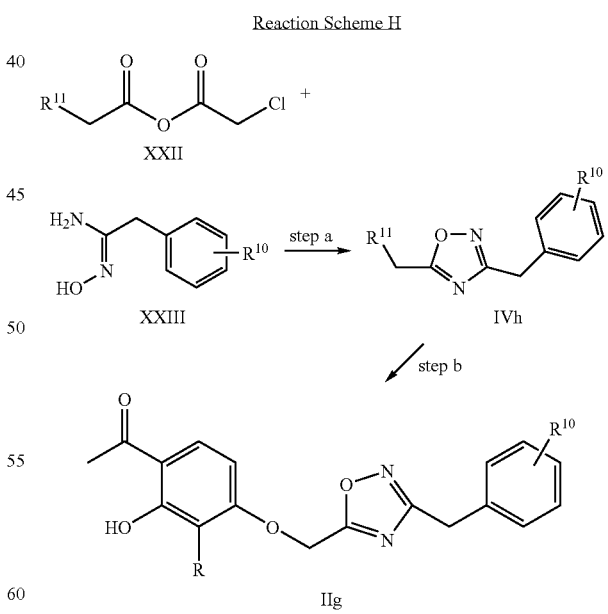

In Reaction Scheme I, a compound of formula XXVII where $Ar_1$ is a heterocyclic ring such as 1,2,4-oxadiazol-3,5-diyl may be prepared by condensing two heterocyclic precursors. More specifically, a carboxylic acid of formula XXV is reacted with an appropriately substituted N-hydroxyacetamide of formula XXVI under conditions of water removal as shown in step a to provide a compound of formula XXVII where $Ar_1$ is the 1,2,4-oxadiazol-3,5-diyl. Compound XXVII ($R^{11}$=OPg) may then be transformed into a compound of formula XXVII where $R^{11}$ is a hydroxyl and coupled to a compound of formula III as described in step b of Scheme A to provide a compound of formula IIh where $Ar_1$ is a heterocyclic ring such as 1,2,4-oxadiazol-3,5-diyl and $R^{10}$ is an ester.

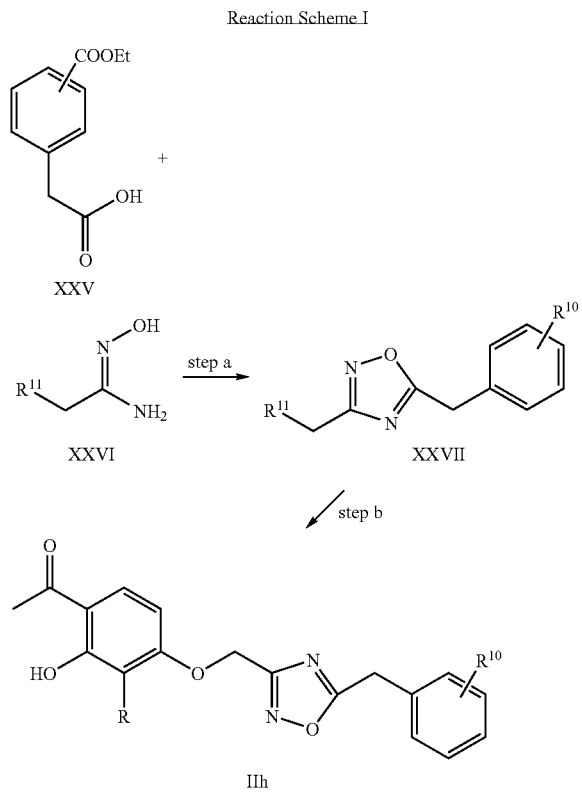

Reaction Scheme I

In Reaction Scheme J, step c, an enantomeric compound of formula XIXb may prepared by resolution of a racemic compound of formula XIX by conventionally procedures including chromatographic separation using a chiral stationary phase. Alternatively, in step b, an enantomeric compound of formula XIXb may be prepared by arylating enantioselectively a compound of formula of XVIII with a compound of formula XXX. More specifically, in step a, a compound of formula XVII where Pg is an hydroxyl protecting group such as tert-butyldimethylsilyl is reacted under borating conditions in which the borating conditions comprise a trialkyl borate such as triisopropyl borate and an alkyl lithium such as n-hexyllithium to provide a borate trimer of formula XXX. The reaction is conveniently carried out in a suitable solvent such as toluene. Also contemplated within the scope of a compound of formula XXX are the corresponding dimer and monomer forms of the aryl boronic acid. In step b, an enantiomeric compound of formula XIXb is prepared by arylating an aldehyde of formula XVIII with a borate trimer of formula XXX in the presence of a chiral catalyst and a dialkyl zinc. More specifically, a compound of formula XXX is reacted with a dialkyl zinc for 12 to 18 hours in a suitable solvent such as toluene at a temperature from 20° C. to 80° C. A temperature of 40° C. to 80° C. is preferred with 60° C. being more preferred. Dialkyl zincs such as dimethyl zinc and diisopropyl zinc are preferred with diethyl zinc being more preferred. Following the reaction with a dialkyl zinc, the reaction is cooled to 10° C. to −20° C. with −10° C. being preferred and a chiral catalyst, preferably in a suitable solvent such as toluene, is added. Preferred chiral catalysts include chiral amino alcohols such as 1-[(R)-[methyl[(1R)-1-phenylethyl]amino]-1-naphthalenylmethyl]-2-naphthalenol, [(S)-1-naphthalenyl[[(1S)-1-phenylethyl]amino]methyl]-2-naphthalenol and [(S)-[methyl[(1S)-1-phenylethyl]amino]phenylmethyl]-2-naphthalenol with (R)-(−)-2-piperidino-1,1,2-triphenyl ethanol being more preferred. The reaction maintained for 15 to 90 minutes with 30 minutes being preferred. A compound of formula XVIII where $R^{10}$ is cyano is added and the reaction is maintained for 2 to 6 hours with 4 hours being preferred. The reaction is quenched and subject to standard extraction techniques to provide an enantomeric compound of formula XIXb where Pg is a hydroxyl protecting group such as tert-butyldimethylsilyl and $R^{10}$ is a suitable precursor to the group Z such as cyano.

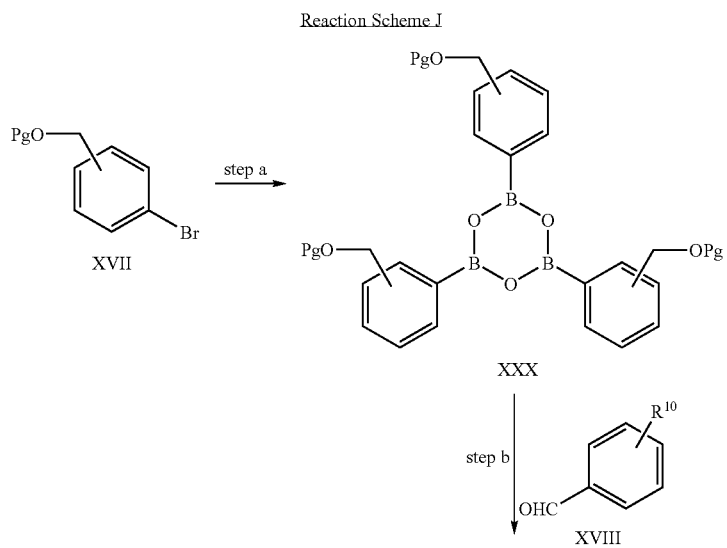

Reaction Scheme J

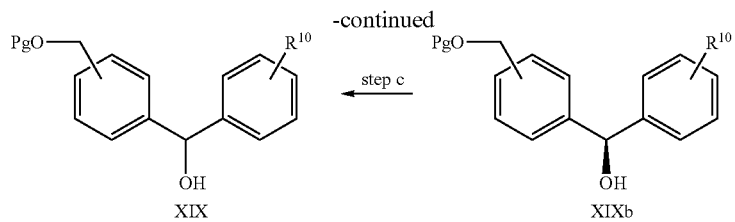

The compounds of the present invention can be administered alone or in the form of a pharmaceutical composition, that is, combined with pharmaceutically acceptable carriers or excipients, the proportion and nature of which are determined by the solubility and chemical properties of the compound selected, the chosen route of administration, and standard pharmaceutical practice. The compounds of the present invention, while effective themselves, may be formulated and administered in the form of their pharmaceutically acceptable salts, for purposes of stability, convenience of crystallization, increased solubility, and the like.

In practice, the compounds of formula I are usually administered in the form of pharmaceutical compositions, that is, in admixture with pharmaceutically acceptable carriers or diluents, the proportion and nature of which are determined by the chemical properties of the selected compound of formula I, the chosen route of administration, and standard pharmaceutical practice.

Thus, the present invention provides pharmaceutical compositions comprising a compound of the formula I and a pharmaceutically acceptable carrier, diluent or excipient.

The compounds of formula I can be administered by a variety of routes. In effecting treatment of a patient afflicted with disorders described above, a compound of formula I can be administered in any form or mode which makes the compound bioavailable in an effective amount, including oral and parenteral routes. For example, compounds of formula I can be administered orally, by inhalation, subcutaneously, intramuscularly, intravenously, transdermally, intranasally, rectally, ocularly, topically, sublingually, buccally, and the like. Oral administration is generally preferred for treatment of the neurological and psychiatric disorders described herein.

One skilled in the art of preparing formulations can readily select the proper form and mode of administration depending upon the particular characteristics of the compound selected, the disorder or condition to be treated, the stage of the disorder or condition, and other relevant circumstances. (*Remington's Pharmaceutical Sciences,* 18th Edition, Mack Publishing Co. (1990)).

The pharmaceutical compositions of the present invention are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solution, suspensions, or the like.

The compounds of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. A person skilled in the art may determine preferred compositions and preparations according to the present invention.

The tablets, pills, capsules, troches, and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations typically contain at least 0.1% of a compound of the invention, but may be varied to be between 0.1 and about 90% of the weight thereof. The amount of the compound of formula I present in such compositions is such that a suitable dosage will be obtained. The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Preferred compositions and preparations are able to be determined by one skilled in the art.

The compounds of the present invention may also be administered topically, and when done so the carrier may suitably comprise a solution, ointment, or gel base. The base, for example, may comprise one or more of the following: petrolatum, lanolin, polyethylene glycols, bees wax, mineral oil, diluents such as water and alcohol, and emulsifiers, and stabilizers. Topical formulations may contain a concentration of the formula I or its pharmaceutical salt from about 0.1 to about 10% w/v (weight per unit volume).

The compounds of formula I are potentiators of metabotropic glutamate (mGlu) receptor function, in particular they are potentiators of mGlu2 receptors. That is the compounds of formula I increase mGlu2 receptor response to glutamate or a glutamate agonist, enhancing the function of the receptors. The behavior of the potentiators of formula I at mGlu2 receptors is shown in Example A which is suitable to identify potentiators useful for carrying out the present invention. Thus, the potentiators of the present invention are expected to be useful in the treatment of various neurological and psychiatric disorders associated with glutamate dysfunction described to be treated herein and others that can be treated by such potentiators as are appreciated by those skilled in the art.

Example A

Potentiation of Glutamate-Induced Increase in Intracellular Calcium with a mGlu2 Expressing Cell Line Cell lines expressing human mGlu2 receptors are derived as previously described (Desai, Burnett, Mayne, Schoepp, *Mol. Pharmacol.* 48, 648-657, 1995) and cultured in DMEM with 5% dialyzed fetal bovine serum, 1 mM glutamine, 1 mM sodium pyruvate, 50 µg/mL Geneticin G418, and 0.2 mg/mL hygromycin B. Confluent cultures are passaged weekly. These cells are referred to as RGT cells for Rat Glutamate Transporter, and have been co-transfected with the glutamate/aspartate transporter GLAST. The RGT cell line expressing the mGlu2 receptors is stably transfected with the promiscuous G-protein, Galpha15 to change the signaling pathway to the mGlu2 receptor to one that could be easily measured through release of intracellular calcium. Thus, intracellular calcium levels are monitored before and after the addition of drugs on a Fluorometric Imaging Plate Reader (i.e. FLIPR, Molecular Devices). The following buffer is used throughout as an assay buffer: 10 mM KCl, 138 mM NaCl, 5 mM $CaCl_2$, 1 mM $MgCl_2$, 4 mM $NaH_2PO_4$, 10 mM Glucose, 10 mM HEPES, pH 7.4. Cells that had been plated 48 hours prior at a density of 30-40,000 cells per well in a 96-well plate are loaded with a calcium-sensitive dye for 90 minutes at 25° C. Fluo-3 (2 mM in DMSO, Molecular Probes) are mixed with a equal volume of 10% pluronic acid in DMSO, and diluted to 8 µM into the buffer described above containing 10% fetal bovine serum to make the loading buffer. Following loading of the cells, the loading buffer is removed and replaced with assay buffer prior to drug addition and monitoring on the FLIPR. The resulting signal from the addition of compounds of formula (I) and submaximal concentrations of a glutamate-site agonist (e.g. 1 µM glutamate) is determined by taking the difference of the maximal fluorescent peak height minus the background fluorescence in each well and expressing the results as a percent of the signal seen with a maximal glutamate response (30 µM glutamate, typically about 30-50, 000 Relative Fluorescent Units). Least squares curve fitting with a four-parameter equation is then applied to the resulting dose-% response curve to determine the resulting $EC_{50}$ values.

Exemplified compounds of formula I typically affect the potentiation of mGlu2 receptors with $EC_{50}$ values less than 12.5 µM. More specifically, examples 47, 65, 81, 82, 83 and 84 affect the potentiation of mGlu2 receptors with $EC_{50}$ values less than 100 nM.

Compounds of formula I are modulators of leukotriene receptor function, in particular they are antagonists of leukotriene receptors. That is the compounds of formula I antagonize the cysteinyl-leukotriene D4 (LTD4) receptor. The behavior of the antagonism of the cysteinyl-leukotriene D4 (LTD4) receptor by compounds of formula I is shown in Example B which is suitable to identify antagonists useful for carrying out the present invention. Thus, the leukotriene antagonists of the present invention are useful in the treatment of various inflammatory and allergic disorders mediated by leukotrienes and described to be treated herein and other disorders that can be treated by such antagonists as are appreciated by those skilled in the art.

Example B

Antagonism of Cysteinyl-Leukotriene D4 (LTD4)-Induced Increase in Intracellular Calcium within a Cysteinyl-Leukotriene 1 (CysLT1) Receptor Expressing Cell Line Cell lines expressing the human CysLT1 receptor [AV12-664 (ATCC-9595)] are derived and maintained in culture media: DMEM with 5% dialyzed fetal bovine serum, 1 mM glutamine, and 1 mM sodium pyruvate. Confluent cultures are passaged weekly. Intracellular calcium levels are monitored in the CysLT1-expressing cells with the addition of LTD4, with or without prior exposure to the compounds being tested as antagonists with a Fluorometric Imaging Plate Reader (FLIPR, Molecular Devices). The following buffer is used throughout as an assay buffer: Hanks Buffered Saline Solution without phenol red (GIBCO), with 10 mM HEPES pH 7.4. Cells that had been plated 48 hours prior at a density of 20-25,000 cells per well in a 96-well plate are loaded with a calcium-sensitive dye for 90 minutes at 25° C. Fluo-3 (2 mM in DMSO, Molecular Probes) is mixed with an equal volume of 10% pluronic acid in DMSO, and diluted to 8 µM in the buffer described above containing 10% fetal bovine serum to make the loading buffer. Following loading of the cells, the buffer is removed and replaced with assay buffer prior to drug addition and monitoring on the FLIPR for several minutes. The resulting signal from the addition of 6 nM LTD4 (provides approximately 90% of the maximal signal with 25 nM LTD4) is determined by taking the difference of the maximal fluorescent peak height minus the background fluorescence in each well and expressing the results as a percent of the signal seen without pretreatment of the test compound(s). Least squares curve fitting with a four-parameter equation is applied to the resulting dose-% inhibition curve to determine the resulting $IC_{50}$ values.

Exemplified compounds of formula I typically affect the antagonism of CysLT1 receptors with $IC_{50}$ values less than 12.5 µM. More specifically, examples 47, 60, 65, 81, 82, 83 and 84 affect the antagonism of CysLT1 receptors with $IC_{50}$ values less than 750 nM.

In one embodiment of the present invention provides methods of treating neurological and psychiatric disorders associated with glutamate dysfunction, comprising administering to a patient in need thereof an effective amount of a potentiator of metabotropic glutamate 2 receptors.

Specifically, the present invention provides a method of treating neurological and psychiatric disorders associated with glutamate dysfunction, comprising administering to a patient in need thereof an effective amount of a potentiator of the mGlu2 receptor and/or antagonist of the CysLT1 receptor, that is, the present invention provides methods using an effective amount of a potentiator of mGlu2 receptors and/or antagonist of the CysLT1 receptor.

In another preferred embodiment the present invention provides a method of treating migraine, comprising administering to a patient in need thereof an effective amount of a compound of formula I.

In another preferred embodiment the present invention provides a method of treating anxiety, comprising administering to a patient in need thereof an effective amount of a compound of formula I.

Particularly preferred anxiety disorders are generalized anxiety disorder, panic disorder, and obsessive compulsive disorder.

In another preferred embodiment the present invention provides a method of treating schizophrenia, comprising administering to a patient in need thereof an effective amount of a compound of formula I.

In yet another preferred embodiment the present invention provides a method of treating epilepsy, comprising administering to a patient in need thereof an effective amount of a compound of formula I.

Because the compounds of formula I enhance the normal physiological function of the mGlu receptors, the compounds of formula I are useful for the treatment of a variety of neurological and psychiatric disorders associated with glutamate dysfunction, including: acute neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, multiple sclerosis, ocular damage, retinopathy, cognitive disorders, idiopathic and drug-induced Parkinson's disease, muscular spasms and disorders associated with muscular spasticity (including tremors) seizures, epilepsy, convulsions, migraine (including migraine headache), urinary incontinence, substance tolerance, substance withdrawal (including, substances such as opiates, nicotine, tobacco products, alcohol, benzodiazepines, cocaine, sedatives, hypnotics, etc.), psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic pain states, severe pain, intractable pain, neuropathic pain, and post-traumatic pain), tardive dyskinesia, sleep disorders (including narcolepsy), attention deficit/hyperactivity disorder, and conduct disorder.

At present, the fourth edition of the Diagnostic and Statistical Manual of Mental Disorders (DSM-IV™) (1994, American Psychiatric Association, Washington, D.C.), provides a diagnostic tool for identifying many of the disorders described herein. The skilled artisan will recognize that there are alternative nomenclatures, nosologies, and classification systems for neurological and psychiatric disorders described herein and that these systems evolve with medical scientific progress.

The compounds of formula I potentiate mGlu receptor response, in particular mGlu2 receptor response, to glutamate and glutamate agonists. Such agonists are easily recognized and some are available in the art. Schoepp, D. D., Jane, D. E., Monn, J. A., *Neuropharmacology* 38: 1431-1476, (1999).

Thus, a more particular embodiment, it is understood that the present invention extends to a method of potentiating the action of a glutamate receptor agonist at the Group II mGlu receptors, comprising administering to a patient in need thereof an effective amount of a mGlu2 potentiator, in particular a compound of formula I, in combination with a potentiated amount of an mGlu receptor agonist. Such a combination may be advantageous in that it may augment the activity and selectivity of mGlu agonist.

As used herein, the term "patient" refers to a warm blooded animal such as a mammal which is afflicted with one or more neurological and psychiatric disorders associated with glutamate dysfunction. It is understood that guinea pigs, dogs, cats, rats, mice, horses, cattle, sheep, and humans, particularly humans, are examples of animals within the scope of the meaning of the term. It is also understood that this invention relates specifically to the potentiation of mammalian metabotropic glutamate receptors.

It is also recognized that one skilled in the art may affect the neurological and psychiatric disorders by treating a patient presently afflicted with the disorders or by prophylactically treating a patient afflicted with the disorders with an effective amount of the compound of formula I. Thus, the terms "treatment" and "treating" are intended to refer to all processes wherein there may be a slowing, interrupting, arresting, controlling, or stopping of the progression of the neurological and psychiatric disorders described herein, but does not necessarily indicate a total elimination of all disorder symptoms, and is intended to include prophylactic treatment of such neurological and psychiatric disorders.

As used herein, the term "effective amount" of a compound of formula I refers to an amount, that is, the dosage which is effective in treating the neurological and psychiatric disorders described herein.

The attending diagnostician, as one skilled in the art, can readily determine an effective amount by the use of conventional techniques and by observing results obtained under analogous circumstances. In determining an effective amount, the dose of a compound of formula I, a number of factors are considered by the attending diagnostician, including, but not limited to: the compound of formula I to be administered; the co-administration of an mGlu agonist, if used; the species of mammal; its size, age, and general health; the specific disorder involved; the degree of involvement or the severity of the disorder; the response of the individual patient; the mode of administration; the bioavailability characteristics of the preparation administered; the dose regimen selected; the use of other concomitant medication; and other relevant circumstances.

An effective amount of a compound of formula I is expected to vary from about 0.01 milligram per kilogram of body weight per day (mg/kg/day) to about 100 mg/kg/day. Preferred amounts may be determined by one skilled in the art.

As used herein, the term "potentiated amount" refers to an amount of an mGlu agonist, that is, the dosage of agonist which is effective in treating the neurological and psychiatric disorders described herein when administered in combination with an effective amount of a compound of formula I. A potentiated amount is expected to be less than the amount that is required to provided the same effect when the mGlu agonist is administered without an effective amount of a compound of formula I.

The attending diagnostician, as one skilled in the art, can readily determine a potentiated amount by the use of conventional techniques and by observing results obtained under analogous circumstances. In determining a potentiated amount, the dose of an mGlu agonist to be administered in combination with a compound of formula I, a number of factors are considered by the attending diagnostician, including, but not limited to: the mGlu agonist selected to be administered, including its potency and selectivity; the compound of formula I to be co-administered; the species of mammal; its size, age, and general health; the specific disorder involved; the degree of involvement or the severity of the disorder; the response of the individual patient; the modes of administration; the bioavailability characteristics of the preparations administered; the dose regimens selected; the use of other concomitant medication; and other relevant circumstances.

A potentiated amount of an mGlu agonist to be administered in combination with an effective amount of a compound of formula I is expected to vary from about 0.1 milligram per kilogram of body weight per day (mg/kg/day) to about 100 mg/kg/day and is expected to be less than the amount that is required to provided the same effect when administered without an effective amount of a compound of formula I. Preferred amounts of a co-administered mGlu agonist are able to be determined by one skilled in the art.

Of the neurological and psychiatric disorders associated with glutamate dysfunction which are treated according to the present invention, the treatment of migraine, anxiety, schizophrenia, and epilepsy are particularly preferred. Particularly preferred anxiety disorders are generalized anxiety disorder, panic disorder, and obsessive compulsive disorder.

Thus, in a preferred embodiment the present invention provides a method of treating migraine, comprising administering to a patient in need thereof an effective amount of a compound of formula I or a pharmaceutical composition thereof.

In one of the available sources of diagnostic tools, *Dorland's Medical Dictionary* (23$^{rd}$ Ed., 1982, W.B. Saunders Company, Philadelphia, Pa.), migraine is defined as a symptom complex of periodic headaches, usually temporal and unilateral, often with irritability, nausea, vomiting, constipation or diarrhea, and photophobia. As used herein the term "migraine" includes these periodic headaches, both temporal and unilateral, the associated irritability, nausea, vomiting, constipation or diarrhea, photophobia, and other associated symptoms. The skilled artisan will recognize that there are alternative nomenclatures, nosologies, and classification systems for neurological and psychiatric disorders, including migraine, and that these systems evolve with medical scientific progress.

In another preferred embodiment the present invention provides a method of treating anxiety, comprising administering to a patient in need thereof an effective amount of a compound of formula I or a pharmaceutical composition thereof.

At present, the fourth edition of the Diagnostic and Statistical Manual of Mental Disorders (DSM-IV™) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified. As used herein the term "anxiety" includes treatment of those anxiety disorders and related disorder as described in the DSM-IV. The skilled artisan will recognize that there are alternative nomenclatures, nosologies, and classification systems for neurological and psychiatric disorders, and particular anxiety, and that these systems evolve with medical scientific progress. Thus, the term "anxiety" is intended to include like disorders that are described in other diagnostic sources.

A number of preclinical laboratory animal models for migraine and anxiety have been described. One commonly used model of migraine is the dural extravasation model that has been described by Phebus et al., Life Sci., 61(21), 2117-2126 (1997) which can be used to evaluate the present compounds.

Example C

Animal Model of Dural Plasma Protein Extravasation (PPE)

Male Harlan Sprague-Dawley rats (250-350 g) are anesthetized with sodium pentobarbital (65 mg/kg, i.p.) and placed in a stereotaxic frame (David Kopf Instruments) with the incisor bar set at −2.5 mm. Following a midline sagittal scalp incision, two pairs of bilateral holes are drilled through the skull (3.2 mm posteriorly, 1.8 and 3.8 mm laterally, all coordinates referenced to bregma). Pairs of stainless steel stimulating electrodes, insulated except at the tips (Rhodes Medical Systems, Inc.), are lowered through the holes in both hemispheres to a depth of 9.2 mm.

The femoral vein is exposed and a dose of the test compound is injected intravenously (i.v.) at a dosing volume of 1 mL/kg. Approximately 8 minutes post i.v. injection, a 20 mg/kg dose of Fluorescein isothiocyanate-bovine serum albumin (FITC-BSA) is also injected intravenously. The FITC-BSA functions as a marker for protein extravasation. Exactly 10 minutes post-injection of the test compound, the left trigeminal ganglion is stimulated for 5 minutes at a current intensity of 1.0 mA (5 Hz, 5 msec duration) with a Model S48 Grass Instrument Stimulator with PSIU6 photoelectric isolation unit (Grass-Telefactor).

Alternatively, rats fasted overnight are dosed orally with test compound via gavage at a volume of 2 mL/kg. Approximately 50 minutes later the animals are anesthetized and placed in the stereotaxic frame as described above. Exactly 58 minutes post-p.o. dosing, the animals are dosed with FITC-BSA (20 mg/kg, i.v.). Exactly one hour post-p.o. dosing, the animals are stimulated as described above.

Five minutes following stimulation, the animals are killed by exsanguination with 40 mL of saline. The top of the skull is removed to facilitate the collection of the dural membranes. The membrane samples are removed from both hemispheres, rinsed with water, and spread flat on microscopic slides. Once dried, the tissues are coverslipped with a 70% glycerol/water solution.

A fluorescence microscope (Zeiss) equipped with a grating monochromator and a spectrophotometer is used to quantify the amount of FITC-BSA in each sample. An excitation wavelength of approximately 490 nm is utilized and the emission intensity at 535 nm was determined. The microscope is equipped with a motorized stage and also interfaced with a personal computer. This facilitates the computer-controlled movement of the stage with fluorescence measurements at 25 points (500 mm steps) on each dural sample. The mean and standard deviation of the measurements are determined by the computer.

The extravasation induced by the electrical stimulation of the trigeminal ganglion is an ipsilateral effect (i.e. occurs only on the side of the dura in which the trigeminal ganglion was stimulated). This allows the use of the other (unstimulated) half of the dura as a control. The ratio of the amount of extravasation in the dura from the stimulated side, over the amount of extravasation in the unstimulated side, is calculated. Control animals dosed only with saline, yield a ratio of approximately 2.0. In contrast, a compound which effectively prevented the extravasation in the dura from the stimulated side would yield a ratio of approximately 1.0.

Examples 60, 65, 83 and 84 affect extravasation in the dura with $ID_{100}$ values less than or equal to 0.1 mg/kg p.o.

The fear potentiated startle response model has been extensively used as a model of anxiety and can be used to evaluate the present compounds. Davis, *Psychopharmacol.*, 62, 1 (1979); Davis, *Behav. Neurosci*, 100, 814 (1986); Davis, *Tr. Pharmacol. Sci.*, 13, 35 (1992).

Example D

Fear Potentiated Startle Paradigm

Male Sprague-Dawley rats weighing 325-400 g are purchased from Harlan Sprague-Dawley, Inc. (Cumberland, Ind.) and given a one week acclimation period before testing. Rats are individually housed with food and water ad libitum in an animal room on a 12-hour light/dark cycle with lights on between 6:00 A.M. and 6:00 P.M. The test compound of formula I is prepared in a suspension of 5% ethanol, 0.5% CMC, 0.5% Tween 80 and 99% water. 2S-2-amino-2-(1S,2S-2-carboxycyclopropan-1-yl)-3-(xanth-9-yl) propionic acid is prepared in sterile water. Control rats are given the respective vehicle.

The fear potentiated startle paradigm is conducted over three consecutive days. All three days begin with a 5-minute adaptation period before the trial starts. On day one (baseline startle) after the adaptation period, the animal receives 30 trials of 120 dB auditory noise. The mean startle amplitude ($V_{max}$) is used to assign animals to groups with similar means before conditioning begins. Day two consists of conditioning the animals. Each animal receives 0.5 mA of shock for 500 msec preceded by a 5 second presentation of light which remains on for the duration of the shock. Ten presentations of the light and shock are administered. Day three is the testing trial where drug administration occurs prior to testing. Twenty-four hours after conditioning, startle testing sessions are conducted. Ten trials of acoustic startle (120 dB), non-light paired, are presented at the beginning of the session. This is followed by 20 random trials of the noise alone and 20 random trials of noise preceded by light. Excluding the first 10 trials, the startle response amplitudes for each trial type are averaged for each animal. Data is presented as the difference between light+noise and noise-alone. Differences in startle response amplitudes are analyzed by JMP statistical software using a One-way Anova (analysis of variance, t-test). Group differences are considered to be significant at $p<0.05$.

In another preferred embodiment the present invention provides a method of treating epilepsy, comprising administering to a patient in need thereof an effective amount of a compound of formula I or a pharmaceutical composition thereof.

At present, there are several types and subtypes of seizures associated with epilepsy, including idiopathic, symptomatic, and cryptogenic. These epileptic seizures can be focal (partial) or generalized. They can also be simple or complex. Epilepsy is described in the art, such as Epilepsy: A comprehensive textbook. Ed. by Jerome Engel, Jr. and Timothy A. Pedley. (Lippincott-Raven, Philadelphia, 1997). At present, the International Classification of Diseases, Ninth Revision, (ICD-9) provides a diagnostic tool including epilepsy and related disorders. These include: generalized nonconvulsive epilepsy, generalized convulsive epilepsy, petit mal status epilepticus, grand mal status epilepticus, partial epilepsy with impairment of consciousness, partial epilepsy without impairment of consciousness, infantile spasms, epilepsy partialis continua, other forms of epilepsy, epilepsy, unspecified, NOS. As used herein the term "epilepsy" includes these all types and subtypes. The skilled artisan will recognize that there are alternative nomenclatures, nosologies, and classification systems for neurological and psychiatric disorders, including epilepsy, and that these systems evolve with medical scientific progress.

Various electroshock-induces models has been extensively used as a model of seizure disorders.

Example E

Electroshock-Induced Seizures

Application of electrical stimulation by corneal electrodes to mice can induce tonic hindlimb-extensor seizures. Blockade of tonic extensor seizures induced by electroshock is considered predictive for drugs which block seizure propagation and may be effective in preventing various seizures in humans, including epileptic seizures.

Vehicle or a dose of a test drug are administered to groups of 5 to 10 mice each. Thirty minutes later, electroshock (10 mA, 0.2 sec duration) is administered by transcorneal electrodes. The number of mice exhibiting tonic extensor seizures in each group is recorded. The data are reported as the percentage of mice that are protected from seizures.

The present invention is further illustrated by the following examples and preparations. These examples and preparations are illustrative only and are not intended to limit the invention in any way.

The chemical nomenclature used in the examples and preparations is derived from one or more standard conventions. The skilled artisan will recognize the technical meaning when names are derived from two or more conventions.

The terms used in the examples and preparations have their normal meanings unless otherwise designated. For example, "C" refers to degrees Celsius; "N" refers to normal or normality; "M" refers to molar or molarity; "mol" refers to mole or moles; "mmol" refers to millimole or millimoles; "mmol" refers to micromole or micromoles; "kg" refers to kilogram or kilograms; "g" refers to gram or grams; "mg" refers to microgram or micrograms; "mg" refers to milligram or milligrams; "mL" refers to microliter or microliters; "mL" refers milliliter or milliliters; "L" refers to liter or liters; "bp" refers to boiling point; "mp" refers to melting point; "brine" refers to a saturated aqueous sodium chloride solution; "h or hr" refers to hour or hours; "min" refers to minute or minutes; "MS" refers to mass spectrometry; "NMR" refers to nuclear magnetic resonance spectroscopy; "TFA" refers to trifluoroacetic acid; "$CH_2Cl_2$" or "DCM" refers to dichloromethane; "DCE" refers to dichloroethane; "MeOH" refers to methanol; "$NH_4OH$" refers to a concentrated aqueous ammonia solution; "HCl" refers to hydrogen chloride; "MTBE" refers to tert-butyl methyl ether; "DSC" refers to differential scanning calorimetery; "DMEM" refers to Dulbecco's modified eagle medium. Chemical shifts are give in δ and NMR spectra were obtained in $CDCl_3$, unless otherwise indicated.

Preparation 1

Synthesis of 2-fluoro-3-methoxy-phenol

A mixture of 2-fluoroanisole (1.8 ml, 15.85 mmol), pentamethyldiethyenetriamine (3.6 mL, 17.45 mmol) and tetrahydrofuran (10 mL) is stirred at −78° C. A 2.5 M solution of n-butyllithium in hexanes (7 ml, 17.45 mmol) is added dropwise and the resulting solution is stirred at −78° C. 2 hr. Trimethylborate (2 mL, 17.45 mmol) is added and the reaction is warmed to room temperature and stirred 1 hr. Acetic acid (1.4 ml, 23.8 mmol) is added followed by an aqueous 30% solution of hydrogen peroxide (1.8 mL, 17.45 mmol) and the resulting mixture is stirred rapidly 18 hr at room temperature. The reaction mixture is diluted with water and extracted with ethyl acetate (3×50 mL). The combined extracts are dried over magnesium sulfate, filtered and concentrated to about 10 mL volume. The resulting mixture is purified via silica chromatography eluting with hexanes to 8:1 hexanes:ethyl acetate to give the title compound (1.65 g, 73%) as a colorless oil. MS ES 141 M−1.

Preparation 2

Synthesis of 1-(3-fluoro-2,4-dihydroxy-phenyl)-ethanone

A solution of 2-fluoro-3-methoxy-phenol (0.5 g, 3.53 mmol) and dichloromethane is stirred at −78° C. A 1M solution of boron tribromide in dichloromethane (3.9 mL, 3.9 mmol) is added slowly and the mixture is stirred 10 min cold, then warmed to 0° C. and stirred 1 hr. The reaction is quenched with ice and stirred at room temperature overnight. The product is extracted with ethyl acetate (2×50 mL), dried over magnesium sulfate, filtered, and concentrated. The resulting residue is combined with boron trifluoride diethyl etherate (1.3 mL, 10.3 mmol) and acetic acid (0.2 mL, 3.28 mmol) and heated to reflux 8 hr. The mixture is cooled to room temperature, diluted with water (50 mL), and extracted with ethyl acetate (3×50 mL). The combined extracts are dried over magnesium sulfate, filtered and concentrated to about 10 mL volume. The resulting mixture is diluted with hexanes (50 mL), cooled to 0° C., and filtered to give the title compound (310 mg, 58%) as a tan solid. MS ES 171 M+1.

Preparation 3

Synthesis of 1-(3-chloro-2,4-dihydroxy-phenyl)-ethanone

A solution of 2,4,-dihydroxyacetophenone (6 g, 39.4 mmol), aqueous 1M sodium hydroxide (41.4 mL, 41.4 mmol) and water (200 mL) is stirred at room temperature. An aqueous 1.6M solution of sodium hypochlorite (32 mL) is added over a 1 hr period. The resulting dark brown solution is stirred 18 hr at room temperature. The reaction mixture is adjusted to a pH of 2-3 with concentrated aqueous hydrochloric acid. The resulting suspension is filtered and washed with water (4×100 mL). The filtered solid was dried under vacuum at 45° C. for 2.5 days to give the title compound (4.8 g, 65%) as a brown solid. LCMS 1 187 M+.

Preparation 4

Synthesis of 1-(3-chloro-2,4-dihydroxy-phenyl)-propan-1-one

The title compound was prepared in a similar manner to 1-(3-chloro-2,4-dihydroxy-phenyl)-ethanone (Preparation 3) employing 2,4-dihydroxypropiophenone to give 4.5 g, 37% of an off-white solid. LCMS 1 201 M+.

Preparation 5

Synthesis of (4-bromo-benzyloxy)-triisopropyl-silane

Stir a solution of 4-bromobenzyl alcohol (50 g, 267.3 mmol), DBU (48 ml, 320.8 mmol) and dichloromethane (600 mL) in an ice/water bath. Add triisopropylsilylchloride (63 mL, 294 mmol) over 10 min via an addition funnel and stir the reaction mixture for 20 hours at room temperature. Wash the mixture with water (2×600 mL), dry over anhydrous magnesium sulfate, filter and concentrate. Purify the residue via silica chromatography eluting with 9:1 hexanes:ethyl acetate to give the title compound (91.5 g, 99%) as a colorless oil. $^1$H NMR (300 MHz, CDCl$_3$) δ 7.47-7.50 (m, 2H), 7.28-7.30 (m, 2H), 4.81 (s, 1.11-1.24 (m, 21H).

Preparation 6

Synthesis of (3-bromo-benzyloxy)-triisopropyl-silane

The title compound is prepared essentially as described in Preparation 5 employing 3-bromobenzyl alcohol to give a colorless oil, 100%. $^1$H NMR (CDCl$_3$) d 7.54 (s, 1H), 7.20-7.42 (m, 3H), 4.84 (s, 2H), 0.99-1.27 (m, 21H).

Preparation 7

Synthesis of 3-[hydroxy-(4-triisopropylsilanyloxymethyl-phenyl)-methyl]-benzonitrile Stir a solution of (4-bromo-benzyloxy)-triisopropyl-silane (72 g, 209.7 mmol) and tetrahydrofuran (500 mL) at −78° C. Add a 1.6 M solution of n-butyllithium in hexanes (143 mL) over 10 min. After addition, allow the reaction mixture to reach −20° C. and stir for 5 minutes. Cool the reaction mixture to −78° C. In another flask, stir a solution of 3-cyanobenzaldehyde (25 g, 190.6 mmol) and tetrahydrofuran (250 mL) at −78° C. Add the lithium anion solution to the aldehyde solution via large cannula at a rate such that the internal aldehyde temperature does not rise above −50° C. After addition is complete, stir the reaction mixture 18 hours at room temperature. Dilute the reaction mixture with aqueous saturated ammonium chloride (500 mL) and ethyl acetate (200 mL). Separate the layers, and extract the aqueous layer with ethyl acetate (3×100 mL). Combine the organic layers, dry over anhydrous magnesium sulfate, filter, and concentrate. Purify the residue via silica gel chromatography eluting with hexanes to 9:1 hexanes:ethyl acetate to afford the title compound (56.1 g, 75%) as a colorless oil. LCMS (m/z) 396 M+1.

Preparation 8

Synthesis of 3-[(tetrahydro-pyran-2-yloxy)-(4-triisopropylsilanyloxymethyl-phenyl)-methyl]-benzonitrile Stir a solution of 3-[hydroxy-(4-triisopropylsilanyloxymethyl-phenyl)-methyl]-benzonitrile (12 g, 30.3 mmol), 3,4-dihydro-2H-pyran (3.6 mL, 39.4 mmol) and dichloromethane (250 mL) at room temperature. Add pyridinium p-toluenesulfonate (0.8 g, 3.03 mmol) and stir the resulting mixture 18 hours at room temperature. Dilute the reaction mixture with aqueous saturated sodium hydrogen carbonate (100 mL) and separate the layers. Extract the aqueous layer is washed with dichloromethane (2×50 mL), combine the organic layers, dry with magnesium sulfate, filter and concentrate. Purify the residue via silica chromatography eluting with hexanes to 8:2 hexanes:ethyl acetate to afford the title compound (14.6 g, 100%) as a colorless oil. LCMS (m/z) 478 M−1.

The following compounds are prepared essentially as described in Preparation 8.

| Prep. No. | Chemical name | Structure | Physical data |
|---|---|---|---|
| 9 | 3-[(Tetrahydro-pyran-2-yloxy)-(3-triisopropylsilanyloxy-methyl-phenyl)-methyl]-benzonitrile | 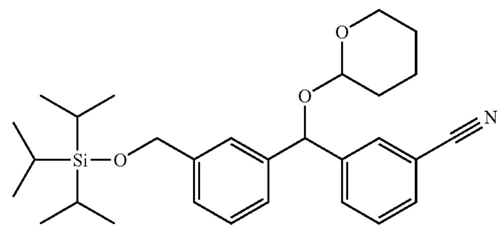 | $^1$H NMR (CDCl$_3$) δ 7.76 (s, 1 H), 7.65 (d, 1 H), 7.58 (d, 1 H), 7.26-7.48 (m, 5 H), 5.89 (s, 1 H), 4.86 (s, 2 H), 2.29 (bs, 1 H), 1.03-1.21 (m, 21 H). |
| 10 | 4-[(Tetrahydro-pyran-2-yloxy)-4-triisopropylsilanyloxy-methyl-phenyl)-methyl]-benzonitrile | 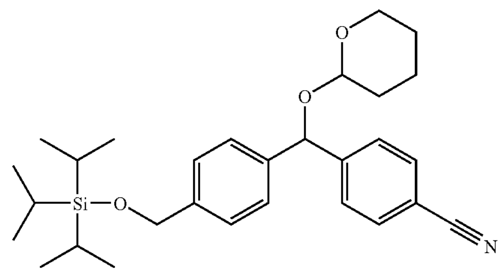 | $^1$H NMR (DMSO-d$_6$) δ 7.79-7.84 (m, 2 H), 7.58-7.63 (m, 2 H), 7.29-7.40 (m, 4 H), 5.88 (d, 1 H), 4.78 (d, 2 H), 4.59-4.60 (m, 1 H), 3.64-3.74 (m, 1 H), 3.39-3.49 (m, 1 H), 1.40-1.89 (m, 6 H), 0.96-1.23 (m, 21 H). |

Preparation 11

Synthesis of 3-[(4-hydroxymethyl-phenyl)-(tetrahydro-pyran-2-yloxy)-methyl]-benzonitrile Add a 1M solution in tetrahydrofuran of tetrabutylammonium fluoride (37 mL, 37 mmol) to a solution of 3-[(tetrahydro-pyran-2-yloxy)-(4-triisopropylsilanyloxymethyl-phenyl)-methyl]-benzonitrile (14.6 g, 30.4 mmol) in tetrahydrofuran (50 mL) and tetrahydrofuran stir at room temperature for 2 hours. Concentrate the reaction, dilute with water (200 mL), and extract with ethyl acetate (2×100 mL). Combine the extracts, dry over magnesium sulfate, filter, and concentrate. Purify the residue via silica chromatography eluting with 9:1 hexanes:ethyl acetate to 1:1 hexanes ethyl acetate to afford the title compound (8.0 g, 82%), as a colorless thick oil. LCMS (m/z) 323 M+1.

The following compounds are prepared essentially as described in Preparation 11.

| Prep. No. | Chemical name | Structure | Physical data |
|---|---|---|---|
| 12 | 3-[(3-Hydroxymethyl-phenyl)-(tetrahydro-pyran-2-yloxy)-methyl]-benzonitrile | 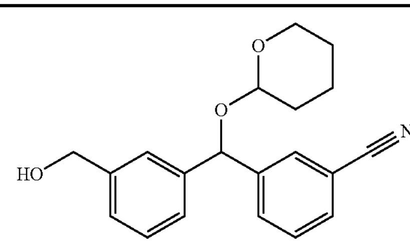 | LCMS 322 M−1 |

-continued

| Prep. No. | Chemical name | Structure | Physical data |
|---|---|---|---|
| 13 | 4-[(4-Hydroxymethyl-phenyl)-(tetrahydro-pyran-2-yloxy)-methyl]-benzonitrile | 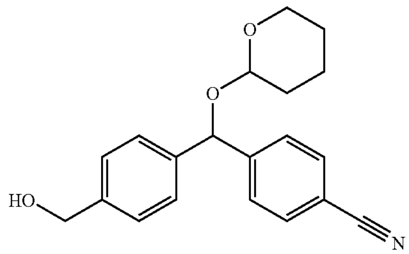 | LCMS 322 M-1 |

Preparation 14

Synthesis of 3-[[4-(4-acetyl-3-hydroxy-2-propyl-phenoxymethyl)-phenyl]-(tetrahydro-pyran-2-yloxy)-methyl]-benzonitrile Stir a solution of 1-(2,4-dihydroxy-3-propyl-phenyl)-ethanone (1.75 g, 9 mmol), 3-[(4-hydroxymethyl-phenyl)-(tetrahydro-pyran-2-yloxy)-methyl]-benzonitrile (2.9 g, 9 mmol), toluene (10 mL), and dichloromethane (10 mL) at −20° C. Add 1,1'-(azodicarbonyl)dipiperidine (4.5 g, 18 mmol) followed by tributylphosphine (4.5 mL, 18 mmol) and allow the resulting yellow solution to stir at room temperature overnight. Concentrate the resulting thick reaction mixture and dilute with ether (50 mL). Cool the slurry to 0° C. with stirring, for 30 minutes. Filter the reaction mixture, concentrate, and purify via silica chromatography eluting with 1:1 hexanes:(5:4:1 hexanes:dichloromethane:ethyl acetate) to give the title compound (3 g, 67%), as an orange thick oil. LCMS (m/z) 498-M−1.

The following compounds are prepared essentially as described in Preparation 14.

| Prep. No. | Chemical name | Structure | Physical data |
|---|---|---|---|
| 15 | 3-[[4-(4-Acetyl-3-hydroxy-2-propyl-phenylsulfanylmethyl)-phenyl]-(tetrahydro-pyran-2-yloxy)-methyl]-benzonitrile | 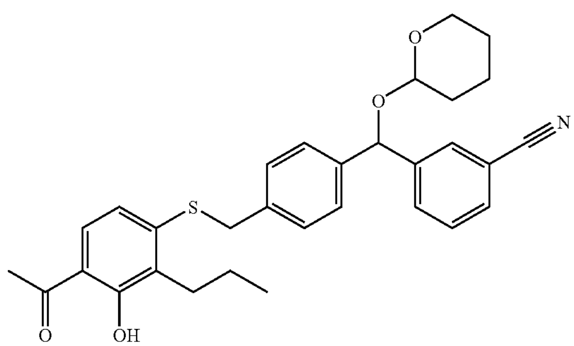 | LCMS (m/z) 514 M − 1. |
| 16 | 3-[[4-(3-Hydroxy-2-methyl-4-propionyl-phenoxymethyl)-phenyl]-(tetrahydro-pyran-2-yloxy)-methyl]-benzonitrile | 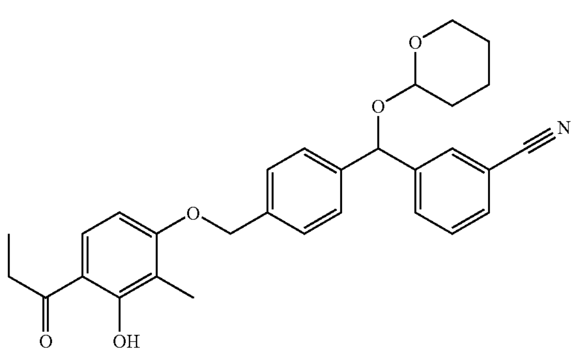 | LCMS (m/z) m-THP 400. |

-continued

| Prep. No. | Chemical name | Structure | Physical data |
|---|---|---|---|
| 17 | 3-[[4-(4-Acetyl-3-hydroxy-2-isopropyl-phenoxymethyl)-phenyl]-(tetrahydro-pyran-2-yloxy)-methyl]-benzonitrile | 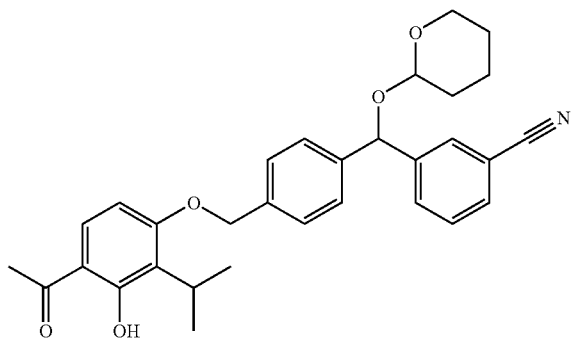 | LCMS 498 M − 1. |
| 18 | 3-[[4-(4-Acetyl-2-fluoro-3-hydroxy-phenoxymethyl)-phenyl]-(tetrahydro-pyran-2-yloxy)-methyl]-benzonitrile | 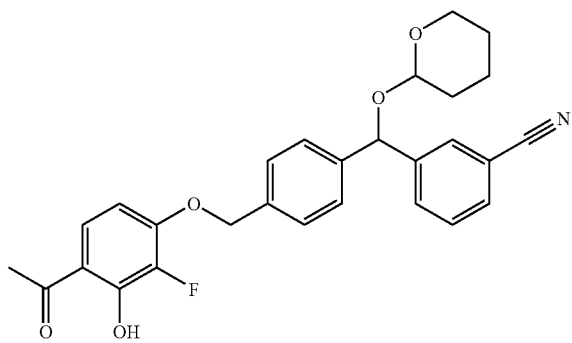 | LC/MS 474 M − 1. |
| 19 | 3-[[4-(4-Acetyl-2-chloro-3-hydroxy-phenoxymethyl)-phenyl]-(tetrahydro-pyran-2-yloxy)-methyl]-benzonitrile | 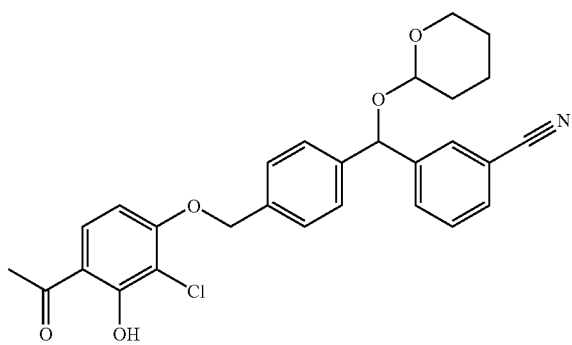 | LCMS 490 M − 1. |
| 20 | 3-[[4-(2-Chloro-3-hydroxy-4-propionyl-phenoxymethyl)-phenyl]-(tetrahydro-pyran-2-yloxy)-methyl]-benzonitrile | 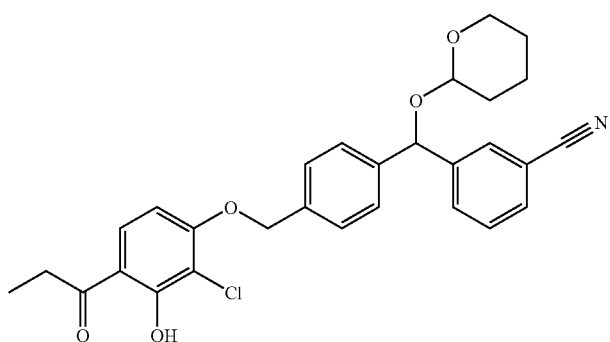 | LCMS 504 M − 1. |

-continued

| Prep. No. | Chemical name | Structure | Physical data |
|---|---|---|---|
| 21 | 3-[[3-(4-Acetyl-3-hydroxy-2-propyl-phenoxymethyl)-phenyl]-(tetrahydro-pyran-2-yloxy)-methyl]-benzonitrile | 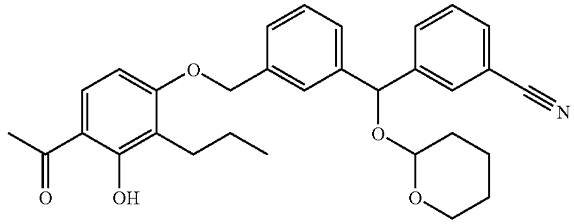 | LCMS 498 M − 1. |
| 22 | 3-[[3-(4-Acetyl-3-hydroxy-2-methyl-phenoxymethyl)-phenyl]-(tetrahydro-pyran-2-yloxy)-methyl]-benzonitrile | 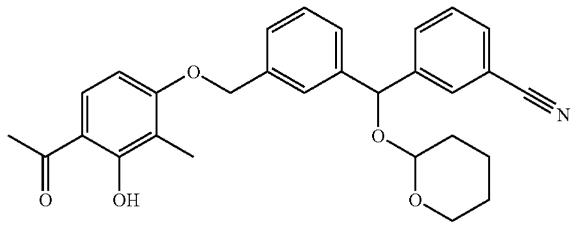 | LCMS 470 M − 1. |
| 23 | 3-[[3-(3-Hydroxy-2-methyl-4-propionyl-phenoxymethyl)-phenyl]-(tetrahydro-pyran-2-yloxy)-methyl]-benzonitrile | 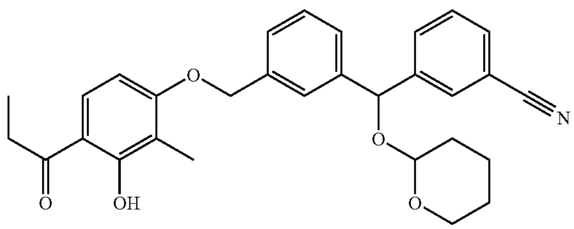 | LCMS 484 M − 1. |
| 24 | 3-[[3-(4-Acetyl-3-hydroxy-2-propyl-phenoxymethyl)-phenyl]-(tetrahydro-pyran-2-yloxy)-methyl]-benzonitrile | 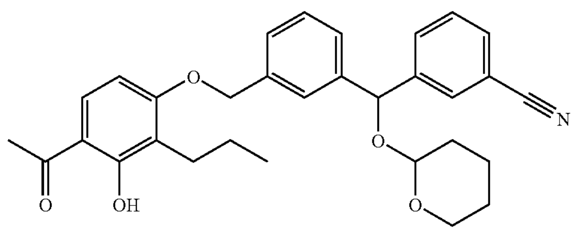 | LCMS 498 M − 1. |
| 25 | 3-[[3-(4-Acetyl-2-chloro-3-hydroxy-phenoxymethyl)-phenyl]-(tetrahydro-pyran-2-yloxy)-methyl]-benzonitrile | 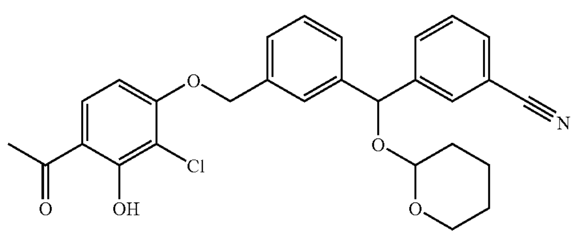 | $^1$H NMR (CDCl$_3$) δ 13.20 (s, 1 H), 7.30-7.70 (m, 9 H), 6.55 (d, 1 H), 5.87 (s, 1 H), 5.28 (s, 2 H), 4.65-4.69 (m, 1 H), 3.80-3.85 (m, 1 H), 3.50-3.60 (m, 1 H), 2.63 (s, 3 H), 1.50-1.80 (m, 6 H). |
| 26 | 4-[[4-(4-Acetyl-3-hydroxy-2-propyl-phenoxymethyl)-phenyl]-(tetrahydro-pyran-2-yloxy)-methyl]-benzonitrile | 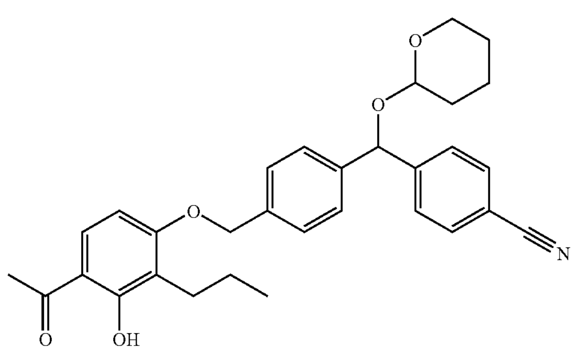 | LCMS 498 M − 1. |

-continued

| Prep. No. | Chemical name | Structure | Physical data |
|---|---|---|---|
| 27 | 3-[[4-(4-Acetyl-3-hydroxy-2-trifluoromethyl-phenoxymethyl)-phenyl]-(tetrahydro-pyran-2-yloxy)-methyl]-benzonitrile | 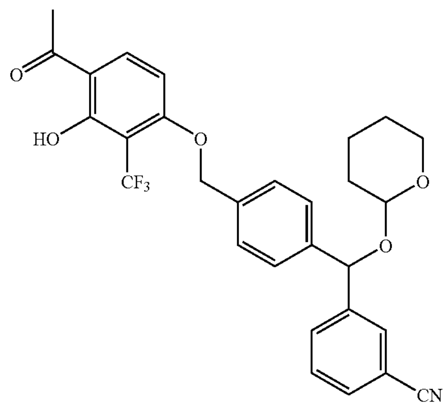 | $^1$H NMR (DMSO-d$_6$) δ 1.43-1.85 (m, 6 H), 2.63 (s, 3 H), 3.42 (m, 1 H), 3.68 (m, 1 H), 4.59 (m, 1 H), 5.34 (d, 2 H), 5.87 (d, 1 H), 6.89 (dd, 1 H), 7.39-7.59 (m, 5 H), 7.73 (m, 2 H), 7.86 (d, 1 H), 8.19 (m, 1 H), 13.77 (s, 1 H). |
| 28 | 3-[[4-(4-Acetyl-2-ethyl-3-hydroxy-phenoxymethyl)-phenyl]-(tetrahydro-pyran-2-yloxy)-methyl]-benzonitrile | 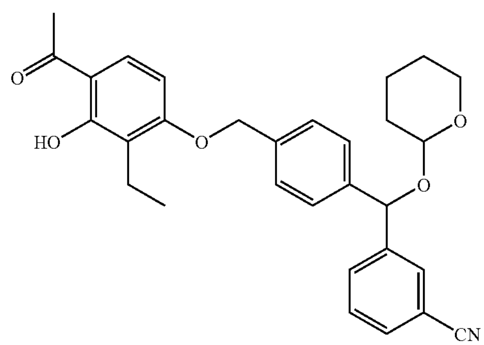 | MS (esi negative) m/z (rel intensity) 484 (100). |
| 29 | 3-[[4-(4-Acetyl-3-hydroxy-2-thiophen-3-yl-phenoxymethyl)-phenyl]-(tetrahydro-pyran-2-yloxy)-methyl]-benzonitrile | 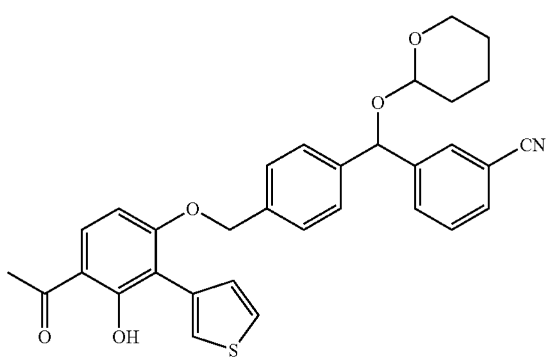 | LCMS 538 M − 1. |
| 30 | 3-[[4-(4-Acetyl-3-hydroxy-2-thiophen-2-yl-phenoxymethyl)-phenyl]-(tetrahydro-pyran-2-yloxy)-methyl]-benzonitrile | 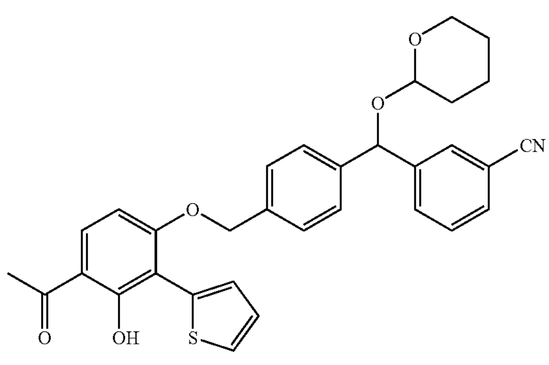 | LCMS 538 M − 1. |

-continued

| Prep. No. | Chemical name | Structure | Physical data |
|---|---|---|---|
| 31 | 3-[[4-(5-Acetyl-4'-fluoro-6-hydroxy-biphenyl-2-yloxymethyl)-phenyl]-(tetrahydro-pyran-2-yloxy)-methyl]-benzonitrile | 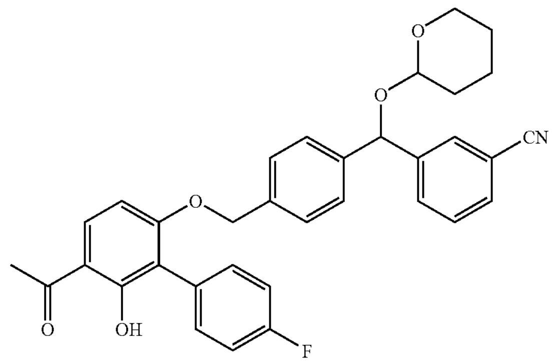 | LCMS 550 M − 1. |
| 32 | 3-[[4-(4-Acetyl-3-hydroxy-2-pyridin-2-yl-phenoxymethyl)-phenyl]-(tetrahydro-pyran-2-yloxy)-methyl]-benzonitrile | 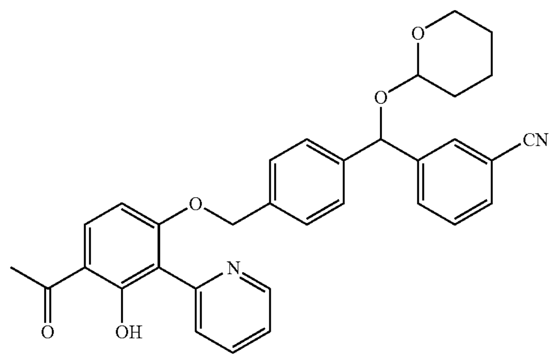 | LCMS 533 M − 1. |

Preparation 33

Synthesis of 3-{[4-(4-acetyl-3-hydroxy-2-propyl-phenoxymethyl)-phenyl]-hydroxy-methyl}-benzonitrile Stir a mixture of 3-[[4-(4-acetyl-3-hydroxy-2-propyl-phenoxymethyl)-phenyl]-(tetrahydro-pyran-2-yloxy)-methyl]-benzonitrile (13.4 g, 26.88 mmol), p-toluenesulfonic acid monohydrate (5.1 g, 26.88 mmol), methanol (100 mL), dichloromethane (50 mL), and ethyl acetate (50 mL) at room temperature for an hour. Concentrate the reaction mixture, dilute with ethyl acetate (150 mL) and wash with water (2×100 mL). Dry the organic phase over magnesium sulfate, filter, and concentrate. Dilute the residue with 5:1 hexanes:dichloromethane (50 mL), cool to 0° C. and filter. Collect a second and third crop to give the title compound (10.3 g, 93%), as a white solid. LCMS 416 M+1. The following compounds are prepared essentially as described in Preparation 33.

| Prep. No. | Chemical name | Structure | Physical data |
|---|---|---|---|
| 34 | 3-{[4-(2-Chloro-3-hydroxy-4-propionyl-phenoxymethyl)-phenyl]-hydroxy-methyl}-benzonitrile | 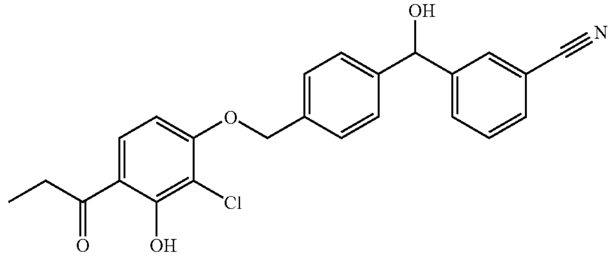 | LCMS 420 M − 1. |

-continued

| Prep. No. | Chemical name | Structure | Physical data |
|---|---|---|---|
| 35 | 3-{[4-(4-Acetyl-2-chloro-3-hydroxy-phenoxymethyl)-phenyl]-hydroxy-methyl}-benzonitrile | 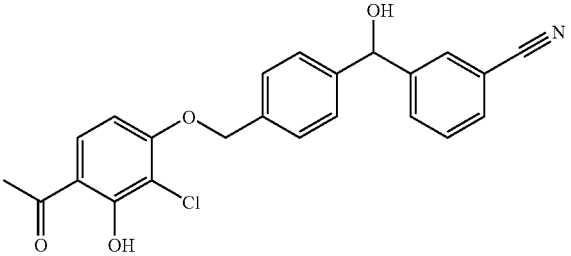 | LCMS 406 M − 1. |
| 36 | 3-{[3-(4-Acetyl-3-hydroxy-2-methyl-phenoxymethyl)-phenyl]-hydroxy-methyl}-benzonitrile | 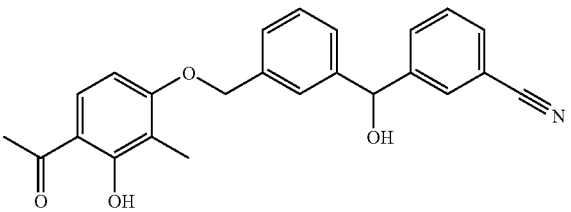 | LCMS 388 M + 1. |
| 37 | 3-{Hydroxy-[3-(3-hydroxy-2-methyl-4-propionyl-phenoxymethyl)-phenyl]-methyl}-benzonitrile | 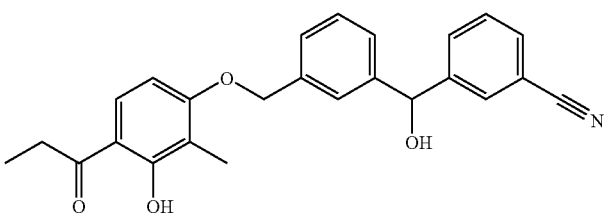 | LCMS 400 M − 1. |
| 38 | 3-{[3-(4-Acetyl-3-hydroxy-2-propyl-phenoxymethyl)-phenyl]-hydroxy-methyl}-benzonitrile | 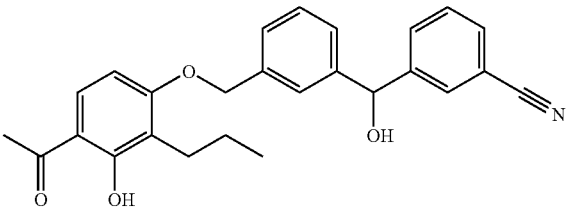 | LCMS 414 M − 1. |
| 39 | 3-{[3-(4-Acetyl-2-chloro-3-hydroxy-phenoxymethyl)-phenyl]-hydroxy-methyl}-benzonitrile | 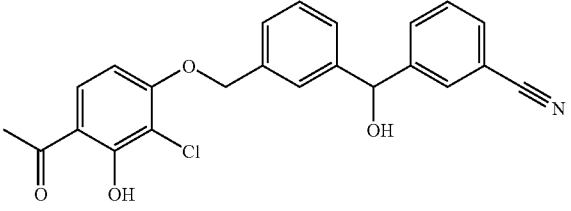 | LCMS 406 M − 1. |
| 40 | 4-{[4-(4-Acetyl-3-hydroxy-2-propyl-phenoxymethyl)-phenyl]-hydroxy-methyl}-benzonitrile | 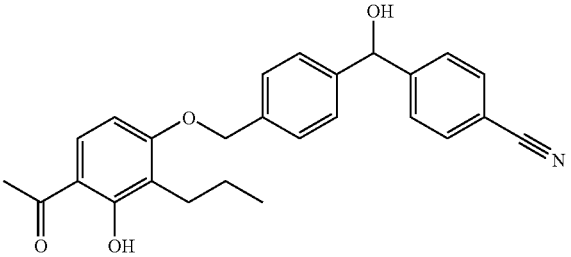 | LCMS 416 M + 1. |

| Prep. No. | Chemical name | Structure | Physical data |
|---|---|---|---|
| 41 | 3-{[4-(4-Acetyl-3-hydroxy-2-trifluoromethyl-phenoxymethyl)-phenyl]-hydroxy-methyl}-benzonitrile | 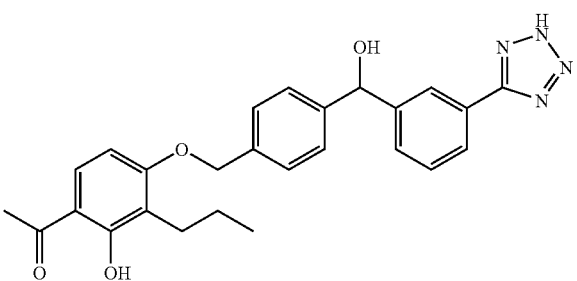 | LC-MS (m/e): 440 (M − 1) |

Example 1

Synthesis of 1-[2-hydroxy-4-(4-{hydroxy-[3-(2H-tetrazol-5-yl)-phenyl]-methyl}-benzyloxy)-3-propyl-phenyl]-ethanone Bring to a heavy reflux, a mixture of 3-[[4-(4-acetyl-3-hydroxy-2-propyl-phenoxymethyl)-phenyl]-(tetrahydro-pyran-2-yloxy)-methyl]-benzonitrile (3.0 g, 6 mmol), zinc (II) bromide (4.1 g, 18 mmol), sodium azide (2.34 g, 36 mmol), water (20 mL) and isopropyl alcohol (20 mL) for 18 hours. Cool and dilute the reaction mixture with water (100 mL) and adjust the pH to 2 with 1M hydrochloric acid. Extract the product with ethyl acetate (2×150 mL), combine the extracts and wash with water (100 mL), brine (100 mL), dry over magnesium sulfate, filter, and concentrate. Stir the residue in methanol (50 mL), and add p-toluenesulfonic acid mono hydrate (4 g, 21 mmol) and stir at room temperature for an hour. Concentrate the mixture and dilute with water (100 mL). Extract the product with ethyl acetate (2×100 mL). Wash the combined extracts with water (2×100 mL), brine (100 mL), dry over magnesium sulfate, filter, and concentrate. Purify the resulting residue via silica chromatography eluting with 1:1 hexanes:ethyl acetate to 1:1 ethyl acetate:acetone to acetone to give the title compound (2.6 g, 95%) as a tan solid. $^1$H NMR (DMSO-$d_6$) d 12.86 (s, 1H), 8.12 (s, 1H), 7.87 (d, 1H), 7.80 (d, 1H), 7.39-7.55 (m, 6H), 6.72 (d, 1H), 6.11 (d, 1H), 5.82 (d, 1H), 5.23 (s, 2H), 2.56 (s, 3H), 2.57-2.60 (m, 2H), 1.44-1.52 (m, 2H), 0.87 (t, 3H). LCMS (m/z) 457 M−1.

The following compounds are prepared essentially as described in Example 1.

| Ex. No. | Chemical name | Structure | Physical data |
|---|---|---|---|
| 2 | 1-[2-Hydroxy-4-(4-{hydroxy-[3-(1H-tetrazol-5-yl-phenyl]-methyl}-benzylsulfanyl)-3-propyl-phenyl]-ethanone | 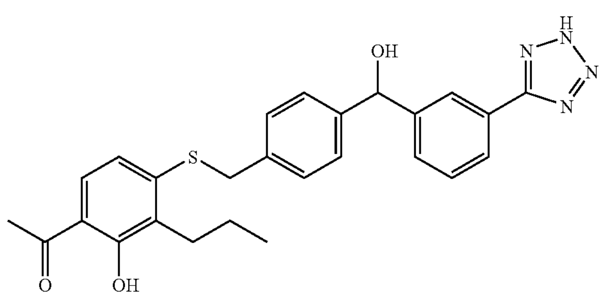 | $^1$H NMR (DMSO-$d_6$) d 12.83 (s, 1 H), 8.13 (s, 1 H), 7.88 (d, 1 H), 7.73 (d, 1 H), 7.56 (m, 2 H), 7.40 (s, 4 H), 6.97 (d, 1 H), 6.11 (d, 1 H), 5.81 (d, 1 H), 4.34 (s, 2 H), 2.60 (m, 5 H), 1.45 (m, 2 H), 0.88 (m, 3 H). LCMS (m/z) 473 M − 1. |

-continued

| Ex. No. | Chemical name | Structure | Physical data |
|---|---|---|---|
| 3 | 1-[2-Hydroxy-4-(4-{hydroxy-[3-(1H-tetrazol-5-yl)-phenyl]-methyl}-phenylmethanesulfonyl)-3-propyl-phenyl]-ethanone | 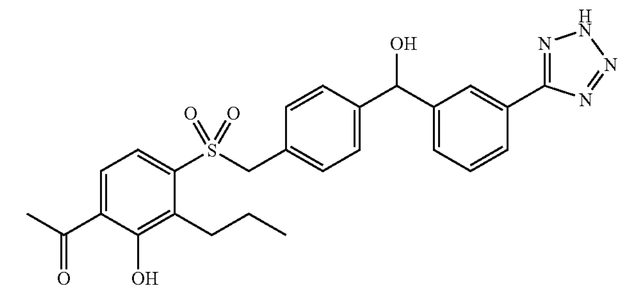 | $^1$H NMR (DMSO-$d_6$) d 12.80 (s, 1 H), 8.09 (s, 1 H), 7.96 (d, 1 H), 7.88-7.89 (m, 1 H), 7.50-7.55 (m, 2 H), 7.37 (d, 2 H), 7.27 (d, 1 H), 7.10 (d, 2 H), 6.14 (d, 1 H), 5.80 (d, 1 H), 4.64 (s, 2 H), 2.68-2.75 (m, 5 H), 1.40-1.50 (m, 2 H), 0.83-91 (m, 3 H). LCMS (m/z) 505 M − 1. |
| 4 | 1-[2-Hydroxy-4-(4-{hydroxy-[3-(1H-tetrazol-5-yl)-phenyl]-methyl}-benzyloxy)-3-methyl-phenyl]-propan-1-one | 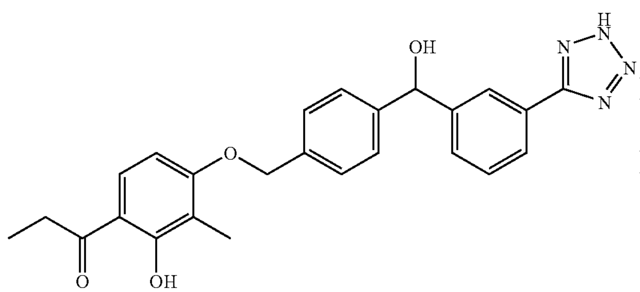 | $^1$H NMR (DMSO-$d_6$) d 12.90 (s, 1 H), 8.15 (s, 1 H), 7.81-7.90 (m, 2 H), 7.52-7.62 (m, 2 H), 7.41-7.49 (m, 4 H), 6.72 (d, 1 H), 6.14 (s, 1 H), 5.84 (s, 1 H), 5.21 (s, 2 H), 3.04 (q, 2 H), 0.88 (t, 3 H). LCMS 443 M − 1. |
| 5 | 1-[2-Hydroxy-4-(4-{hydroxy-[3-(1H-tetrazol-5-yl)-phenyl]-methyl}-benzyloxy)-3-isopropyl-phenyl]-ethanone | 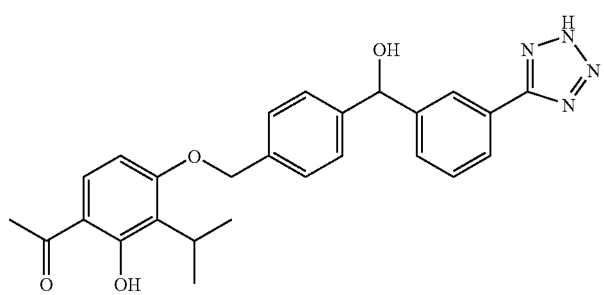 | $^1$H NMR (DMSO-$d_6$) d 13.06 (s, 1 H), 8.15 (s, 1 H), 7.89 (d, 1 H), 7.78 (d, 1 H), 7.52-7.62 (m, 2 H), 7.41-7.49 (m, 4 H), 6.71 (d, 1 H), 6.14-6.15 (m, 1 H), 5.84-5.85 (m, 1 H), 5.21 (s, 2 H), 3.52-3.59 (m, 1 H), 2.57 (s, 3 H), 1.24 (d, 6 H). LCMS 457 M − 1. |
| 6 | 1-[3-Fluoro-2-hydroxy-4-(4-{hydroxy-[3-(1H-tetrazol-5-yl)-phenyl]-methyl}-benzyloxy)-phenyl]-ethanone | 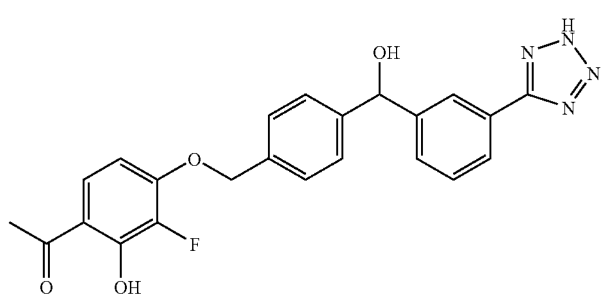 | $^1$H NMR (DMSO-$d_6$) d 12.34 (s, 1 H), 8.14 (s, 1 H), 7.85 (m, 1 H), 7.69-7.75 (2 H), 7.39-7.58 (m, 5 H), 6.85-6.91 (m, 1 H) 6.15-6.19 (m, 1 H), 5.77-5.85 (m, 1 H), 5.28 (s, 2 H), 2.60 (s, 3 H). LCMS 433 M − 1. |
| 7 | 1-[3-Chloro-2-hydroxy-4-(4-{hydroxy-[3-(1H-tetrazol-5-yl)-phenyl]-methyl}-benzyloxy)-phenyl]-ethanone | 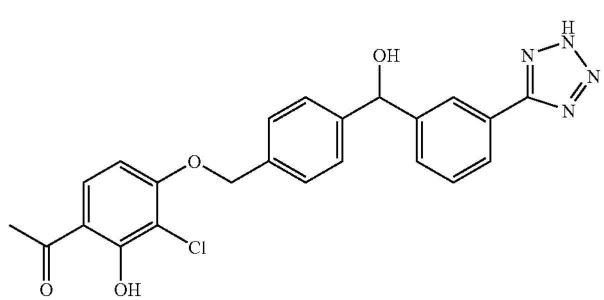 | $^1$H NMR (DMSO-$d_6$) d 12.14 (s, 1 H), 7.75-7.95 (m, 2 H), 7.69-7.75 (m, 2 H), 7.42-7.56 (m, 5 H), 6.90 (d, 1 H), 6.17-6.19 (m, 1 H), 5.80-5.82 (m, 1 H), 5.33 (s, 2 H), 2.62 (s, 3 H). LCMS 449 M − 1. |

-continued

| Ex. No. | Chemical name | Structure | Physical data |
|---|---|---|---|
| 8 | 1-[2-Hydroxy-4-(3-{hydroxy-[3-(2H-tetrazol-5-yl)-phenyl]-methyl}-benzyloxy)-3-propyl-phenyl]-ethanone | 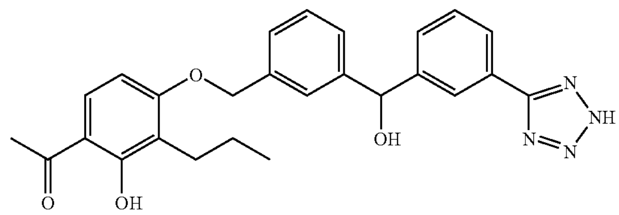 | $^1$H NMR (DMSO-d$_6$) d 12.84 (s, 1 H), 8.15 (s, 1 H), 7.87-7.91 (m, 1 H), 7.79 (d, 1 H), 7.51-7.59 (m, 3 H), 7.30-7.45 (m, 3 H), 6.72 (d, 1 H), 5.85 (s, 1 H), 5.24 (s, 2 H), 2.56-2.59 (m, 5 H), 1.39-1.47 (m, 2 H), 0.81 (t, 3 H). LCMS 457 M − 1. |
| 9 | 1-[2-Hydroxy-4-(4-{hydroxy-[4-(2H-tetrazol-5-yl)-phenyl]-methyl}-benzyloxy)-3-propyl-phenyl]-ethanone | 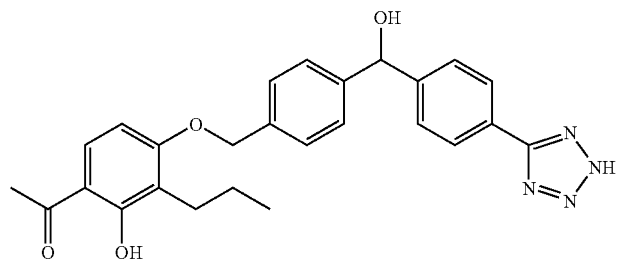 | $^1$H NMR (DMSO-d$_6$) δ 12.85 (s, 1 H), 7.99 (d, 2 H), 7.79 (d, 1 H), 7.63 (d, 2 H), 7.39-7.47 (m, 4 H), 6.72 (d, 1 H), 6.10 (m, 1 H), 5.82 (s, 1 H), 5.23 (s, 2 H), 2.56-2.65 (m, 5 H), 1.45-1.53 (m, 2 H), 0.87 (t, 3 H). LCMS 459 M + 1. |
| 10 | 1-[2-Hydroxy-4-(4-{hydroxy-[3-(2H-tetrazol-5-yl)-phenyl]-methyl}-benzyloxy)-3-trifluoromethyl-phenyl]-ethanone | 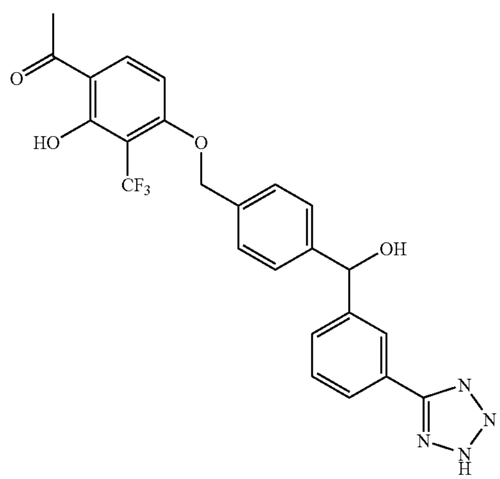 | $^1$H NMR (DMSO-d$_6$) δ 2.62 (s, 3 H), 5.33 (s, 2 H), 5.83 (d, 1 H), 6.13 (d, 1 H), 6.91 (d, 1 H), 7.35-7.59 (m, 6 H), 7.87 (d, 1 H), 8.13 (s, 1 H), 8.18 (d, 1 H), 13.77 (s, 1 H); MS (esi negative) m/z 483 (M − 1). |
| 11 | 1-[3-Ethyl-2-hydroxy-4-(4-{hydroxy-[3-(2H-tetrazol-5-yl)-phenyl]-methyl}-benzyloxy)-phenyl]-ethanone | 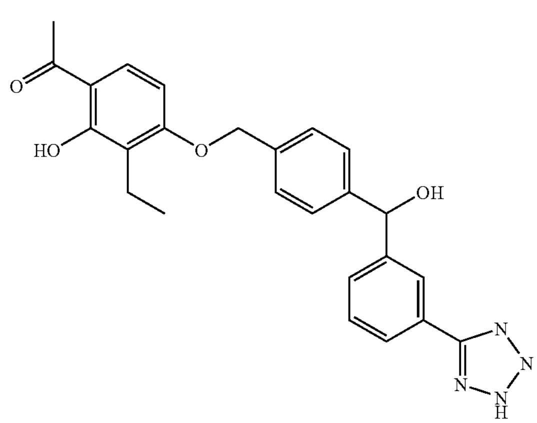 | $^1$H NMR (DMSO-d$_6$) δ 1.02 (t, 3 H), 2.56 (s, 3 H), 2.58 (q, 2 H), 5.22 (s, 2 H), 5.82 (d, 1 H), 6.12 (d, 1 H), 6.71 (d, 1 H), 7.39-7.47 (m, 4 H), 7.51-7.60 (m, 2 H), 7.87 (dt, 1 H), 8.13 (s, 1 H), 12.82 (s, 1 H); MS (esi negative) m/z 443 (M − 1). |

| Ex. No. | Chemical name | Structure | Physical data |
|---|---|---|---|
| 12 | 3-[4-(4-Acetyl-2-chloro-3-hydroxy-phenylsulfanylmethyl)-benzyl]-benzoic acid | 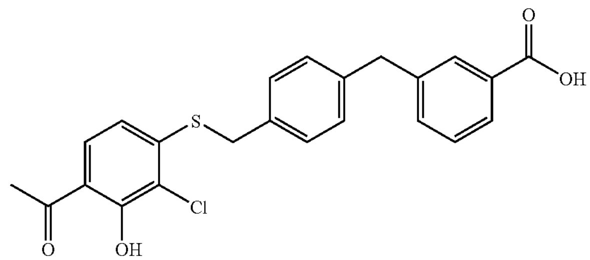 | $^1$H NMR (acetone-$d_6$) δ 13.10 (s, 1 H), 7.80-7.89 (m, 3 H), 7.49 (d, 1 H), 7.41-7.43 (m, 3 H), 7.25 (d, 2 H), 6.99 (d, 1 H), 4.34 (s, 2 H), 4.05 (s, 2 H), 2.63 (s, 3 H). LCMS 425 M − 1. |

Preparation 42

Synthesis of dimethyl-thiocarbamic acid S-(4-acetyl-3-hydroxy-2-propyl-phenyl) ester Stir a mixture of 1-(2,4-dihydroxy-3-propyl-phenyl)-ethanone (2 g, 10.3 mmol), triethylamine (1.6 mL 11.3 mmol), and dichloromethane (40 mL) at room temperature. Add dimethylthiocarbamoyl chloride (1.27 g, 10.3 mmol) and stir at room temperature overnight. Wash the mixture with 1M hydrochloric acid (25 mL), dry over magnesium sulfate, filter and concentrate. Purify the residue via silica chromatography eluting with hexanes to 7:3 hexanes:ethyl acetate to afford dimethyl-thiocarbamic acid O-(4-acetyl-3-hydroxy-2-propyl-phenyl) ester (1.2 g, 41%) as a light yellow solid. Stir the yellow solid in tetradecane (10 mL) at 250° C. for an hour and purify by silica chromatography eluting with hexanes to 6:4 hexanes:ethyl acetate to give the title compound (1.08 g, 90%) as a white solid. LCMS (m/z) 280 M−1.

Preparation 43

Synthesis of 1-(2-hydroxy-4-mercapto-3-propyl-phenyl)-ethanone

Reflux a stirred mixture of dimethyl-thiocarbamic acid S-(4-acetyl-3-hydroxy-2-propyl-phenyl) ester (1.08 g, 3.84 mmol), potassium hydroxide (1.1 g, 19.2 mmol), ethanol (25 mL), and water (10 mL) for 2 hours. Cool the reaction in an ice/water bath and adjust the pH to 2 with aqueous 5N hydrochloric acid. Extract the mixture with ethyl acetate (3×50 mL). Combine the extracts and wash with water (50 mL) and brine (50 mL) and dry over magnesium sulfate, filter, and concentrate to afford the title compound (0.76 g, 94%) as a brown oil which solidifies on standing. LCMS (m/z) 211 M−1.

Preparation 44

Synthesis of 3-[[4-(4-acetyl-3-hydroxy-2-propyl-benzenesulfonylmethyl)-phenyl]-(tetrahydro-pyran-2-yloxy)-methyl]-benzonitrile Stir a mixture of 3-[[4-(4-acetyl-3-hydroxy-2-propyl-phenylsulfanylmethyl)-phenyl]-(tetrahydro-pyran-2-yloxy)-methyl]-benzonitrile (140 mg, 0.271 mmol) and dichloromethane (5 mL) at room temperature. Add 3-chloroperoxybenzoic acid (50-55% pure) (100 mg, 0.29 mmol) and stir the reaction for 10 minutes. Add an additional portion of 3-chloroperoxybenzoic acid (50-55% pure) (280 mg, 0.81 mmol) and stir the reaction for an additional hour at room temperature. Dilute the reaction with aqueous saturated sodium hydrogen carbonate (50 mL) and water (50 mL). Extract the product with dichloromethane (2×50 mL). Wash the combined extracts with water (50 mL), brine (50 mL), and dry over sodium sulfate, filter, and concentrate. Purify the product via silica chromatography eluting with hexanes to 3:1 ethyl acetate:hexanes to give the title compound (147 mg, 99%) as a white solid. LCMS (m/z) 546 M−1.

Preparation 45

Synthesis of 3-[3-(4-acetyl-3-hydroxy-2-propyl-phenylsulfanylmethyl)-benzyl]-benzoic acid methyl ester Stir a mixture of 1-(2-Hydroxy-4-mercapto-3-propyl-phenyl)-ethanone (132 mg, 0.63 mmol), 3-(3-Iodomethyl-benzyl)-benzoic acid methyl ester (230 mg, 0.63 mmol), and cesium carbonate (410 mg, 1.26 mmol) in 2-butanone (6 ml) at room temperature under argon for 20 hours. Pour the mixture into water (60 ml) and extract with ethyl acetate (2×30 ml). Combine the organic extracts and wash with water, brine, then dry over sodium sulfate, filter and concentrate. Purify the crude product via silica chromatography eluting with 1:4 ethyl acetate:hexanes to give the title compound (240 mg, 85%). MS (m/z) 447 (M−H).

Example 13

Synthesis of 3-[3-(4-acetyl-3-hydroxy-2-propyl-phenylsulfanylmethyl)-benzyl]-benzoic acid

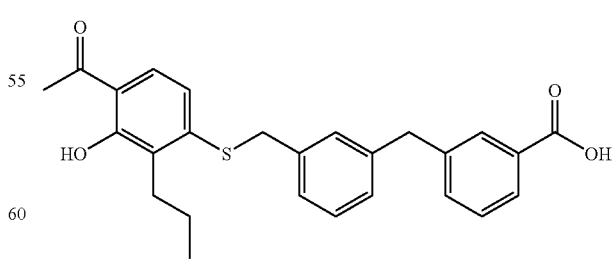

Dissolve 3-[3-(4-Acetyl-3-hydroxy-2-propyl-phenylsulfanylmethyl)-benzyl]-benzoic acid methyl ester (238 mg, 0.53 mmol) in tetrahydrofuran (5 ml) and methanol (4 ml). Add lithium hydroxide monohydrate (89 mg, 2.1 mmol) and water (1.5 ml), then stir at room temperature for 18 hours. Cool at 0° C. and adjust to pH 3 with 1 N hydrochloric acid. Dilute with water (35 ml) and extract with ethyl acetate (2×20 ml). Combine the organic extracts, dry over sodium sulfate, filter and concentrate to a solid. Purify the crude product via reverse phase HPLC using a gradient of 90:10 to 20:80 (water/0.1% TFA):acetonitrile as eluent to give the title compound (196 mg, 85%).

MS (m/z) 433 (M−H). $^1$H NMR (400 MHz, DMSO-$d_6$) 12.85 (s, 1H), 7.80-7.75 (m, 2H). 7.68 (d, 1H), 7.47-7.38 (m, 2H), 7.31-7.26 (m, 3H), 7.17-7.14 (m, 1H), 6.94 (d, 1H), 4.32 (s, 2H), 4.02 (s, 2H), 2.63-2.59 (m, 5H), 1.43 (sextet, 2H), 0.90 (t, 3H).

The following compounds are prepared essentially as described in Example 13.

| Ex. No. | Chemical name | Structure | Physical data |
|---|---|---|---|
| 14 | 4-[3-(4-Acetyl-3-hydroxy-2-propyl-phenylsulfanylmethyl)-benzyl]-benzoic acid | 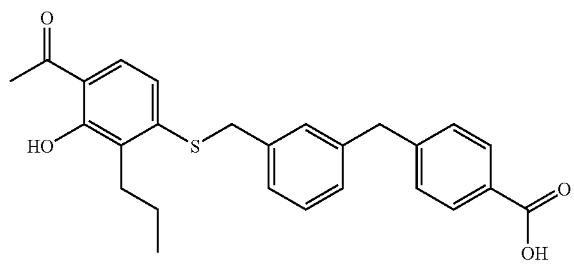 | $^1$H NMR (400 MHz, DMSO-$d_6$) 12.85 (s, 1 H), 7.85-7.83 (m, 2 H), 7.68 (d, 1 H), 7.32-7.24 (m, 5 H), 7.17-7.13 (m, 1 H), 6.90 (d, 1 H), 4.32 (s, 2 H), 4.00 (s, 2 H), 2.63-2.59 (m, 5 H), 1.44 (sextet, 2 H), 0.90 (t, 3 H), MS (m/z) 433 (M − H). |
| 15 | 3-[4-(4-Acetyl-3-hydroxy-2-propyl-phenylsulfanylmethyl)-benzyl]-benzoic acid | 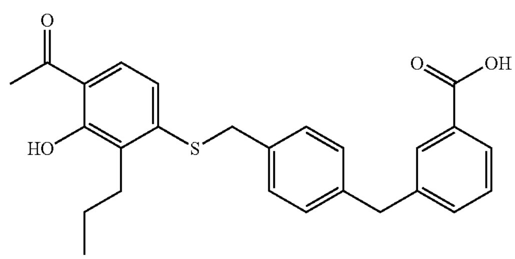 | $^1$H NMR (400 MHz, DMSO-$d_6$) 12.8 (s, 1 H), 7.80-7.7.76 (m, 2 H), 7.73 (d, 1 H), 7.50-7.35 (m, 4 H), 7.23-7.20 (m, 2 H), 6.96 (d, 1 H), 4.32 (s, 2 H), 4.00 (s, 2 H), 2.63-2.60 (m, 5 H), 1.45 (sextet, 2 H), 0.90 (t, 3 H). MS (m/z) 433 (M − H). |
| 16 | 4-[4-(4-Acetyl-3-hydroxy-2-propyl-phenylsulfanylmethyl)-benzyl]-benzoic acid | 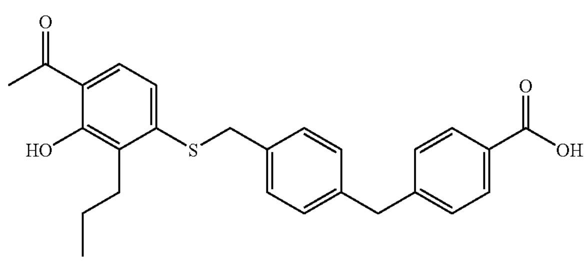 | $^1$H NMR (400 MHz, DMSO-$d_6$) 12.75 (2 H), 7.86 (d, 2 H), 7.72 (d, 1 H), 7.37-7.33 (m, 4 H), 7.21 (d, 2 H), 6.97 (d, 1 H), 4.30 (s, 2 H), 4.00 (s, 2 H), 2.62-2.60 (m, 5 H), 1.45 (sextet, 2 H), 0.90 (t, 3 H). MS (m/z) 433 (M − H). |
| 17 | 3-[3-(4-Acetyl-3-hydroxy-2-methyl-phenylsulfanylmethyl)-benzyl]-benzoic acid | 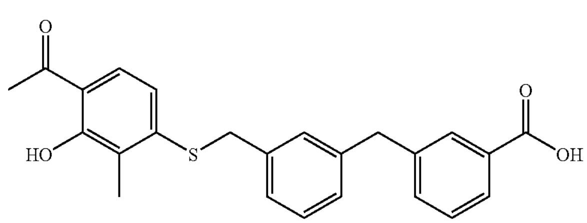 | $^1$H NMR (400 MHz, DMSO-$d_6$) 12.9 (s, 1 H), 12.8 (s, 1 H), 7.80-7.76 (m, 2 H), 7.69 (d, 1 H), 7.49-7.39 (m, 2 H), 7.33-7.32 (m, 1 H), 7.28-7.27 (m, 2 H), 7.17-7.14 (m, 1 H), 6.93 (d, 1 H), 4.33 (s, 2 H), 4.01 (s, 2 H), 2.60 (s, 3 H), 2.09 (s, 3 H). MS (m/z) 405 (M − H). |
| 18 | 4-[3-(4-Acetyl-3-hydroxy-2-methyl-phenylsulfanylmethyl)-benzyl]-benzoic acid | 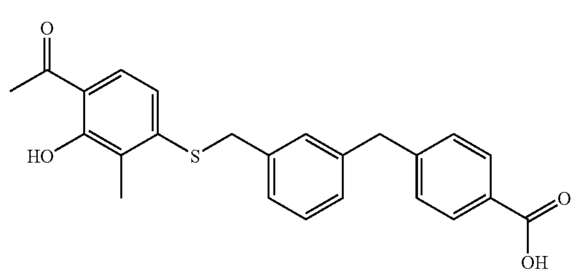 | $^1$H NMR (DMSO-d6) δ 12.81 (s, 2 H), 7.83 (d, J = 8.3 Hz, 2 H), 7.67 (d, J = 8.8 Hz, 1 H), 7.31-7.22 (m, 5 H), 7.13 (d, J = 6.0 Hz, 1 H), 6.90 (d, J = 8.8 Hz, 1 H), 4.30 (s, 2 H), 3.98 (s, 2 H), 2.58 (s, 3 H), 2.06 (s, 3 H); MS (m/e): 407 (M + 1). |

-continued

| Ex. No. | Chemical name | Structure | Physical data |
|---|---|---|---|
| 19 | 3-[4-(4-Acetyl-3-hydroxy-2-methyl-phenylsulfanylmethyl)-benzyl]-benzoic acid | 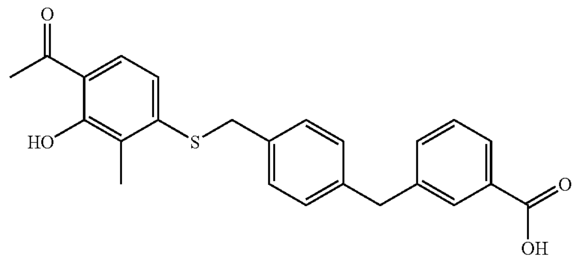 | ¹H NMR (DMSO-d6) δ 12.85 (s, 1 H), 12.81 (s, 1 H), 7.77-7.69 (m, 3 H), 7.47 (m, 1 H), 7.41-7.34 (m, 3 H), 7.19 (d, J = 8.2 Hz, 2 H), 6.92 (d, J = 8.7 Hz, 1 H), 4.30 (s, 2 H), 3.97 (s, 2 H), 2.57 (s, 3 H), 2.07 (s, 3 H); MS (m/e): 407 (M + 1). |
| 20 | 4-[4-(4-Acetyl-3-hydroxy-2-methyl-phenylsulfanylmethyl)-benzyl]-benzoic acid | 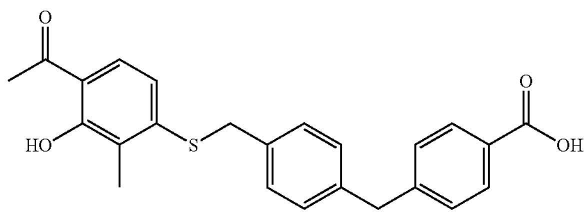 | ¹H NMR (DMSO-d6) δ 12.81 (s, 1 H), 12.78 (s, 1 H), 7.80 (d, J = 8.0 Hz, 2 H), 7.71 (d, J = 8.7 Hz, 1 H), 7.34 (d, J = 8.0 Hz, 2 H), 7.24 (d, J = 8.2 Hz, 2 H), 7.18 (d, J = 8.0 Hz, 2 H), 6.92 (d, J = 8.7 Hz, 1 H), 4.30 (s, 2 H), 3.94 (s, 2 H), 2.57 (s, 3 H), 2.07 (s, 3 H); MS (m/e): 407 (M + 1). |
| 21 | 1-(2-Hydroxy-3-methyl-4-{4-[3-(1H-tetrazol-5-yl)-benzyl]-benzylsulfanyl}-phenyl)-ethanone | 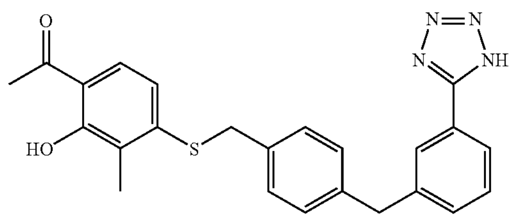 | ¹H NMR (400 MHz, DMSO-d₆) 12.85 (s, 1 H), 7.94-7.93 (m, 1 H), 7.87-7.85 (m, 1 H), 7.73 (d, 1 H), 7.55-7.45 (m, 2 H), 7.39 (d, 2 H), 7.26 (d, 2 H), 6.95 (d, 1 H), 4.33 (s, 2 H), 4.03 (s, 2 H), 2.60 (s, 3 H), 2.09 (s, 3 H). MS (m/z) 429 (M − H). |
| 22 | 1-(2-Hydroxy-3-propyl-4-{4-[3-(1H-tetrazol-5-yl)-benzyl]-benzylsulfanyl}-phenyl)-ethanone | 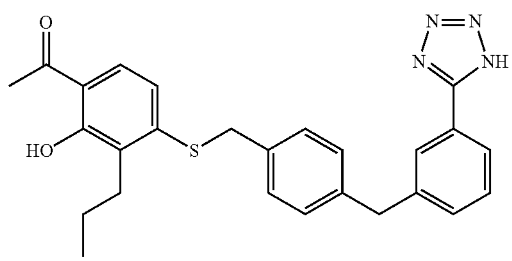 | ¹H NMR (400 MHz, DMSO-d₆) 12.80 (s, 1 H), 7.94-7.93 (m, 1 H), 7.87-7.84 (m, 1 H), 7.72 (d, 1 H), 7.55-7.51 (m, 1 H), 7.48-7.45 (m, 1 H), 7.39-7.37 (m, 1 H), 7.27-7.25 (m, 1 H), 6.96 (d, 1 H), 4.32 (s, 2 H), 4.03 (s, 2 H), 2.63-2.60 (m, 5 H), 1.45 (sextet, 2 H), 0.89 (t, 3 H). MS (m/z) 457 (M − H). |

Preparation 46

Synthesis of (S)-3-[(4-Iodomethyl-phenyl)-(tetrahydro-pyran-2-yloxy)-methyl]-benzonitrile

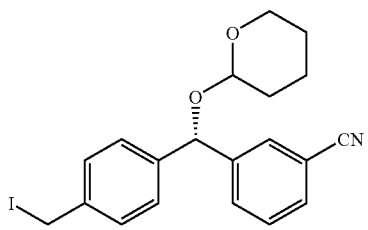

Add sequentially a solution of (S)-3-[(4-hydroxymethyl-phenyl)-(tetrahydro-pyran-2-yloxy)-methyl]-benzonitrile (2.0 g, 6.18 mmol) dichloromethane (20 ml) and a solution of iodine (1.72 g, 6.80 mmol) in dichloromethane (30 ml) to a cooled (0° C.) solution of triphenylphosphine (1.78 g, 6.80 mmol) and imidazole (635 mg, 9.33 mmol) in dichloromethane (20 ml). Allow to warm to room temperature, then stir for 1.5 hours. Pour the mixture into a cold (0° C.) solution of sodium thiosulfate (3.63 g, 23 mmol) in an ice/water mixture (250 g) and stir for 30 minutes. Extract the aqueous layer with dichloromethane (30 ml). Combine the organic extracts and wash with water, dry with sodium sulfate, filter and concentrate. Purify the crude product via silica chromatography eluting with 15:85 ethyl acetate:hexanes to give the title compound (2.19 g, 82%). MS (m/z). Parent ion not observed.

Preparation 47

Synthesis of (S)-3-[[4-(4-Acetyl-3-hydroxy-2-propyl-phenylsulfanylmethyl)-phenyl]-(tetrahydro-pyran-2-yloxy)-methyl]-benzonitrile Stir a mixture of 1-(2-Hydroxy-4-mercapto-3-propyl-phenyl)-ethanone (250 mg, 1.18 mmol), (S)-3-[(4-Iodomethyl-phenyl)-(tetrahydro-pyran-2-yloxy)-methyl]-benzonitrile (515 mg, 1.18 mmol) and cesium carbonate (769 mg, 2.36 mmol) in 2-butanone (10 ml) at room temperature under argon for 24 hours. Pour the mixture into water (85 ml) and extract with ethyl acetate (3×25 ml). Combine the organic extracts and wash with water, brine, then dry over sodium sulfate, filter and concentrate. Purify the crude product via silica chromatography eluting with 1:4 ethyl acetate:hexanes to give the title compound (325 mg, 53%). MS (m/z) 514 (M–H).

Preparation 48

Synthesis of (S)-3-{[4-(4-Acetyl-3-hydroxy-2-propyl-phenylsulfanylmethyl)-phenyl]-hydroxy-methyl}-benzonitrile Add p-toluenesulfonic acid monohydrate (78 mg, 0.41 mmol) to a solution of (S)-3-[[4-(4-Acetyl-3-hydroxy-2-propyl-phenylsulfanylmethyl)-phenyl]-(tetrahydro-pyran-2-yloxy)-methyl]-benzonitrile (177 mg, 0.34 mmol) in methanol (5 ml) at room temperature. Stir the mixture for 1.5 hours, concentrate, and dissolve the residue in ethyl acetate (25 ml) and saturated aqueous sodium bicarbonate (35 ml). Wash the organic layer with saturated aqueous sodium bicarbonate, brine, dry over sodium sulfate and concentrate. Purify the crude product via silica chromatography eluting with 1:2 ethyl acetate:hexanes to give the title compound (122 mg, 84%). MS (m/z) 430 (M–H).

Example 23

Synthesis of (S)-1-[2-hydroxy-4-(4-{hydroxy-[3-(1H-tetrazol-5-yl)-phenyl]-methyl}-benzylsulfanyl)-3-propyl-phenyl]-ethanone

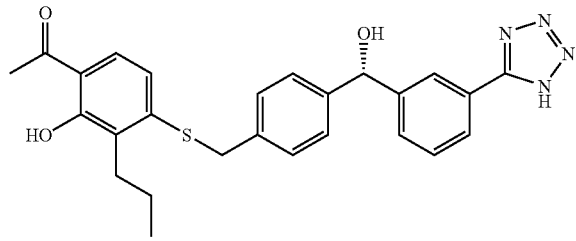

Add sodium azide (66 mg, 0.25 mmol) and zinc bromide (131 mg, 0.50 mmol) to a solution of (S)-3-{[4-(4-Acetyl-3-hydroxy-2-propyl-phenylsulfanylmethyl)-phenyl]-hydroxy-methyl}-benzonitrile (110 mg, 0.25 mmol) in N-methylpyr-rolidinone (2.0 ml). Heat the mixture at 140° C. for 12 hours, then cool to room temperature and stir for 18 hours. Pour the mixture into water (25 ml) and stir the solid suspension for 20 minutes. Filter and wash the filtered solid with water. Dissolve the solid in a 1N HCl (25 ml) and ethyl acetate (20 ml) mixture. Extract the aqueous layer with ethyl acetate (25 ml), combine the organic extracts, then wash with water, brine, dry over sodium sulfate and concentrate. Purify the crude product via reverse phase HPLC using a gradient of 90:10 to 20:80 (water/0.1% TFA):acetonitrile as eluent to give the title compound (37 mg, 31%). MS (m/z) 473 (M–H). $^1$H NMR (400 MHz, DMSO-$d_6$) 12.83 (s, 1H), 8.13-8.11 (m, 1H), 7.89-7.86 (m, 1H), 7.72 (d, 1H), 7.59-7.51 (m, 2H), 7.41-7.37 (m, 4H), 6.96 (d, 1H), 5.60 (s, 1H), 4.30 (s, 2H), 2.65-2.60 (m, 5H), 1.45 (sextet, 2H), 0.90 (t, 3H).

Preparation 49

Synthesis of 1-(2-Hydroxy-3-methyl-4-nitro-phenyl)-ethanone

To a solution of 2-methyl-3-nitrophenol (2.0 g, 13 mmol) in nitrobenzene (16 mL) at RT under Ar gas is added AlCl$_3$ (3.9 g, 29 mmol). The reddish mixture is heated to 50° C. To the reddish mixture is added dropwise via addition funnel a solution of acetyl chloride (1.2 mL, 17 mmol) in nitrobenzene (10 mL). The reaction is heated to 120° C. After 2 h at 120° C., the reaction mixture is cooled to RT and quenched slowly into a 1N HCl/ice mixture. The resulting mixture is stirred for 30 min and extracted with EtOAc (3×). The organic layers are combined and concentrated. Water is used to azeotrope off the nitrobenzene. The resulting residue is purified by flash column chromatography using 20% EtOAc/hexane. Obtained is the title compound as reddish oil (1.2 g). The title compound is 60% pure by LC-MS. Compound is used as is in the next step. LC-MS (m/e): 194 (M−1).

Preparation 50

Synthesis of 1-(4-Amino-2-hydroxy-3-methyl-phenyl)-ethanone

To a solution of 1-(2-hydroxy-3-methyl-4-nitro-phenyl)-ethanone (720 mg, 3.7 mmol) in EtOH (30 mL) are consecutively added Fe powder (4 g, 74 mmol), water (7.2 mL), and conc. HCl (145 μL). The reaction mixture is heated at 95° C. for 4 h. The iron is filtered through celite and the filtrate poured slowly into saturated aqueous NaHCO$_3$. After the bubbling subsides, the mixture is extracted with EtOAc (3×). The organic layers are combined, washed with brine, dried over Na$_2$SO$_4$, and concentrated. The residue is purified by 25% EtOAc/hexane. Obtained is the title compound as a white solid (455 mg). LC-MS (m/e): 166 (M+1).

Preparation 51

Synthesis of 1-(4-Amino-2-hydroxy-3-propyl-phenyl)-ethanone

To N1-(4-acetyl-3-hydroxy-2-propylphenyl)acetamide (1.0 g, 4.3 mmol) in absolute ethanol (15 mL) is added 6N HCl (15 mL). The reaction mixture is refluxed for 3 h. The reaction mixture is cooled to RT and quenched into saturated aqueous NaHCO$_3$. The mixture is extracted with EtOAc (3×). The organic layers are combined, washed with brine, dried over Na$_2$SO$_4$ and concentrated. Obtained is the title compound (827 mg, 99%). LC-MS (m/e): 194 (M+1).

Preparation 52

Synthesis of 3-[{4-[(4-Acetyl-3-hydroxy-2-methyl-phenylamino)-methyl]-phenyl}-(tetrahydro-pyran-2-yloxy)-methyl]-benzonitrile To a solution of 1-(4-amino-2-hydroxy-3-methyl-phenyl)-ethanone (300 mg, 1.8 mmol) and 3-[(4-Iodomethyl-phenyl)-(tetrahydro-pyran-2-yloxy)-methyl]-benzonitrile (865 mg, 2.0 mmol)) in anhydrous DMF (1.5 mL) under Ar gas at RT is added K$_2$CO$_3$ (303 mg, 2.2 mmol). The reaction mixture is heated at 50° C. overnight. The reaction mixture is quenched into water and extracted with EtOAc (3×). The organic layers are combined, washed with brine, dried over $Na_2SO_4$ and concentrated. The residue is purified by flash chromatography using 25% EtOAc/hexane as eluent. Obtained is the title compound as a yellow foam (538 mg, 64%). LC-MS (m/e): 469 (M−1).

The following compounds are prepared essentially by the method of preparation 52.

| Prep. No. | Chemical name | Structure | Physical data |
|---|---|---|---|
| 53 | 3-{3-[(4-Acetyl-3-hydroxy-2-methyl-phenylamino)-methyl]-benzyl}-benzoic acid methyl ester | 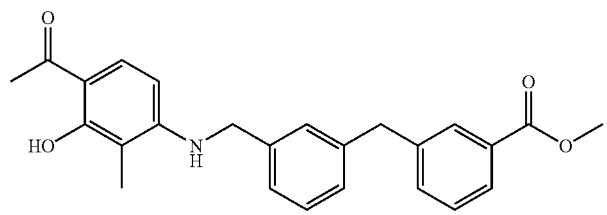 | LC-MS (m/e): 404 (M + 1). |
| 54 | 4-{4-[(4-Acetyl-3-hydroxy-2-methyl-phenylamino)-methyl]-benzyl}-benzoic acid methyl ester | 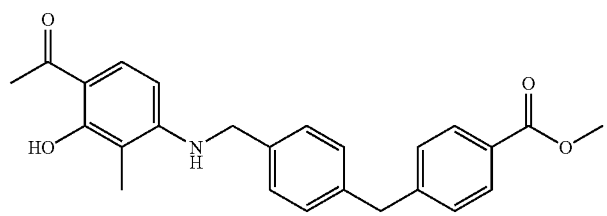 | LC-MS (m/e): 404 (M + 1). |
| 55 | 4-{3-[(4-Acetyl-3-hydroxy-2-methyl-phenylamino)-methyl]-benzyl}-benzoic acid methyl ester | 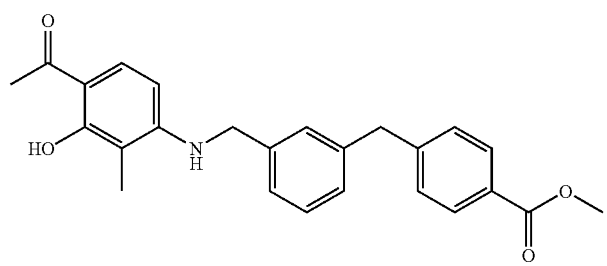 | LC-MS (m/e): 404 (M + 1). |
| 56 | 3-{4-[(4-Acetyl-3-hydroxy-2-methyl-phenylamino)-methyl]-benzyl}-benzoic acid methyl ester | 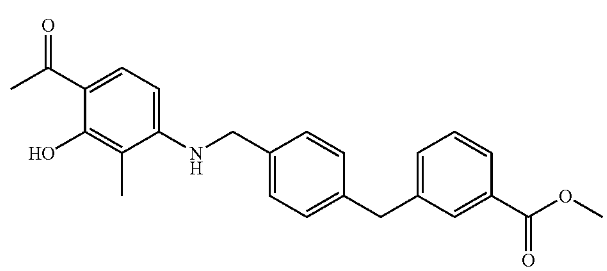 | LC-MS (m/e): 404 (M + 1). |
| 57 | 3-{4-[(4-Acetyl-3-hydroxy-2-methyl-phenylamino)-methyl]-benzyl}-benzonitrile | 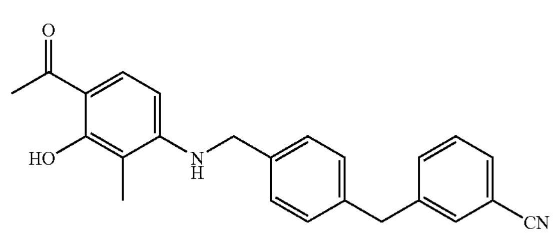 | LC-MS (m/e): 414 (M + 1). |

| Prep. No. | Chemical name | Structure | Physical data |
|---|---|---|---|
| 58 | 3-{4-[(4-Acetyl-3-hydroxy-2-propyl-phenylamino)-methyl]-benzyl}-benzoic acid methyl ester | 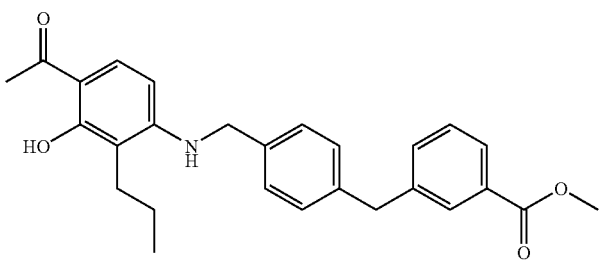 | LC-MS (m/e): 432 (M + 1). |
| 59 | 3-[{4-[(4-Acetyl-3-hydroxy-2-propyl-phenylamino)-methyl]-phenyl}-(tetrahydro-pyran-2-yloxy)-methyl]-benzonitrile | 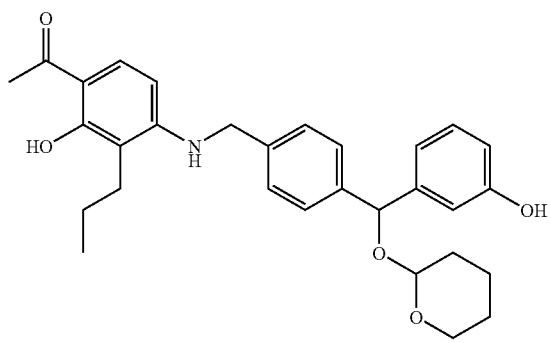 | LC-MS (m/e): 499 (M + 1). |
| 60 | 4-[{4-[(4-Acetyl-3-hydroxy-2-methyl-phenylamino)-methyl]-phenyl}-(tetrahydro-pyran-2-yloxy)-methyl]-benzonitrile | 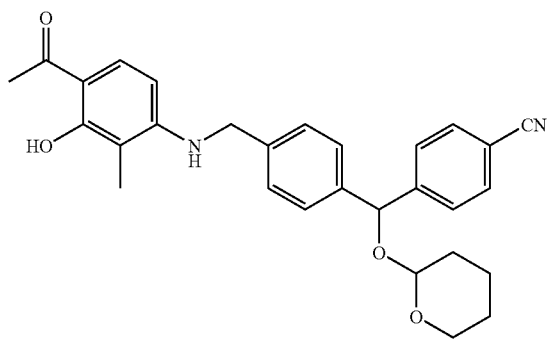 | LC-MS (m/e): 469 (M − 1). |

Preparation 61

Synthesis of 3-({4-[(4-acetyl-3-hydroxy-2-methyl-phenylamino)-methyl]-phenyl}-hydroxy-methyl)-benzonitrile To 3-[{4-[(4-acetyl-3-hydroxy-2-methyl-phenylamino)-methyl]-phenyl}-(tetrahydro-pyran-2-yloxy)-methyl]-benzonitrile (538 mg, 1.1 mmol) in MeOH (5 mL) is added conc. HCl (0.33 mL). The reaction mixture is stirred at RT for 6 h. The reaction mixture is concentrated and the residue partitioned between saturated aqueous NaHCO₃ and EtOAc. The organic layer is separated and the aqueous extracted with EtOAc (2×). The organic layers are combined, washed with brine, dried over Na₂SO₄, and concentrated. The residue is purified by flash column chromatography using 40% EtOAc/hexane as eluent. Obtained is the title compound as yellow foam (305 mg, 72%). LC-MS (m/e): 385 (M−1).

Example 24

Synthesis of 3-({4-[(4-acetyl-3-hydroxy-2-methyl-phenylamino)-methyl]-phenyl}-hydroxy-methyl)-benzoic acid

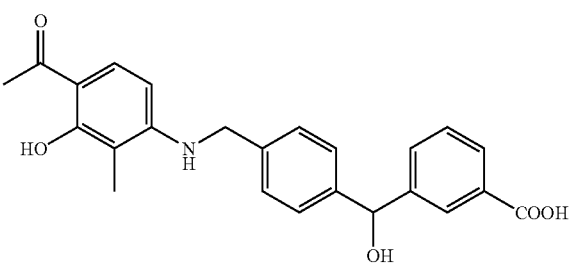

To 3-({4-[(4-Acetyl-3-hydroxy-2-methyl-phenylamino)-methyl]-phenyl}-hydroxy-methyl)-benzonitrile (160 mg, 0.41 mmol) in EtOH/H₂O (6:1, 2.1 mL) in a microwave tube is added powdered KOH (140 mg, 2.0 mmol). The tube is sealed, placed in a microwave reactor, and heated at 150° C. for 30 min. The reaction mixture is acidified to pH=7 and concentrated. The residue is purified by reverse phase HPLC using 90:10 to 20:80 (H₂O/0.1% TFA)/CH₃CN. Obtained is the title compound as a brownish solid (86 mg, 52%). LC-MS (m/e): 404 (M−1); ¹H NMR (DMSO-d₆) δ 13.16 (1H, s), 12.85 (1H, bs), 7.90 (1H, m), 7.73 (1H, m), 7.56 (1H, m), 7.32-7.45 (2H, m), 7.27 (2H, d), 7.20 (2H, d), 6.76 (1H, t), 6.00 (1H, d), 5.69 (1H, s), 4.38 (2H, d), 2.35 (3H, s), 1.93 (3H, s).

Preparation 62

Synthesis of 3-[(4-{[(4-acetyl-3-hydroxy-2-methyl-phenyl)-methyl-amino]-methyl}-phenyl)-hydroxy-methyl]-benzonitrile To 3-({4-[(4-acetyl-3-hydroxy-2-methyl-phenylamino)-methyl]-phenyl}-hydroxy-methyl)-benzonitrile (138 mg, 0.36 mmol) in acetonitrile (14 mL) are added 37% aqueous solution of formaldehyde (140 μL) and NaCNBH₃ (69 mg, 1.1 mmol). The pH of the mixture is adjusted to approximately 2 by dropwise addition of 1 N HCl over a 15 min period. The reaction was complete after 1.5 h, during which time the pH of the reaction mixture is monitored every 15 min using pH paper and kept at around 2 by addition of 1N HCl. The reaction mixture is quenched into H₂O and basified with saturated aqueous NaHCO₃. The mixture is extracted with EtOAc (3×), washed with brine, dried over Na₂SO₄, and concentrated. Obtained is the title compound as a yellow oil (135 mg, 94%). LC-MS (m/e): 399 (M−1).

The following compound is prepared essentially by the method of preparation 62.

| Prep. No. | Chemical name | Structure | Physical data |
|---|---|---|---|
| 63 | 3-(4-{[(4-Acetyl-3-hydroxy-2-methyl-phenyl)-methyl-amino]-methyl}-benzyl)-benzonitrile | 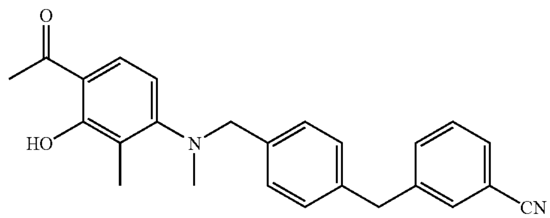 | LC-MS (m/e): 404 (M − 1). |

Example 25

Synthesis of 3-[(4-{[(4-acetyl-3-hydroxy-2-methyl-phenyl)-methyl-amino]-methyl}-phenyl)-hydroxy-methyl]-benzoic acid The title compound is prepared essentially as described for 3-({4-[(4-acetyl-3-hydroxy-2-methyl-phenylamino)-methyl]-phenyl}-hydroxy-methyl)-benzoic acid employing 3-[(4-{[(4-acetyl-3-hydroxy-2-methyl-phenyl)-methyl-amino]-methyl}-phenyl)-hydroxy-methyl]-benzonitrile. LC-MS (m/e): 420 (M+1). ¹H NMR (DMSO-d₆) δ 12.87 (1H, s), 7.91 (1H, m), 7.73 (1H, m), 7.63 (1H, d), 7.57 (1H, m), 7.37 (1H, dd), 7.29 (2H, d), 7.19 (2H, d), 6.55 (1H, d), 5.71 (1H, s), 4.17 (2H, s), 2.62 (3H, s), 2.50 (s, 3H), 2.08 (3H, s).

The following compounds are prepared essentially by the method described in Example 25.

| Ex. No. | Chemical name | Structure | Physical data |
|---|---|---|---|
| 26 | 4-({4-[(4-Acetyl-3-hydroxy-2-methyl-phenylamino)-methyl]-phenyl}-hydroxy-methyl)-benzoic acid | 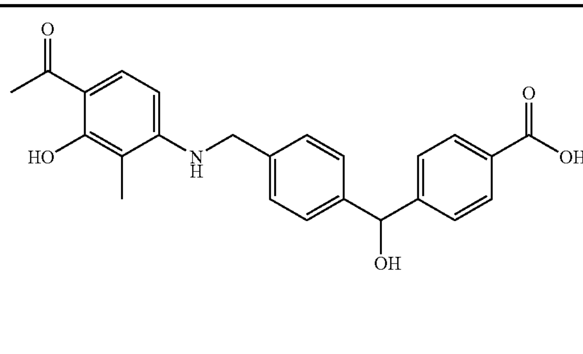 | LC-MS (m/e): 404 (M − 1); ¹H NMR (DMSO-d₆) δ 13.16 (1 H s), 12.75 (1 H, bs), 7.81 (2 H, d), 7.43 (3 H, m), 7.15-7.30 (4 H, m), 6.77 (1 H, m), 5.99 (1 H, d), 5.68 (1 H, s), 4.37 (2 H, d), 2.35 (3 H, s), 1.93 (3 H, s). |

-continued

| Ex. No. | Chemical name | Structure | Physical data |
|---|---|---|---|
| 27 | 3-({4-[(4-Acetyl-3-hydroxy-2-propyl-phenylamino)-methyl]-phenyl}-hydroxy-methyl)-benzoic acid | 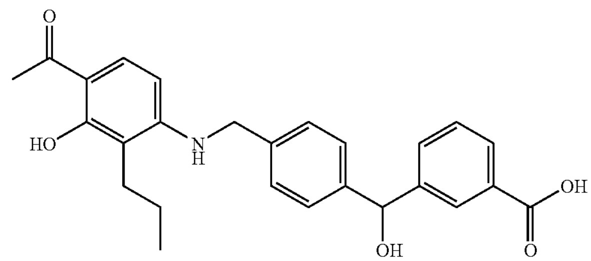 | LC-MS (m/e): 432 (M − 1); $^1$H NMR (DMSO-d$_6$) δ 13.15 (1 H, s), 12.85 (1 H, bs), 7.89 (1 H, m), 7.72 (1 H, m), 7.55 (1 H, m), 7.34-7.43 (2 H, m), 7.27 (2 H, d), 7.18 (2 H, d), 6.87 (1 H, t), 5.97 (1 H, d), 5.69 (1 H, s), 4.37 (2 H, d), 2.48 (2 H, m), 2.34 (3 H, s), 1.41 (2 H, m), 0.90 (3 H, t). |
| 28 | 3-(4-{[(4-Acetyl-3-hydroxy-2-methyl-phenyl)-methyl-amino]-methyl}-benzyl)-benzoic acid | 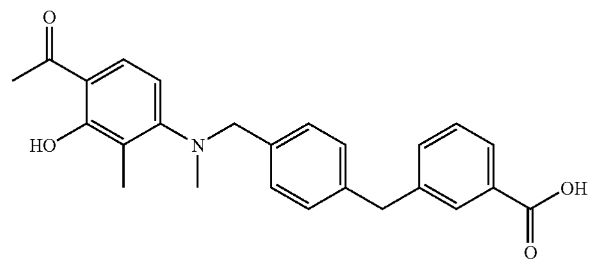 | LC-MS (m/e): 404 (M + 1); $^1$H NMR (DMSO-d$_6$) δ 12.87 (1 H, s), 12.85 (1 H, s), 7.73 (2 H, m), 7.63 (1 H, d), 7.44 (1 H, m), 7.37 (1 H, dd), 7.16 (4 H, s), 6.54 (1 H, d), 4.17 (2 H, s), 3.95 (2 H, s), 2.63 (3 H, s), 2.51 (3 H, s), 2.08 (3 H, s). |
| 29 | 1-(2-Hydroxy-3-methyl-4-{4-[3-(2H-tetrazol-5-yl)-benzyl]-benzylamino}-phenyl)-ethanone | 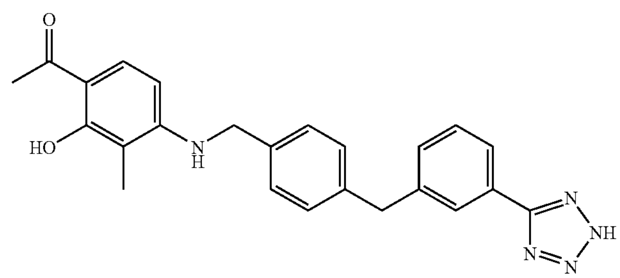 | LC-MS (m/e): 414 (M + 1); $^1$H NMR (DMSO-d$_6$) δ 13.16 (1 H, s), 7.87 (1 H, s), 7.79 (1 H, m), 7.47 (1 H, dd), 7.41 (2 H, m), 7.19 (4 H, m), 6.76 (1 H, t), 6.01 (1 H, d), 4.39 (2 H, d), 3.96 (2 H, s), 2.35 (3 H, s), 1.94 (3 H, s) |

Example 30

Synthesis of 3-{4-[(4-Acetyl-3-hydroxy-2-methyl-phenylamino)-methyl]-benzyl}-benzoic acid To 3-{4-[(4-acetyl-3-hydroxy-2-methyl-phenylamino)-methyl]-benzyl}-benzoic acid methyl ester (356 mg, 0.88 mmol) in THF (14 mL) is added a solution of LiOH·H$_2$O (185 mg, 4.4 mmol) in H$_2$O (7 mL). The reaction mixture is stirred at RT overnight. The reaction mixture is acidified to pH=7 and concentrated. The residue is purified by reverse phase HPLC using 90:10 to 20:80 (H$_2$O/0.1% TFA)/CH$_3$CN. Obtained is the title compound as a brownish solid (158 mg, 46%). LC-MS (m/e): 390 (M+1); $^1$H NMR (DMSO-d$_6$) δ 13.16 (1H, s), 12.84 (1H, bs), 7.71 (2H, m), 7.43 (2H, m), 7.36 (1H, dd), 7.19 (2H, d), 7.14 (2H, d), 6.75 (1H, t), 6.05 (1H, d), 4.38 (2H, d), 3.92 (2H, s), 2.35 (3H, s), 1.94 (3H, s).

The following compounds are prepared essentially by the method described in Example 30.

| Ex. No. | Chemical name | Structure | Physical data |
|---|---|---|---|
| 31 | 4-{3-[(4-Acetyl-3-hydroxy-2-methyl-phenylamino)-methyl]-benzyl}-benzoic acid | 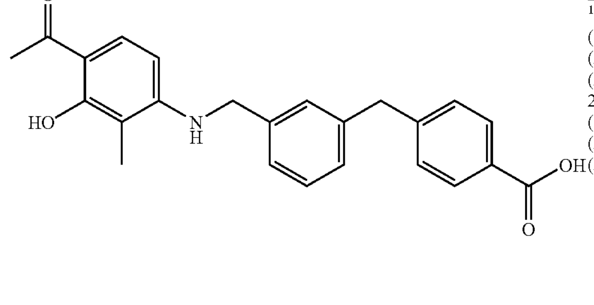 | LC-MS (m/e): 390 (M + 1); $^1$H NMR (DMSO-d$_6$) δ 13.17 (1 H, s) 12.75 (1 H, s), 7.79 (2 H, d), 7.41 (1 H, d), 7.25 (2 H, d), 7.17 (2 H, m), 7.07 (2 H, m), 6.74 (1 H, t), 5.99 (1 H, d), 4.39 (2 H, d), 3.93 (2 H, s), 2.36 (3 H, s), 1.93 (3 H, s). |

-continued

| Ex. No. | Chemical name | Structure | Physical data |
|---|---|---|---|
| 32 | 3-{3-[(4-Acetyl-3-hydroxy-2-methyl-phenylamino)-methyl]-benzyl}-benzoic acid | 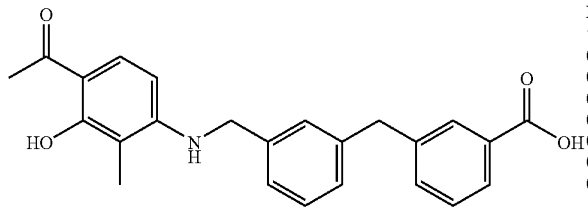 | LC-MS (m/e): 390 (M + 1); $^1$H NMR (DMSO-d$_6$) δ 13.16 (1 H s), 12.85 (1 H, bs), 7.72 (2 H, m), 7.40 (2 H, m), 7.35 (1 H, dd), 7.19 (1 H, dd), 7.15 (1 H, s), 7.17 (2 H, m), 6.75 (1 H, t), 6.00 (1 H, d) 4.38 (2 H, d), 3.93 (2 H, s), 2.36 (3 H, s), 1.93 (3 H, s). |
| 33 | 4-{4-[(4-Acetyl-3-hydroxy-2-methyl-phenylamino)-methyl]-benzyl}-benzoic acid | 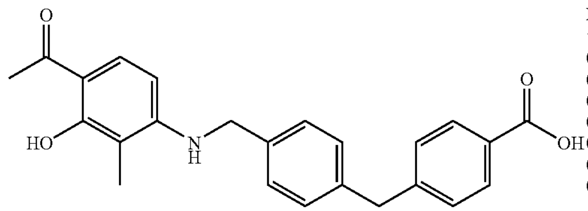 | LC-MS (m/e): 390 (M + 1); $^1$H NMR (DMSO-d$_6$) δ 13.17 (1 H, s), 12.75 (1 H, s), 7.80 (2 H, d), 7.42 (1 H, d), 7.28 (2 H, d), 7.19 (2 H, d), 7.14 (2 H, d), 6.75 (1 H, t), 6.01 (1 H, d), 4.38 (2 H, d), 3.92 (2 H, s), 2.35 (3 H, s), 1.94 (3 H, s). |
| 34 | 3-{4-[(4-Acetyl-3-hydroxy-2-propyl-phenylamino)-methyl]-benzyl}-benzoic acid | 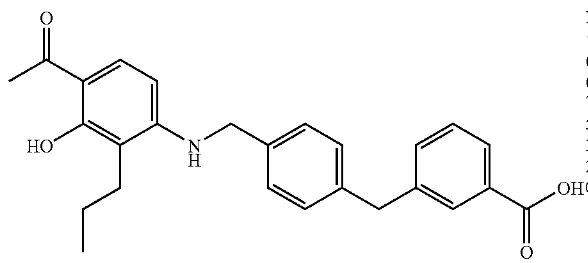 | LC-MS (m/e): 418 (M + 1); $^1$H NMR (DMSO-d$_6$) δ 13.15 (1 H, s), 12.84 (1 H, s), 7.72 (2 H, m), 7.32-7.47 (3 H, m), 7.15 (4 H, m), 6.86 (1 H, t), 5.98 (1 H, d), 4.38 (2 H, d), 3.91 (2 H, s), 2.48 (2 H, m), 2.33 (3 H, s), 1.41 (2 H, m), 0.90 (3 H, t). |

Example 35

Synthesis of 3-{[4-(4-acetyl-3-hydroxy-2-propyl-phenoxymethyl)-phenyl]-hydroxy-methyl}-benzoic acid A mixture of 3-{[4-(4-acetyl-3-hydroxy-2-propyl-phenoxymethyl)-phenyl]-hydroxy-methyl}-benzonitrile (320 mg, 0.772 mmol), potassium hydroxide (1.0 g, 17.85 mmol), water (2 mL), and ethanol (10 mL) is stirred at reflux overnight. The reaction is cooled, the pH is adjusted to 2 with aqueous 5N hydrochloric acid and diluted with water (50 mL). The product is extracted with ethyl acetate (2×50 mL). The combined extracts are washed with water (50 mL), dried over magnesium sulfate, filtered and concentrated to give the title compound (250 mg, 75%) as a white powder. $^1$H NMR (DMSO-d$_6$) δ 12.85 (bs, 2H), 7.98 (s, 1H), 7.80 (d, 2H), 7.64 (d, 1H), 7.38-7.47 (m, 5H), 6.72 (d, 1H), 6.05 (d, 1H), 5.81 (d, 1H), 5.23 (s, 2H), 2.56-2.61 (m, 5H), 1.45-1.53 (m, 2H), 0.87 (t, 3H). LCMS 433 M−1.

The following compounds are prepared essentially by the method described in Example 35.

| Ex. No. | Chemical name | Structure | Physical data |
|---|---|---|---|
| 36 | 3-{[4-(4-Acetyl-2-chloro-3-hydroxy-phenoxymethyl)-phenyl]-hydroxy-methyl}-benzoic acid | 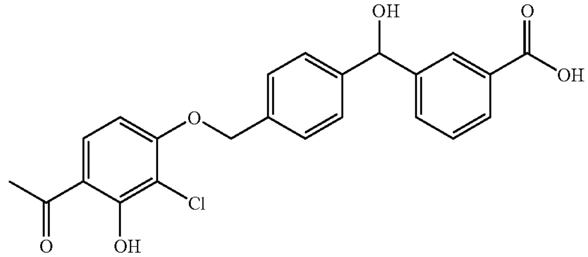 | $^1$H NMR (DMSO-d$_6$) d 13.14 (s, 1 H), 12.9 (bs, 1 H), 9.93-7.99 (m, 2 H), 7.80 (d, 1 H), 7.64 (d, 1 H), 7.43-7.47 (m, 5 H), 6.89 (d, 1 H), 6.07 (s, 1 H), 5.82 (s, 1 H), 5.33 (s, 2 H), 2.62 (s, 3 H). LCMS 425 M − 1. |

-continued

| Ex. No. | Chemical name | Structure | Physical data |
|---|---|---|---|
| 37 | 3-{[4-(2-Chloro-3-hydroxy-4-propionyl-phenoxymethyl)-phenyl]-hydroxy-methyl}-benzoic acid | 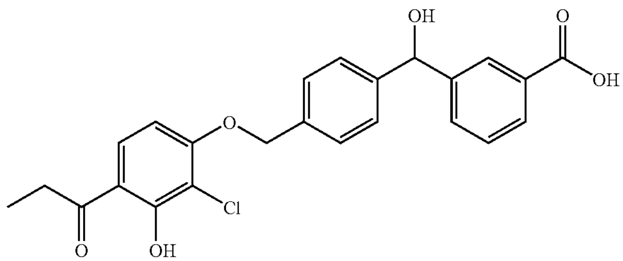 | $^1$H NMR (DMSO-$d_6$) d 13.20 (bs, 1 H), 13.18 (s, 1 H), 7.94-7.98 (m, 3 H), 7.80 (d, 1 H), 7.64 (d, 1 H), 7.42-7.47 (m, 4 H), 6.88 (d, 1 H), 6.08 (s, 1 H), 5.81 (s, 1 H), 5.31 (s, 2 H), 3.06-3.11 (m, 2 H), 1.08 (t, 3 H). LCMS 439 M − 1. |
| 38 | 3-{Hydroxy-[4-(3-hydroxy-2-methyl-4-propionyl-phenoxymethyl)-phenyl]-methyl}-benzoic acid | 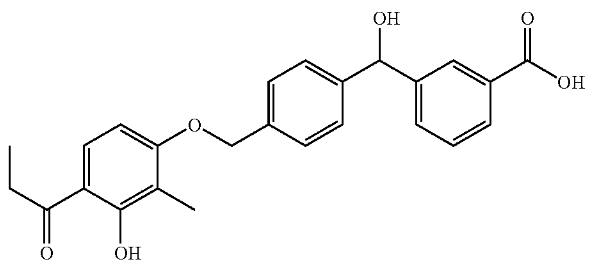 | $^1$H NMR (DMSO-$d_6$) d 12.99 (s, 1 H), 12.91 (s, 1 H), 7.96 (s, 1 H), 7.83 (d, 2 H), 7.63 (d, 1 H), 7.40-7.51 (m, 5 H), 6.72 (d, 1 H), 5.47 (s, 1 H), 5.22 (s, 2 H), 3.30 (s, 3 H), 3.01-3.09 (m, 2 H), 2.04 (s, 3 H), 1.10 (t, 3 H). LCMS 419 M − 1. |
| 39 | 3-{[4-(4-Acetyl-3-hydroxy-2-isopropyl-phenoxymethyl)-phenyl]-hydroxy-methyl}-benzoic acid | 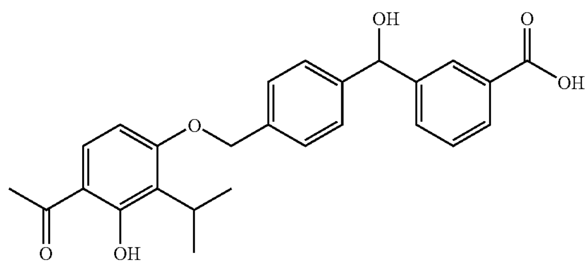 | $^1$H NMR (DMSO-$d_6$) d 13.06 (s, 1 H), 12.92 (s, 1 H), 7.78-7.82 (m, 3 H), 7.51-7.52 (m, 1 H), 7.39-7.46 (m, 3 H), 7.29-7.32 (m, 2 H), 6.72 (d, 1 H), 6.14-6.15 (m, 1 H), 5.84-5.85 (m, 1 H), 5.21 (s, 2 H), 3.52-3.59 (m, 1 H), 2.58 (s, 3 H), 1.24 (d, 6 H). LCMS 433 M − 1. |
| 40 | 3-{[3-(4-Acetyl-3-hydroxy-2-methyl-phenoxymethyl)-phenyl]-hydroxy-methyl}-benzoic acid | 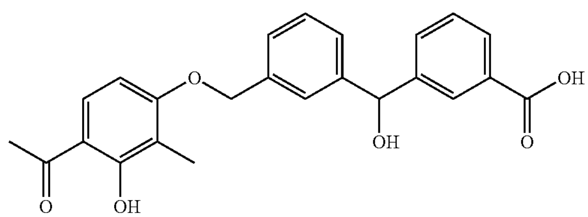 | $^1$H NMR (DMSO-$d_6$) δ 12.9 (s, 1 H), 12.85 (s, 1 H), 7.99 (s, 1 H), 7.78-7.81 (m, 2 H), 7.62-7.64 (m, 1 H), 7.31-7.48 (m, 5 H), 6.73 (d, 1 H), 6.08 (d, 1 H), 5.81 (d, 1 H), 5.24 (s, 2 H), 2.59 (s, 3 H), 2.01 (s, 3 H). LCMS 405 M − 1. |
| 41 | 3-{Hydroxy-[3-(3-hydroxy-2-methyl-4-propionyl-phenoxymethyl)-phenyl]-methyl}-benzoic acid | 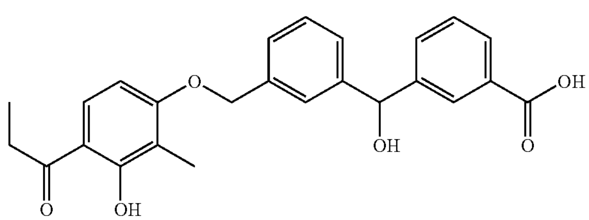 | $^1$H NMR (DMSO-$d_6$) δ 12.93 (s, 1 H), 12.91 (s, 1 H), 7.99 (s, 1 H), 7.72-7.84 (m, 2 H), 7.63 (d, 1 H), 7.30-7.48 (m, 5 H), 6.72 (d, 1 H), 6.08 (d, 1 H), 5.82 (d, 1 H), 5.23 (s, 1 H), 3.05 (q, 2 H), 2.02 (s, 3 H), 1.11 (t, 3 H). LCMS 419 M − 1. |
| 42 | 3-{[3-(4-Acetyl-3-hydroxy-2-propyl-phenoxymethyl)-phenyl]-hydroxy-methyl}-benzoic acid | 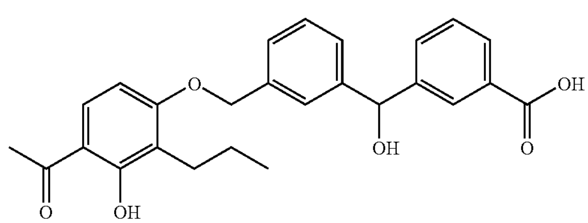 | $^1$H NMR (DMSO-$d_6$) δ 12.93 (s, 1 H), 12.85 (s, 1 H), 7.99 (s, 1 H), 7.79 (d, 2 H), 7.62 (d, 1 H), 7.29-7.48 (m, 5 H), 6.72 (d, 1 H), 6.07 (d, 1 H), 5.81 (d, 1 H), 5.23 (s, 2 H), 2.53-2.58 (m, 5 H), 1.43-1.50 (m, 2 H), 0.85 (t, 3 H). LCMS 433 M − 1. |

-continued

| Ex. No. | Chemical name | Structure | Physical data |
|---|---|---|---|
| 43 | 3-{[3-(4-Acetyl-2-chloro-3-hydroxy-phenoxymethyl)-phenyl]-hydroxy-methyl}-benzoic acid | 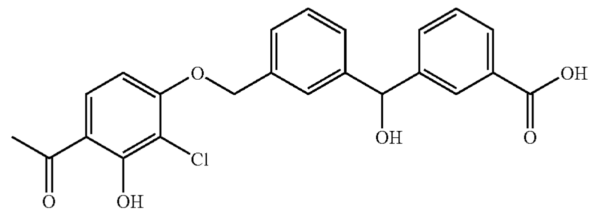 | $^1$H NMR (DMSO-$d_6$) δ 13.15 (s, 1 H), 12.92 (bs, 1 H), 7.98 (s, 1 H), 7.93 (d, 1 H), 7.80 (d, 1 H), 7.62 (d, 1 H), 7.35-7.51 (m, 5 H), 6.89 (d, 1 H), 6.10 (d, 1 H), 5.81 (d, 1 H), 5.34 (s, 2 H), 2.63 (s, 3 H). LCMS 425 M − 1. |
| 44 | 3-{[4-(4-Acetyl-3-hydroxy-2-iodo-phenoxymethyl)-phenyl]-hydroxy-methyl}-benzoic acid | 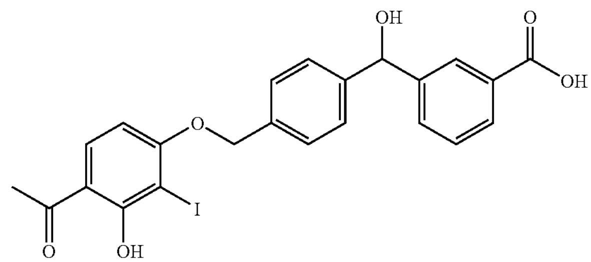 | $^1$H NMR (DMSO-$d_6$) δ 7.97-7.90 (m, 2 H), 7.77-7.71 (m, 1 H), 7.57-7.50 (m, 1 H), 7.46-7.32 (m, 5 H), 6.72 (d, J = 8.8 Hz, 1 H), 5.75 (s, 1 H), 5.27 (s, 2 H), 2.58 (s, 3 H); MS (m/e): 517 (M − 1). |

Preparation 64

Synthesis of 2-fluoro-5-formyl-benzonitrile

Add freshly ground magnesium (1.72 g, 70.7 mmol) to a solution of 5-chloro-2-fluoro-benzonitrile (10.0 g, 64.3 mmol) and N,N-dimethylformamide (5.64 g, 77.1 mmol) in tetrahydrofuran (0.2 M). Add iodine (0.816 g, 3.21 mmol). Heat the solution at reflux for 6 h. Quench the reaction with 1N hydrochloric acid and extract the mixture with ethyl acetate (3×). Dry the combined organic layers with sodium sulfate and concentrate to afford the title compound (9.20 g, 61.7 mmol, 96%): $^1$H NMR (CDCl$_3$, 400 MHz) δ 7.15 (m, 1H), 7.59 (m, 1H), 7.66 (m, 1H), 10.4 (s, 1H).

Preparation 65

Synthesis of 5-{[4-(tert-butyl-dimethyl-silanyloxymethyl)-phenyl]-hydroxy-methyl}-2-fluoro-benzonitrile Add freshly ground magnesium (0.887 g, 36.5 mmol) to a solution of (4-bromo-benzyloxy)-tert-butyl-dimethyl-silane (10.0 g, 33.2 mmol) in tetrahydrofuran (0.2 M). Add iodine (0.400 g, 1.50 mmol). Heat the solution at reflux for 6 h. Add 2-fluoro-5-formyl-benzonitrile (4.95 g, 33.2 mmol) at −40° C. and stir the reaction for 18 h while warming the reaction to room temperature. Quench the reaction with ammonium chloride (sat) and extract the mixture with ethyl acetate (3×). Dry the combined organic layers with sodium sulfate and concentrate. Purify the residue with flash chromatography, eluting with hexanes, ramping to 50% ethyl acetate/hexanes to elute the title compound (8.60 g, 23.1 mmol, 70%): $^1$H NMR (400 MHz, CDCl$_3$) δ 0.10 (s, 6H), 0.94 (s, 9H), 4.73 (s, 2H), 5.81 (m, 1H), 7.15 (t, J=8.6 Hz, 1H), 7.27 (d, J=10.9 Hz, 2H), 7.33 (d, J=8.2 Hz, 2H), 7.57 (m, 1H), 7.65 (m, 1H).

Preparation 66

Synthesis of 5-[[4-(tert-butyl-dimethyl-silanyloxymethyl)-phenyl]-(tetrahydro-pyran-2-yloxy)-methyl]-2-fluoro-benzonitrile Add 3,4-dihydro-2H-pyran (0.340 g, 4.04 mmol) to a solution of 5-{[4-(tert-butyl-dimethyl-silanyloxymethyl)-phenyl]-hydroxy-methyl}-2-fluoro-benzonitrile (1.00 g, 2.69 mmol) and pyridiniuM-toluenesulfonate (0.068 g, 0.269 mmol) in dichloromethane (0.2M). Stir the reaction for 3 h at room temperature. Evaporate solvent and filter through a short pad of silica gel. The title compound (1.20 g, 2.63 mmol, 98%) is taken directly onto the next step (Preparation 58). MS (m/z): 456 (M+1).

Preparation 67

Synthesis of 2-fluoro-5-[(4-hydroxymethyl-phenyl)-(tetrahydro-pyran-2-yloxy)-methyl]-benzonitrile Add tetrabutylammonium fluoride (1.0M in tetrahydrofuran, 5.27 mL, 5.27 mmol) to 5-[[4-(tert-butyl-dimethyl-silanyloxymethyl)-phenyl]-(tetrahydro-pyran-2-yloxy)-methyl]-2-fluoro-benzonitrile (1.20 g, 2.64 mmol) and stir the solution overnight. Dilute with dichloromethane and wash with water and brine. Dry the organic layer and concentrate the solution to afford the title compound (0.890 g, 2.60 mmol, 99%, mixture of diastereomers): $^1$H NMR (400 MHz, CDCl$_3$) δ 1.55 (m, 2H), 1.68 (m, 2H), 1.74 (m, 2H), 3.46 (m, 1H), 3.77 (m, 1H), 4.60 (m, 1H), 4.67 (s, 2H), 5.78 (s, 1H), 7.10 (m, 1H), 7.27 (m, 4H), 7.55 (m, 1H), 7.64 (m, 1H).

Preparation 68

Synthesis of 5-[[4-(4-acetyl-3-hydroxy-2-propyl-phenoxymethyl)-phenyl]-(tetrahydro-pyran-2-yloxy)-methyl]-2-fluoro-benzonitrile Employing the method as described essentially in Preparation 14 using 2-fluoro-5-[(4-hydroxymethyl-phenyl)-(tetrahydro-pyran-2-yloxy)-methyl]-benzonitrile (1.00 g, 2.93 mmol), the title compound is obtained (0.400 g, 0.773 mmol, 26%): MS (m/z): 516 (M−1).

Preparation 69

Synthesis of 1-(4-{4-[[4-fluoro-3-(2H-tetrazol-5-yl)-phenyl]-(tetrahydro-pyran-2-yloxy)-methyl]-benzyloxy}-2-hydroxy-3-propyl-phenyl)-ethanone Employing the method described essentially in Example 1 using 5-[[4-(4-acetyl-3-hydroxy-2-propyl-phenoxymethyl)-phenyl]-(tetrahydro-pyran-2-yloxy)-methyl]-2-fluoro-benzonitrile (0.400 g, 0.773 mmol), the title compound was obtained (0.120 g, 0.214 mmol, 28%): MS (m/z): 559 (M−1).

Example 45

Synthesis of 1-[4-(4-{[4-fluoro-3-(2H-tetrazol-5-yl)-phenyl]-hydroxy-methyl}-benzyloxy)-2-hydroxy-3-propyl-phenyl]-ethanone

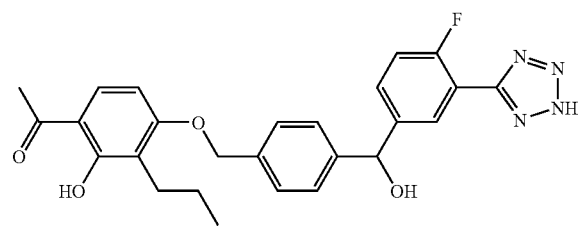

Add p-toluenesulfonic acid (2.00 mg, 0.012 mmol) to a solution of 1-(4-{4-[[4-fluoro-3-(2H-tetrazol-5-yl)-phenyl]-(tetrahydro-pyran-2-yloxy)-methyl]-benzyloxy}-2-hydroxy-3-propyl-phenyl)-ethanone (0.130 g, 0.232 mmol) in methanol (0.2 M) and stir for 24 h. Evaporate solvent and filter through a pad of silica gel to afford the title compound (0.100 g, 0.220 mmol, 91%): MS (m/z): 475 (M−1).

Example 46

Synthesis of 1-[4-(4-{[4-fluoro-3-(2Na-tetrazol-5-yl)-phenyl]-hydroxy-methyl}-benzyloxy)-2-hydroxy-3-propyl-phenyl]-ethanone sodium salt

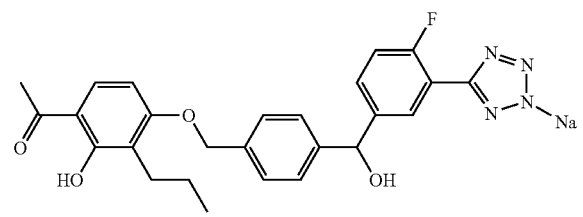

Add excess sodium methoxide 0.5 M solution in methanol) to a solution of 1-[4-(4-{[4-fluoro-3-(2H-tetrazol-5-yl)-phenyl]-hydroxy-methyl}-benzyloxy)-2-hydroxy-3-propyl-phenyl]-ethanone, and stir for 30 min. Evaporate solvent. Add 1:10 tetrahydrofuran/ether and sonicate the residue. Filter and collect the solid product. The title compound is obtained: $^1$H NMR (400 MHz, DMSO-$d_6$) δ 0.86 (t, J=7.4 Hz, 3H), 1.45-1.50 (m, 2H), 2.56 (s, 3H), 3.37-3.39 (m, 2H), 5.21 (s, 2H), 5.74 (s, 1H), 6.70 (d, J=9.0 Hz, 1H), 7.11-7.15 (m, 1H), 7.29 (br s, 1H), 7.37 (m, 4H), 7.78 (d, J=9.0 Hz, 1H), 7.91 (d, J=6.6 Hz, 1H), 12.8 (s, 1H). MS (m/z): 475 (M−1).

Preparation 70

Synthesis of 5-formyl-2-methoxy-benzonitrile

Add copper (I) cyanide (4.58 g, 51.2 mmol) to a solution of 3-bromo-4-methoxy-benzaldehyde (10.0 g, 46.5 mmol) in N,N-dimethylformamide (0.2 M). Heat the solution to 120° C. and stir the solution for 1 d. Quench with potassium carbonate (sat) and extract with diethyl ether (5×). Wash organic layers with water, dry with sodium sulfate, and concentrate to afford the title compound (5.00 g, 31.0 mmol, 67%): $^1$H NMR (400 MHz, DMSO-$d_6$) δ 4.04 (s, 3H), 7.47 (d, J=8.6 Hz, 1H), 8.20 (m, 1H), 8.33 (m, 1H), 9.91 (s, 1H).

Preparation 71

Synthesis of 5-{[4-(tert-butyl-dimethyl-silanyloxymethyl)-phenyl]-hydroxy-methyl}-2-methoxy-benzonitrile The title compound is prepared essentially as described in Preparation 65 employing 5-formyl-2-methoxy-benzonitrile (2.67 g, 16.6 mmol) and (4-bromo-benzyloxy)-tert-butyl-dimethyl-silane (5.00 g, 16.6 mmol), the title compound is obtained (3.50 g, 9.12 mmol, 55%): $^1$H NMR (400 MHz, CDCl$_3$) δ 0.10 (s, 6H), 0.94 (s, 9H), 4.66 (s, 2H), 5.78 (m, 1H), 6.96 (m, 1H), 7.27 (m, 4H), 7.53 (m, 2H).

Preparation 72

Synthesis of 5-[[4-(tert-butyl-dimethyl-silanyloxymethyl)-phenyl]-(tetrahydro-pyran-2-yloxy)-methyl]-2-methoxy-benzonitrile The title compound is prepared essentially as described in Preparation 66 employing 5-{[4-(tert-butyl-dimethyl-silanyloxymethyl)-phenyl]-hydroxy-methyl}-2-methoxy-benzonitrile (2.00 g, 5.21 mmol), the title compound is obtained (2.44 g, 5.21 mmol, 99%): MS (m/z): 468 (M+1).

Preparation 73

Synthesis of 5-[(4-hydroxymethyl-phenyl)-(tetrahydro-pyran-2-yloxy)-methyl]-2-methoxy-benzonitrile The title compound is prepared essentially as described in Preparation 67 employing 5-[[4-(tert-butyl-dimethyl-silanyloxymethyl)-phenyl]-(tetrahydro-pyran-2-yloxy)-methyl]-2-methoxy-benzonitrile (2.44 g, 5.22 mmol), the title compound is obtained (1.60 g, 4.53 mmol, 87%, mixture of diastereomers): $^1$H NMR (400 MHz, CDCl$_3$) δ 1.55 (m, 2H), 1.68 (m, 2H), 1.84 (m, 2H), 3.49 (m, 1H), 3.81 (m, 1H), 3.93 (s, 3H), 4.60 (m, 1H), 4.65 (s, 2H), 5.79 (s, 1H), 6.85 (m, 1H), 7.35 (m, 4H), 7.50 (m, 1H), 7.59 (m, 1H).

Preparation 74

Synthesis of 5-[[4-(4-Acetyl-3-hydroxy-2-propyl-phenoxymethyl)-phenyl]-(tetrahydro-pyran-2-yloxy)-methyl]-2-methoxy-benzonitrile The title compound is prepared essentially as described in Preparation 68 employing 5-[(4-hydroxymethyl-phenyl)-(tetrahydro-pyran-2-yloxy)-methyl]-2-methoxy-benzonitrile (1.60 g, 4.53 mmol), the title compound is obtained (2.28 g, 4.83 mmol, 95%, mixture of diastereomers): MS (m/z): 528 (M−1).

Preparation 75

Synthesis of 1-(2-hydroxy-4-{4-[[4-methoxy-3-(2H-tetrazol-5-yl)-phenyl]-(tetrahydro-pyran-2-yloxy)-methyl]-benzyloxy}-3-propyl-phenyl)-ethanone Using the method of tetrazole formation described in Example 1 with 5-[[4-(4-acetyl-3-hydroxy-2-propyl-phenoxymethyl)-phenyl]-(tetrahydro-pyran-2-yloxy)-methyl]-2-methoxy-benzonitrile (1.00 g, 1.89 mmol), the title compound is obtained (0.620 g, 1.10 mmol, 58%): MS (m/z): 571 (M−1).

Preparation 76

Synthesis of 1-[2-hydroxy-4-(4-{(tetrahydro-pyran-2-yloxy)-[3-(2H-tetrazol-5-yl)-phenyl]-methyl}-benzyloxy)-3-trifluoromethyl-phenyl]-ethanone Employing the procedure of Example 1 using 3-[[4-(4-acetyl-3-hydroxy-2-trifluoromethyl-phenoxymethyl)-phenyl]-(tetrahydro-pyran-2-yloxy)-methyl]-benzonitrile (384 mg, 0.731 mmol), sodium azide (475 mg, 7.31 mmol), and triethylamine hydrochloride (1.01 g, 7.31 mmol) to yield the title compound as a tan solid (400 mg, 96%): $^1$H NMR (CD$_3$CN) 61.44-1.91 (m, 6H), 2.56 (s, 3H), 3.44 (m, 1H), 3.78 (m, 1H), 4.66 (q, 1H), 5.23 (d, 2H), 5.91 (d, 1H), 6.73 (dd, 1H), 7.39-7.62 (m, 5H), 7.89-8.08 (m, 3H), 13.75 (s, 1H).

Preparation 77

Synthesis of 1-[3-ethyl-2-hydroxy-4-(4-{(tetrahydro-pyran-2-yloxy)-[3-(2H-tetrazol-5-yl)-phenyl]-methyl}-benzyloxy)-phenyl]-ethanone Employing the procedure of Example 1 using 3-[[4-(4-acetyl-2-ethyl-3-hydroxy-phenoxymethyl)-phenyl]-(tetrahydro-pyran-2-yloxy)-methyl]-benzonitrile (869 mg, 1.79 mmol), sodium azide (1.16 g, 17.9 mmol), and triethylamine hydrochloride (2.46 g, 17.9 mmol), the title product is obtained as a clear oil (900 mg, 66%): MS (esi negative) m/z (rel intensity) 527 (100).

Example 47

Synthesis of 1-[2-hydroxy-4-(4-{hydroxy-[4-methoxy-3-(2H-tetrazol-5-yl)-phenyl]-methyl}-benzyloxy)-3-propyl-phenyl]-ethanone

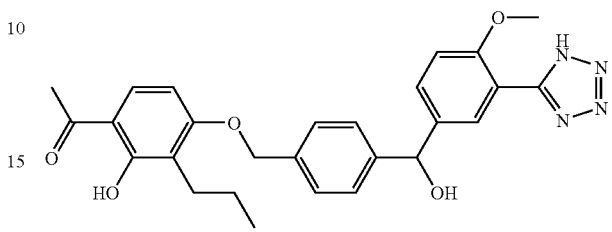

The title compound is prepared essentially as described in Example 45 employing 1-(2-hydroxy-4-{4-[[4-methoxy-3-(2H-tetrazol-5-yl)-phenyl]-(tetrahydro-pyran-2-yloxy)-methyl]-benzyloxy}-3-propyl-phenyl)-ethanone (0.620 g, 1.10 mmol) to afford the title compound (0.350 g, 0.700 mmol, 72%): $^1$H NMR (400 MHz, DMSO-d$_6$) δ 0.86 (t, J=7.4 Hz, 3H), 1.47 (m, 2H), 2.50 (m, 2H), 2.56 (s, 3H), 3.94 (s, 3H), 5.21 (s, 2H), 5.78 (s, 1H), 6.70 (d, J=9.4 Hz, 1H), 7.21 (d, J=8.6 Hz, 1H), 7.39 (d, J=8.2 Hz, 2H), 7.43 (d, J=8.2 Hz, 2H), 7.56 (q, J=7.0 Hz, 1H), 7.78 (d, J=9.0 Hz, 1H), 8.12 (d, J=2.3 Hz, 1H), 12.83 (s, 1H). MS (m/z): 487 (M−1).

Preparation 78

Synthesis of 5-[[4-(4-acetyl-3-hydroxy-2-propyl-phenoxymethyl)-phenyl]-(tetrahydro-pyran-2-yloxy)-methyl]-2-methoxy-benzoic acid Heat a solution of 5-[[4-(4-acetyl-3-hydroxy-2-propyl-phenoxymethyl)-phenyl]-(tetrahydro-pyran-2-yloxy)-methyl]-2-methoxy-benzonitrile (0.650 g, 1.23 mmol) and potassium hydroxide (1.38 g, 24.6 mmol) in ethanol (0.2 M) at reflux for 96 h. Evaporate solvent, acidify with 1N hydrochloric acid, then extract with dichloromethane (5×). Dry the combined organic layers and concentrate to afford the title compound (0.600 g, 1.09 mmol, 89%): MS (m/z): 547 (M−1).

Preparation 79

Synthesis of 5-[[4-(4-acetyl-3-hydroxy-2-propyl-phenoxymethyl)-phenyl]-(tetrahydro-pyran-2-yloxy)-methyl]-2-methoxy-benzamide Add N,N-diisopropylcarbodiimide (0.114 g, 0.902 mmol) to a solution of 5-[[4-(4-acetyl-3-hydroxy-2-propyl-phenoxymethyl)-phenyl]-(tetrahydro-pyran-2-yloxy)-methyl]-2-methoxy-benzoic acid (0.450 g, 0.820 mmol) and 1-hydroxybenzotriazole hydrate (0.122 g, 0.902 mmol) in dichloromethane (0.2M). Stir the solution for 1 h at room temperature. Saturate the solution with ammonia gas and stir the solution for 24 h. Collect the precipitate as the title compound (0.440 g, 0.815 mmol, 98%): MS (m/z): 546 (M−1).

Example 48

Synthesis of 1-[2-hydroxy-4-(4-{hydroxy-[4-methoxy-3-(2Na-tetrazol-5-yl)-phenyl]-methyl}-benzyloxy)-3-propyl-phenyl]-ethanone sodium salt

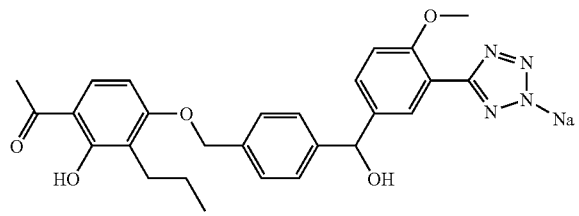

Employing the general method 3 with 1-[2-hydroxy-4-(4-{hydroxy-[4-methoxy-3-(2H-tetrazol-5-yl)-phenyl]-methyl}-benzyloxy)-3-propyl-phenyl]-ethanone (0.200 g, 0.409 mmol), the title compound is obtained (0.190 g, 0.372 mmol, 91%): $^1$H NMR (400 MHz, DMSO-$d_6$) δ 0.86 (t, J=7.4 Hz, 3H), 1.47 (m, 2H), 2.50 (s, 3H), 2.56 (m, 2H), 3.70 (s, 3H), 5.16 (s, 2H), 5.67 (s, 1H), 5.80 (br s, 1H), 6.54 (br s, 1H), 6.96 (d, J=8.6 Hz, 1H), 7.26 (q, J=7.2 Hz, 1H), 7.35 (d, J=7.8 Hz, 2H), 7.39 (d, J=8.2 Hz, 2H), 7.56 (d, J=2.3 Hz, 1H), 7.70 (d, J=8.2 Hz, 1H), 12.76 (br s, 1H). MS (m/z): 487 (M−1).

Preparation 80

Synthesis of 3-[4-(4-acetyl-3-hydroxy-2-propyl-phenoxymethyl)-benzoyl]-benzonitrile Stir a solution of 3-{[4-(4-acetyl-3-hydroxy-2-propyl-phenoxymethyl)-phenyl]-hydroxy-methyl}-benzonitrile (110 mg, 0.264 mmol) in dichloromethane (5 mL) at 0° C. Add Dess-Martin periodinane (1,1,1-triacetoxy-1,1-dihydro-1,2-benziodoxol-3(H)-one) (120 mg, 0.29 mmol) and stir the reaction for 1.5 hr at room temperature. Dilute the reaction mixture with aqueous saturated sodium bicarbonate (50 mL) and extract with ethyl acetate (3×50 mL). Dry the combined extracts over sodium sulfate, filter and concentrate. Purify the residue via silica gel chromatography, eluting with 7:3 hexanes:ethyl acetate to afford the title compound as a white solid (105 mg, 95%). Mass spectrum (M+H) 414.

Example 49

Synthesis of 1-(2-hydroxy-3-propyl-4-{4-[3-(1H-tetrazol-5-yl)-benzoyl]-benzyloxy}-phenyl)-ethanone

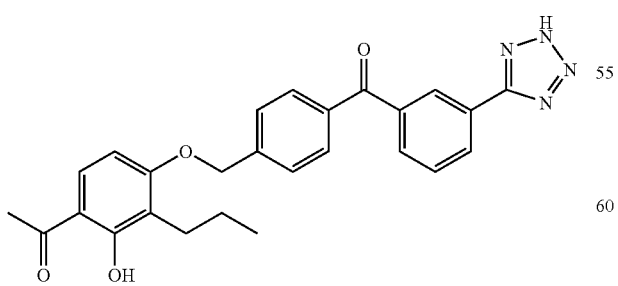

The title compound is prepared essentially as described for 1-[4-(4-{fluoro-[3-(1H-tetrazol-5-yl)-phenyl]-methyl}-benzyloxy)-2-hydroxy-3-propyl-phenyl]-ethanone. The title compound is isolated as a tan solid, 115 mg, 99%. $^1$H NMR (DMSO-$d_6$) δ 12.89 (s, 1H), 8.42 (s, 1H), 8.36 (d, 1H), 7.95 (d, 1H), 7.80-7.89 (m, 4H), 7.68 (d, 2H), 6.76 (d, 1H), 5.42 (s, 2H), 2.66 (t, 2H), 2.60 (s, 3H), 1.54 (q, 2H), 0.92 (t, 3H). LC/MS M−1 455.

Example 50

Synthesis of 3-[4-(4-acetyl-3-hydroxy-2-propyl-phenoxymethyl)-benzoyl]-benzoic acid

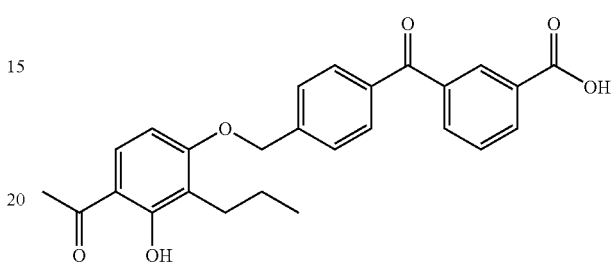

The title compound is prepared essentially as described for 3-{[4-(4-acetyl-3-hydroxy-2-propyl-phenoxymethyl)-phenyl]-hydroxy-methyl}-benzoic acid employing 3-[4-(4-acetyl-3-hydroxy-2-propyl-phenoxymethyl)-benzoyl]-benzonitrile, to give the title compound (52 mg, 100%), as a white powder. $^1$H NMR (DMSO-$d_6$) δ 13.34 (bs, 1H), 12.89 (s, 1H), 8.22-8.26 (m, 2H), 8.01 (d, 1H), 7.82-7.87 (m, 3H), 7.75 (t, 1H), 7.65-7.68 (m, 2H), 6.75 (d, 1H), 5.42 (s, 2H), 2.60-2.68 (m, 5H), 1.50-1.55 (m, 2H), 0.91 (t, 3H). LCMS M−1 431.

Preparation 81

Synthesis of 5-bromo-N-methoxy-N-methyl-nicotinamide

Heat a solution of 5-bromo-nicotinic acid (50 g, 248 mmol) in thionyl chloride (200 mL) to reflux. After 4 hours, cool to ambient temperature and concentrate under reduced pressure to give a residue. Dissolve residue in dichloromethane (1.0 L). Add pyridine (58.7 g, 743 mmol) followed by O,N-dimethyl-hydroxylamine hydrochloride (26.6 g, 272 mmol) and stir. After 18 hours add water (1.0 L) and extract with dichloromethane. Combine organic layers, dry with sodium sulfate, filter and concentrate under reduced pressure to yield the title compound as a clear oil (59.1 g, 97%): $^1$H NMR (DMSO-$d_6$) δ 3.29 (bs, 3H), 3.57 (bs, 3H), 8.24 (dd, 1H), 8.75 (d, 1H), 8.83 (d, 1H).

Preparation 82

Synthesis of (5-bromo-pyridin-3-yl)-[4-(tert-butyl-dimethyl-silanyloxymethyl)-phenyl]-methanone Add n-butyllithium (4.56 mL, 7.30 mmol) to a solution of (4-bromo-benzyloxy)-tert-butyl-dimethyl-silane (2.0 g, 6.64 mmol) in tetrahydrofuran (60 mL) cooled to −78° C. After 2 hours, add 5-bromo-N-methoxy-N-methyl-nicotinamide (1.63 g, 6.64 mmol), and allow solution to warm gradually to ambient temperature. After 2 hours, add 1% aqueous hydrochloric acid (60 mL) and stir. After 20 minutes, extract solution with ethyl acetate. Combine organic layers, dry over sodium sulfate, filter and concentrate under reduced pressure to give a residue. Purify the residue by flash chromatography eluting with 12.5% ethyl acetate:hexanes to yield the title compound as a white solid (1.10 g, 41%): $^1$H NMR (DMSO-d$_6$) δ 0.11 (s, 6H), 0.93 (s, 9H), 4.84 (bs, 2H), 7.52 (d, 2H), 7.79 (d, 2H), 8.31 (t, 1H), 8.82 (d, 1H), 8.98 (d, 1H).

Preparation 83

Synthesis of 5-[4-(tert-butyl-dimethyl-silanyloxymethyl)-benzoyl]-nicotinonitrile Add tetrakis(triphenylphosphine)palladium (284 mg, 0.246 mmol) to a solution of (5-bromo-pyridin-3-yl)-[4-(tert-butyl-dimethyl-silanyloxymethyl)-phenyl]-methanone (1.0 g, 2.46 mmol) and zinc cyanide (578 mg, 4.92 mmol) in dimethylformamide (25 mL) and stir. Purge solution with nitrogen and heat to 80° C. After 18 hours, add water (100 mL) and extract with ethyl acetate. Combine organic layers, dry over sodium sulfate, filter and concentrate under reduced pressure to give a residue. Purify the residue with flash chromatography eluting with 12.5% ethyl acetate:hexanes to yield the title compound as a white solid (550 mg, 63%): $^1$H NMR (DMSO-d$_6$) δ 0.11 (s, 6H), 0.93 (s, 9H), 4.84 (bs, 2H), 7.53 (d, 2H), 7.83 (d, 2H), 8.61 (t, 1H), 9.09 (d, 1H), 9.26 (d, 1H).

Preparation 84

Synthesis of 5-(4-hydroxymethyl-benzoyl)-nicotinonitrile

Dissolve 5-[4-(tert-butyl-dimethyl-silanyloxymethyl)-benzoyl]-nicotinonitrile (510 mg, 1.45 mmol) in 10% aqueous hydrochloric acid (10 mL) and tetrahydrofuran (50 mL) and stir. After 1 hour, add saturated aqueous sodium bicarbonate (50 mL) and extract with ethyl acetate. Combine organic layers, dry over sodium sulfate, filter and concentrate under reduced pressure to yield the title compound as a white solid (325 mg, 94%): $^1$H NMR (DMSO-d$_6$) δ 4.64 (d, 2H), 5.44 (t, 1H), 7.53 (d, 2H), 7.80 (d, 2H), 8.59 (t, 1H), 9.09 (d, 1H), 9.27 (d, 1H).

Preparation 85

Synthesis of 5-[4-(4-acetyl-3-hydroxy-2-propyl-phenoxymethyl)-benzoyl]-nicotinonitrile The title compound is prepared essentially as described in Preparation 14 employing 5-(4-hydroxymethyl-benzoyl)-nicotinonitrile (325 mg, 1.36 mmol) to afford the title compound as a white solid (448 mg, 79%): $^1$H NMR (DMSO-d$_6$) δ 0.90 (t, 3H), 1.52 (sextet, 2H), 2.58 (s, 3H), 2.64 (t, 2H), 5.41 (bs, 2H), 6.74 (d, 1H), 7.66 (d, 2H), 7.83 (d, 1H), 7.89 (d, 2H), 8.62 (t, 1H), 9.11 (d, 1H), 9.27 (d, 1H), 12.86 (s, 1H).

Example 51

Synthesis of 1-(2-hydroxy-3-propyl-4-{4-[5-(2H-tetrazol-5-yl)-pyridine-3-carbonyl]-benzyloxy}-phenyl)-ethanone

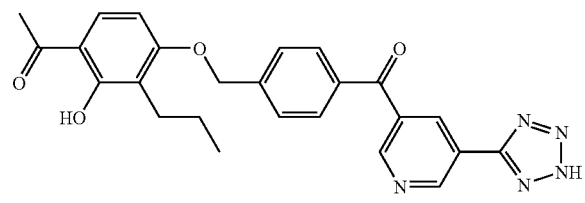

The title compound is prepared essentially as described in Example 1 using 5-[4-(4-acetyl-3-hydroxy-2-propyl-phenoxymethyl)-benzoyl]-nicotinonitrile (448 mg, 1.08 mmol), sodium azide (703 mg, 10.8 mmol), and triethylamine hydrochloride (1.49 g, 10.8 mmol) to yield the title product as a white solid (338 mg, 66%): $^1$H NMR (DMSO-d$_6$) δ 0.90 (t, 3H), 1.53 (sextet, 2H), 2.59 (s, 3H), 2.64 (t, 2H), 5.43 (s, 2H), 6.76 (d, 1H), 7.67 (d, 2H), 7.84 (d, 1H), 7.92 (d, 2H), 8.68 (t, 1H), 9.05 (d, 1H), 9.46 (d, 1H), 12.86 (s, 1H); MS (esi negative) m/z (rel intensity) 456 (100).

Example 52

Synthesis of 5-[4-(4-acetyl-3-hydroxy-2-propyl-phenoxymethyl)-benzoyl]-nicotinic acid

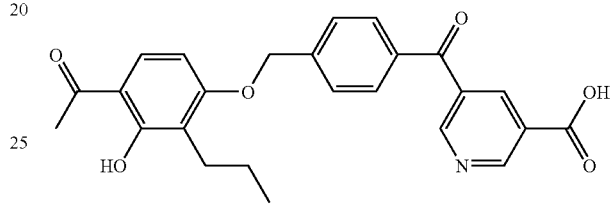

Add lithium hydroxide (289 mg, 12.06 mmol) to a solution of 5-[4-(4-acetyl-3-hydroxy-2-propyl-phenoxymethyl)-benzoyl]-nicotinonitrile (500 mg, 1.21 mmol) in dioxane (10 mL) and water (10 mL) and stir. Heat solution to reflux. After 1 hour cool to ambient temperature, add water (100 mL) and wash with ethyl acetate. Acidify with 10% aqueous hydrochloric acid (15 mL), and extract with ethyl acetate. Combine organic layers, dry with sodium sulfate, filter and concentrate under reduced pressure to give a residue. Purify residue by sonicating in ether for 1 hour. Filter the resulting precipitate to yield the title compound as a beige solid (262 mg, 50%): $^1$H NMR (DMSO-d$_6$) δ 0.86 (t, 3H), 1.48 (sextet, 2H), 2.54 (s, 3H), 2.59 (t, 2H), 5.38 (s, 2H), 6.70 (d, 1H), 7.62 (d, 2H), 7.79 (d, 1H), 7.84 (d, 2H), 8.42 (s, 1H), 9.05 (s, 1H), 9.24 (s, 1H), 12.82 (s, 1H), 13.72 (bs, 1H); MS (esi negative) m/z (rel intensity) 432 (100).

Preparation 86

Synthesis of 3-{[4-(4-acetyl-3-hydroxy-2-propyl-phenoxymethyl)-phenyl]-fluoro-methyl}-benzonitrile A solution of 3-{[4-(4-acetyl-3-hydroxy-2-propyl-phenoxymethyl)-phenyl]-hydroxy-methyl}-benzonitrile (5.0 g, 12.06 mmol) and dichloromethane (100 mL) is stirred at −78° C. Diethylaminosulfur trifluoride (1.8 mL, 13.74 mmol) is added, the cold bath is removed, and the reaction is stirred at room temperature 1 hr. The reaction mixture is diluted with water (100 mL), the layers are separated, and the aqueous layer is extracted with dichloromethane (2×100 mL). The organic layers are combined, washed with water (50 mL), dried over magnesium sulfate, filtered, and concentrated to give 5.1 g, 100%, of the title compound as a tan solid. LCMS M+1=418.

Example 53

Synthesis of 1-[4-(4-{fluoro-[3-(1H-tetrazol-5-yl)-phenyl]-methyl}-benzyloxy)-2-hydroxy-3-propyl-phenyl]-ethanone

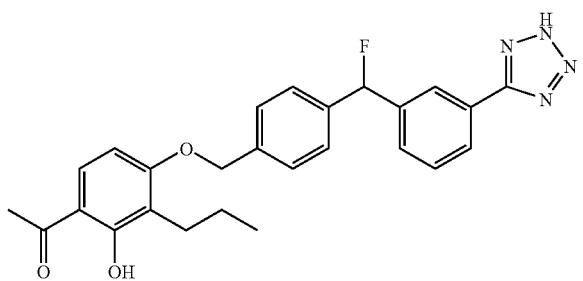

A mixture of 3-{[4-(4-Acetyl-3-hydroxy-2-propyl-phenoxymethyl)-phenyl]-fluoro-methyl}-benzonitrile (4.7 g, 11.26 mmol), zinc (II) bromide (10.1 g, 45 mmol), sodium azide (5.85 g, 90 mmol), and N-methylpyrrolidinone (50 ml) is heated to 140° C. and stirred 1 hr. The reaction is cooled to room temperature and diluted with water (200 mL). The pH is adjusted to 2 with 5N aqueous hydrochloric acid and extracted with ethyl acetate (3×100 mL). The extracts are combined, dried over magnesium sulfate, filtered, and concentrated. The residue is purified via reversed phase C18 chromatography eluting with 4:6 acetonitrile:(0.1% trifluoroacetic acid) water to 7:3 acetonitrile:(0.1% trifluoroacetic acid) water in 8 runs to give 3.08 g, 59%, of the title compound as fine white needles. $^1$H NMR (DMSO-$d_6$) δ 12.86 (s, 1H), 8.13 (s, 1H), 8.03 (d, 1H), 7.81 (d, 1H), 7.61-7.70 (m, 2H), 7.48 (m, 4H), 6.78-6.93 (d, 1H), 6.72 (d, 1H), 5.29 (s, 2H), 2.58-2.63 (m, 5H), 1.46-1.53 (m, 2H), 0.88 (t, 3H). LCMS M−1 459.

Example 54

Synthesis of 1-[4-(4-{azido-[3-(2H-tetrazol-5-yl)-phenyl]-methyl}-benzyloxy)-2-hydroxy-3-propyl-phenyl]-ethanone

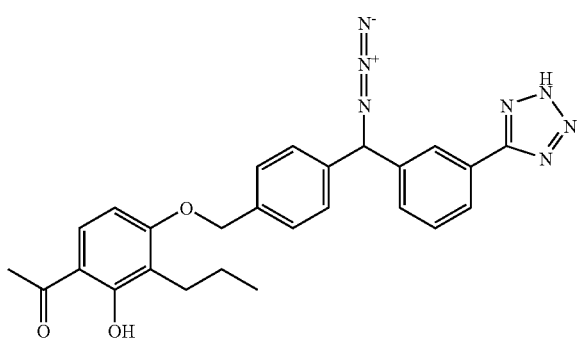

The title compound is obtained as an additional product in the purification of Example 53 1-[4-(4-{fluoro-[3-(1H-tetrazol-5-yl)-phenyl]-methyl}-benzyloxy)-2-hydroxy-3-propyl-phenyl]-ethanone, as a white solid, 340 mg, 7%. $^1$H NMR (DMSO-$d_6$) δ 12.86 (s, 1H), 8.11 (s, 1H), 7.99 (d, 1H), 7.80 (d, 1H), 7.59-7.68 (m, 2H), 7.45-7.51 (m, 4H), 6.73 (d, 1H), 6.32 (s, 1H), 5.28 (2H), 2.58-2.62 (m, 5H), 1.45-1.53 (m, 2H), 0.87 (t, 3H). LC/MS M−1 482.

Preparation 87

Synthesis of 3-{[4-(4-acetyl-3-hydroxy-2-methyl-phenoxymethyl)-phenyl]-fluoro-methyl}-benzonitrile A mixture of 3-{[4-(4-acetyl-3-hydroxy-2-methyl-phenoxymethyl)-phenyl]-hydroxy-methyl}-benzonitrile (0.5 g, 1.29 mmol) and dichloromethane (15 mL) is stirred at −78° C. Diethylaminosulfur trifluoride (0.2 mL, 1.48 mmol) is added and the reaction is warmed to room temperature and stirred 30 min. The mixture is cooled to 0° C. and diluted with water (50 mL). The layers are separated, and the aqueous layer is extracted with dichloromethane (3×50 mL). The organic layers are combined, dried on magnesium sulfate, filtered, and concentrated. The residue is purified via silica chromatography eluting with hexanes to 7:3 hexanes:ethyl acetate to give the title compound (400 mg, 80%) as a white solid. LCMS M+1 390.

Example 55

Synthesis of 1-[4-(4-{fluoro-[3-(1H-tetrazol-5-yl)-phenyl]-methyl}-benzyloxy)-2-hydroxy-3-methyl-phenyl]-ethanone

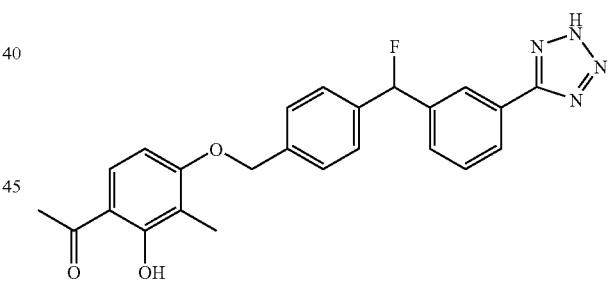

A mixture of 3-{[4-(4-acetyl-3-hydroxy-2-methyl-phenoxymethyl)-phenyl]-fluoro-methyl}-benzonitrile (400 mg, 1.03 mmol), zinc (II) bromide (280 mg, 1.24 mmol), sodium azide (160 mg, 2.48 mmol) and N-methylpyrrolidinone (10 mL) is stirred at 140° C. 1 hr. The reaction mixture is cooled, diluted with water, and the pH is adjusted to 2 with aqueous hydrochloric acid. The product is extracted with ethyl acetate, dried over magnesium sulfate, filtered, and concentrated. The residue is purified via reversed phase C-18 chromatography eluting with 4:6 acetonitrile:(0.1% trifluoroacetic acid) water to acetonitrile to give the title compound (100 mg, 22%) as a white solid. $^1$H NMR (DMSO-$d_6$) δ 12.85 (s, 1H), 8.13 (s, 1H), 8.03 (d, 1H), 7.80 (d, 1H), 7.6107.70 (m, 2H), 7.48-7.55 (m, 4H), 6.78-6.94 (d, 1H), 6.73 (d, 1H), 5.29 (s, 2H), 2.59 (s, 3H), 2.05 (s, 3H). LCMS M−1 431.

Example 56

Synthesis of 3-{[4-(4-acetyl-3-hydroxy-2-methyl-phenoxymethyl)-phenyl]-fluoro-methyl}-benzoic acid

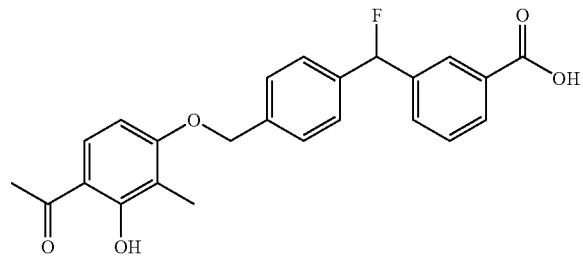

A suspension of 3-{[4-(4-acetyl-3-hydroxy-2-methyl-phenoxymethyl)-phenyl]-hydroxy-methyl}-benzoic acid (100 mg, 0.246 mmol) and dichloromethane (5 mL) is stirred at −78° C. Dimethylamino sulfur trifluoride (35 µL, 0.271 mmol) is added and the mixture is warmed to room temperature. An additional portion of dimethylamino sulfur trifluoride (35 µL, 0.271 mmol) is added and suspension becomes a solution. The reaction mixture is diluted with aqueous 2N sodium hydroxide (5 mL) and tetrahydrofuran (2 mL) and stirred 10 min. The pH is adjusted to 2 with aqueous 5N hydrochloric acid and extracted with ethyl acetate (2×20 mL). The combined extracts are concentrated and the resulting residue is purified via silica chromatography eluting with hexanes to 1:1 hexanes:ethyl acetate to give the title compound (70 mg, 70%) as a white solid. $^1$H NMR (DMSO-$d_6$) δ 13.12 (s, 1H), 12.86 (s, 1H), 7.93-7.95 (m, 2H), 7.82 (d, 1H), 7.68 (d, 1H), 7.44-7.59 (m, 5H), 6.75-6.90 (d, 1H), 6.72 (d, 1H), 5.29 (s, 2H), 2.59 (s, 3H), 2.06 (s, 3H). LCMS M−1 407.

Preparation 88

Synthesis of 3-[4-(4-acetyl-3-hydroxy-2-trifluoromethyl-phenoxymethyl)-benzyl]-benzonitrile To 3-{[4-(4-acetyl-3-hydroxy-2-trifluoromethyl-phenoxymethyl)-phenyl]-hydroxy-methyl}-benzonitrile (211 mg, 0.48 mmol) in anhydrous CH$_2$Cl$_2$ (5 mL) at room temperature under Ar is added Et$_3$SiH (0.61 mL, 3.8 mmol) and BF$_3$.ether complex (0.12 mL, 0.96 mmol). The reaction mixture is stirred at room temperature for 2 h and quenched into saturated aqueous NH$_4$Cl (20 mL). The aqueous mixture is extracted with CH$_2$Cl$_2$ (3×25 mL). The organic layers are combined, washed with brine, dried over sodium sulfatesodium sulfate, and concentrated. The residue is purified by flash column chromatography using 50% ethyl acetate/hexane as eluent to give the title compound (108 mg, 53%). LC-MS (m/e): 424 (M−1)

Example 57

Synthesis of 1-(2-hydroxy-4-{4-[3-(2H-tetrazol-5-yl)-benzyl]-benzyloxy}-3-trifluoromethyl-phenyl)-ethanone

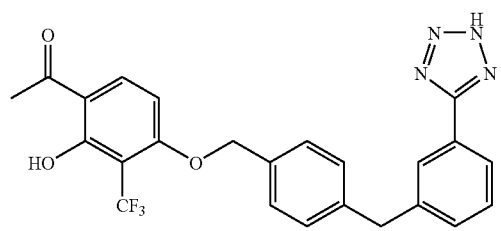

The title compound is prepared essentially as described for 1-(2-hydroxy-4-{4-[3-(2H-tetrazol-5-yl)-phenoxy]-benzyloxy}-3-trifluoromethyl-phenyl)-ethanone employing 3-[4-(4-acetyl-3-hydroxy-2-trifluoromethyl-phenoxymethyl)-benzyl]-benzonitrile (58%). LC-MS (m/e): 467 (M−1); $^1$H NMR (DMSO-$d_6$) δ 13.79 (1H, s), 8.21 (1H, d), 7.80-8.00 (2H, m), 7.30-7.60 (6H, m), 6.92 (1H, d), 5.35 (2H, s), 4.08 (2H, s), 2.65 (3H, s).

Example 58

Synthesis of 1-(2-hydroxy-3-isopropyl-4-{4-[3-(2H-tetrazol-5-yl)-benzyl]-benzyloxy}-phenyl)-ethanone

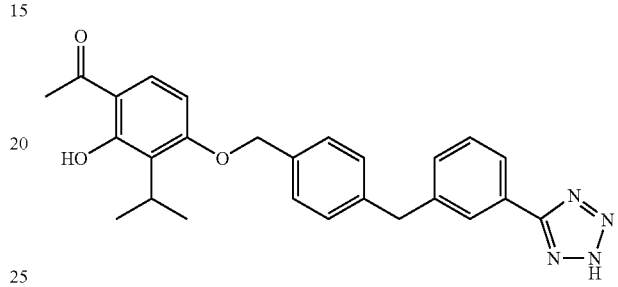

To 1-[2-Hydroxy-4-(4-{hydroxy-[3-(2H-tetrazol-5-yl)-phenyl]-methyl}-benzyloxy)-3-isopropyl-phenyl]-ethanone (100 mg, 0.22 mmol) in anhydrous CH$_2$Cl$_2$ (5.4 mL) is added Et$_3$SiH (281 µL, 1.76 mmol) and BF$_3$.ether complex (56 µL, 0.44 mmol). The reaction mixture is stirred for 1.5 h. The reaction mixture is quenched into saturated aqueous NH$_4$Cl (10 mL) and extracted with a 50% tetrahydrofuran/ethyl acetate solution (3×30 mL). The organic layers are combined, washed with brine, dried over sodium sulfatesodium sulfate, and concentrated to an oil. The residue is purified by reverse phase HPLC using a gradient of 90:10 to 20:80 (H$_2$O/0.1% TFA):CH$_3$CN as eluent to give the title compound (29 mg, 30%). LC-MS (m/e): 441 (M−1); $^1$H NMR (DMSO-$d_6$) δ 13.1 (1H, s), 7.82-8.00 (2H, m), 7.78 (1H, d), 7.30-7.55 (6H, m), 6.72 (1H, d), 5.22 (2H, s), 4.08 (2H, s), 3.57 (1H, m), 2.57 (3H, s), 1.26 (3H, s), 1.23 (3H, s).

Example 59

Synthesis of 1-(3-fluoro-2-hydroxy-4-{4-[3-(2H-tetrazol-5-yl)-benzyl]-benzyloxy}-phenyl)-ethanone

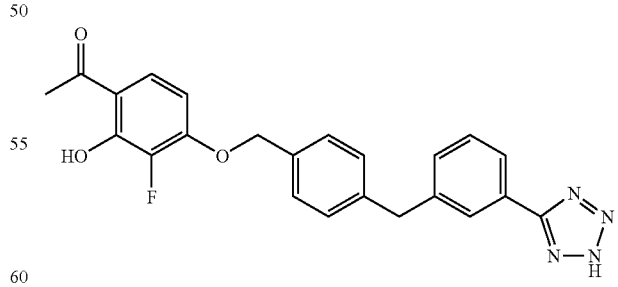

The title compound is prepared essentially as described in Example 57 employing 1-[3-fluoro-2-hydroxy-4-(4-{hydroxy-[3-(2H-tetrazol-5-yl)-phenyl]-methyl}-benzyloxy)-phenyl]-ethanone and stirring 2 h at room temperature. Obtained is the title compound (18 mg, 27%). LC-MS (m/e): 417 (M−1); $^1$H NMR (DMSO-$d_6$) δ 12.34 (1H, s), 7.82-8.00

(2H, m), 7.73 (1H, dd), 7.47-7.60 (2H, m), 7.42 (2H, d), 7.34 (2H, d), 6.89 (1H, dd), 5.28 (2H, s), 4.08 (2H, s), 2.61 (3H, s).

Example 60

Synthesis of 1-(2-hydroxy-3-propyl-4-{4-[3-(1H-tetrazol-5-yl)-benzyl]-benzyloxy}-phenyl)-ethanone

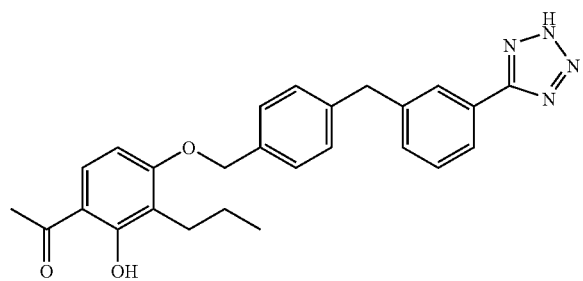

The title compound is prepared in a similar manner to 1-[4-(4-{fluoro-[3-(1H-tetrazol-5-yl)-phenyl]-methyl}-benzyloxy)-2-hydroxy-3-propyl-phenyl]-ethanone employing 3-[4-(4-acetyl-3-hydroxy-2-propyl-phenoxymethyl)-benzyl]-benzonitrile. The crude product is purified via reversed phase C18 preparative chromatography over 8 runs to provide the title compound as a tan solid (6.3 g, 58%). $^1$H NMR (DMSO-$d_6$) δ 12.86 (s, 1H), 7.96 (s, 1H), 7.86-7.89 (m, 1H), 7.81 (d, 1H), 7.48-7.58 (m, 2H), 7.33-7.42 (m, 4H), 6.73 (d, 1H), 5.23 (s, 2H), 4.08 (s, 2H), 2.56-2.61 (m, 5H), 1.45-1.53 (m, 2H), 0.88 (t, 3H). LCMS M−1 441.

Example 61

Synthesis of 3-[4-(4-acetyl-3-hydroxy-2-methyl-phenoxymethyl)-benzyl]-benzoic acid A solution of 3-{[4-(4-acetyl-3-hydroxy-2-methyl-phenoxymethyl)-phenyl]-hydroxy-methyl}-benzoic acid (80 mg, 0.197 mmol), triethylsilane (250 μL, 1.57 mmol), boron trifluoride diethyl etherate (70 μL, 0.542 mmol), and dichloromethane (2 mL) is stirred 1 hr at room temperature. The mixture is diluted with water and extracted with ethyl acetate (2×10 mL). The combined extracts are dried over magnesium sulfate, filtered and concentrated. The residue is recrystallized from dichloromethane/hexanes to give (54 mg, 70%) the title compound, as a white solid. $^1$H NMR (DMSO-$d_6$) δ 12.92 (bs, 1H), 12.85 (s, 1H), 7.78-7.82 (m, 3H), 7.27-7.49 (m, 6H), 6.72 (d, 1H), 5.23 (s, 2H), 4.06 (s, 2H), 2.52 (s, 3H), 2.04 (s, 3H). LCMS M−1 389.

The following compounds are prepared essentially as described for Example 61.

| Ex. No. | Chemical name | Structure | Physical data |
|---|---|---|---|
| 62 | 3-[4-(3-Hydroxy-2-methyl-4-propionyl-phenoxymethyl)-benzyl]-benzoic acid | 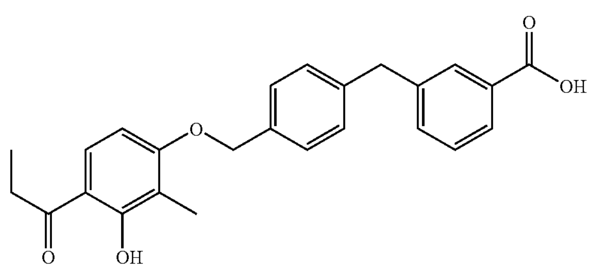 | $^1$H NMR (DMSO-$d_6$) δ 12.92 (bs, 1H), 12.91 (s, 1H), 7.77-7.85 (m, 3H), 7.28-7.60 (m, 5H), 7.15 (s, 1H), 6.72 (d, 1H), 5.22 (s, 2H), 4.04 (s, 2H), 3.02-3.09 (m, 2H), 2.04 (s, 3H), 1.08 (t, 3H). LCMS M−1 403. |
| 63 | 3-[4-(4-Acetyl-3-hydroxy-2-isopropyl-phenoxymethyl)-benzyl]-benzoic acid | 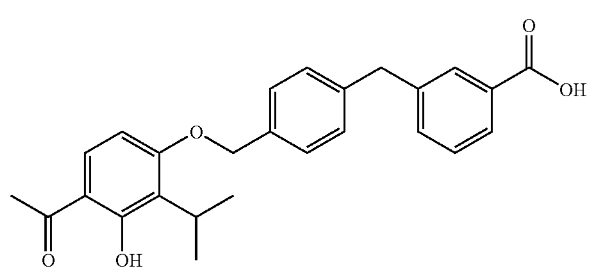 | $^1$H NMR (DMSO-$d_6$) δ 13.06 (s, 1H), 12.92 (s, 1H), 7.78-7.82 (m, 3H), 7.51-7.52 (m, 1H), 7.39-7.46 (m, 3H), 7.29-7.32 (m, 2H), 6.72 (d, 1H), 5.21 (s, 2H), 4.05 (s, 2H), 3.57 (m, 1H), 2.58 (s, 3H), 1.24 (d, 6H). LCMS M−1 417. |
| 64 | 3-[4-(2-Chloro-3-hydroxy-4-propionyl-phenoxymethyl)-benzyl]-benzoic acid | 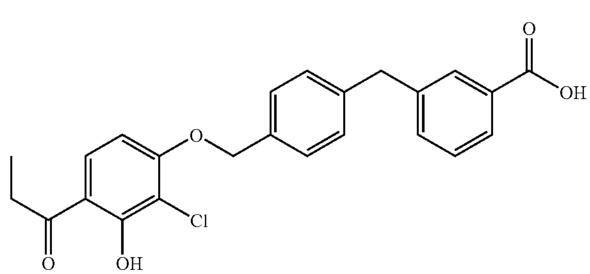 | $^1$H NMR (DMSO-$d_6$) δ 13.19 (s, 1H), 12.92 (bs, 1H), 7.96 (d, 1H), 7.77-7.82 (m, 2H), 7.53-7.55 (m, 1H), 7.40-7.46 (m, 3H), 7.29-7.32 (m, 2H), 6.89 (d, 1H), 5.32 (s, 2H), 4.05 (s, 2H), 3.06-3.14 (m, 2H), 1.11 (t, 3H). LCMS M−1 423. |

-continued

| Ex. No. | Chemical name | Physical data |
|---|---|---|
| 65 | 3-[4-(4-Acetyl-2-chloro-3-hydroxy-phenoxymethyl)-benzyl]-benzoic acid | $^1$H NMR (DMSO-d$_6$) δ 13.15 (s, 1H), 12.94 (bs, 1H), 7.94 (d, 1H), 7.77-7.82 (m, 2H), 7.30-7.51 (m, 6H), 6.91 (d, 1H), 5.33 (s, 2H), 4.05 (s, 2H), 2.63 (s, 3H). LCMS M − 1 409. |
| 66 | 3-[3-(4-Acetyl-3-hydroxy-2-methyl-phenoxymethyl)-benzyl]-benzoic acid | $^1$H NMR (DMSO-d$_6$) δ 12.92 (bs, 1H), 12.85 (s, 1H), 7.78-7.82 (m, 3H), 7.27-7.49 (m, 6H), 6.72 (d, 1H), 5.23 (s, 2H), 4.06 (s, 2H), 2.59 (s, 3H), 2.01 (s, 3H). LCMS M − 1 389. |
| 67 | 3-[3-(4-Acetyl-3-hydroxy-2-propyl-phenoxymethyl)-benzyl]-benzoic acid | $^1$H NMR (DMSO-d$_6$) δ 12.92 (bs, 1H), 12.85 (s, 1H), 7.78-7.82 (m, 3H), 7.27-7.49 (m, 6H), 6.72 (d, 1H), 5.22 (s, 2H), 4.05 (s, 2H), 2.53-2.59 (m, 5H), 1.41-1.47 (m, 2H), 0.83 (t, 3H). LCMS M − 1 417. |
| 68 | 3-[3-(3-Hydroxy-2-methyl-4-propionyl-phenoxymethyl)-benzyl]-benzoic acid | $^1$H NMR (DMSO-d$_6$) δ 12.90 (bs, 1H), 12.90 (s, 1H), 7.78-7.82 (m, 3H), 7.27-7.49 (m, 6H), 6.72 (d, 1H), 5.23 (s, 2H), 4.06 (s, 2H), 3.02-3.09 (m, 2H), 2.01 (s, 3H), 1.11 (t, 3H). LCMS M − 1 403. |
| 69 | 3-[3-(4-Acetyl-2-chloro-3-hydroxy-phenoxymethyl)-benzyl]-benzoic acid | $^1$H NMR (DMSO-d$_6$) δ 13.15 (s, 1H), 12.93 (bs, 1H), 7.94 (d, 1H), 7.77-7.82 (m, 2H), 7.25-7.46 (m, 6H), 6.89 (d, 1H), 5.33 (s, 2H), 2.63 (s, 3H). LCMS M + 1 411. |

Preparation 89

Synthesis of 3-[methoxy-(4-triisopropylsilanyloxymethyl-phenyl)-methyl]-benzonitrile A solution of 3-[hydroxy-(4-triisopropylsilanyloxymethyl-phenyl)-methyl]-benzonitrile (0.64 g, 1.62 mmol) and tetrahydrofuran (10 mL) is stirred at 0° C. Sodium hydride, 60% in mineral oil, (80 mg, 1.95 mmol) is added and the mixture is stirred at room temperature 10 min. The mixture is cooled to 0° C. and iodomethane (0.12 mL, 1.8 mmol) is added. The resulting mixture is stirred at room temperature 18 hr. The mixture is diluted with aqueous saturated sodium hydrogen carbonate, extracted with ethyl acetate, and the organic layer concentrated. The residue is purified via silica chromatography eluting with hexanes to 9:1 hexanes:ethyl acetate to provide 400 mg, 60% the title compound, as a colorless oil. $^1$H NMR (CDCl$_3$) δ 7.70 (s, 1H), 7.55-7.69 (m, 2H), 7.27-7.46 (m, 5H), 5.27 (s, 1H), 4.88 (s, 2H), 3.41 (s, 3H), 1.05-1.29 (m, 21H).

Preparation 90

Synthesis of 3-[(4-hydroxymethyl-phenyl)-methoxymethyl]-benzonitrile

A solution of 3-[methoxy-(4-triisopropylsilanyloxymethyl-phenyl)-methyl]-benzonitrile (0.4 g, 0.976 mmol), tetrahydrofuran (10 mL) and a 1M tetrahydrofuran solution of tetrabutylammonium fluoride (1.2 mL, 1.2 mmol) is stirred at room temperature 18 hr. The mixture is diluted with water (100 mL) and extracted with ethyl acetate (2×50 mL) and the combined extracts are concentrated. The residue is purified via silica chromatography eluting with hexanes to 1:1 hexanes:ethyl acetate to give the title compound (188 mg, 76%) as a colorless oil. LCMS M+1 254.

Preparation 91

Synthesis of 3-{[4-(4-acetyl-3-hydroxy-2-propyl-phenoxymethyl)-phenyl]-methoxy-methyl}-benzonitrile The title compound is prepared in a similar manner to 3-[[4-(4-acetyl-3-hydroxy-2-propyl-phenoxymethyl)-phenyl]-(tetrahydro-pyran-2-yloxy)-methyl]-benzonitrile employing 3-[(4-Hydroxymethyl-phenyl)-methoxy-methyl]-benzonitrile to afford 248 mg, 78%, as a colorless oil. LCMS M+1 430.

Example 70

Synthesis of 1-[2-hydroxy-4-(4-{methoxy-[3-(1H-tetrazol-5-yl)-phenyl]-methyl}-benzyloxy)-3-propyl-phenyl]-ethanone

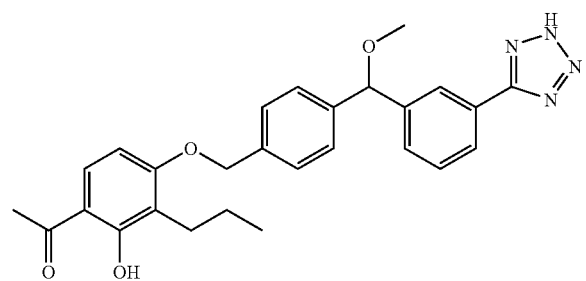

The title compound is prepared essentially as described for 1-[4-(4-{fluoro-[3-(1H-tetrazol-5-yl)-phenyl]-methyl}-benzyloxy)-2-hydroxy-3-propyl-phenyl]-ethanone, employing 3-{[4-(4-acetyl-3-hydroxy-2-propyl-phenoxymethyl)-phenyl]-methoxy-methyl}-benzonitrile to give (129 mg, 47%) of the title compound as a lavender foam. $^1$H NMR (DMSO-d$_6$) δ 12.85 (s, 1H), 8.12 (s, 1H), 7.93 (m, 1H), 7.80 (d, 1H), 7.59 (d, 2H), 7.42-7.49 (m, 4H), 6.71 (d, 1H), 5.50 (s, 1H), 5.25 (s, 2H), 2.57-2.61 (m, 5H), 2.09 (s, 3H), 1.47-1.56 (m, 2H), 0.84-0.92 (m, 3H). LCMS M−1 471.

Example 71

Synthesis of 3-{[4-(4-acetyl-3-hydroxy-2-propyl-phenoxymethyl)-phenyl]-methoxy-methyl}-benzoic acid

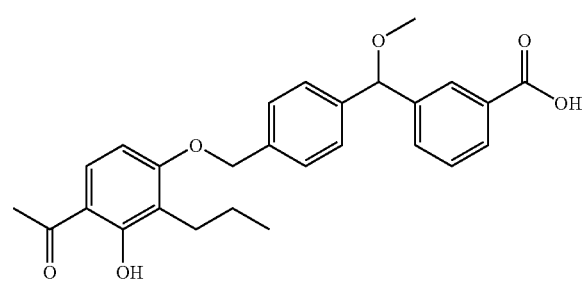

The title compound is prepared essentially as described for 3-{[4-(4-acetyl-3-hydroxy-2-propyl-phenoxymethyl)-phenyl]-hydroxy-methyl}-benzoic acid employing 3-{[4-(4-acetyl-3-hydroxy-2-propyl-phenoxymethyl)-phenyl]-methoxy-methyl}-benzonitrile to give a white solid, 82%. $^1$H NMR (DMSO-d$_6$) δ 13.00 (bs, 1H), 12.85 (s, 1H), 7.96 (s, 1H), 7.79-7.85 (m, 2H), 7.63 (d, 1H), 7.40-7.48 (m, 5H), 6.72 (d, 1H), 5.50 (s, 1H), 5.24 (s, 2H), 3.30 (s, 3H), 2.58-2.61 (m, 5H), 1.44-1.52 (m, 2H), 0.84-0.88 (m, 3H). LCMS M+1 449.

Preparation 92

Synthesis of 3-(4-triisopropylsilanyloxymethyl-benzoyl)-benzonitrile

A solution of 3-[hydroxy-(4-triisopropylsilanyloxymethyl-phenyl)-methyl]-benzonitrile (2.06 g, 5.21 mmol), Dess-Martin periodinane (1,1,1-triacetoxy-1,1-dihydro-1,2-benziodoxol-3(H)-one) (2.7 g, 6.25 mmol), and dichloromethane (50 mL) is stirred at room temperature 24 hr. The mixture is diluted with aqueous saturated sodium hydrogen carbonate and extracted with dichloromethane (2×50 ml). The combined extracts are dried over magnesium sulfate, filtered, and concentrated. The residue is purified via silica chromatography eluting with hexanes to 8:2 hexanes:ethyl acetate to give the title compound (1.2 g, 60%) as a white solid. $^1$H NMR (CDCl$_3$) δ 8.06-8.10 (m, 2H), 7.89-7.91 (m, 1H), 7.79-7.81 (m, 2H), 7.66 (t, 1H), 7.54-7.56 (m, 2H), 4.97 (s, 2H), 1.17-1.31 (m, 21H).

Preparation 93

Synthesis of 3-[1-(4-triisopropylsilanyloxymethyl-phenyl)-vinyl]-benzonitrile

A mixture of methyltriphenylphosphonium bromide (0.2 g, 0.56 mmol) and tetrahydrofuran (10 mL) is stirred at 0° C. Potassium tert-butoxide (72 mg, 0.64 mmol) is added and the yellow solution is stirred 10 min at room temperature. The solution is cooled to 0° C. and 3-(4-Triisopropylsilanyloxymethyl-benzoyl)-benzonitrile (0.2 g, 0.51 mmol) is added. The resulting orange reaction is stirred 1 hr at room temperature. The reaction is diluted with water and extracted with ethyl acetate (2×50 mL). The extracts are combined, dried on magnesium sulfate, filtered, and concentrated. The residue is purified via silica chromatography eluting with hexanes to 9:1 hexanes:ethyl acetate to give 90 mg, 45%, as a colorless wax. $^1$H NMR (CDCl$_3$) δ 7.60-7.67 (m, 3H), 7.47 (t, 1H), 7.37-7.40 (m, 2H) 7.27-7.28 (2H), 5.60 (s, 1H), 5.50 (s, 1H), 1.10-1.29 (m, 21H).

Preparation 94

Synthesis of 3-{1-[4-(4-acetyl-3-hydroxy-2-propyl-phenoxymethyl)-phenyl]-vinyl}-benzonitrile The title compound is prepared in a similar manner as 3-[[4-(4-acetyl-3-hydroxy-2-propyl-phenoxymethyl)-phenyl]-(tetrahydro-pyran-2-yloxy)-methyl]-benzonitrile, employing 3-[1-(4-triisopropylsilanyloxymethyl-phenyl)-vinyl]-benzonitrile to give 0.46 g, 47%, of the title compound as a white solid. LCMS M+1 412.

Example 72

Synthesis of 1-[2-hydroxy-3-propyl-4-(4-{1-[3-(1H-tetrazol-5-yl)-phenyl]-vinyl}-benzyloxy)-phenyl]-ethanone

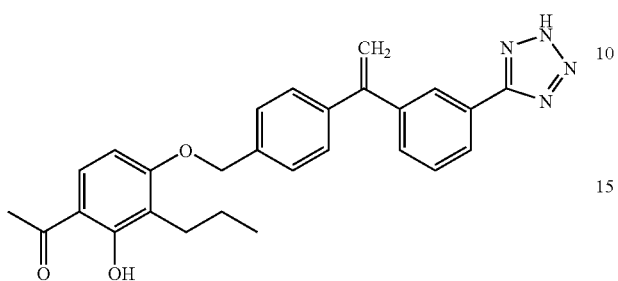

The title compound is prepared essentially as described for 1-[4-(4-{fluoro-[3-(1H-tetrazol-5-yl)-phenyl]-methyl}-benzyloxy)-2-hydroxy-3-propyl-phenyl]-ethanone employing 3-{1-[4-(4-acetyl-3-hydroxy-2-propyl-phenoxymethyl)-phenyl]-vinyl}-benzonitrile to give 72 mg, of the title compound as a tan solid 65%. $^1$H NMR (CDCl$_3$) δ 12.87 (s, 1H), 8.00-8.07 (m, 2H), 7.83-7.86 (m, 2H), 7.65 (t, 1H), 7.39-7.54 (m, 4H), 6.76 (d, 1H), 5.68 (s, 1H), 5.63 (s, 1H), 5.32 (s, 2H), 2.58-2.65 (m, 5H), 1.48-1.53 (m, 2H), 0.89 (t, 3H). LCMS M−1 453.

Preparation 95

Synthesis of 3-{1-[4-(4-acetyl-3-hydroxy-2-propyl-phenoxymethyl)-phenyl]-ethyl}-benzonitrile Add 3-{1-[4-(4-acetyl-3-hydroxy-2-propyl-phenoxymethyl)-phenyl]-vinyl}-benzonitrile (0.105 g, 0.255 mmol), ethyl acetate (50 ml) and PtO$_2$ (0.010 g) to a Parr pressure vessel. Purge the reaction vessel with nitrogen, pressurize the reaction mixture with hydrogen (400 KPa), seal the vessel and agitate the reaction at ambient temperature. Continue the reaction for 2.5 hours. Vent the excess hydrogen from the vessel and purge the vessel with nitrogen. Filter the reaction mixture to remove the platinum catalyst. Add the filtrate and PtO$_2$ (0.019 g) to a Parr pressure vessel. Purge the reaction vessel with nitrogen, pressurize the reaction mixture with hydrogen (400 KPa), seal the vessel and agitate the reaction at ambient temperature. Continue the reaction for 6 hours. Vent the excess hydrogen from the vessel and purge the vessel with nitrogen. Filter the reaction mixture to remove the platinum catalyst and remove the solvent under vacuum. Add the concentrate, ethyl acetate (50 ml) and PtO$_2$ (0.022 g) to a Parr pressure vessel. Purge the reaction vessel with nitrogen, pressurize the reaction mixture with hydrogen (400 KPa), seal the vessel and agitate the reaction at ambient temperature. Continue the reaction for 18 hours. Vent the excess hydrogen from the vessel and purge the vessel with nitrogen. Filter the reaction mixture to remove the platinum catalyst and remove the solvent under vacuum. Add the concentrate, ethyl acetate (150 ml), Pt catalyst from previous filtrations and PtO$_2$ (0.105 g) to a Parr pressure vessel. Purge the reaction vessel with nitrogen, pressurize the reaction mixture with hydrogen (400 KPa), seal the vessel and agitate the reaction at ambient temperature. Continue the reaction for 22.5 hours. Vent the excess hydrogen from the vessel and purge the vessel with nitrogen. Filter the reaction mixture to remove the platinum catalyst. The mixture is filtered and concentrated to give 25 mg, 25%, as a film. LCMS M−1 412.

Example 73

Synthesis of 1-[2-hydroxy-3-propyl-4-(4-{1-[3-(1H-tetrazol-5-yl)-phenyl]-ethyl}-benzyloxy)-phenyl]-ethanone

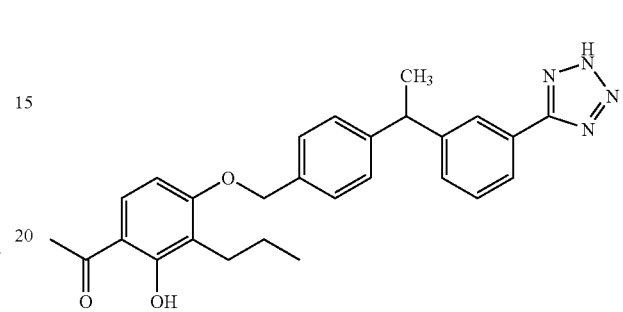

The title compound is prepared essentially as described for 1-[4-(4-{fluoro-[3-(1H-tetrazol-5-yl)-phenyl]-methyl}-benzyloxy)-2-hydroxy-3-propyl-phenyl]-ethanone employing 3-{1-[4-(4-acetyl-3-hydroxy-2-propyl-phenoxymethyl)-phenyl]-ethyl}-benzonitrile. The title compound is obtained (12.5 mg, 45%) as a white solid. $^1$H NMR (DMSO-d$_6$) δ 12.85 (s, 1H), 8.00 (s, 1H), 7.75-7.85 (m, 2H), 7.35-7.54 (m, 6H), 6.73 (d, 1H), 5.23 (s, 2H), 4.32 (m, 1H), 2.55-2.60 (m, 5H), 1.66 (d, 3H), 1.46-1.50 (m, 2H), 0.87 (t, 3H). LCMS M+1 457.

Example 74

Synthesis of 1-[4-(4-{amino-[3-(1H-tetrazol-5-yl)-phenyl]-methyl}-benzyloxy)-2-hydroxy-3-propyl-phenyl]-ethanone

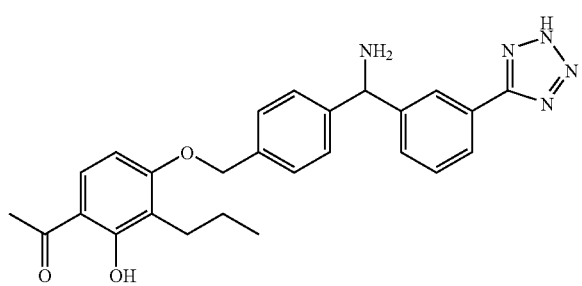

A mixture of 1-[4-(4-{azido-[3-(2H-tetrazol-5-yl)-phenyl]-methyl}-benzyloxy)-2-hydroxy-3-propyl-phenyl]-ethanone (340 mg, 0.703 mmol), triphenylphosphine (195 mg, 0.74 mmol), water (0.5 mL), and tetrahydrofuran (5 mL) is stirred at room temperature 48 hr. The mixture is filtered, the cake is washed with tetrahydrofuran (2 mL) and dried under vacuum to give the title compound 169 mg, 52%, as a white solid. $^1$H NMR (DMSO-d$_6$) δ 12.86 (s, 1H), 8.9 (bs, 2H), 8.18 (s, 1H), 7.98 (d, 1H), 7.80 (d, 1H), 7.35-7.58 (m, 6H), 6.72 (d, 1H), 5.74 (s, 1H), 5.28 (s, 2H), 2.58-2.62 (m, 5H), 1.46-1.54 (m, 2H), 0.88 (t, 3H). LCMS M−1 456.

Example 75

Synthesis of N-{[4-(4-acetyl-3-hydroxy-2-propyl-phenoxymethyl)-phenyl]-[3-(1H-tetrazol-5-yl)-phenyl]-methyl}-acetamide

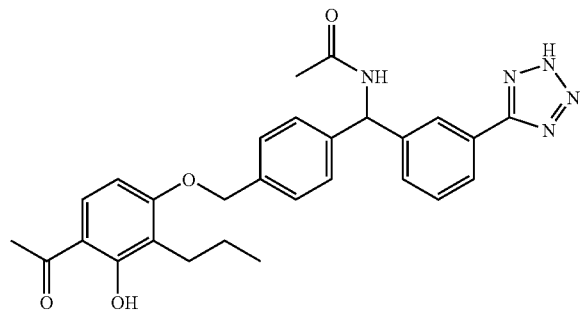

A mixture of 1-[4-(4-{amino-[3-(1H-tetrazol-5-yl)-phenyl]-methyl}-benzyloxy)-2-hydroxy-3-propyl-phenyl]-ethanone (80 mg, 0.175 mmol), acetyl chloride (15 μL, 0.211 mmol) and dichloromethane (1.5 mL) is stirred at room temperature. Pyridine (50 μL, 0.62 mmol) is added and the mixture is stirred at room temperature 24 hr. An additional portion of acetyl chloride (20 μL, 0.28 mmol) is added and the reaction is stirred an additional 24 hr. The reaction mixture is purified as is via reversed phase C18 preparative chromatography eluting with 4:6 acetonitrile:water (0.1% trifluoroacetic acid) to 8:2 acetonitrile:water (0.1% trifluoroacetic acid) to give the title compound (53 mg, 61%), as a white solid. $^1$H NMR (DMSO-d$_6$) δ 12.85 (s, 1H), 8.92 (d, 1H), 8.03 (s, 1H), 7.92 (d, 1H), 7.80 (d, 1H), 7.36-7.61 (m, 6H), 6.73 (d, 1H), 6.23 (d, 1H), 5.25 (s, 2H), 2.59-2.62 (m, 5H), 1.97 (s, 3H), 1.46-1.53 (m, 2H), 0.88 (t, 3H). LCMS M−1=498.

Example 76

Synthesis of N-{[4-(4-acetyl-3-hydroxy-2-propyl-phenoxymethyl)-phenyl]-[3-(1H-tetrazol-5-yl)-phenyl]-methyl}-methanesulfonamide

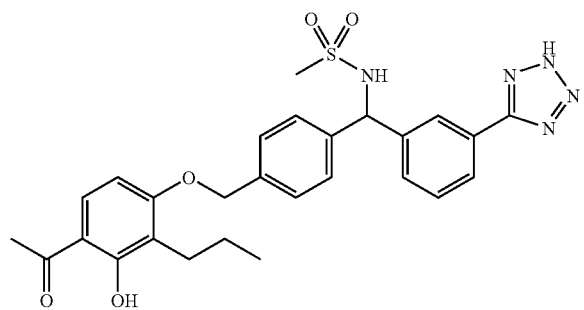

The title compound is prepared essentially as described in Example 74 employing methane sulfonyl chloride and 1-[4-(4-{amino-[3-(1H-tetrazol-5-yl)-phenyl]-methyl}-benzyloxy)-2-hydroxy-3-propyl-phenyl]-ethanone to give 22 mg, 28%, as a white solid. $^1$H NMR (DMSO-d$_6$) δ 12.86 (s, 1H), 8.49 (d, 1H), 8.17 (s, 1H), 7.91-7.94 (m, 1H), 7.80 (d, 1H), 7.60-7.62 (m, 2H), 7.44-7.51 (m, 4H), 6.72 (d, 1H), 5.81 (d, 1H), 5.25 (s, 2H), 2.75 (s, 3H), 2.57-2.62 (m, 5H), 1.46-1.53 (m, 2H), 0.87 (t, 3H). LCMS M+1 536.

Preparation 96

Synthesis of 3-{[4-(4-acetyl-3-hydroxy-2-propyl-phenoxymethyl)-phenyl]-azido-methyl}-benzonitrile A mixture of 3-{[4-(4-acetyl-3-hydroxy-2-propyl-phenoxymethyl)-phenyl]-hydroxy-methyl}-benzonitrile (3 g, 7.22 mmol), 1,8-diazabicyclo[5.4.0]undec-7-ene (2.3 mL, 15.2 mmol), diphenylphosphoryl azide (3.3 mL, 152 mmol) and tetrahydrofuran (20 mL) is stirred at 50° C. 2 hr. The mixture is concentrated and the crude residue is purified via silica chromatography eluting with hexanes to 7:3 hexanes: ethyl acetate to give the title compound 1.77 g, 56% as a white solid. LCMS M−1 439.

Preparation 97

Synthesis of 3-{[4-(4-acetyl-3-hydroxy-2-propyl-phenoxymethyl)-phenyl]-amino-methyl}-benzonitrile A mixture of 3-{[4-(4-acetyl-3-hydroxy-2-propyl-phenoxymethyl)-phenyl]-azido-methyl}-benzonitrile (1.77 g, 4.02 mmol), triphenylphosphine (1.16 g, 4.42 mmol), water (0.5 mL) and tetrahydrofuran (25 mL) is stirred 18 hr. The mixture is concentrated, diluted with water (100 mL) and extracted to ethyl acetate (3×50 mL). The combined extracts are dried over sodium sulfate, filtered, and concentrated to a bright yellow residue. The compound is used without further purification. LCMS M−1 413.

Example 77

Synthesis of 3-{[4-(4-acetyl-3-hydroxy-2-propyl-phenoxymethyl)-phenyl]-amino-methyl}-benzoic acid

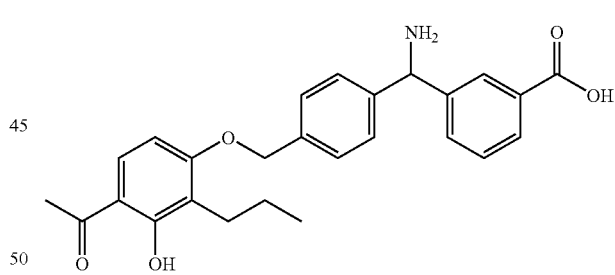

A solution of 3-{[4-(4-acetyl-3-hydroxy-2-propyl-phenoxymethyl)-phenyl]-amino-methyl}-benzonitrile aqueous 5N sodium hydroxide (15 mL, 75 mmol), and ethanol (50 mL) is stirred at reflux 3 hr. The pH is adjusted to 2 with concentrated aqueous hydrochloric acid and extracted with ethyl acetate (3×50 mL). The combined extracts are washed with water (50 mL) and brine (50 mL), dried over magnesium sulfate, filtered, and concentrated. The residue is purified in 4 runs via reversed phase C18 preparatory chromatography eluting with 8:2 water (0.1% trifluoroacetic acid):acetonitrile to acetonitrile to give 1.5 g, 87% as a white crystalline solid. $^1$H NMR (DMSO-d$_6$) δ 13.25 (bs, 1H), 12.86 (s, 1H), 9.00 (bs, 2H), 8.14 (s, 1H), 7.97 (d, 1H), 7.82 (d, 1H), 7.72 (d, 1H), 7.51-7.62 (m, 5H), 6.73 (d, 1H), 5.83 (s, 1H), 5.28 (s, 2H), 2.57-2.62 (m, 5H), 1.46-1.53 (m, 2H), 0.88 (t, 3H). LCMS M−1 432.

Example 78

Synthesis of 3-{acetylamino-[4-(4-acetyl-3-hydroxy-2-propyl-phenoxymethyl)-phenyl]-methyl}-benzoic acid

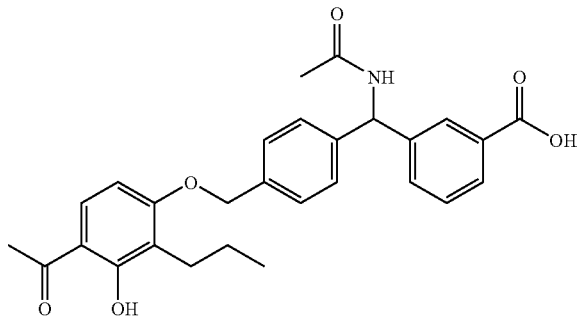

The title compound is prepared in a similar manner to N-{[4-(4-acetyl-3-hydroxy-2-propyl-phenoxymethyl)-phenyl]-[3-(1H-tetrazol-5-yl)-phenyl]-methyl}-acetamide employing 3-{[4-(4-Acetyl-3-hydroxy-2-propyl-phenoxymethyl)-phenyl]-amino-methyl}-benzoic acid to give a white solid (48%). $^1$H NMR (DMSO-$d_6$) δ 13.01 (bs, 1H), 12.86 (s, 1H), 8.89 (d, 1H), 7.80-7.88 (m, 3H), 7.37-7.57 (m, 6H), 6.72 (d, 1H), 6.20 (d, 1H), 5.25 (s, 2H), 2.57-2.62 (m, 5H), 1.95 (s, 3H), 1.46-1.53 (m, 2H), 0.88 (t, 3H). LCMS M+1 476.

General Method 1

General Procedure for the Chromatographic Separation of a Racemic Mixture into Individual Enantiomers The appropriate racemic compound such as 1-[2-hydroxy-4-(4-{hydroxy-[3-(1H-tetrazol-5-yl)-phenyl]-methyl}-benzyloxy)-3-methyl-phenyl]-propan-1-one (56 mg, 0.126 mmol) is dissolved in a solution of acetone, tetrahydrofuran, and isopropyl alcohol. The solution is concentrated to an oil and diluted with isopropyl alcohol (1 mL). The solution is separated via chiral chromatography in two injections utilizing a Chiralcel OD, 2×25 cm column eluting isochratically with 3:1 heptane:isopropyl alcohol at a flow rate of 14 mL/min, to afford 27 mg of the first eluting fraction, designated isomer 1 (Example 79, 100% ee) and 25 mg of the second eluting fraction, designated isomer 2 (Example 80, 95% ee).

The following examples are prepared essentially as described in General Method 1. In Examples 83 and 84, the stereochemistry provided is a correction of the priority document representation.

| Example No. | Chemical Name | Structure | Physical Data |
|---|---|---|---|
| 79 | 1-[2-Hydroxy-4-(4-{hydroxy-[3-(1H-tetrazol-5-yl)-phenyl]-methyl}-benzyloxy)-3-methyl-phenyl]-propan-1-one isomer 1 | 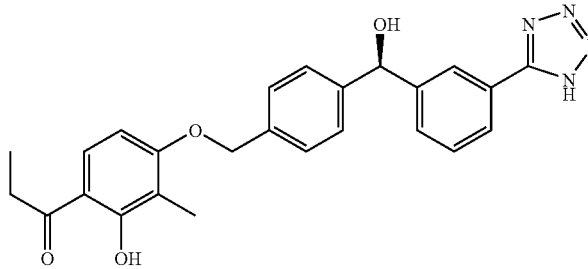 | 100% e.e. ES MS 443 M − 1. |
| 80 | 1-[2-Hydroxy-4-(4-{hydroxy-[3-(1H-tetrazol-5-yl)-phenyl]-methyl}-benzyloxy)-3-methyl-phenyl]-propan-1-one isomer 2 | 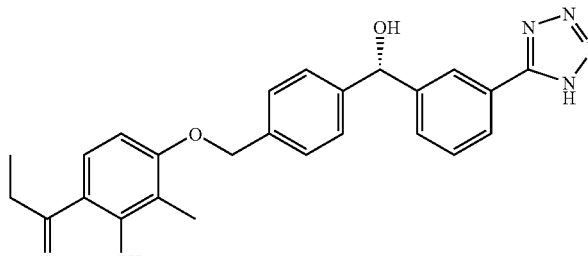 | 95% e.e. ES MS 443 M − 1. |
| 81 | 1-[4-(4-{Fluoro-[3-(1H-tetrazol-5-yl)-phenyl]-methyl}-benzyloxy)-2-hydroxy-3-propyl-phenyl]-ethanone isomer 1 | 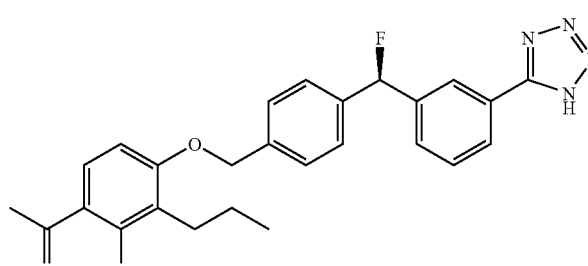 | 100% e.e. ES MS 459 M − 1. |

-continued

| Example No. | Chemical Name | Structure | Physical Data |
|---|---|---|---|
| 82 | 1-[4-(4-{Fluoro-[3-(1H-tetrazol-5-yl)-phenyl]-methyl}-benzyloxy)-2-hydroxy-3-propyl-phenyl]-ethanone isomer 2 | 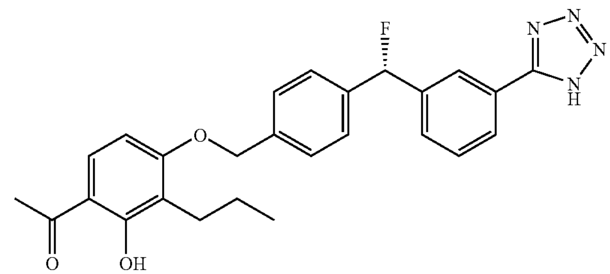 | 95.5% e.e. ES MS 459 M − 1. |
| 83 | (+)-3-{[4-(4-Acetyl-3-hydroxy-2-propyl-phenoxymethyl)-phenyl]-hydroxy-methyl}-benzoic acid isomer 1 | 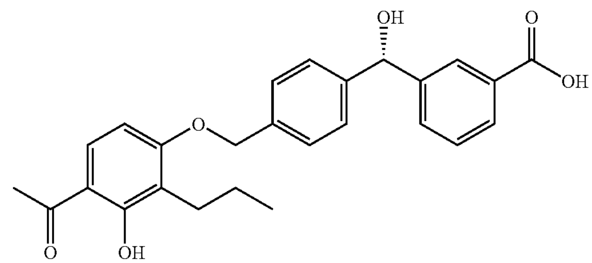 | 100% e.e. ES MS 433 M − 1. $[\alpha]_D^{20} = +12.6°$ (C = 1.0, DMSO) |
| 84 | (−)-3-{[4-(4-Acetyl-3-hydroxy-2-propyl-phenoxymethyl)-phenyl]-hydroxy-methyl}-benzoic acid isomer 2 | 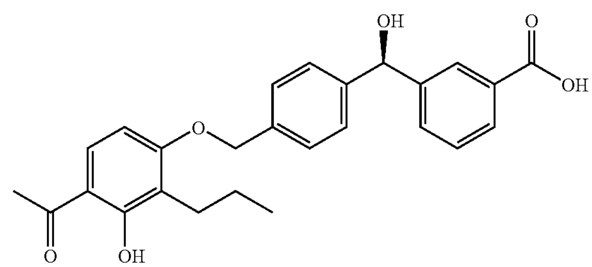 | 100% e.e. ES MS (m/z) (m ± 1) 433. $[\alpha]_D^{20} = -11.4°$ (C = 1.0, DMSO) |

Example 85

Synthesis of sodium 3-{[4-(4-acetyl-3-hydroxy-2-propyl-phenoxymethyl)-phenyl]-hydroxy-methyl}-benzoate

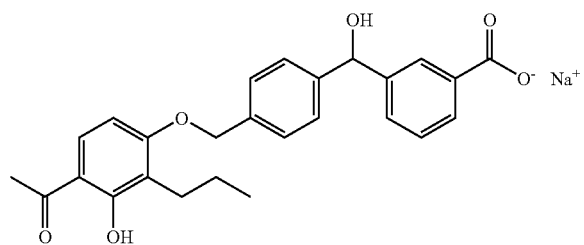

Compound 3-{[4-(4-Acetyl-3-hydroxy-2-propyl-phenoxymethyl)-phenyl]-hydroxy-methyl}-benzoic acid (357 mg, 0.822 mmol) is stirred in a solution of ethyl acetate (4 mL) and tetrahydrofuran (4 mL) at room temperature. A solution of sodium 2-ethylhexanoate (150 mg, 0.904 mmol) in ethyl acetate (2 mL) is added and the reaction is stirred overnight. The reaction is concentrated and the resulting thick oil is diluted with ether (5 mL) and stirred vigorously. The resulting white precipitate is filtered, and dried under vacuum to give the title compound as a white solid (94%). $^1$H NMR (DMSO-d$_6$) δ 12.85 (s, 1H), 7.86 (s, 1H), 7.81 (d, 1H), 7.69 (d, 1H), 7.38-7.39 (m, 4H), 7.33 (d, 1H), 7.19 (t, 1H), 6.72 (d, 1H), 5.84 (d, 1H), 5.70 (d, 1H), 5.22 (s, 2H), 2.57-2.62 (m, 5H), 1.46-1.53 (m, 2H), 0.88 (t, 3H). LCMS M−1 433 (parent acid).

Preparation 98

Synthesis of 1-(2,6-dihydroxy-biphenyl-3-yl)-ethanone

To a solution of 1-(2,4-dihydroxy-3-iodo-phenyl)-ethanone (1.0 g, 3.59 mmol; 581938, may be prepared as described in G. Batu and R. Stevenson, *J. Org. Chem.* 1979, 44, 3948) in tetrahydrofuran/water (15 mL/3 mL) at room temperature is added phenyl boronic acid (0.877 g, 7.19 mmol), Pd(dppf)$_2$Cl$_2$ (0.088 g, 0.107 mmol), and cesium hydroxide monohydrate (1.81 g, 10.8 mmol). After stirring for 15 hours, the mixture is filtered through a pad of Celite®, washing with ethyl acetate. The residue is diluted with 30 mL of 1N hydrochloric acid and extracted with ethyl acetate. The combined organic phases are washed with brine; dried over magnesium sulfate; filtered and concentrated under reduced pressure. The resulting residue is purified by flash chromatography, eluting with 30% ethyl acetate/hexanes to give the title compound as a colorless solid: MS (m/z) 228 (M+); $^1$H NMR (DMSO-d$_6$) δ 13.1 (s, 1H), 10.6 (bs, 1H), 7.81 (d, J=8.8 Hz, 1H), 7.41-7.28 (m, 5H), 6.61 (d, J=8.8 Hz, 1H), 2.58 (s, 3H); R$_f$=0.58 in 40% ethyl acetate/hexanes.

The following compounds are prepared essentially as described in Preparation 98.

| Prep. No. | Chemical name | Structure | Physical data |
|---|---|---|---|
| 99 | 1-(2,4-Dihydroxy-3-thiophen-3-yl-phenyl)-ethanone | 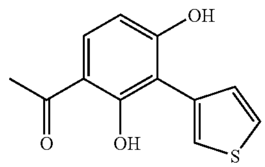 | MS (m/e): 235 (M + 1) |
| 100 | 1-(2,4-Dihydroxy-3-thiophen-2-yl-phenyl)-ethanone | 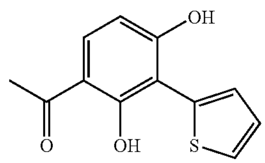 | MS (m/e): 235 (M + 1) |
| 101 | 1-(4'-Fluoro-2,6-dihydroxy-biphenyl-3-yl)-ethanone | 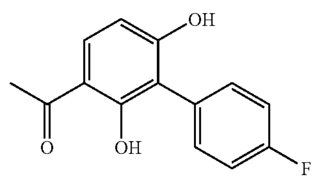 | MS (m/e): 247 (M + 1) |
| 102 | 1-(2,4-Dihydroxy-3-pyridin-2-yl-phenyl)-ethanone | 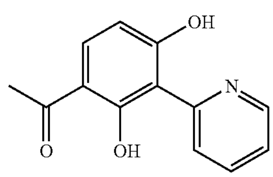 | MS (m/e): 230 (M + 1) |

Preparation 103

Synthesis of 3-[[4-(5-acetyl-6-hydroxy-biphenyl-2-yloxymethyl)-phenyl]-(hydroxy-methyl]-benzonitrile To a solution of 1-(2,6-dihydroxy-biphenyl-3-yl)-ethanone (446 mg, 1.95 mmol) and 3-[(4-iodomethyl-phenyl)-(tetrahydro-pyran-2-yloxy)-methyl]-benzonitrile (848 mg, 1.95 mmol) in acetone (50 mL) is added potassium carbonate (450 mg, 3.25 mmol). The suspension is heated at 50° C. for 14 hours. After cooling to room temperature, the mixture is poured onto saturated ammonium chloride (15 mL) and extracted with ethyl acetate (4×20 mL). The combined organic extracts are combined; washed with brine; dried over magnesium sulfate; filtered and concentrated under reduced pressure to a light-yellow oil: MS (m/z): 523 (M+). The residue is then dissolved in methanol and p-toluenesulfonic acid monohydrate is added. After 1 hour, the solvent is removed under reduced pressure. The resulting residue is purified by flash chromatography (20% to 45% ethyl acetate/hexanes) to give the title compound as a foam: MS (m/z): 449 (M+), 432 (M−OH).

Preparation 104

Synthesis of 3-[4-(5-acetyl-6-hydroxy-biphenyl-2-yloxymethyl)-benzoyl]-benzonitrile To a solution of 3-[[4-(5-acetyl-6-hydroxy-biphenyl-2-yloxymethyl)-phenyl]-(hydroxy-methyl]-benzonitrile (100 mg, 0.22 mmol) in dichloromethane (10 mL) is added Dess-Martin periodinane (113.5 mg, 0.266 mmol) and potassium carbonate (33.8 mg). After five minutes, the mixture is directly loaded onto a silica cartridge. Purification by flash chromatography (linear gradient from hexanes to 50% ethyl acetate/hexanes) gives the title compound as a white solid (98% yield): $^1$H NMR (CDCl$_3$) δ 12.8 (2, 1H), 8.02-7.98 (m, 2H), 7.87-7.84 (m, 1H), 7.76-7.70 (m, 3H), 7.64-7.60 (m, 1H), 7.48-7.33 (m, 7H), 6.58 (d, J=8.8 Hz, 1H), 5.22 (s, 2H), 2.59 (2, 3H); R$_f$=0.29 in 40% ethyl acetate/hexanes.

Preparation 105

Synthesis of 1-(2-hydroxy-6-{4-[3-(2H-tetrazol-5-yl)-benzoyl]-benzyloxy}-biphenyl-3-yl)-ethanone To a −10° C. solution of 3-[[4-(5-acetyl-6-hydroxy-biphenyl-2-yloxymethyl)-phenyl]-(hydroxymethyl]-benzonitrile (100 mg, 0.22 mmol) in dichloromethane (10 mL) is added triethylsilane (2.0 equiv.) and BF$_3$.Et$_2$O (2.0 equiv). After 30 minutes, an additional 2 equivalents of each reagent is added. The reaction is complete within 1 hour. The mixture is quenched with 3 mL of 1N NaOH and extracted with ethyl acetate. The combined organic extracts are washed with brine; dried over magnesium sulfate; filtered, and concentrated to dryness. The resulting residue is purified by flash chromatography (15% to 35% ethyl acetate/hexanes) to give the title compound as a colorless solid: $^1$H NMR (CDCl$_3$) δ 12.8 (2, 1H), 7.72 (d, J=9.2 Hz, 1H), 7.50-7.32 (m, 8H), 7.19-7.08 (m, 4H), 6.58 (d, J=9.2 Hz, 1H), 5.12 (s, 2H), 3.97 (s, 2H), 2.59 (s, 3H).

Example 86

Synthesis of 1-[2-hydroxy-6-(4-{hydroxy-[3-(2H-tetrazol-5-yl)-phenyl]-methyl}-benzyloxy)-biphenyl-3-yl]-ethanone

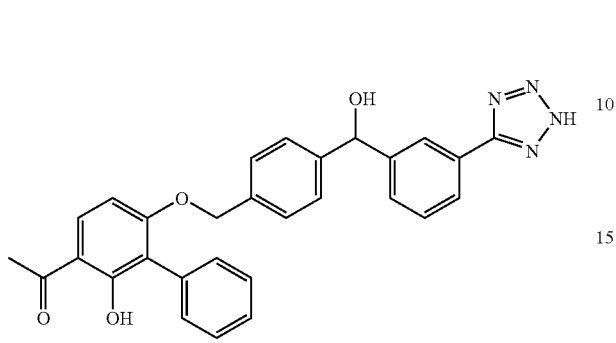

To a solution of 3-[[4-(5-acetyl-6-hydroxy-biphenyl-2-yloxymethyl)-phenyl]-(hydroxymethyl]-benzonitrile 185 (230 mg, 0.430 mmol) in iso-propanol/water (9 mL, 2/1) is added sodium azide (4.0 equiv.) and zinc bromide (2.0 equiv.). The solution is then heated at 110° C. for 2.5 days. After cooling to room temperature, 5 mL of 1N hydrochloric acid is added and the mixture is extracted with ethyl acetate (5×20 mL). The combined organic extracts are combined, washed with brine; dried over magnesium sulfate; filtered, and concentrated under reduced pressure to dryness. The resulting residue is purified by flash chromatography (linear gradient from dichloromethane to 9/1/0/0.2 dichloromethane/ACN/AcOH) to give the title compound as a white residue: MS (m/z): 492 (M+); $^1$H NMR (acetone-$d_6$) δ 12.9 (s, 1H), 8.21 (s, 1H), 8.00-7.96 (m, 1H), 7.90 (d, J=8.8 Hz, 1H), 7.62-7.50 (m, 5H), 7.29-7.25 (m, 4H), 6.79 (d, J=8.8 Hz, 1H), 5.93 (s, 1H), 5.18 (s, 2H), 2.60 (s, 3H).

Example 87

Synthesis of 1-[4'-fluoro-2-hydroxy-6-(4-{hydroxy-[3-(2H-tetrazol-5-yl)-phenyl]-methyl}-benzyloxy)-biphenyl-3-yl]-ethanone

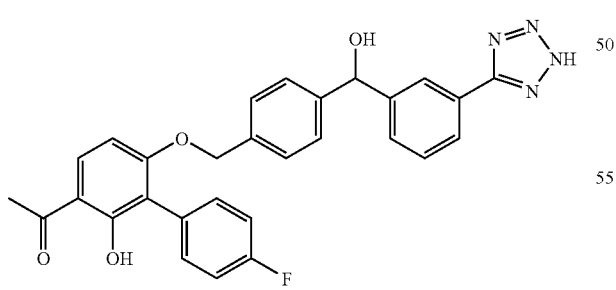

The title compound is prepared essentially as described above for Example 86 using the corresponding benzonitrile: MS (m/z): 509 (M−1); $^1$H NMR (DMSO-$d_6$) δ 12.8 (bs, 1H), 8.07 (s, 1H), 7.93 (d, J=8.8 Hz, 1H), 7.85-7.82 (m, 1H), 7.53-7.15 (m, 10H), 6.79 (d, J=9.6 Hz, 1H), 6.07 (bs, 1H), 5.77 (s, 1H), 5.16 (s, 2H), 2.59 (s, 3H).

Example 88

Synthesis of 1-(2-hydroxy-6-{4-[3-(2H-tetrazol-5-yl)-benzoyl]-benzyloxy}-biphenyl-3-yl)-ethanone

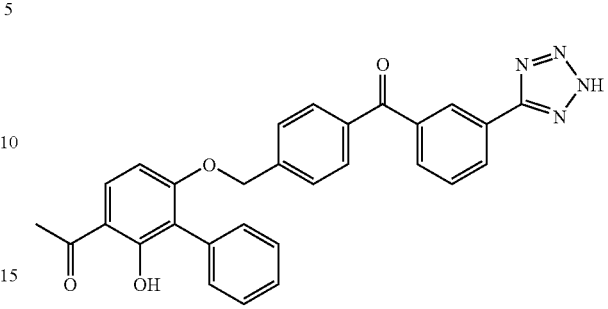

The title compound is prepared essentially as described for Example 86 using 3-[4-(5-Acetyl-6-hydroxy-biphenyl-2-yloxymethyl)-benzoyl]-benzonitrile: MS (m/z): 489 (M−1); $^1$H NMR (DMSO-$d_6$) δ 12.8 (s, 1H), 8.34-8.30 (m, 2H), 7.97 (d, J=8.8 Hz, 1H), 7.88-7.73 (m, 4H), 7.46-7.27 (m, 7H), 6.83 (d, J=8.8 Hz, 1H), 5.35 (s, 2H), 2.61 (s, 3H).

Example 89

Synthesis of 1-(2-hydroxy-6-{4-[3-(2H-tetrazol-5-yl)-benzyl]-benzyloxy}-biphenyl-3-yl)-ethanone

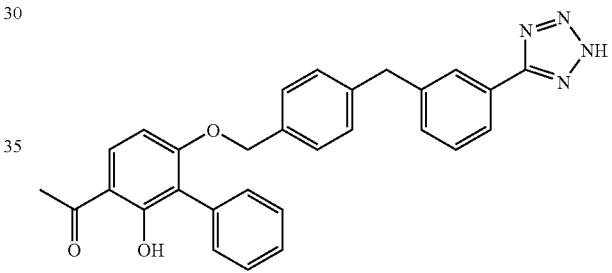

The title compound may be prepared essentially as described for Example 61 using 1-(2-hydroxy-6-{4-[3-(2H-tetrazol-5-yl)-benzoyl]-benzyloxy}-biphenyl-3-yl)-ethanone of preparation 187: MS (m/z): 475 (M−1).

Example 90

Synthesis of 1-(4'-fluoro-2-hydroxy-6-{4-[3-(2H-tetrazol-5-yl)-benzyl]-benzyloxy}-biphenyl-3-yl)-ethanone

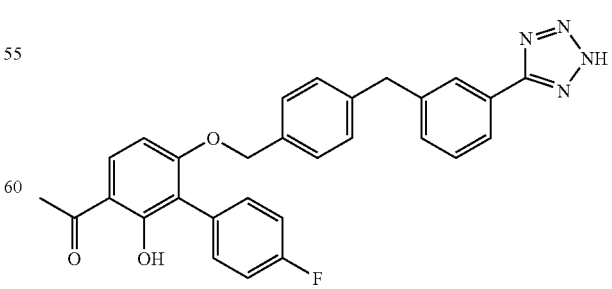

The title compound may be prepared essentially as described above for Example 61 using the corresponding hydroxyl compound of Example 87: MS (m/z): 495 (M+1); $^1$H NMR (DMSO-$d_6$) δ 12.8 (s, 1H), 7.93 (d, J=8.8 Hz, 1H), 7.90-7.81 (m, 2H), 7.51-7.41 (m, 2H), 7.35-7.29 (m, 2H), 7.24-7.14 (m, 6H0, 6.80 (d, J=9.6 Hz, 1H), 5.33 (s, 2H), 4.00 (s, 1H), 2.58 (s, 3H).

Example 91

Synthesis of 3-{3-[[4-(4-acetyl-3-hydroxy-2-propyl-phenoxymethyl)-phenyl]-(tetrahydro-pyran-2-yloxy)-methyl]-phenyl}-4H-[1,2,4]oxadiazol-5-one

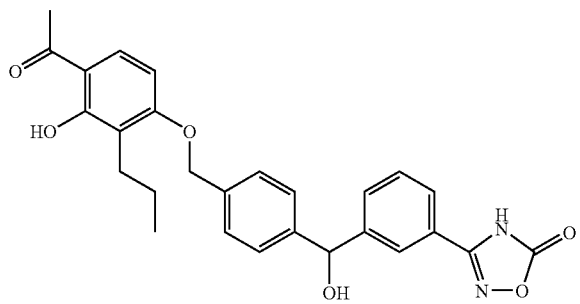

Add hydroxylamine (50% solution in water, 0.128 mL, 2.09 mmol) to a solution of 3-[[4-(4-acetyl-3-hydroxy-2-propyl-phenoxymethyl)-phenyl]-(tetrahydro-pyran-2-yloxy)-methyl]-benzonitrile (950 mg, 1.90 mmol) in ethanol (20 mL) and stir. Heat the solution to reflux for 3 hours. Cool the reaction to ambient temperature and concentrate to dryness. Dissolve the resulting residue in tetrahydrofuran (20 mL) and cool to 0° C. Add pyridine (226 mg, 2.85 mmol) and 2-ethylhexyl chloroformate (403 mg, 2.09 mmol) and stir. After 30 minutes, add water (50 mL) and extract with ethyl acetate. Combine the organic extracts, dry with sodium sulfate, filter and concentrate to dryness. Dissolve the resulting residue in xylenes (20 mL) and heat to 130° C. After 4 hours, cool to ambient temperature and concentrate under reduced pressure to dryness. Purify the resulting residue by flash chromatography eluting with acetone:acetic acid:hexanes (25%:1%:74%) to give a white solid. Dissolve the solid in a solution of 1% aqueous hydrochloric acid:methanol, and stir. After 1 hour, concentrate under reduced pressure to dryness. Purify the resulting residue by reverse phase chromatography eluting with methanol:acetic acid:water to yield the title compound as a white solid (22 mg, 2.4%): $^1$H NMR (DMSO-$d_6$) δ 0.86 (t, 3H), 1.48 (sextet, 2H), 2.56 (m, 5H), 5.21 (s, 2H), 5.79 (d, 1H), 6.11 (d, 1H), 6.70 (d, 1H), 7.41 (m, 4H), 7.49 (t, 1H), 7.63 (m, 2H), 7.79 (d, 1H), 7.89 (s, 1H), 12.83 (s, 1H), 12.96 (bs, 1H); MS (esi negative) m/z (rel intensity) 473 (100).

Preparation 106

Synthesis of 1-[4-(4-bromomethyl-benzyloxy)-3-chloro-2-hydroxy-phenyl]-ethanone

Combine 1-(3-chloro-2,4-dihydroxy-phenyl)-ethanone (6.00 g, 32.2 mmol) and 1,4-bis-bromomethyl-benzene (8.48 g, 31.2 mmol) and potassium carbonate (4.44 g, 32.2 mmol) in acetone (400 ml) and heat to reflux. After 1 h, cool to room temperature and add 10% hydrochloric acid (300 mL). Filter to collect and triturate resultant solid in 1:1 ether/hexanes. Purify by column chromatography, eluting with 40% tetrahydrofuran/hexanes to obtain 1-[4-(4-bromomethyl-benzyloxy)-3-chloro-2-hydroxy-phenyl]-ethanone (3.00 g, 8.12 mmol) as a white solid. MS (m/z): 368.9 (M−1).

Preparation 107

Synthesis of 1-(3-bromo-phenyl)-3-dimethylamino-propenone

Combine 1-(3-bromo-phenyl)-ethanone (10 g, 50.2 mmol) and dimethylformamide dimethylacetal (60 g, 502 mmol) in a sealed tube, heat to 150° C. for 12 hours. Cool the solution and evaporate the excess dimethylformamide dimethylacetal. Purify residue by column chromatography to obtain the title compound (3.05 g, 12.0 mmol) as a white solid. MS (m/z): 254.1 (M).

Preparation 108

Synthesis of 4-(3-bromo-phenyl)-pyrimidin-2-ol

Combine 1-(3-bromo-phenyl)-3-dimethylamino-propenone (3.00 g, 11.8 mmol), urea (544 mg, 11.8 mmol), sodium ethoxide (4.00 g, 21% wt in ethanol) and ethanol (24 mL) and heat to 150° C. in sealed tube overnight. Cool to room temperature and pour into 1% hydrochloric acid (50 mL). Collect white solid by filtration to obtain 4-(3-bromo-phenyl)-pyrimidin-2-ol (2.60 g, 10.4 mmol). MS (m/z): 251.2 (M+1).

Preparation 109

Synthesis of 4-[3-(5,5-dimethyl-[1,3,2]dioxaborinan-2-yl)-phenyl]-pyrimidin-2-ol Combine 4-(3-bromo-phenyl)-pyrimidin-2-ol (1.50 g, 5.97 mmol), bis(neopentyl glycolato)diboron (1.62 g, 7.17 mmol), Pd(dppf)Cl$_2$ (505 mg, 0.597 mmol) and potassium acetate (1.76 g, 17.9 mmol) in a purged (N2) flask, add dry DMSO (50 mL) and plunge into a 80° C. bath. Heat overnight, then pour into 1% hydrochloric acid (100 mL). Neutralize with sodium bicarbonate, and extract with ethyl acetate, dry, filter and condense to afford 4-[3-(5,5-dimethyl-[1,3,2]dioxaborinan-2-yl)-phenyl]-pyrimidin-2-ol (300 mg) as a brown solid. MS (m/z): 173.1 (M−$C_5H_{10}BO_2$+1).

Example 92

Synthesis of 1-(3-chloro-2-hydroxy-4-{4-[3-(2-hydroxy-pyrimidin-4-yl)-benzyl]-benzyloxy}-phenyl)-ethanone

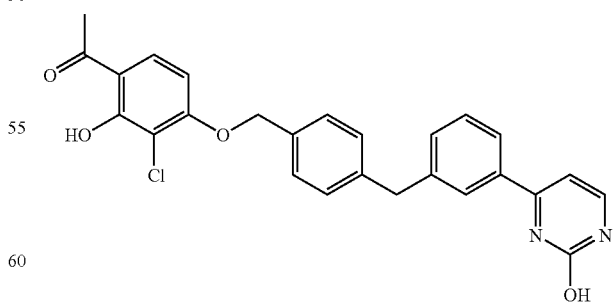

Prepare a solution of 1-[4-(4-bromomethyl-benzyloxy)-3-chloro-2-hydroxy-phenyl]-ethanone (402 mg, 1.06 mmol) and boronic ester (300 mg, 1.05 mmol) in aqueous sodium carbonate (2 M, 3 mL) and DME (10 ml). Treat with tetrakis(triphenylphosphine)palladium(0) (61 mg, 0.05 mmol) and degas five times (house vacuum/nitrogen). Heat the light yellow partition to 70° C., at which time it turns from yellow to black. Cool the mixture to rt, then dilute with water and ethyl acetate. Separate the layers and extract the aqueous layer with ethyl acetate. Combine the organic layers and wash with brine, dry (MgSO$_4$), filter, and concentrate in vacuo to afford a solid residue. Purify the residue by reverse phase HPLC (C-18 column) eluting with a 15 to 85% acetonitrile/water gradient to afford 1-(3-chloro-2-hydroxy-4-{4-[3-(2-hydroxy-pyrimidin-4-yl)-benzyl]-benzyloxy}-phenyl)-ethanone (5 mg, 0.01 mmol) as a white solid: $^1$H NMR (DMSO-d$_6$) δ 2.60 (s, 3H), 5.10 (s, 2H), 5.34 (s, 2H), 6.86 (d, 1H), 7.12 (d, 1H), 7.40 (d, 2H), 7.46 (d, 2H), 7.55 (m, 3H), 7.92 (d, 1H), 8.12 (d, 2H), 8.45 (d, 1H), 13.12 (s, 1H); MS (m/z): 459.1 (M−1).

Preparation 110

Synthesis of 4-(3-bromo-phenyl)-pyrimidin-2-ylamine

Combine 1-(3-bromo-phenyl)-3-dimethylamino-propanone (3.00 g, 11.8 mmol) and guanidinium chloride (1.12 g, 11.8 mmol), sodium ethoxide (5 mL, 21% wt solution in ethanol), absolute EtOH (24 mL) and heat to reflux overnight. Cool to room temperature and pour into 1% hydrochloric acid (200 mL). Extract with ethyl acetate, dry over sodium sulfate and condense to afford 4-(3-bromo-phenyl)-pyrimidin-2-ylamine (930 mg, 3.72 mmol) as a white solid. MS (m/z): 250.2 (M).

Preparation 111

Synthesis of 4-[3-(5,5-dimethyl-[1,3,2]dioxaborinan-2-yl)-phenyl]-pyrimidin-2-ylamine The title compound is prepared essentially as described for Preparation 109 using 4-(3-bromo-phenyl)-pyrimidin-2-ylamine (2.00 g, 8.00 mmol). The title compound is isolated (1.71 g, 6.04 mmol) as a brown solid. MS (m/z): 216.2 (M−C$_5$H$_8$+1).

Example 93

Synthesis of 1-(4-{4-[3-(2-amino-pyrimidin-4-yl)-benzyl]-benzyloxy}-3-chloro-2-hydroxy-phenyl)-ethanone

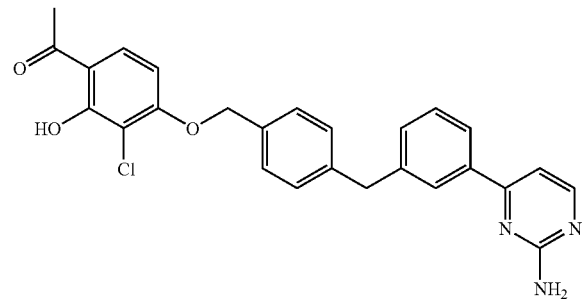

The title compound is prepared essentially as described in Example 92 using 4-[3-(5,5-dimethyl-[1,3,2]dioxaborinan-2-yl)-phenyl]-pyrimidin-2-ylamine (327 mg, 1.15 mmol) and 1-[4-(4-bromomethyl-benzyloxy)-3-chloro-2-hydroxy-phenyl]-ethanone (400 mg, 1.08 mmol). The title compound is isolated (109 mg, 0.237 mmol) as a yellow solid: $^1$H NMR (DMSO-d$_6$) δ 2.10 (s, 3H), 4.04 (s, 2H), 5.30 (s, 2H), 6.62 (m, 2H), 6.88 (d, 1H), 7.08 (m, 1H), 7.29 (m, 2H), 7.40 (m, 4H), 7.92 (m, 3H), 8.28 (d, 1H), 13.12 (s, 1H); MS (m/z): 458.2 (M−1).

Preparation 112

Synthesis of 3-[[4-(4-acetyl-2-chloro-3-hydroxy-phenoxymethyl)-phenyl]-(tetrahydro-pyran-2-yloxy)-methyl]-benzonitrile Add diisopropylazodicarboxylate (DIAD, 5.418 g, 26.80 mmol) to a solution of 1-(3-chloro-2,4-dihydroxy-phenyl) ethanone (5.000 g, 26.80 mmol), 3-[(4-hydroxymethyl-phenyl)-(tetrahydro-pyran-2-yloxy)-methyl]-benzonitrile (8.666 g, 26.80 mmol), and triphenylphosphine (7.028 g, 26.80 mmol) in tetrahydrofuran (0.200M) at 0° C. Stir for 2 hours while warming to room temperature. Add silica gel and evaporate solvent. Chromatograph with Biotage Flash 75, eluting with 50-90% ethyl acetate/hexanes to afford the title compound as a white solid (13.00 g, 26.42 mmol, 98%): MS (m/z): 490 (M−H).

Preparation 113

Synthesis of 3-[[4-(4-acetyl-2-chloro-3-hydroxy-phenoxymethyl)-phenyl]-(tetrahydro-pyran-2-yloxy)-methyl]-benzoic acid Heat a solution of 3-[[4-(4-acetyl-2-chloro-3-hydroxy-phenoxymethyl)-phenyl]-(tetrahydro-pyran-2-yloxy)-methyl]-benzonitrile (10.00 g, 20.33 mmol) and potassium hydroxide (22.81 g, 406.5 mmol) in ethanol (100 mL) and water (25 mL) at reflux for 3 days. Evaporate volatiles and acidify with 1N hydrochloric acid and extract with CH$_2$Cl$_2$ (3×). Combine organic layers, dry (sodium sulfatesodium sulfate) and evaporate to afford the title compound as a white solid (10.00 g, 19.57 mmol, 96%): MS (m/z): 510 (M−H).

Example 94

Synthesis of 3-{[4-(4-acetyl-2-chloro-3-hydroxy-phenoxymethyl)-phenyl]-hydroxy-methyl}-benzoic acid

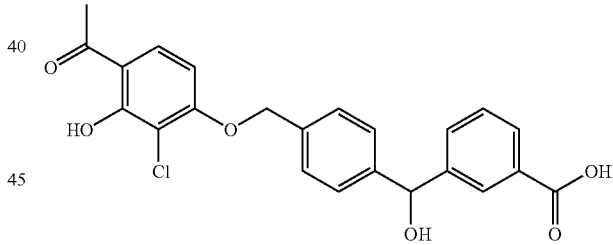

Add p-toluenesulfonic acid (16.8 mg, 0.098 mmol) to a solution of 3-[[4-(4-acetyl-2-chloro-3-hydroxy-phenoxymethyl)-phenyl]-(tetrahydro-pyran-2-yloxy)-methyl]-benzoic acid (1.00 g, 1.96 mmol) in methanol (0.20M) and stir overnight. Evaporate solvents, dilute with ethyl acetate and wash with water (1×) and brine (1×). Dry and concentrate to afford the title compound as a white solid (0.786 mg, 1.84 mmol, 94%): MS (m/z): 426 (M−H).

Preparation 114

Synthesis of 1-(3-{[4-(4-acetyl-2-chloro-3-hydroxy-phenoxymethyl)-phenyl]-hydroxy-methyl}-phenyl)-2-chloro-ethanone Add oxalyl chloride (256 mg, 2.02 mmol) to a solution of 3-{[4-(4-acetyl-2-chloro-3-hydroxy-phenoxymethyl)-phenyl]-hydroxy-methyl}-benzoic acid (0.786 mg, 1.84 mmol) in tetrahydrofuran (0.20M). Add dimethylformamide (5 drops). Add ethereal solution of diazomethane (1.90 mmol)

and stir for 2 hours. Add hydrochloric acid (4N in dioxane) to quench unreacted diazomethane and evaporate solvents to afford the title compound (0.786 mg, 1.84 mmol, 94%): MS (m/z): 457 (M−H).

Example 95

Synthesis of 4-(3-{[4-(4-acetyl-2-chloro-3-hydroxy-phenoxymethyl)-phenyl]-hydroxy-methyl}-phenyl)-3H-thiazol-2-one

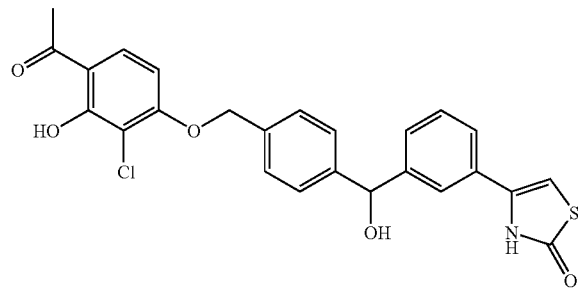

Heat a solution of 1-(3-{[4-(4-acetyl-2-chloro-3-hydroxy-phenoxymethyl)-phenyl]-hydroxy-methyl}-phenyl)-2-chloro-ethanone (0.075 mg, 0.163 mmol) and potassium thiocyanate (159 mg, 1.63 mmol) in ethanol (0.20M) overnight at 70° C. Evaporate solvents and chromatograph residue. Major fraction isolated was the title compound (0.005 g, 0.010 mmol, 6.1%): $^1$H NMR (400 MHz, DMSO-$d_6$) δ 2.61 (s, 3H), 5.10 (s, 2H), 5.30 (s, 2H), 5.82 (s, 1H), 6.11 (s, 1H), 6.88 (d, J=9.8 Hz, 1H), 7.41 (m, 4H), 7.49 (m, 1H), 7.71 (d, J=7.4 Hz, 1H), 7.87 (d, J=7.8 Hz, 1H), 7.92 (d, J=9.4 Hz, 1H), 8.04 (s, 1H), 13.12 (s, 1H). MS (m/z): 480 (M−H).

Preparation 115

Synthesis of 3-[[4-(3-hydroxy-2-methyl-4-propionyl-phenoxymethyl)-phenyl]-(tetrahydro-pyran-2-yloxy)-methyl]-benzonitrile The title compound is prepared essentially as described in Preparation 112 employing 1-(2,4-dihydroxy-3-methyl-phenyl)-propan-1-one (5.00 g, 27.7 mmol). The title compound is isolated as a white powder (10.0 g, 20.5 mmol, 74%). MS (m/z): 484 (M−H).

Preparation 116

Synthesis of 3-[[4-(3-hydroxy-2-methyl-4-propionyl-phenoxymethyl)-phenyl]-(tetrahydro-pyran-2-yloxy)-methyl]-benzoic acid The title compound is prepared essentially as described in Preparation 113 employing 3-[[4-(3-hydroxy-2-methyl-4-propionyl-phenoxymethyl)-phenyl]-(tetrahydro-pyran-2-yloxy)-methyl]-benzonitrile (5.00 g, 10.3 mmol) and potassium hydroxide (11.6 g, 206 mmol) in ethanol (100 mL) and water (25 mL) at reflux for 3 days. Concentrate the reaction mixture and acidify with 1N hydrochloric acid, then extract with dichloromethane (3×). Combine organic layers, dry (sodium sulfatesodium sulfate) and evaporate to afford the title compound as a white solid (2.11 g, 4.18 mmol, 40%): MS (m/z): 503 (M−H).

Preparation 117

Synthesis of 1-(4-{4-[[3-(2-chloro-acetyl)-phenyl]-(tetrahydro-pyran-2-yloxy)-methyl]-benzyloxy}-2-hydroxy-3-methyl-phenyl)-propan-1-one Add oxalyl chloride (0.660 mg, 5.20 mmol) to a solution of 3-[[4-(3-hydroxy-2-methyl-4-propionyl-phenoxymethyl)-phenyl]-(tetrahydro-pyran-2-yloxy)-methyl]-benzoic acid (2.50 g, 5.00 mmol) in tetrahydrofuran (0.20M). Add dimethylformamide (5 drops). Add ethereal solution of diazomethane (15.0 mmol) and stir for 2 hours. Add hydrochloric acid (4N in dioxane) to quench unreacted diazomethane and evaporate solvents to afford the title compound (2.25 g, 4.19 mmol, 85%): MS (m/z): 536 (M−H).

Example 96

Synthesis of 4-(3-{hydroxy-[4-(3-hydroxy-2-methyl-4-propionyl-phenoxymethyl)-phenyl]-methyl}-phenyl)-3H-thiazol-2-one

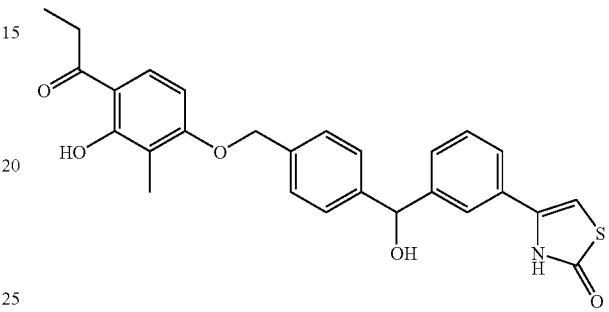

Heat a solution of 1-(4-{4-[[3-(2-chloro-acetyl)-phenyl]-(tetrahydro-pyran-2-yloxy)-methyl]-benzyloxy}-2-hydroxy-3-methyl-phenyl)-propan-1-one (0.250 mg, 0.466 mmol) and potassium thiocyanate (90.5 mg, 0.931 mmol) in ethanol (0.20 M) overnight at 70° C. Add p-toluenesulfonic acid (10 mg) and stir overnight. Evaporate solvents and chromatograph residue. Major fraction isolated was the title compound (0.086 g, 0.179 mmol, 39%): $^1$H NMR (400 MHz, DMSO-$d_6$) δ 1.09 (t, J=7.2 Hz, 3H), 2.02 (s, 3H), 3.03 (q, J=9.6 Hz, 2H), 5.10 (s, 2H), 5.20 (s, 2H), 5.82 (d, J=3.9 Hz, 1H), 6.11 (d, J=3.9 Hz, 1H), 6.70 (d, J=9.0 Hz, 1H), 7.42 (q, J=11.2 Hz, 4H), 7.51 (t, J=7.8 Hz, 1H), 7.71 (d, J=7.8 Hz, 1H), 7.81 (d, J=9.0 Hz, 1H), 7.87 (d, J=8.2 Hz, 1H), 8.04 (s, 1H), 12.88 (s, 1H). MS (m/z): 474 (M−H).

Example 97

Synthesis of 1-[4-(4-{[3-(2-amino-thiazol-4-yl)-phenyl]-hydroxy-methyl}-benzyloxy)-2-hydroxy-3-methyl-phenyl]-propan-1-one

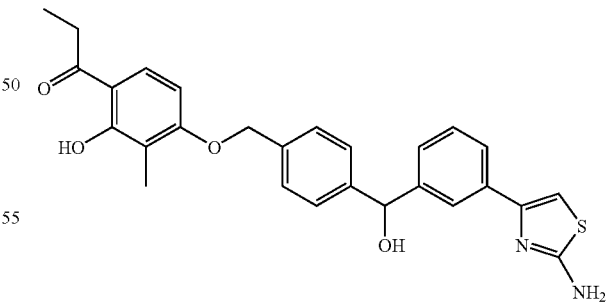

Heat a solution of 1-(4-{4-[[3-(2-chloro-acetyl)-phenyl]-(tetrahydro-pyran-2-yloxy)-methyl]-benzyloxy}-2-hydroxy-3-methyl-phenyl)-propan-1-one (0.250 mg, 0.466 mmol) and thiourea (71 mg, 0.931 mmol) in ethanol (0.20 M) overnight at 70° C. Add p-toluenesulfonic acid (10 mg) and stir overnight. Evaporate solvents and chromatograph residue. Major fraction isolated was the title compound (0.115 g, 0.243 mmol, 52%): $^1$H NMR (400 MHz, DMSO-$d_6$) δ 1.09 (t, J=10.5 Hz, 3H), 2.02 (s, 3H), 3.03 (q, J=14.4 Hz, 2H), 5.20 (s, 2H), 5.75 (s, 1H), 6.70 (d, J=9.0 Hz, 1H), 7.14 (s, 1H), 7.37 (d, J=6.43 Hz, 1H), 7.42 (m, 6H), 7.60 (m, 1H), 7.80 (m, 2H), 12.89 (s, 1H). MS (m/z): 473 (M−H).

Preparation 118

Synthesis of 3-[[4-(4-acetyl-3-hydroxy-2-methyl-phenoxymethyl)-phenyl]-(tetrahydro-pyran-2-yloxy)-methyl]-benzonitrile The title compound is prepared essentially as described in Preparation 112 employing 1-(2,4-dihydroxy-3-methyl-phenyl)-ethanone (5.00 g, 30.1 mmol). The title compound is isolated as a white powder (3.20 g, 6.79 mmol, 23%). MS (m/z): 470 (M−H).

Preparation 119

Synthesis of 3-[[4-(4-acetyl-3-hydroxy-2-methyl-phenoxymethyl)-phenyl]-(tetrahydro-pyran-2-yloxy)-methyl]-benzoic acid The title compound is prepared essentially as described in Preparation 113 employing 3-[[4-(4-acetyl-3-hydroxy-2-methyl-phenoxymethyl)-phenyl]-(tetrahydro-pyran-2-yloxy)-methyl]-benzonitrile (3.20 g, 6.79 mmol) and potassium hydroxide (7.62 g, 136 mmol) in ethanol (100 mL) and water (25 mL) at reflux for 3 days. Evaporate volatiles and acidify with 1N hydrochloric acid and extract with three portions of methylene chloride. Combine organic layers, dry (sodium sulfate) and evaporate to afford the title compound as a white solid (1.10 g, 2.24 mmol, 33%): MS (m/z): 490 (M−H).

Preparation 120

Synthesis of 3-[[4-(4-acetyl-3-hydroxy-2-methyl-phenoxymethyl)-phenyl]-(tetrahydro-pyran-2-yloxy)-methyl]-benzoic acid thiosemicarbazide Add oxalyl chloride (0.660 mg, 5.20 mmol) to a solution of 3-[[4-(4-acetyl-3-hydroxy-2-methyl-phenoxymethyl)-phenyl]-(tetrahydro-pyran-2-yloxy)-methyl]-benzoic acid, 1.00 g, 2.04 mmol) in tetrahydrofuran (0.20M). Add dimethylformamide (5 drops). Add pyridine (0.322 g, 4.08 mmol) and thiosemicarbazide (0.223 g, 2.45 mmol). Stir the reaction overnight. Evaporate solvents. Dissolve brown tar in acetone/water. Extract with CH$_2$Cl$_2$ (3×) and ethyl acetate (3×). Combine organic extracts, dry and concentrate to afford the title compound, which was used without further purification (1.20 g, 2.04 mmol, 99%): MS (m/z): 563 (M−H).

Preparation 121

Synthesis of 1-(2-hydroxy-4-{4-[[3-(5-mercapto-4H-[1,2,4]triazol-3-yl)-phenyl]-(tetrahydro-pyran-2-yloxy)-methyl]-benzyloxy}-3-methyl-phenyl)-ethanone Heat a solution of 3-[[4-(4-acetyl-3-hydroxy-2-methyl-phenoxymethyl)-phenyl]-(tetrahydro-pyran-2-yloxy)-methyl]-benzoic acid thiosemicarbazide (1.20 g, 2.04 mmol) and potassium hydroxide (0.228 g, 4.08 mmol) in acetone (5.0 mL) and water (5.0 mL) overnight. Acidify with 2N hydrochloric acid and extract with ethyl acetate (5×). Combine organic layers and wash with brine, dry, and concentrate to afford the title compound which was used without further purification (1.12 g, 2.04 mmol, 99%). MS (m/z): 544 (M−H).

Example 98

Synthesis of 1-[2-hydroxy-4-(4-{hydroxy-[3-(5-mercapto-4H-[1,2,4]triazol-3-yl)-phenyl]-methyl}-benzyloxy)-3-methyl-phenyl]-ethanone

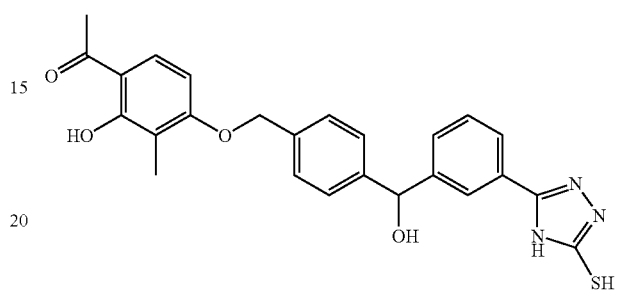

Stir a solution of 1-(2-hydroxy-4-{4-[[3-(5-mercapto-4H-[1,2,4]triazol-3-yl)-phenyl]-(tetrahydro-pyran-2-yloxy)-methyl]-benzyloxy}-3-methyl-phenyl)-ethanone (1.12 g, 2.04 mmol) and p-toluenesulfonic acid (50 mg) in methanol (0.2M). Dilute with ethyl acetate and wash with water. Dry the organic layer and concentrate to afford the title compound (0.250 g, 0.551 mmol, 27% overall from acid chloride). $^1$H NMR (400 MHz, DMSO-d$_6$) δ 2.02 (s, 3H), 2.50 (s, 3H), 5.21 (s, 2H), 5.76 (s, 1H), 6.05 (s, 1H), 6.71 (d, J=9.4 Hz, 1H), 7.39 (m, 6H), 7.53 (m, 1H), 7.73 (m, 1H), 7.78 (d, J=9.0 Hz, 1H), 7.98 (s, 1H), 12.83 (s, 1H). MS (m/z): 460 (M−H).

Example 99

Synthesis of 3-{3-[[4-(4-acetyl-3-hydroxy-2-propyl-phenoxymethyl)-phenyl]-(tetrahydro-pyran-2-yloxy)-methyl]-phenyl}-4H-[1,2,4]oxadiazol-5-one

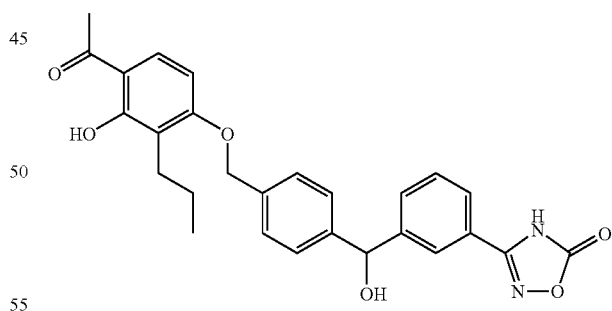

Add hydroxylamine (50% solution in water, 0.128 mL, 2.09 mmol) to a solution of 3-[[4-(4-acetyl-3-hydroxy-2-propyl-phenoxymethyl)-phenyl]-(tetrahydro-pyran-2-yloxy)-methyl]-benzonitrile (950 mg, 1.90 mmol) in ethanol (20 mL) and stir. Heat solution to reflux. After 3 hours, cool to ambient temperature and concentrate to give a residue. Dissolve the residue in tetrahydrofuran (20 mL) and cool to 0° C. Add pyridine (226 mg, 2.85 mmol) and 2-ethylhexyl chloroformate (403 mg, 2.09 mmol) and stir. After 30 minutes, add water (50 mL) and extract with ethyl acetate. Combine the organic layers, dry with sodium sulfate filter and concentrate to give a residue. Dissolve the residue in xylenes (20 mL) and heat to 130° C. After 4 hours, cool to ambient temperature and concentrate under reduced pressure to give a residue. Purify the residue by flash chromatography eluting with acetone:acetic acid:hexanes (25%:1%:74%) to give a white solid. Dissolve the solid in a solution of 1% aqueous hydrochloric acid:methanol, and stir. After 1 hour, concentrate under reduced pressure to give a residue. Purify the residue by reverse phase chromatography eluting with methanol:acetic acid:water to yield the title compound as a white solid (22 mg, 2.4%): $^1$H NMR (DMSO-d$_6$) δ 0.86 (t, 3H), 1.48 (sextet, 2H), 2.56 (m, 5H), 5.21 (s, 2H), 5.79 (d, 1H), 6.11 (d, 1H), 6.70 (d, 1H), 7.41 (m, 4H), 7.49 (t, 1H), 7.63 (m, 2H), 7.79 (d, 1H), 7.89 (s, 1H), 12.83 (s, 1H), 12.96 (bs, 1H); MS (esi negative) m/z (rel intensity) 473 (100).

Preparation 122

Synthesis of 3-(tetrahydro-pyran-2-yloxymethyl)-benzonitrile

Add p-toluene sulphonic acid (2.11 g, 12.2 mmol) to a solution of 3-hydroxymethyl-benzonitrile (16.30 g, 122.4 mmol) and 3,4-dihydro-2H-pyran (51.5 g, 612 mmol) in dichloromethane (500 ml) and stir. After 90 minutes, pour reaction into saturated sodium bicarbonate, remove organics, dry with sodium sulfate, filter and concentrate to give a dark brown oil. Purify the residue by flash chromatography eluting with a gradient of 10-15% ethyl acetate:hexanes to yield the title product as a clear oil (16.20 g, 61%): $^1$H NMR (CDCl$_3$) δ 1.53-1.91 (m, 6H), 3.56 (m, 1H), 3.88 (m, 1H), 4.53 (d, 1H), 4.72 (t, 1H), 4.81 (d, 1H), 7.45 (t, 1H), 7.58 (m, 2H), 7.69 (s, 1H)

Preparation 123

Synthesis of 3-[3-(tetrahydro-pyran-2-yloxymethyl)-phenyl]-4H-[1,2,4]oxadiazol-5-one Add 50% aqueous hydroxylamine (9.73 g, 147 mmol) dropwise to a refluxing solution of 3-(tetrahydro-pyran-2-yloxymethyl)-benzonitrile (8.00 g, 36.8 mmol) in isopropanol (0.1M). After 2 hours, cool to room temperature and concentrate under reduced pressure to give a residue. Dissolve the residue in dioxane (0.1M). Add carbonyldiimidazole (7.16 g, 44.2 mmol) and heat to 110° C. After 30 minutes, cool to room temperature and pour into water. Extract with ethyl acetate. Combine the organic layers, dry with sodium sulfate, filter and concentrate under reduced pressure to yield the title product as a white solid (90.10 g, 89%): $^1$H NMR (CDCl$_3$) δ 1.53-1.95 (m, 6H), 3.59 (m, 1H), 3.93 (m, 1H), 4.58 (d, 1H), 4.77 (t, 1H), 4.88 (d, 1H), 7.52 (t, 1H), 7.57 (d, 1H), 7.71 (d, 1H), 7.82 (s, 1H), 11.16 (bs, 1H)

Preparation 124

Synthesis of 3-(3-hydroxymethyl-phenyl)-4H-[1,2,4]oxadiazol-5-one

Add 10% hydrochloric acid (100 ml) to a solution of 3-[3-(tetrahydro-pyran-2-yloxymethyl)-phenyl]-4H-[1,2,4]oxadiazol-5-one (4.50 g, 16.3 mmol) in tetrahydrofuran (0.1M) and stir. After 18 hours, pour reaction into brine and extract with ethyl acetate. Combine the organic layers, dry with sodium sulfate, filter and concentrate under reduced pressure to yield the title product as a white solid (3.10 g, 99%): $^1$H NMR (DMSO-d$_6$) δ 4.57 (s, 2H), 7.55 (m, 2H), 7.67 (dt, 1H), 7.81 (m, 1H), 12.95 (bs, 1H).

Preparation 125

Synthesis of 3-(5-oxo-4,5-dihydro-[1,2,4]oxadiazol-3-yl)-benzaldehyde

Add PCC (5.22 g, 24.2 mmol) to a solution of 3-(3-hydroxymethyl-phenyl)-4H-[1,2,4]oxadiazol-5-one (3.10 g, 16.1 mmol) in tetrahydrofuran:dichloromethane (125 mL:125 mL) and stir. After 4 hours concentrate under reduced pressure to give a residue. Purify the residue by flash chromatography eluting with ethyl acetate:hexanes:acetic acid (50%:50%:0.1%) to yield the title product as a white solid (2.20 g, 72%): $^1$H NMR (DMSO-d$_6$) δ 7.83 (t, 1H), 8.10-8.17 (m, 2H), 8.35 (m, 1H), 10.09 (s, 1H), 13.15 (bs, 1H).

Preparation 126

Synthesis of 1-[2-hydroxy-4-(4-iodo-benzyloxy)-3-propyl-phenyl]-ethanone

Add 1-bromomethyl-4-iodo-benzene (10.00 g, 33.7 mmol) to a solution of 1-(2,4-dihydroxy-3-propyl-phenyl)-ethanone (6.54 g, 33.7 mmol) and cesium carbonate (13.2 g, 40.4 mmol) in acetone (500 mL) and stir. After 48 hours, pour the reaction into water and extract with ethyl acetate. Combine the organic layers, dry with sodium sulfate, filter and concentrate under reduced pressure to give a residue. Purify the residue by flash chromatography eluting with a gradient of ethyl acetate:hexanes to yield the title product as a yellow solid (7.20 g, 52%): $^1$H NMR (CDCl$_3$) δ 0.95 (t, 3H), 1.56 (sextet, 2H), 2.56 (s, 3H), 2.69 (t, 2H), 5.09 (s, 2H), 6.43 (d, 1H), 7.15 (d, 2H), 7.57 (d, 1H), 7.73 (d, 2H), 12.74 (s, 1H).

Preparation 127

Synthesis of 1-(4-iodo-benzyloxy)-2-propyl-3-trimethylsilanyloxy-4-(1-trimethyl-silanyloxy-vinyl)-benzene Add lithium hexamethyldisilazide (1M solution in tetrahydrofuran, 5.36 ml, 5.36 mmol) to a solution of 1-[2-hydroxy-4-(4-iodo-benzyloxy)-3-propyl-phenyl]-ethanone (1.00 g, 2.44 mmol) in tetrahydrofuran (25 mL) cooled to −78° C. After 1 hour, add trimethylsilyl chloride (794 mg, 7.31 mmol). After 1 hour, warm reaction to room temperature and stir overnight. Pour the reaction into saturated sodium bicarbonate and extract with ethyl acetate. Combine the organic layers, dry with sodium sulfate, filter, and concentrate. Dry on high-vac overnight to yield the title product as a dark yellow oil (1.35 g, 99%): $^1$H NMR (CDCl$_3$) δ 0.16 (s, 9H), 0.23 (s, 9H), 0.94 (t, 3H), 1.52 (sextet, 2H), 2.60 (t, 2H), 4.49 (s, 1H), 4.53 (s, 1H), 4.99 (s, 2H), 6.49 (d, 1H), 7.10 (d, 1H), 7.17 (d, 2H), 7.71 (d, 2H).

Example 100

Synthesis of 3-(3-{[4-(4-acetyl-3-hydroxy-2-propyl-phenoxymethyl)-phenyl]-hydroxy-methyl}-phenyl)-4H-[1,2,4]oxadiazol-5-one

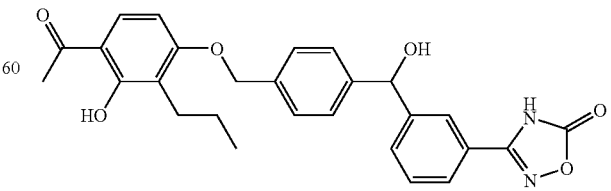

Add isopropyl magnesium chloride (2M solution in tetrahydrofuran, 0.496 ml, 0.992 mmol) to a solution of 1-(4- iodo-benzyloxy)-2-propyl-3-trimethylsilanyloxy-4-(1-trimethylsilanyloxy-vinyl)-benzene (500 mg, 0.901 mmol) in tetrahydrofuran (0.1M) at 0° C. After 15 minutes, warm to room temperature. After 1 hour, cool to −78° C. Add sodium hydride (60% dispersion, 24 mg, 0.992 mmol) to a solution of 3-(5-oxo-4,5-dihydro-[1,2,4]oxadiazol-3-yl)-benzaldehyde (189 mg, 0.992 mmol) in tetrahydrofuran (0.1M). Sonicate the solution for 5 minutes, then add it via syringe to the gringard reagent. After 30 minutes warm the reaction to room temperature. Quench with 10% aq hydrochloric acid (3 mL). Pour the reaction into brine and extract with 25% isopropyl alcohol:75% dichloromethane. Combine organic layers, dry with sodium sulfate, filter and concentrate under reduced pressure to give a residue. Purify the residue by flash chromatography eluting with ethyl acetate:hexanes:acetic acid 50%:50%:0.1% to yield the title product as a off white solid (110 mg, 26%): $^1$H NMR (DMSO-$d_6$) δ 0.86 (t, 3H), 1.47 (sextet, 2H), 2.56 (m, 5H), 5.21 (s, 2H), 5.79 (d, 1H), 6.11 (d, 1H), 6.70 (d, 1H), 7.41 (q, 4H), 7.51 (t, 1H), 7.63 (t, 2H), 7.78 (d, 1H), 7.90 (s, 1H), 12.83 (s, 1H), 12.97 (bs, 1H); MS (esi negative) m/z (rel intensity) 473 (100).

Preparation 128

Synthesis of 1-[3-chloro-2-hydroxy-4-(4-iodo-benzyloxy)-phenyl]-ethanone

Add 1-bromomethyl-4-iodo-benzene (10.00 g, 33.7 mmol) to a solution of 1-(3-chloro-2,4-dihydroxy-phenyl)-ethanone (7.92 g, 42.4 mmol) and cesium carbonate (16.6 g, 50.9 mmol) in dimethylformamide (250 mL) and stir. After 18 hours, pour reaction into water and extract with ethyl acetate. Combine organic layers and wash with 2N NaOH. Dry with sodium sulfate, filter, and concentrate under reduced pressure to give a residue. Purify the residue by flash chromatography eluting with a gradient of ethyl acetate:hexanes to yield the title product as a tan solid (4.00 g, 23%): $^1$H NMR (DMSO-$d_6$) δ 2.62 (s, 3H), 5.33 (s, 2H), 6.87 (d, 1H), 7.27 (d, 2H), 7.78 (d, 2H), 7.94 (d, 1H), 13.13 (s, 1H).

Preparation 129

Synthesis of 2-chloro-1-(4-iodo-benzyloxy)-3-trimethylsilanyloxy-4-(1-trimethyl-silanyloxy-vinyl)-benzene Add sodium hexamethyldisilazide (1M solution in tetrahydrofuran, 21.9 mL, 21.9 mmol) to a solution of 1-[3-chloro-2-hydroxy-4-(4-iodo-benzyloxy)-phenyl]-ethanone (4.00 g, 9.94 mmol) in tetrahydrofuran (100 mL) chilled to −78° C. After 1 hour, add trimethylsilyl chloride (3.24 g, 29.8 mmol). After 1 hour, warm reaction to room temperature and stir overnight. Pour reaction into saturated sodium bicarbonate and extract with ethyl acetate. Combine organic layers, dry with sodium sulfate, filter, and concentrate. Dry in vacuo overnight to yield the title product as a dark yellow oil (5.30 g, 98%): $^1$H NMR (CDCl$_3$) δ 0.21 (s, 9H), 0.28 (s, 9H), 4.55 (s, 1H), 4.79 (s, 1H), 5.08 (s, 2H), 6.56 (d, 1H), 7.22 (m, 3H), 7.71 (d, 2H).

Preparation 130

Synthesis of 3-(3-{[4-(4-acetyl-2-chloro-3-hydroxy-phenoxymethyl)-phenyl]-hydroxy-methyl}-phenyl-4H-[1,2,4]oxadiazol-5-one Add isopropyl magnesium chloride (2M solution in tetrahydrofuran, 1.01 ml, 2.02 mmol) to a solution of 2-chloro-1-(4-iodo-benzyloxy)-3-trimethylsilanyloxy-4-(1-trimethylsilanyloxy-vinyl)-benzene (1.00 g, 1.83 mmol) in tetrahydrofuran (0.1M) at 0° C. After 15 minutes, warm to room temperature. After 1 hour, cool to −78° C. Add sodium hydride (60% dispersion, 80 mg, 2.01 mmol) to a solution of 3-(5-oxo-4,5-dihydro-[1,2,4]oxadiazol-3-yl)-benzaldehyde (348 mg, 1.83 mmol) in tetrahydrofuran (0.1M). Sonicate the solution for 5 minutes, then add it via syringe to the gringard reagent. After 30 minutes, warm the reaction to room temperature. Quench with 10% aq hydrochloric acid. Pour the reaction into brine and extract with 25% isopropyl alcohol: 75% dichloromethane. Combine the organic layers, dry with sodium sulfate, filter, and concentrate under reduced pressure to give a residue. Purify the residue by flash chromatography eluting with 5% methanol:methylene chloride to yield the title product as a off white solid (389 mg, 46%): $^1$H NMR (DMSO-$d_6$) δ 2.61 (s, 3H), 5.31 (s, 2H), 5.80 (d, 1H), 6.12 (d, 1H), 6.87 (d, 1H), 7.43 (m, 4H), 7.51 (t, 1H), 7.64 (tt, 2H), 7.90 (t, 1H), 7.91 (d, 1H), 12.96 (bs, 1H), 13.12 (s, 1H); MS (esi negative) m/z (rel intensity) 465 (100).

Preparation 131

Synthesis of 3-(tert-butyl-dimethyl-silanyloxymethyl)-benzonitrile

Add tert-butyl-chloro-dimethyl-silane (11.9 g, 78.9 mmol) to a solution of 3-hydroxymethyl-benzonitrile (10.00 g, 75.10 mmol) and imidazole (6.14 g, 90.1 mmol) in dichloromethane (1 L) and stir. After 18 hours, pour reaction into 1% hydrochloric acid. Remove organic layer, dry with sodium sulfate, filter, and concentrate under reduced pressure to yield the title product as a clear yellow oil (18.5 g, 99%): $^1$H NMR (CDCl$_3$) δ 0.12 (s, 6H), 0.95 (s, 9H), 4.75 (s, 2H), 7.43 (t, 1H), 7.53 (d, 2H), 7.63 (s, 1H).

Preparation 132

Synthesis of [3-(2-oxo-2,3-dihydro-2-[1,2,3,5]oxathiadiazol-4-yl)-phenyl]-methanol Add hydroxylamine (50% aqueous solution, 5.34 g, 80.8 mmol) dropwise to a refluxing solution of 3-(tert-butyl-dimethyl-silanyloxymethyl)-benzonitrile (5.00 g, 20.2 mmol) in isopropanol (0.1 M). After 2 hours, concentrate the reaction under reduced pressure and azeotrope with toluene. Add dichloromethane (0.1 M) and pyridine (1.92 g, 24.3 mmol) and cool reaction to −78° C. Add thionyl chloride (2.64 g, 22.2 mmol) via syringe. After 4 hours, warm the reaction to room temperature. Concentrate the reaction under reduced pressure. Add tetrahydrofuran (0.1M) and 10% hydrochloric acid (0.1M) and stir. After 18 hours, add brine and extract with 25% isopropyl alcohol:75% dichloromethane. Combine organic layers, dry with sodium sulfate, filter and concentrate under reduced pressure to yield the title product as a yellow solid (3.90 g, 91%): $^1$H NMR (DMSO-$d_6$) δ 4.63 (s, 2H), 5.42 (bs, 1H), 7.59 (m, 2H), 7.75 (dt, 1H), 7.88 (s, 1H), 12.23 (bs, 1H).

Preparation 133

Synthesis of 3-(2-oxo-2,3-dihydro-2$\lambda^4$-[1,2,3,5]oxathiadiazol-4-yl)-benzaldehyde Add PCC (5.94 g, 27.6 mmol) to a solution of [3-(2-oxo-2,3-dihydro-214-[1,2,3,5]oxathiadiazol-4-yl)-phenyl]-methanol (3.90 g, 18.4 mmol) in dichloromethane (100 mL):

tetrahydrofuran (100 mL) and stir. After 2 hours, concentrate the reaction under reduced pressure and purify the residue by flash chromatography eluting with 35% acetone:hexanes to yield the title product as a white solid (2.0 g, 52%): $^1$H NMR (DMSO-d$_6$) δ 7.83 (t, 1H), 8.16 (m, 2H), 8.38 (t, 1H), 10.10 (s, 1H), 12.42 (bs, 1H).

Example 101

Synthesis of 1-[3-chloro-2-hydroxy-4-(4-{hydroxy-[3-(2-oxo-2,3-dihydro-2λ$^4$-[1,2,3,5]oxathiadiazol-4-yl)-phenyl]-methyl}-benzyloxy)-phenyl]-ethanone

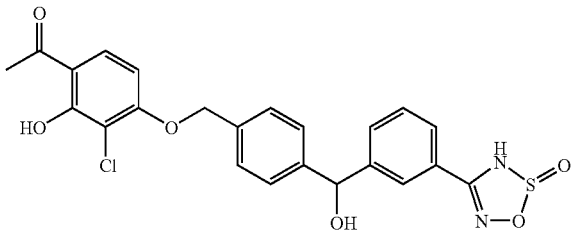

Add isopropyl magnesium chloride (2 M solution in tetrahydrofuran, 1.16 ml, 2.31 mmol) to a solution of 2-chloro-1-(4-iodo-benzyloxy)-3-trimethylsilanyloxy-4-(1-trimethylsilanyloxy-vinyl)-benzene (1.15 g, 2.10 mmol) in tetrahydrofuran (0.1M) chilled to 0° C. After 15 minutes warm to room temperature. After 1 hour cool the reaction to −78° C. Add sodium hydride (60% dispersion, 101 mg, 2.52 mmol) to a solution of 3-(2-oxo-2,3-dihydro-2,4-[1,2,3,5]oxathiadiazol-4-yl)-benzaldehyde (442 mg, 2.10 mmol) in tetrahydrofuran (0.1M). Sonicate the solution for 5 minutes, then add it via syringe to the gringard reagent. After 30 minutes warm the reaction to room temperature. Quench with 10% aq hydrochloric acid. Pour the reaction into brine and extract with 25% isopropyl alcohol:75% dichloromethane. Combine the organic layers, dry with sodium sulfate, filter and concentrate under reduced pressure to give a residue. Purify the residue by flash chromatography eluting with methanol:dichloromethane to yield the title product as a white solid (142 mg, 14%): $^1$H NMR (DMSO-d$_6$) δ 2.61 (s, 3H), 5.31 (s, 2H), 5.81 (s, 1H), 6.13 (bs, 1H), 6.88 (d, 1H), 7.43 (m, 4H), 7.51 (t, 1H), 7.60 (d, 1H), 7.68 (dt, 1H), 7.92 (m, 2H), 12.19 (bs, 1H), 13.12 (s, 1H); MS (esi negative) m/z (rel intensity) 484.9 (100).

Preparation 134

Synthesis is of 1-[3-chloro-2-hydroxy-4-(3-iodo-benzyloxy)-phenyl]-ethanone

Add triphenylphosphine (13.6 g, 51.7 mmol) and DIAD (10.5 g, 51.7 mmol) to a solution of (3-iodo-phenyl)-methanol (11.0 g, 47.0 mmol) and 1-(3-Chloro-2,4-dihydroxy-phenyl)-ethanone (8.77 g, 47.0 mmol) in dichloromethane:tetrahydrofuran (250 ml:250 ml) and stir. After 18 hours, concentrate the reaction, and load directly onto silica. Purify the residue by flash chromatography eluting with acetone:hexanes to yield the title product as a white solid (12.2 g, 64%): $^1$H NMR (DMSO-d$_6$) δ 2.62 (s, 3H), 5.34 (s, 2H), 6.88 (d, 1H), 7.23 (t, 1H), 7.48 (d, 1H), 7.72 (d, 1H), 7.87 (s, 1H), 7.96 (d, 1H), 13.14 (s, 1H).

Preparation 135

Synthesis of 2-chloro-1-(3-iodo-benzyloxy)-3-trimethylsilanyloxy-4-(1-trimethylsilanyloxy-vinyl)-benzene Add sodium hexamethyldisilazide (1 M solution in tetrahydrofuran, 20.2 ml, 20.2 mmol) to a solution of 1-[3-chloro-2-hydroxy-4-(4-iodo-benzyloxy)-phenyl]-ethanone (3.70 g, 9.19 mmol) in tetrahydrofuran (100 mL) chilled to −78° C. After 1 hour, add trimethylsilyl chloride (3.00 g, 27.6 mmol). After 1 hour, warm reaction to room temperature and stir overnight. Pour reaction into saturated sodium bicarbonate and extract with ethyl acetate. Combine organic layers, dry with sodium sulfate, filter, and concentrate. Dry on highvac overnight to yield the title product as a dark yellow oil (5.0 g, 99%): $^1$H NMR (CDCl$_3$) δ 0.21 (s, 9H), 0.28 (s, 9H), 4.55 (d, 1H), 4.79 (d, 1H), 5.08 (s, 2H), 6.56 (d, 1H), 7.12 (t, 1H), 7.24 (d, 1H), 7.42 (d, 1H), 7.65 (d, 1H), 7.82 (s, 1H).

Example 102

Synthesis of 3-(3-{[3-(4-acetyl-2-chloro-3-hydroxy-phenoxymethyl)-phenyl]-hydroxy-methyl}-phenyl)-4H-[1,2,4]oxadiazol-5-one

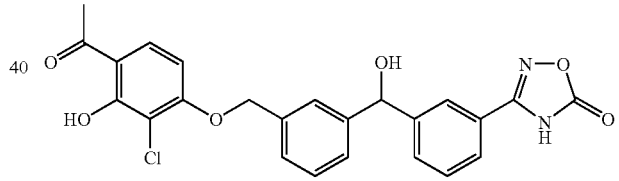

Add isopropyl magnesium chloride (2M solution in tetrahydrofuran, 1.01 mL, 2.02 mmol) to a solution of 2-chloro-1-(3-iodo-benzyloxy)-3-trimethylsilanyloxy-4-(1-trimethylsilanyloxy-vinyl)-benzene (1.00 g, 1.83 mmol) in tetrahydrofuran (0.1M) chilled to 0° C. After 15 minutes, warm to room temperature. After 1 hour, cool to −78° C. Add sodium hydride (60% dispersion, 80 mg, 2.01 mmol) to a solution of 3-(5-oxo-4,5-dihydro-[1,2,4]oxadiazol-3-yl)-benzaldehyde (348 mg, 1.83 mmol) in tetrahydrofuran (0.1 M). Sonicate the solution for 5 minutes then add it via syringe to the gringard reagent. After 30 minutes, warm the reaction to room temperature. Quench with 10% aq hydrochloric acid. Pour the reaction into brine and extract with 25% isopropyl alcohol:75% dichloromethane. Combine the organic layers, dry with sodium sulfate, filter and concentrate under reduced pressure to give a residue. Purify the residue by flash chromatography eluting with ethyl acetate:hexanes:acetic acid (50%:50%:0.1%) to yield the title product as a white solid (120 mg, 14%): $^1$H NMR (DMSO-d$_6$) δ 2.61 (s, 3H), 5.32 (s, 2H), 5.79 (d, 1H), 6.15 (d, 1H), 6.87 (d, 1H), 7.32-7.41 (m, 3H), 7.49 (m, 2H), 7.59 (dt, 1H), 7.64 (dt, 1H), 7.89-7.92 (m, 2H), 12.96 (bs, 1H), 13.13 (s, 1H); MS (esi negative) m/z (rel intensity) 465 (100).

Preparation 136

Synthesis of 5-bromo-N-methoxy-N-methyl-nicotinamide

Heat a solution of 5-bromo-nicotinic acid (50 g, 248 mmol) in thionyl chloride (200 mL) to reflux. After 4 hours, cool to ambient temperature and concentrate under reduced pressure to give a residue. Dissolve residue in dichloromethane (1.0 L). Add pyridine (58.7 g, 743 mmol) followed by O,N-dimethyl-hydroxylamine hydrochloride (26.6 g, 272 mmol) and stir. After 18 hours, add water (1.0 L) and extract with dichloromethane. Combine the organic layers, dry with sodium sulfate, filter and concentrate under reduced pressure to yield the title product as a clear oil (59.1 g, 97%): $^1$H NMR (DMSO-$d_6$) δ 3.29 (bs, 3H), 3.57 (bs, 3H), 8.24 (dd, 1H), 8.75 (d, 1H), 8.83 (d, 1H).

Preparation 137

Synthesis of (5-bromo-pyridin-3-yl)-[4-(tert-butyl-dimethyl-silanyloxymethyl)-phenyl]-methanone Add n-butyllithium (4.56 mL, 7.30 mmol) to a solution of (4-bromo-benzyloxy)-tert-butyl-dimethyl-silane (2.0 g, 6.64 mmol) in tetrahydrofuran (60 mL) cooled to −78° C. After 2 hours, add 5-bromo-N-methoxy-N-methyl-nicotinamide (1.63 g, 6.64 mmol), and allow solution to warm gradually to ambient temperature. After 2 hours, add 1% aqueous hydrochloric acid (60 mL) and stir. After 20 minutes, extract solution with ethyl acetate. Combine the organic layers, dry with sodium sulfate, filter and concentrate under reduced pressure to give a residue. Purify the residue by flash chromatography eluting with 12.5% ethyl acetate:hexanes to yield the title product as a white solid (1.10 g, 41%): $^1$H NMR (DMSO-$d_6$) δ 0.11 (s, 6H), 0.93 (s, 9H), 4.84 (bs, 2H), 7.52 (d, 2H), 7.79 (d, 2H), 8.31 (t, 1H), 8.82 (d, 1H), 8.98 (d, 1H).

Preparation 138

Synthesis of 5-[4-(tert-butyl-dimethyl-silanyloxymethyl)-benzoyl]-nicotinonitrile Add tetrakis(triphenylphosphine)palladium (284 mg, 0.246 mmol) to a solution of (5-bromo-pyridin-3-yl)-[4-(tert-butyl-dimethyl-silanyloxymethyl)-phenyl]-methanone (1.0 g, 2.46 mmol) and zinc cyanide (578 mg, 4.92 mmol) in dimethylformamide (25 mL) and stir. Purge solution with nitrogen and heat to 80° C. After 18 hours, add water (100 mL) and extract with ethyl acetate. Combine the organic layers, dry with sodium sulfate, filter and concentrate under reduced pressure to give a residue. Purify the residue with flash chromatography eluting with 12.5% ethyl acetate:hexanes to yield the title product as a white solid (550 mg, 63%): $^1$H NMR (DMSO-$d_6$) δ 0.11 (s, 6H), 0.93 (s, 9H), 4.84 (bs, 2H), 7.53 (d, 2H), 7.83 (d, 2H), 8.61 (t, 1H), 9.09 (d, 1H), 9.26 (d, 1H).

Preparation 139

Synthesis of 5-(4-hydroxymethyl-benzoyl)-nicotinonitrile

Dissolve 5-[4-(tert-butyl-dimethyl-silanyloxymethyl)-benzoyl]-nicotinonitrile (510 mg, 1.45 mmol) in 10% aqueous hydrochloric acid (10 mL) and tetrahydrofuran (50 mL) and stir. After 1 hour, add saturated aqueous sodium bicarbonate (50 mL) and extract with ethyl acetate. Combine the organic layers, dry with sodium sulfate, filter and concentrate under reduced pressure to yield the title product as a white solid (325 mg, 94%): $^1$H NMR (DMSO-$d_6$) δ 4.64 (d, 2H), 5.44 (t, 1H), 7.53 (d, 2H), 7.80 (d, 2H), 8.59 (t, 1H), 9.09 (d, 1H), 9.27 (d, 1H).

Preparation 140

Synthesis of 5-[4-(4-acetyl-3-hydroxy-2-propyl-phenoxymethyl)-benzoyl]-nicotinonitrile The title compound is prepared essentially as described in Preparation 14 employing 5-(4-hydroxymethyl-benzoyl)-nicotinonitrile (325 mg, 1.36 mmol) to afford the title compound as an white solid (448 mg, 79%): $^1$H NMR (DMSO-$d_6$) δ 0.90 (t, 3H), 1.52 (sextet, 2H), 2.58 (s, 3H), 2.64 (t, 2H), 5.41 (bs, 2H), 6.74 (d, 1H), 7.66 (d, 2H), 7.83 (d, 1H), 7.89 (d, 2H), 8.62 (t, 1H), 9.11 (d, 1H), 9.27 (d, 1H), 12.86 (s, 1H).

Example 103

Synthesis of 1-(2-hydroxy-3-propyl-4-{4-[5-(2H-tetrazol-5-yl)-pyridine-3-carbonyl]-benzyloxy}-phenyl)-ethanone

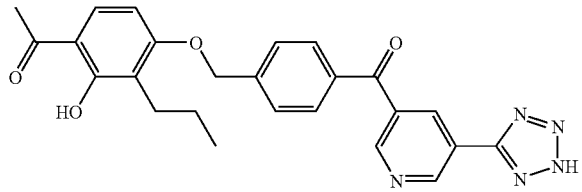

Using the general procedure of Example 1 using 5-[4-(4-acetyl-3-hydroxy-2-propyl-phenoxymethyl)-benzoyl]-nicotinonitrile (448 mg, 1.08 mmol), sodium azide (703 mg, 10.8 mmol), and triethylamine hydrochloride (1.49 g, 10.8 mmol) to yield the title product as a white solid (338 mg, 66%): $^1$H NMR (DMSO-$d_6$) δ 0.90 (t, 3H), 1.53 (sextet, 2H), 2.59 (s, 3H), 2.64 (t, 2H), 5.43 (s, 2H), 6.76 (d, 1H), 7.67 (d, 2H), 7.84 (d, 1H), 7.92 (d, 2H), 8.68 (t, 1H), 9.05 (d, 1H), 9.46 (d, 1H), 12.86 (s, 1H); MS (esi negative) m/z (rel intensity) 456 (100).

Example 104

Synthesis of 5-[4-(4-acetyl-3-hydroxy-2-propyl-phenoxymethyl)-benzoyl]-nicotinic acid

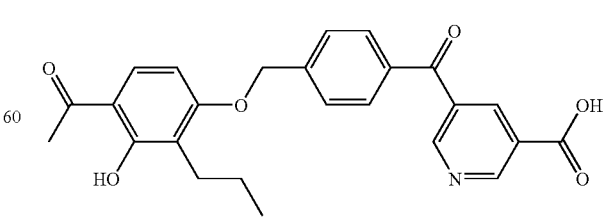

Add lithium hydroxide (289 mg, 12.06 mmol) to a solution of 5-[4-(4-acetyl-3-hydroxy-2-propyl-phenoxymethyl)-benzoyl]-nicotinonitrile (500 mg, 1.21 mmol) in dioxane (10 mL) and water (10 mL) and stir. Heat solution to reflux. After 1 hour cool to ambient temperature, add water (100 mL) and wash with ethyl acetate. Acidify with 10% aqueous hydrochloric acid (15 mL), and extract with ethyl acetate. Combine organic layers, dry with sodium sulfate, filter and concentrate under reduced pressure to give a residue. Purify residue by sonicating in ether for 1 hour. Filter the resulting precipitate to yield the title compound as a beige solid (262 mg, 50%): $^1$H NMR (DMSO-d$_6$) δ 0.86 (t, 3H), 1.48 (sextet, 2H), 2.54 (s, 3H), 2.59 (t, 2H), 5.38 (s, 2H), 6.70 (d, 1H), 7.62 (d, 2H), 7.79 (d, 1H), 7.84 (d, 2H), 8.42 (s, 1H), 9.05 (s, 1H), 9.24 (s, 1H), 12.82 (s, 1H), 13.72 (bs, 1H); MS (esi negative) m/z (rel intensity) 432 (100).

Preparation 141

Synthesis of 5-{[4-(4-acetyl-3-hydroxy-2-propyl-phenoxymethyl)-phenyl]-hydroxy-methyl}-nicotinonitrile Add zinc dust (5.00 g, 76.5 mmol) to a solution of 5-[4-(4-acetyl-3-hydroxy-2-propyl-phenoxymethyl)-benzoyl]-nicotinonitrile (4.50 g, 10.9 mmol) in acetic acid (70 ml) and stir vigorously. After 1 hour, cool reaction in an ice bath and add 1N hydrochloric acid (200 ml). Extract with ethyl acetate. Combine the organic layers, dry with sodium sulfate, filter, and concentrate under reduced pressure to give a residue. Purify the residue by flash chromatography eluting with acetone:hexanes to yield the title product as a white solid (2.80 g, 62%): $^1$H NMR (DMSO-d$_6$) δ 0.86 (t, 3H), 1.47 (sextet, 2H), 2.56 (m, 5H), 5.22 (s, 2H), 5.88 (m, 1H), 6.32 (d, 1H), 6.71 (d, 1H), 7.44 (q, 4H), 7.79 (d, 1H), 8.27 (t, 1H), 8.88 (dd, 1H), 12.84 (s, 1H).

Example 105

Synthesis of 1-[2-hydroxy-4-(4-{hydroxy-[5-(2H-tetrazol-5-yl)-pyridin-3-yl]-methyl}-benzyloxy)-3-propyl-phenyl]-ethanone

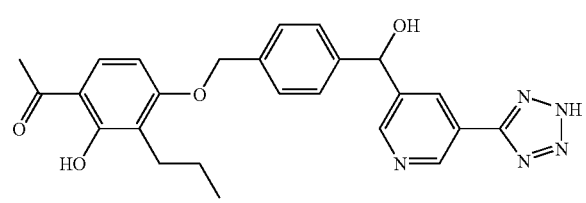

Using the general procedure of Example 1 using 5-{[4-(4-Acetyl-3-hydroxy-2-propyl-phenoxymethyl)-phenyl]-hydroxy-methyl}-nicotinonitrile (473 mg, 1.14 mmol), sodium azide (738 mg, 11.4 mmol), and triethylamine hydrochloride (1.56 g, 11.4 mmol) to yield the title product as a white solid (170 mg, 33%): $^1$H NMR (DMSO-d$_6$) δ 0.85 (t, 3H), 1.35 (s, 1H), 1.47 (sextet, 2H), 2.56 (m, 5H), 5.22 (bs, 2H), 5.93 (d, 1H), 6.29 (d, 1H), 6.71 (d, 1H), 7.45 (q, 4H), 7.78 (d, 1H), 8.39 (t, 1H), 8.77 (d, 1H), 9.07 (d, 1H), 12.83 (s, 1H); MS (esi negative) m/z (rel intensity) 458 (100).

Example 106

Synthesis of 5-{[4-(4-acetyl-3-hydroxy-2-propyl-phenoxymethyl)-phenyl]-hydroxy-methyl}-nicotinic acid

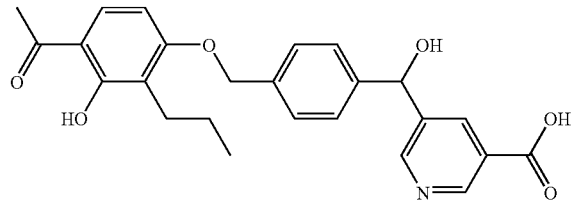

Add lithium hydroxide (1M aqueous solution, 11.4 mL, 11.4 mmol) to a solution of 5-{[4-(4-acetyl-3-hydroxy-2-propyl-phenoxymethyl)-phenyl]-hydroxy-methyl}-nicotinonitrile (473 mg, 1.14 mmol) in dioxane (10 mL). Heat reaction to 80° C. After 2 hours, cool to room temperature and pour into water (50 ml). Wash solution with ethyl acetate (25 mL), and discard. Acidify the aqueous layer with 10% hydrochloric acid, and extract with 25% isopropyl alcohol:75% dichloromethane. Combine the organic layers, dry with sodium sulfate, filter and concentrate under reduced pressure to give a residue. Sonicate the residue in acetonitrile (10 mL), and filter to yield the title compound as a beige solid (210 mg, 42%): $^1$H NMR (DMSO-d$_6$) δ 0.86 (t, 3H), 1.47 (sextet, 2H), 2.55-2.59 (m, 5H), 5.22 (bs, 2H), 5.90 (bs, 1H), 6.70 (d, 1H), 7.43 (q, 4H), 7.79 (d, 1H), 8.21 (t, 1H), 8.82 (d, 1H), 8.92 (d, 1H), 12.84 (s, 1H); MS (esi negative) m/z (rel intensity) 434 (100).

Preparation 142

Synthesis of 2-hydroxymethyl-isonicotinonitrile

Add ammonium persulfate (70.1 g, 307 mmol) to a solution of isonicotinonitrile (16.00 g, 154 mmol) in methanol:water:sulfuric acid (275 mL:135 mL:11 mL). Heat solution to reflux. After 24 hours, pour reaction onto ice and neutralize with ammonium hydroxide (70 ml). Extract solution with chloroform (3×600 ml). Combine the organic layers, dry with sodium sulfate, filter, and concentrate under reduced pressure to give a residue. Purify the residue by flash chromatography eluting with acetone:dichloromethane (1:6) to yield the title compound as a white solid (5.86 g, 28%): $^1$H NMR (CDCl$_3$) δ 3.17 (t, 1H), 4.84 (d, 1H), 7.45 (m, 1H), 7.58 (s, 1H), 8.74 (d, 1H).

Preparation 143

Synthesis of 2-formyl-isonicotinonitrile

Add selenium dioxide (2.69 g, 24.2 mmol) to a solution of 2-hydroxymethyl-isonicotinonitrile (5.86 g, 43.7 mmol) in dioxane (120 mL). Heat reaction to 80° C. After 4 hours, cool to room temperature. Add dichloromethane (500 mL) and celite and stir. After 15 minutes, filter through a plug of silica eluting with dichloromethane. Concentrate filtrate under reduced pressure to yield the title compound as an orange solid (5.30 g, 92%): $^1$H NMR (DMSO-d$_6$) δ 8.19 (dd, 1H), 8.34 (t, 1H), 9.07 (dd, 1H), 10.01 (s, 1H).

Preparation 144

Synthesis of 2-{[4-(4-acetyl-3-hydroxy-2-propyl-phenoxymethyl)-phenyl]-hydroxy-methyl}-isonicotinonitrile Add isopropyl magnesium chloride (2M solution in tetrahydrofuran, 2.98 mL, 5.95 mmol) to a solution of 1-(4-iodo-benzyloxy)-2-propyl-3-trimethylsilanyloxy-4-(1-trimethylsilanyloxy-vinyl)-benzene (3.00 g, 5.41 mmol) in tetrahydrofuran (0.1M) cooled to 0° C. After 15 minutes, warm reaction to room temperature. After 1 hour, cool the reaction to −78° C. Add a solution of 2-formyl-isonicotinonitrile (612 mg, 5.95 mmol) in tetrahydrofuran (10 mL) via syringe. After 1 hour, warm the reaction to room temperature. Add 10% hydrochloric acid (30 mL). After 5 minutes, pour the reaction into water and extract with ethyl acetate. Combine organics, dry with sodium sulfate, filter and concentrate under reduced pressure to give a residue. Purify the residue by flash chromatography eluting with methanol:dichlormethane followed by trituration with acetonitrile to yield the title product as a white solid (1.71 g, 76%): $^1$H NMR (CDCl$_3$) δ 0.95 (t, 3H), 1.56 (sextet, 2H), 2.56 (s, 3H), 2.69 (t, 2H), 4.50 (d, 1H), 5.16 (s, 2H), 5.84 (d, 1H), 6.46 (d, 1H), 7.41 (m, 4H), 7.51 (s, 1H), 7.55 (d, 1H), 8.76 (d, 1H), 12.74 (s, 1H).

Example 107

Synthesis of 2-{[4-(4-acetyl-3-hydroxy-2-propyl-phenoxymethyl)-phenyl]-hydroxy-methyl}-isonicotinic acid

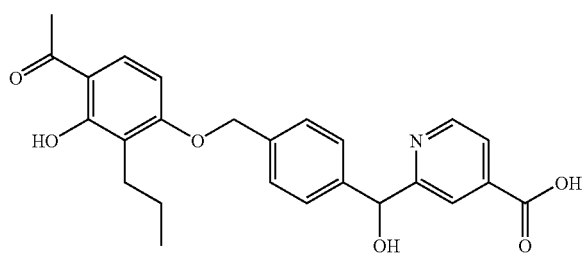

Add lithium hydroxide (2M aqueous solution, 20.4 mL, 40.8 mmol) to a solution of 2-{[4-(4-acetyl-3-hydroxy-2-propyl-phenoxymethyl)-phenyl]-hydroxy-methyl}-isonicotinonitrile (1.70 g, 4.08 mmol) in dioxane (40 mL) and stir. Heat the reaction to reflux. After 4 hours, cool reaction to room temperature, acidify with 1N hydrochloric acid and extract with ethyl acetate. Combine organic layers, dry with sodium sulfate, filter and concentrate under reduced pressure to give a residue. Sonicate the residue in acetonitrile and filter to yield the title product as a beige solid (1.60 g, 90%): $^1$H NMR (DMSO-d$_6$) δ 0.86 (t, 3H), 1.46 (sextet, 2H), 2.56 (m, 5H), 5.21 (s, 2H), 5.82 (s, 1H), 6.69 (d, 1H), 7.41 (m, 4H), 7.68 (dd, 1H), 7.78 (d, 1H), 8.04 (s, 1H), 8.64 (d, 1H), 12.83 (s, 1H); MS (esi negative) m/z (rel intensity) 434 (100).

Preparation 145

Synthesis of 3-(4-hydroxymethyl-benzyl)-benzoic acid methyl ester

Tetrakis(triphenylphosphine)palladium(0) (550 mg, 0.476 mmol) is added to a mixture of 3-bromomethyl-benzoic acid methyl ester (3.0 g, 13.09 mmol) and 4-(hydroxymethyl)-phenylboronic acid (2.99 g, 19.68 mmol) in a mixture of toluene (125 mL) and 2M sodium carbonate (62 mL). The mixture was degassed, placed under nitrogen and heated at 85° C. for 16 hours. After cooling to room temperature, the mixture is concentrated in vacuo and the black residue is partitioned between saturated sodium bicarbonate and dichloromethane. After the layers are separated, the aqueous layer is extracted two more times with dichloromethane. The combined organic layers are washed with brine, dried over magnesium sulfate, filtered and concentrated in vacuo. The residue is purified by flash chromatography (20% tetrahydrofuran in hexanes) to give 2.71 g of the title compound as a yellow oil: MS (m/z): 239 (M−OH); $^1$H NMR (CDCl$_3$) δ 7.92 (m, 2H), 7.42-7.36 (m, 2H), 7.34-7.29 (m, 2H), 7.21 (d, J=8.0 Hz, 2H), 4.69 (s, 2H), 4.05 (s, 2H), 3.93 (s, 3H), 1.79 (s, 1H).

The following compounds are prepared by an analogous procedure for coupling as described in Preparation 145.

Preparation 146

4-(3-hydroxymethyl-benzyl)-benzoic acid methyl ester: MS (m/z): 239 (M−OH)

Preparation 147

3-(3-hydroxymethyl-benzyl)-benzoic acid methyl ester: MS (m/z): 239 (M−OH)

Preparation 148

4-(4-hydroxymethyl-benzyl)-benzoic acid methyl ester: MS (m/z): 239 (M−OH)

Preparation 149

3-[(4-hydroxymethyl-benzyl)-benzonitrile: MS (m/z): 206 (M−OH)

Preparation 150

Synthesis of 3-(4-Iodomethyl-benzyl)-benzoic acid methyl ester

The resin-bound triphenylphosphine (7.59 g, 22.77 mmol), iodine (5.79 g, 22.81 mmol) and imidazole (1.55 g, 22.76 mmol) in dichloromethane (65 mL) are gently stirred for 1 hour at room temperature. A solution of alcohol of preparation 284 (2.92 g, 11.39 mmol) in dichloromethane (65 mL) is then added, and stirring is continued for another 1 hour. The solids are removed by filtration through Celite. The mother liquor is washed with saturated sodium bisulfite, water, and brine, then dried over magnesium sulfate, filtered and concentrated in vacuo to give the title compound as a yellow solid: $^1$H NMR δ (CDCl3); 9.24 (m, 2H), 7.39 (m, 2H), 7.36-7.32 (m, 2H), 7.14 (d, J=8.0 Hz, 2H), 4.47 (s, 2H), 4.02 (s, 2H), 3.94 (s, 3H).

The following compounds are prepared by an analogous procedure as described in Preparation 150.

Preparation 151

4-(3-iodomethyl-benzyl)-benzoic acid methyl ester: MS (m/z): 239 (M–I)

Preparation 152

3-[(4-iodomethyl-benzyl)]-benzonitrile: MS (m/z): 206 (M–I)

Preparation 153

3-(3-iodomethyl-benzyl)-benzoic acid methyl ester: MS (m/z): 239 (M–I)

Preparation 154

4-(4-iodomethyl-benzyl)-benzoic acid methyl ester: MS (m/z): 239 (M–I)

Preparation 155

Synthesis of 3-[4-(4-acetyl-3-hydroxy-2-iodo-phenoxymethyl)-benzyl]-benzoic acid methyl ester Potassium carbonate (675 mg, 4.88 mmol) is added to a solution of 4-acetyl-3-hydroxy-2-iodo-phenol (925 mg, 3.33 mmol) and 3-(4-iodomethyl-benzyl)-benzoic acid methyl ester (1.21 g, 3.30 mmol) in acetone (65 mL). The resulting suspension is heated at 50° C. for 16 hours. The reaction mixture is cooled to room temperature and concentrated in vacuo. The residue is taken up in dichloromethane, washed with 1N hydrochloric acid, brine, dried over magnesium sulfate, filtered and concentrated to give a yellow solid. This solid is dissolved in dichloromethane and a white precipitate forms upon addition of ethyl acetate. The white solid is filtered off and the mother liquor is purified by flash chromatography, eluting with 20% ethyl acetate in hexanes. The precipitate and chromatographed materials are combined to give 1.04 g of the title compound as a pale yellow solid: MS (m/z) 517 (M+1), 515 (M–1); $^1$H NMR δ (CDCl$_3$); 13.58 (s, 1H), 7.93 (m, 2H), 7.74 (d, J=9.0 Hz, 1H), 7.45-7.38 (m, 4H), 7.25 (d, J=8.0 Hz, 2H), 6.50 (d, J=9.0 Hz, 1H), 5.27 (s, 2H), 4.07 (s, 2H), 3.94 (s, 3H), 2.63 (s, 3H).

The following compounds are prepared by an analogous procedure as described in Preparation 155.

Preparation 156

3-{[4-(4-acetyl-3-hydroxy-2-iodo-phenoxymethyl)-phenyl]-hydroxy-methyl}-benzonitrile: MS (m/z) 500 (M+1)

Preparation 157

3-[4-(4-acetyl-3-hydroxy-2-iodo-phenoxymethyl)-benzyl]-benzonitrile: MS (m/z) 484 (M+1)

Preparation 158

Synthesis of 3-[4-(4-acetyl-3-hydroxy-2-pyridin-2-yl-phenoxymethyl)-benzyl]-benzoic acid methyl ester A mixture of 3-[4-(4-acetyl-3-hydroxy-2-iodo-phenoxymethyl)-benzyl]-benzoic acid methyl ester (417 mg, 0.808 mmol), 2-tributylstannanyl-pyridine (1.72 g, 4.67 mmol), and tetrakis(triphenylphosphine)palladium(0) (111 mg, 0.096 mmol) in toluene (19 mL) is thoroughly degassed, placed under nitrogen and heated at 100° C. for 16 hours. After cooling to room temperature, the reaction mixture is concentrated in vacuo. The residue thus obtained is purified by flash chromatography (20% to 40% ethylacetate in hexanes) to give 230 mg of the title compound as a yellow oil: MS (m/z): 468 (M+1); $^1$H NMR (CDCl$_3$) δ 8.74 (m, 1H), 7.87 (m, 2H), 7.78 (m, 2H), 7.56 (d, J=8.0 Hz, 1H), 7.36-7.27 (m, 3H), 7.17 (d, J=8.0 Hz, 2H), 7.11 (d, J=8.0 Hz, 2H), 6.60 (d, J=9.0 Hz, 1H), 5.14 (s, 2H), 3.99 (s, 2H), 3.89 (s, 3H), 2.61 (s, 3H).

The following compounds are prepared by an analogous procedure as described in Preparation 158.

Preparation 159

3-[4-(4-acetyl-3-hydroxy-2-pyridin-2-yl-phenoxymethyl)-benzyl]-benzoic acid methyl ester: MS (m/z) 468 (M+1)

Preparation 160

3-[4-(4-acetyl-3-hydroxy-2-pyridin-3-yl-phenoxymethyl)-benzyl]-benzoic acid methyl ester: MS (m/z) 468 (M+1)

Preparation 161

3-[4-(4-acetyl-3-hydroxy-2-pyridin-4-yl-phenoxymethyl)-benzyl]-benzoic acid methyl ester: MS (m/z) 468 (M+1)

Preparation 162

3-{[4-(4-acetyl-3-hydroxy-2-thiazol-2-yl-phenoxymethyl)-phenyl]-hydroxy-methyl}-benzonitrile: MS (m/z) 457 (M+1)

Preparation 163

3-[4-(4-acetyl-3-hydroxy-2-thiophen-2-yl-phenoxymethyl)-benzyl]-benzoic acid methyl ester: MS (m/z) 473 (M+1)

Preparation 164

4-[4-(4-acetyl-3-hydroxy-2-thiophen-2-yl-phenoxymethyl)-benzyl]-benzoic acid methyl ester: MS (m/z) 473 (M+1)

Preparation 165

3-[3-(4-acetyl-3-hydroxy-2-thiophen-2-yl-phenoxymethyl)-benzyl]-benzoic acid methyl ester: MS (m/z) 473 (M+1)

Preparation 166

4-[3-(4-acetyl-3-hydroxy-2-thiophen-2-yl-phenoxymethyl)-benzyl]-benzoic acid methyl: MS (m/z) 473 (M+1)

Preparation 167

3-[4-(4-Acetyl-3-hydroxy-2-thiazol-2-yl-phenoxymethyl)-benzyl]-benzoic acid methyl ester: MS (m/z) 474 (M+1)

Examples 107-123

The Examples in the following table are prepared essentially as described initially in Preparation 158, followed by an analogous procedure described in Example 1 for compounds of formula I where Z is tetrazolyl or an analogous procedure described Example 35 for compounds of formula I where Z is carboxylic acid.

| Ex. No. | Chemical Name | Structure | Physical Data |
|---|---|---|---|
| 107 | 3-[4-(4-Acetyl-3-hydroxy-2-thiophen-2-yl-phenoxymethyl)-benzyl]-benzoic acid | 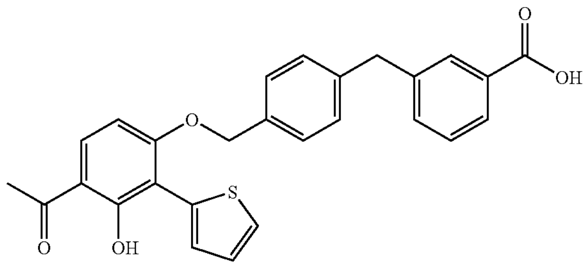 | $^1$H NMR (DMSO-$d_6$) δ 13.46 (s, 1H), 12.79 (bs, 1H), 7.93 (d, J = 8.8 Hz, 1H), 7.77-7.73 (m, 2H), 7.54 (dd, J = 5.0 Hz and 1.0 Hz, 1H), 7.49-7.37 (m, 4H), 7.33 (m, 1H), 7.23 (m, 2H), 7.08-7.05 (m, 1H), 6.84 (d, J = 9.0 Hz, 1H), 5.27 (s, 2H), 3.99 (s, 2H), 2.60 (s, 3H); MS (m/e): 459 (M + 1). |
| 108 | 4-[4-(4-Acetyl-3-hydroxy-2-thiophen-2-yl-phenoxymethyl)-benzyl]-benzoic acid | 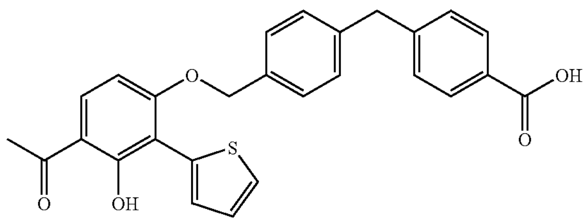 | $^1$H NMR (DMSO-$d_6$) δ 13.45 (s, 1H), 12.78 (s, 1H), 7.93 (d, J = 9.3 Hz, 1H), 7.84 (m, 2H), 7.55 (m, 1H), 7.44 (m, 1H), 7.33 (m, 4H), 7.23 (d, J = 8.0 Hz, 2H), 7.08-7.05 (m, 1H), 6.84 (d, J = 9.0 Hz, 1H), 5.27 (s, 2H), 3.99 (s, 2H), 2.60 (s, 3H); MS (m/e): 459 (M + 1). |
| 109 | 3-[3-(4-Acetyl-3-hydroxy-2-thiophen-2-yl-phenoxymethyl)-benzyl]-benzoic acid | 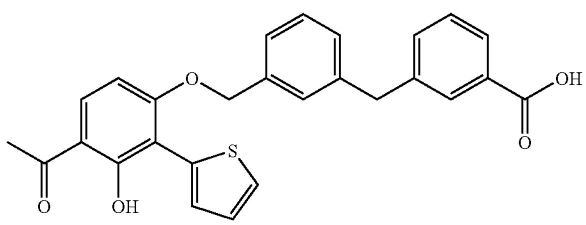 | $^1$H NMR (DMSO-$d_6$) δ 13.45 (s, 1H), 12.91 (s, 1H), 7.93 (d, J = 9.0 Hz, 1H), 7.76 (m, 2H), 7.52 (m, 1H), 7.46-7.37 (m, 3H), 7.31-7.19 (m, 4H), 7.04 (m, 1H), 6.84 (d, J = 9.0 Hz, 1H), 5.26 (s, 2H), 3.99 (s, 2H), 2.61 (s, 3H); MS (m/e): 459 (M + 1). |
| 110 | 4-[3-(4-Acetyl-3-hydroxy-2-thiophen-2-yl-phenoxymethyl)-benzyl]-benzoic acid | 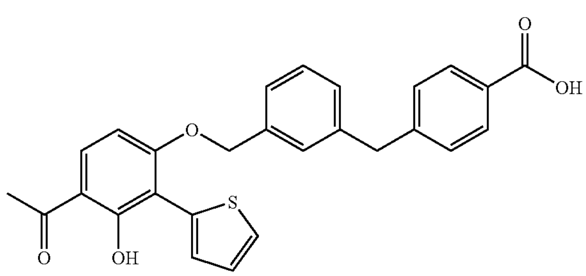 | $^1$H NMR (DMSO-$d_6$) δ 13.45 (s, 1H) 12.79 (bs, 1H), 7.93 (d, J = 9.0 Hz, 1H), 7.84 (d, J = 8.2 Hz, 2H), 7.52 (m, 1H), 7.39 (m, 1H), 7.31-7.18 (m, 6H), 7.04 (m, 1H), 6.83 (d, J = 9.2 Hz, 1H), 5.26 (s, 2H), 3.98 (s, 2H), 2.61 (s, 3H); MS (m/e): 459 (M + 1). |
| 111 | 1-(2-Hydroxy-3-pyridin-2-yl-4-{4-[3-(2H-tetrazol-5-yl)-benzyl]-benzyloxy}-phenyl)-ethanone | 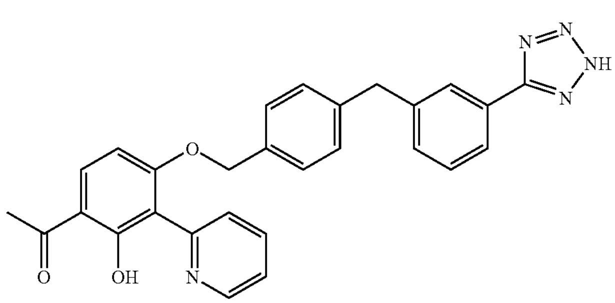 | $^1$H NMR (DMSO-$d_6$) δ 13.09 (s, 1H), 8.62 (m, 1H), 7.95-7.78 (m, 4H), 7.51-7.41 (m, 3H), 7.31 (m, 2H), 7.23-7.17 (m, 4H), 6.79 (d, J = 9.3 Hz, 1H), 5.17 (s, 2H), 4.0 (s, 2H), 2.59 (s, 3H); MS (m/e): 478 (M + 1). |

-continued

| Ex. No. | Chemical Name | Structure | Physical Data |
|---|---|---|---|
| 112 | 1-(2-Hydroxy-4-{4-[3-(2H-tetrazol-5-yl)-benzyl]-benzyloxy}-3-thiophen-2-yl-phenyl)-ethanone | 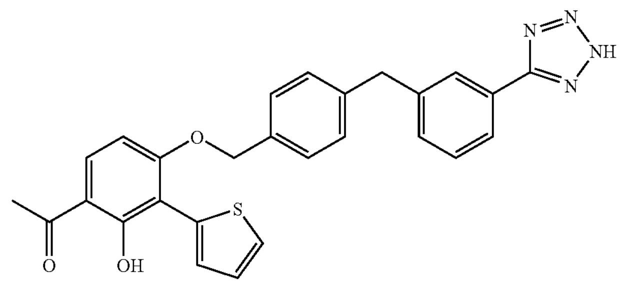 | $^1$H NMR (DMSO-d$_6$) δ 13.46 (s, 1H), 7.92 (m, 2H), 7.83 (m, 1H), 7.55-7.42 (m, 4H), 7.34 (d, J = 7.1 Hz, 2H), 7.27 (d, J = 8.2 Hz, 2H), 7.06 (m, 1H), 6.84 (d, J = 8.2 Hz, 1H), 5.27 (s, 2H), 4.03 (s, 2H), 2.60 (s, 3H); MS (m/e): 483 (M + 1). |
| 113 | 3-[4-(4-Acetyl-2-cyano-3-hydroxy-phenoxymethyl)-benzyl]-benzoic acid | 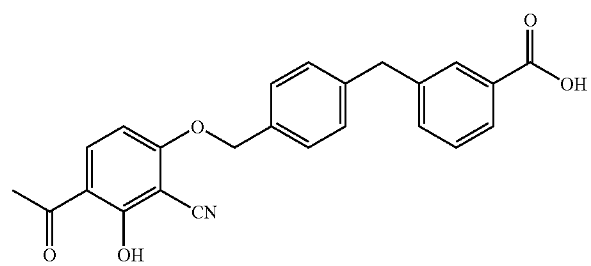 | $^1$H NMR (DMSO-d$_6$) δ 12.86 (bs, 1H), 12.58 (s, 1H), 7.83-7.73 (m, 3H), 7.48 (d, J = 7.5 Hz, 1H), 7.42-7.34 (m, 3H), 7.25 (d, J = 8.0 Hz, 2H), 6.57-6.51 (m, 2H), 5.12 (s, 2H), 4.0 (s, 2H), 2.53 (s, 3H); MS (m/e): 375 (M − CN). |
| 114 | 3-[4-(4-Acetyl-3-hydroxy-2-pyridin-4-yl-phenoxymethyl)-benzyl]-benzoic acid | 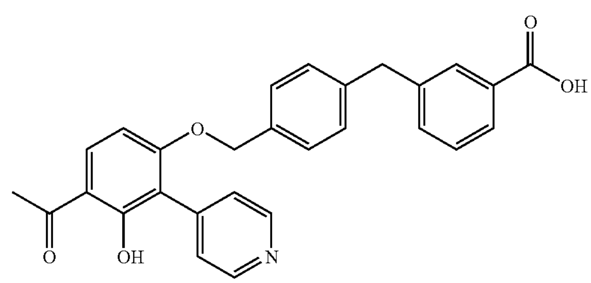 | $^1$H NMR (DMSO-d$_6$) δ 13.2 (s, 1H), 8.87-8.85 (m, 2H), 8.12 (d, J = 9.0 Hz, 1H), 8.02 (d, J = 6.8 Hz, 2H), 7.76-7.73 (m, 2H), 7.48-7.45 (m, 1H), 7.42-7.37 (m, 1H), 7.27-7.19 (m, 4H), 6.94 (d, J = 9.2 Hz, 1H), 5.24 (s, 2H), 3.98 (s, 2H), 2.63 (s, 3H); MS (m/e): 454 (M + 1). |
| 115 | 3-[4-(4-Acetyl-3-hydroxy-2-pyridin-2-yl-phenoxymethyl)-benzyl]-benzoic acid | 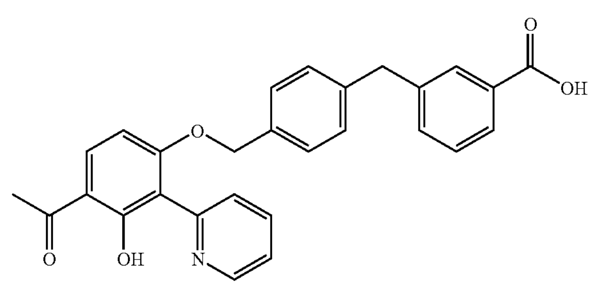 | $^1$H NMR (DMSO-d$_6$) δ 13.12 (bs, 1H), 8.9 (d, J = 5.2 Hz, 1H), 8.47 (m, 1H), 8.16 (d, J = 9.2 Hz, 1H), 8.0 (d, J = 7.7 Hz, 1H), 7.88 (m, 1H), 7.75-7.73 (m, 2H), 7.46 (m, 1H), 7.41-7.36 (m, 1H), 7.25-7.17 (m, 4H), 6.95 (d, J = 9.0 Hz, 1H), 5.24 (s, 2H), 3.97 (s, 2H), 2.64 (s, 3H); MS (m/e): 454 (M + 1). |
| 116 | 3-[4-(4-Acetyl-3-hydroxy-2-thiazol-2-yl-phenoxymethyl)-benzyl]-benzoic acid | 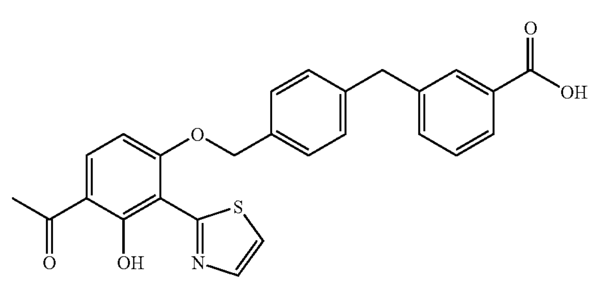 | $^1$H NMR (DMSO-d$_6$) δ 12.85 (bs, 1H), 8.03 (d, 3.6 Hz, 1H), 7.85 (d, J = 3.5 Hz, 1H), 7.79-7.74 (m, 3H), 7.50-7.38 (m, 4H), 7.28 (d, J = 8.0 Hz, 2H), 6.92 (d, J = 9.0 Hz, 1H), 5.42 (s, 2H), 4.02 (s, 2H), 2.60 (s, 3H); MS (m/e): 460 (M + 1). |

| Ex. No. | Chemical Name | Structure | Physical Data |
| --- | --- | --- | --- |
| 117 | 3-[4-(4-Acetyl-3-hydroxy-2-pyridin-3-yl-phenoxymethyl)-benzyl]-benzoic acid | 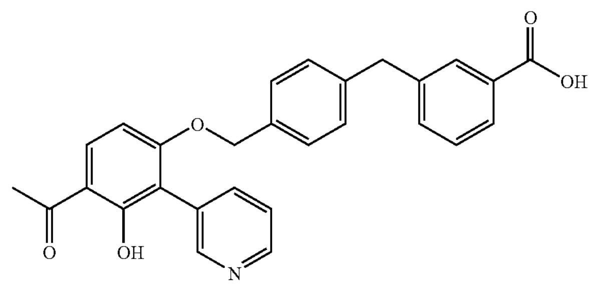 | $^1$H NMR (DMSO-d$_6$) δ 12.93 (s, 1H), 8.52 (s, 1H), 8.48 (d, J = 5.0 Hz, 1H), 8.0 (d, J = 9.2 Hz, 1H), 7.78-7.73 (m, 3H), 7.47-7.36 (m, 3H), 7.20 (s, 4H), 6.86 (d, J = 9.2 Hz, 1H), 5.18 (s, 2H), 3.97 (s, 2H), 2.61 (s, 3H); MS (m/e): 454 (M + 1). |
| 118 | 4-[4-(4-Acetyl-3-hydroxy-2-pyridin-4-yl-phenoxymethyl)-benzyl]-benzoic acid | 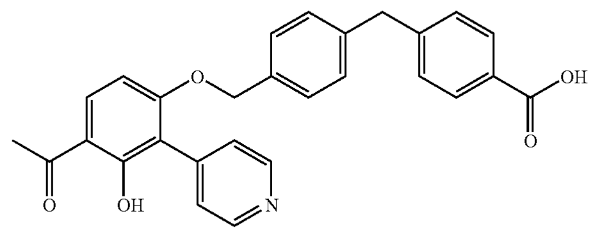 | $^1$H NMR (DMSO-d$_6$) δ 13.24 (s, 1H), 8.88 (m, 2H), 8.13 (d, J = 9.3 Hz, 1H), 8.05 (m, 2H), 7.83 (m, 2H), 7.32 (d, J = 8.3 Hz, 2H), 7.27-7.19 (m, 4H), 6.99 (d, J = 9.3 Hz, 1H), 5.24 (s, 2H), 3.98 (s, 2H), 2.63 (s, 3H); MS (m/e): 454 (M + 1). |
| 119 | 3-[3-(4-Acetyl-3-hydroxy-2-pyridin-4-yl-phenoxymethyl)-benzyl]-benzoic acid | 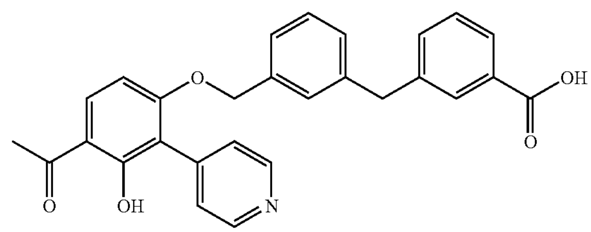 | $^1$H NMR (DMSO-d$_6$) δ 13.20 (s, 1H), 8.83 (dd, J = 6.6 Hz and 1.3 Hz, 2H), 8.1 (d, J = 9.3 Hz, 1H), 7.94 (d, J = 6.5 Hz, 2H), 7.75 (m, 2H), 7.45-7.37 (m, 2H), 7.27 (m, 1H), 7.16 (m, 3H), 6.92 (d, J = 9.0 Hz, 1H), 5.24 (s, 2H), 3.97 (s, 2H), 2.64 (s, 3H); MS (m/e): 454 (M + 1). |
| 120 | 4-[3-(4-Acetyl-3-hydroxy-2-pyridin-4-yl-phenoxymethyl)-benzyl]-benzoic acid | 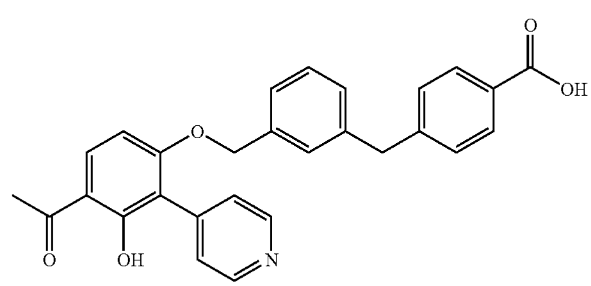 | $^1$H NMR (DMSO-d$_6$) δ 13.23 (s, 1H), 8.88 (d, J = 6.5 Hz, 2H), 8.12 (d, J = 9.0 Hz, 1H), 8.01 (d, J = 6.5 Hz, 2H), 7.84 (d, J = 8.2 Hz, 2H), 7.29-7.24 (m, 3H), 7.18-7.14 (m, 3H), 6.92 (d, J = 9.0 Hz, 1H), 5.24 (s, 2H), 3.97 (s, 2H), 2.64 (s, 3H); MS (m/e): 454 (M + 1). |
| 121 | 1-(2-Hydroxy-3-pyridin-4-yl-4-{4-[3-(2H-tetrazol-5-yl)-benzyl]-benzyloxy}-phenyl)-ethanone | 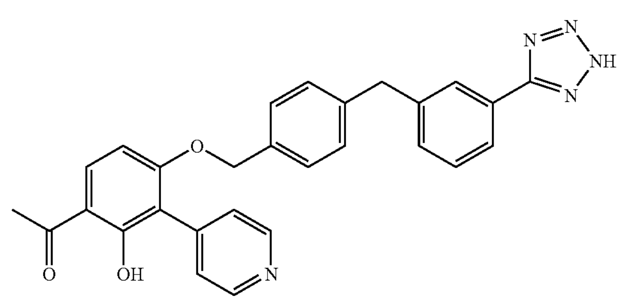 | $^1$H NMR (DMSO-d$_6$) δ 12.96 (s, 1H), 8.65 (bs, 1H), 8.01 (d, J = 9.0 Hz, 1H), 7.90 (s, 1H), 7.83 (d, J = 7.1 Hz, 1H), 7.52-7.42 (m, 5H), 7.23 (s, 5H), 6.86 (d, J = 9.0 Hz, 1H), 5.20 (s, 2H), 4.01 (s, 2H), 2.60 (s, 3H); MS (m/e): 478 (M + 1). |

-continued

| Ex. No. | Chemical Name | Structure | Physical Data |
|---|---|---|---|
| 122 | 1-(2-Hydroxy-3-pyridin-3-yl-4-{4-[3-(2H-tetrazol-5-yl)-benzyl]-benzyloxy}-phenyl)-ethanone | 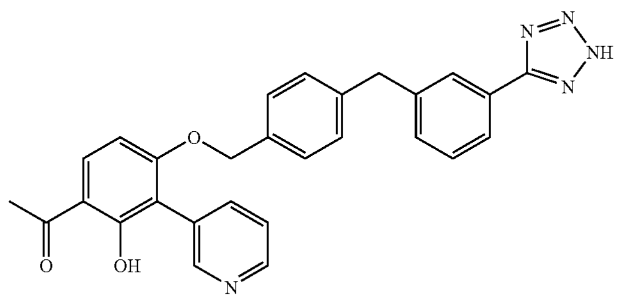 | $^1$H NMR (DMSO-d$_6$) δ 12.98 (s, 1H), 8.66-8.53 (m, 2H), 8.03 (d, J = 9.0 Hz, 1H), 7.96 (d, J = 7.5 Hz, 1H), 7.89 (s, 1H), 7.83 (d, J = 7.5 Hz, 1H), 7.61-7.42 (m, 3H), 7.23 (m, 4H), 6.88 (d, J = 9.0 Hz, 1H), 5.20 (s, 2H), 4.01 (s, 2H), 2.61 (s, 3H); MS (m/e): 478 (M + 1). |
| 123 | 1-(2-Hydroxy-3-pyridin-2-yl-4-{4-[3-(2H-tetrazol-5-yl)-benzyl]-benzyloxy}-phenyl)-ethanone | 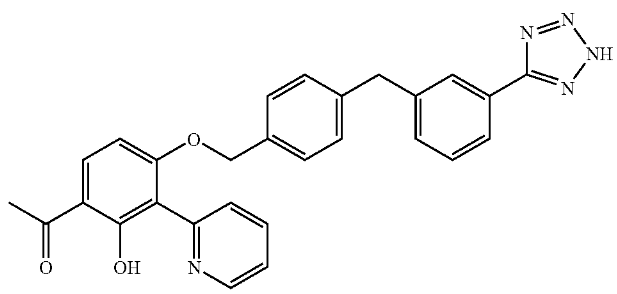 | $^1$H NMR (DMSO-d$_6$) δ 13.09 (s, 1H), 8.62 (m, 1H), 7.95-7.78 (m, 4H), 7.51-7.41 (m, 3H), 7.31 (m, 2H); 7.23-7.17 (m, 4H), 6.79 (d, J = 9.3 Hz, 1H), 5.17 (s, 2H), 4.0 (s, 2H), 2.59 (s, 3H); MS (m/e): 478 (M + 1). |

Examples 124-126

The examples in the following table are prepared by an analogous procedure for coupling as described in Preparation 158 followed by an analogous procedure for ester hydrolysis as described Example 35.

| Ex. No. | Chemical Name | Structure | Physical Data |
|---|---|---|---|
| 124 | 3-{[4-(4-Acetyl-3-hydroxy-2-thiazol-2-yl-phenoxymethyl)-phenyl]-hydroxy-methyl}-benzoic acid | 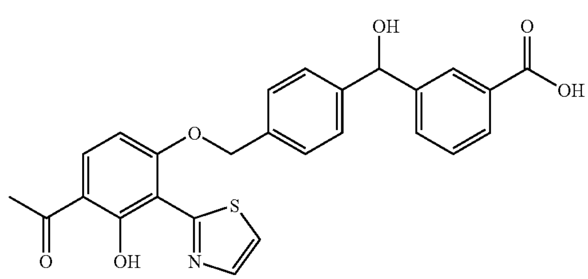 | $^1$H NMR (DMSO-d$_6$) □ 8.03 (d, J = 3.0 Hz, 1H), 7.95-7.92 (m, 1H), 7.85 (d, J = 3.5 Hz, 1H), 7.81-7.74 (m, 2H), 7.62-7.57 (m, 1H), 7.50-7.46 (m, 2H), 7.44-7.37 (m, 3H), 6.91 (d, J = 9.2 Hz, 1H), 6.05-6.00 (bs, 1H), 5.78 (s, 1H), 5.42 (s, 2H), 2.59 (s, 3H); MS (m/e): 474 (M − 1). |
| 125 | 3-{[4-(4-Acetyl-3-hydroxy-2-pyridin-3-yl-phenoxymethyl)-phenyl]-hydroxy-methyl}-benzoic acid | 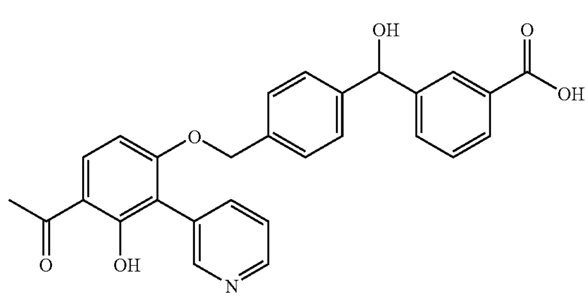 | $^1$H NMR (DMSO-d$_6$) δ 12.9 (s, 1H), 8.71-8.53 (m, 2H), 8.06-7.97 (m, 2H), 7.93-7.89 (m, 1H), 7.79-7.73 (m, 1H), 7.64-7.54 (m, 2H), 7.44-7.36 (m, 1H), 7.36-7.29 (m, 2H), 7.26-7.18 (m, 2H), 6.87 (d, J = 9.2 Hz, 1H), 5.73 (s, 1H), 5.19 (s, 2H), 2.61 (s, 3H); MS (m/e): 468 (M − 1). |

| Ex. No. | Chemical Name | Structure | Physical Data |
|---|---|---|---|
| 126 | 3-{[4-(4-Acetyl-3-hydroxy-2-pyridin-4-yl-phenoxymethyl)-phenyl]-hydroxy-methyl}-benzoic acid | 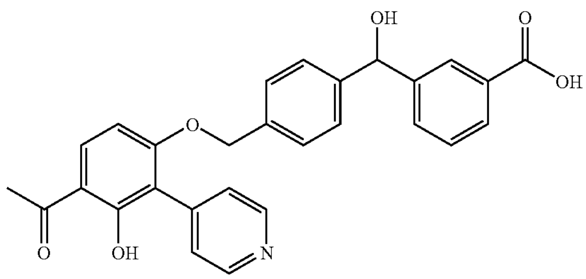 | $^1$H NMR (DMSO-d$_6$) δ 8.60 (bs, 2H), 8.03 (d, J = 9.2 Hz, 1H), 7.98-7.92 (bs, 1H), 7.79 (d, J = 7.5 Hz, 1H), 7.60 (d, J = 7.9 Hz, 1H), 7.47-7.33 (m, 5H), 7.29-7.23 (m, 2H), 6.87 (d, J = 9.2 Hz, 1H), 6.02 (bs, 1H), 5.76 (s, 1H), 5.22 (s, 2H), 2.63 (s, 3H); MS (m/e): 468 (M − 1). |

Examples 127-131

The examples in the following table are prepared by an analogous alkylation procedure as in described in Preparation 155. Followed by, for compounds of formula I where Z is tetrazolyl, the examples are prepared by an analogous procedure as described in Example 1 or, for compounds of formula I where Z is carboxylic acid, the examples are prepared by an analogous procedure for deprotection as described in Preparation 33 followed by an analogous procedure for ester hydrolysis as described Example 35.

| Ex. No. | Chemical name | Structure | Physical data |
|---|---|---|---|
| 127 | 1-[2-Hydroxy-4-(4-{hydroxy-[3-(2H-tetrazol-5-yl)-phenyl]-methyl}-benzyloxy)-3-thiophen-3-yl-phenyl]-ethanone | 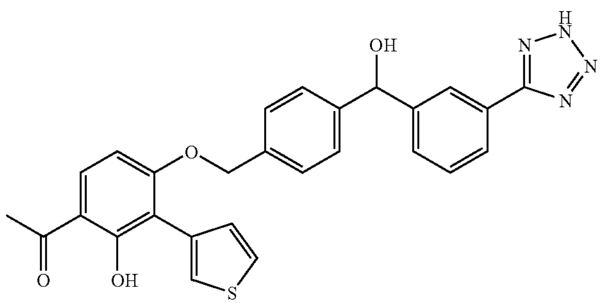 | $^1$H NMR (DMSO-d$_6$) δ 13.1 (s, 1H), 8.12 (bs, 1H), 7.94 (d, J = 9.2 Hz, 1H), 7.91-7.87 (m, 1H), 7.60-7.48 (m, 4H), 7.45-7.42 (m, 2H), 7.36-7.34 (m, 2H), 7.28-7.25 (m, 1H), 6.13-6.10 (m, 1H), 5.83-5.80 (m, 1H), 5.23 (m, 2H), 2.62 (m, 3H); MS (m/e): 497 (M − 1). |
| 128 | 3-{[4-(4-Acetyl-3-hydroxy-2-thiophen-3-yl-phenoxymethyl)-phenyl]-hydroxy-methyl}-benzoic acid | 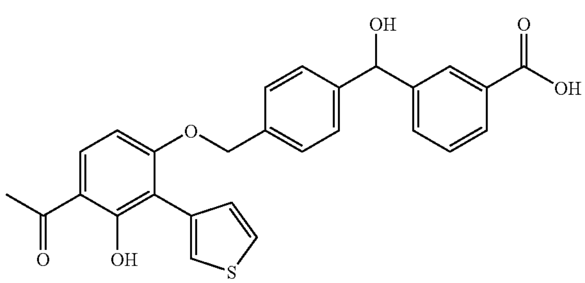 | $^1$H NMR (DMSO-d$_6$) δ 7.96-7.93 (m, 2H), 7.80-7.76 (m, 1H), 7.61-7.56 (m, 2H), 7.53-7.50 (m, 1H), 7.44-7.25 (m, 6H), 6.83 (d, J = 9.2 Hz, 1H), 5.77 (s, 1H), 5.23 (s, 2H), 2.63 (s, 3H); MS (m/e): 473 (M − 1). |
| 129 | 1-[2-Hydroxy-4-(4-{hydroxy-[3-(2H-tetrazol-5-yl)-phenyl]-methyl}-benzyloxy)-3-thiophen-2-yl-phenyl]-ethanone | 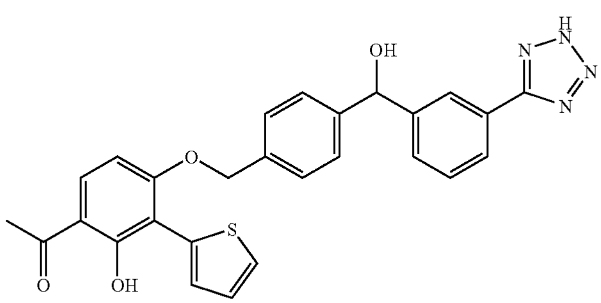 | $^1$H NMR (DMSO-d$_6$) δ 13.5 (bs, 1H), 8.16-8.10 (bs, 1H), 7.95 (d, J = 8.8 Hz, 1H), 7.92-7.86 (m, 1H), 7.62-7.50 (m, 3H), 7.49-7.36 (m, 5H), 7.14-7.07 (m, 1H), 6.87 (d, J = 9.2 Hz, 1H), 6.14-6.11 (m, 1H), 5.84-5.82 (m, 1H), 5.31 (m, 2H), 2.64 (s, 3H); MS (m/e): 497 (M − 1). |

-continued

| Ex. No. | Chemical name | Structure | Physical data |
|---|---|---|---|
| 130 | 3-{[4-(4-Acetyl-3-hydroxy-2-thiophen-2-yl-phenoxymethyl)-phenyl]-hydroxy-methyl}-benzoic acid | 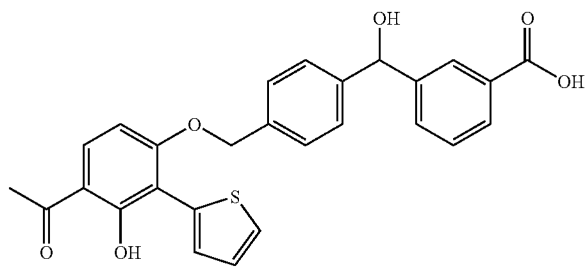 | $^1$H NMR (DMSO-d$_6$) δ 13.5 (s, 1H), 7.97-7.90 (m, 2H), 7.79-7.73 (m, 1H), 7.62-7.58 (m, 1H), 7.56-7.53 (m, 1H), 7.46-7.31 (m, 6H), 7.10-7.04 (m, 1H), 6.83 (d, J = 9.2 Hz, 1H), 6.00 (bs, 1H), 5.75 (s, 1H), 5.27 (s, 2H), 2.60 (s, 3H); MS (m/e): 473 (M − 1). |
| 131 | 1-[2-Hydroxy-4-(4-{hydroxy-[3-(2H-tetrazol-5-yl)-phenyl]-methyl}-benzyloxy)-3-pyridin-2-yl-phenyl]-ethanone | 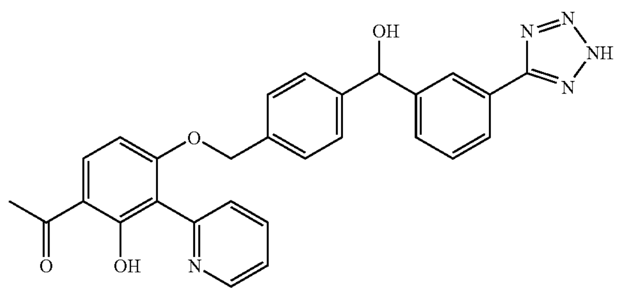 | $^1$H NMR (DMSO-d$_6$) δ 13.1 (bs, 1H), 8.68-8.60 (m, 1H), 8.12-8.02 (bs, 1H), 7.97 (d, J = 9.2 Hz, 1H), 7.88-7.78 (m, 2H), 7.50-7.43 (m, 3H), 7.41-7.31 (m, 3H), 7.27-7.21 (m, 2H), 6.82 (d, J = 9.2 Hz, 1H), 6.03 (bs, 1H), 5.76 (s, 1H), 5.20 (s, 2H), 2.62 (s, 3H); MS (m/e): 492 (M − 1). |

Examples 132-141

The examples in the following table are prepared an analogous alkylation procedure as described in Preparation 155, followed by an analogous procedure described in Example 1 for compounds of formula I where Z is tetrazolyl or an analogous procedure described Example 13 for compounds of formula I where Z is carboxylic acid.

| Ex No. | Chemical Name | Structure | Physical Data |
|---|---|---|---|
| 132 | 3-[4-(4-Acetyl-3-hydroxy-2-iodo-phenoxymethyl)-benzyl]-benzoic acid | 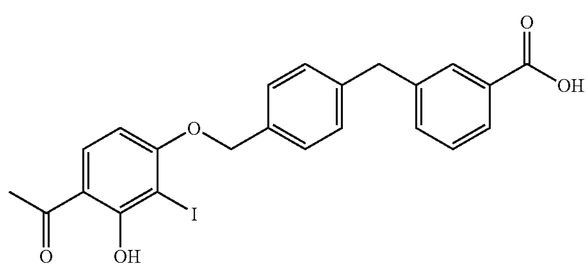 | $^1$H NMR (DMSO-d$_6$) δ 13.5(s, 1H), 12.9 (bs, 1H), 8.0 (d,J = 9.0 Hz, 1H), 7.84-7.77(m, 2H), 7.54 (d, J = 7.8 Hz,1H), 7.46-7.41 (m, 3H), 7.31(d, J = 8.0 Hz, 2H), 6.78 (d, J =9.0 Hz), 5.33 (s, 2H), 4.05 (s, 2H), 2.63 (s, 3H); MS(m/e): 501 (M − 1). |
| 133 | 3-[4-(4-Acetyl-3-hydroxy-2-propyl-phenoxymethyl)-benzyl]-benzoic acid | 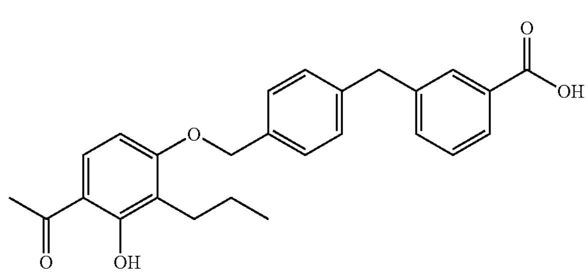 | $^1$H NMR (DMSO-d$_6$) δ 12.90(bs, 1H), 12.82 (s, 1H), 7.79-7.73 (m, 3H), 7.49 (m, 1H),7.41-7.33 (m, 3H), 7.26 (d, J =8.0 Hz, 2H), 6.69 (d, J =9.0 Hz, 1H), 5.19 (s, 2H), 4.0(s, 2H), 2.54 (s, 5H), 1.50-1.40 (m, 2H), 0.84 (t, J = 7.5 Hz, 3H); MS (m/e): 419(M + 1). |

| Ex No. | Chemical Name | Structure | Physical Data |
|---|---|---|---|
| 134 | 4-[4-(4-Acetyl-3-hydroxy-2-propyl-phenoxymethyl)-benzyl]-benzoic acid | 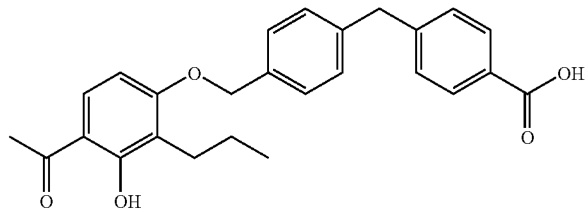 | $^1$H NMR (DMSO-d$_6$) δ 12.82 (s, 1H), 12.73 (bs, 1H), 7.85(m, 2H), 7.77 (d, J = 9.2 Hz,1H), 7.36-7.32 (m, 4H), 7.26(d, J = 8.0 Hz, 2H), 6.69 (d, J =9.0 Hz, 1H), 5.19 (s, 2H),4.0 (s, 2H), 2.57-2.53 (m,5H), 1.50-1.40 (m, 2H), 1.15 (t, J = 7.0 Hz, 3H); MS(m/e): 419 (M + 1). |
| 135 | 4-[4-(4-Acetyl-3-hydroxy-2-methyl-phenoxymethyl)-benzyl]-benzoic acid | 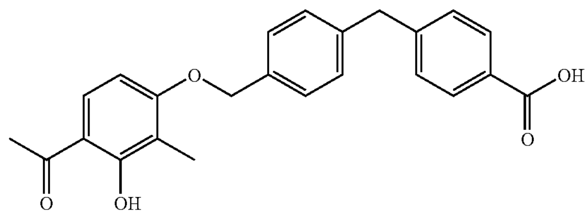 | $^1$H NMR (DMSO-d$_6$) δ 12.82(s, 1H), 12.77 (bs, 1H), 7.84(m, 2H), 7.77 (d, J = 9.0 Hz,1H), 7.38-7.32 (m, 4H), 7.25(d, J = 7.0 Hz, 2H), 6.70 (d, J =9.0 Hz, 1H), 5.20 (s, 2H),4.0 (s, 2H), 2.55 (s, 3H), 2.0 (s, 3H); MS (m/e): 389 (M − 1). |
| 136 | 4-[4-(4-Acetyl-2-chloro-3-hydroxy-phenoxymethyl)-benzyl]-benzoic acid | 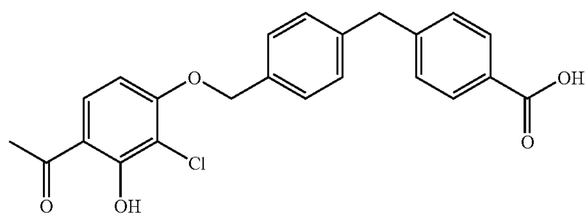 | $^1$H NMR (DMSO-d$_6$) δ 13.11(s, 1H), 12.83 (s, 1H), 7.91(d, J = 9.2 Hz, 1H), 7.74 (m,2H), 7.39-7.32 (m, 4H), 7.27(d, J = 8.2 Hz, 2H), 6.87 (d, J =9.2 Hz, 1H), 5.29 (s, 2H),4.0 (s, 2H), 2.59 (s, 3H); MS(m/e): 411 (M + 1). |
| 137 | 1-(2-Hydroxy-3-iodo-4-{4-[3-(2H-tetrazol-5-yl)-benzyl]-benzyloxy}-phenyl)-ethanone | 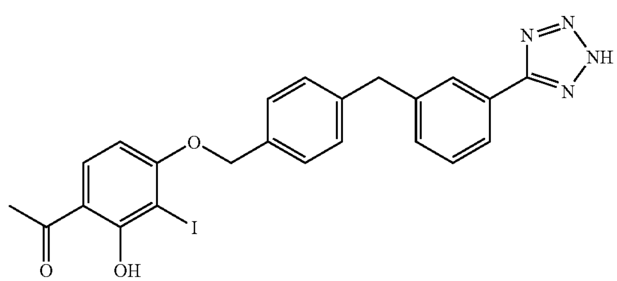 | $^1$H NMR (DMSO-d$_6$) δ 13.48(s, 1H), 7.95 (m, 2H), 7.84(d, J = 7.0 Hz, 1H), 7.53-7.41 (m, 4H), 7.31 (d, J = 8.0 Hz, 2H), 6.74 (d, J = 9.0 Hz, 1H), 5.29 (s, 2H), 4.05 (s, 2H), 2.59 (s, 3H); MS (m/e):527 (M + 1). |
| 138 | 4-[3-(4-Acetyl-3-hydroxy-2-propyl-phenoxymethyl)-benzyl]-benzoic acid | 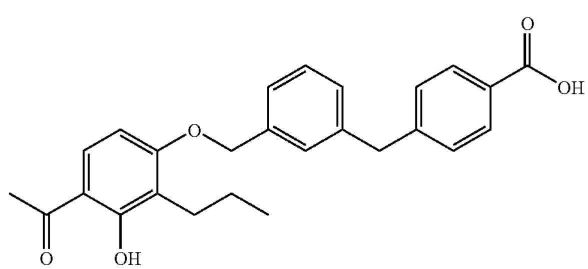 | $^1$H NMR (DMSO-d$_6$) δ12.82 (s, 1H), 12.79 (s, 1H),7.83 (m, 2H), 7.76 (d, J = 9.0Hz, 1H), 7.34-7.30 (m, 3H),7.27-7.20 (m, 3H), 6.67 (d, J =9.2 Hz, 1H), 5.18 (s, 2H), 4.01 (s, 2H), 2.54-2.47 (m, 5H), 1.45-1.36 (m, 2H), 0.80(t, J = 7.5 Hz, 3H); MS (m/e): 419 (M + 1). |
| 139 | 4-[3-(4-Acetyl-3-hydroxy-2-methyl-phenoxymethyl)-benzyl]-benzoic acid | 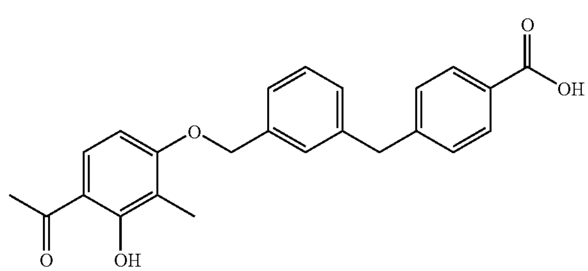 | $^1$H NMR (DMSO-d$_6$) δ12.82 (s, 1H), 12.75 (s, 1H),7.84 (d, J = 8.1 Hz, 2H), 7.77(d, J = 9.0 Hz, 1H), 7.34-7.25(m, 5H), 7.20 (d, J = 7.5 Hz, 1H), 6.68 (d, J = 9.1 Hz, 1H), 5.19 (s, 2H) 4.02 (s, 2H), 2.55 (s, 3H), 1.97 (s, 3H); MS (m/e): 391 (M + 1). |

-continued

| Ex No. | Chemical Name | Structure | Physical Data |
|---|---|---|---|
| 140 | 4-[3-(4-Acetyl-2-chloro-3-hydroxy-phenoxymethyl)-benzyl]-benzoic acid | 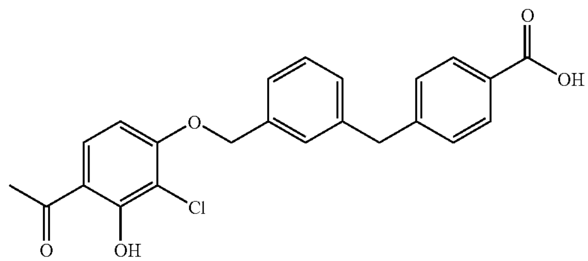 | $^1$H NMR (DMSO-d$_6$) δ13.12 (s, 1H) 12.83 (s, 1H),7.90 (d, J 9.1 Hz, 1H), 7.84(d, J = 8.3 Hz, 2H), 7.35-7.27(m, 5H), 7.22 (d, J = 7.1 Hz, 1H), 6.85 (d, J = 9.0 Hz, 1H), 5.29 (s, 2H), 4.02 (s, 2H), 2.60 (s, 3H); MS (m/e): 409(M − 1). |
| 141 | 3-[4-(4-Acetyl-3-hydroxy-2-thiophen-3-yl-phenoxymethyl)-benzyl]-benzoic acid | 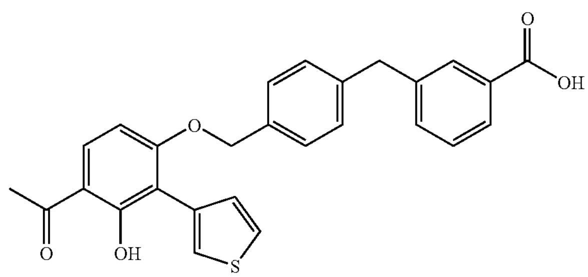 | $^1$H NMR (DMSO-d$_6$) δ13.1 (bs, 1H), 7.95 (d, J = 9.2Hz, 1H), 7.84-7.75 (m, 2H),7.59-7.55 (m, 1H), 7.53-7.48(m, 2H), 7.46-7.39 (m, 1H),7.34-7.22 (m, 5H), 6.84 (d, J =8.8 Hz, 1H), 5.23 (s, 2H), 4.02 (s, 2H), 2.63 (s, 3H); MS (m/e): 457 (M − 1). |

Preparation 168

Synthesis of N-hydroxy-2-(4-methoxy-phenoxy)-acetamidine

Add sodium acetate (5.1 g, 62 mmol) to 4-methoxyphenoxyacetonitrile (5.0 g, 31 mmol) and hydroxylamine hydrochloride (4.3 g, 62 mmol) in methanol (100 mL). Stir the resulting mixture at room temperature for 20 hours. Filter the resulting mixture through Celite, concentrate, stir in chloroform for 18 hours and filter. Concentrate the resulting solution to the title compound (5.1 g). LC-MS (m/e): 197 (M+1).

Preparation 169

Synthesis of 4-[3-(4-methoxy-phenoxymethyl)-[1,2,4]oxadiazol-5-ylmethyl]-benzoic acid ethyl ester Add oxaxyl chloride (1.25 mL, 14 mmol) to 4-carboxymethyl-benzoic acid ethyl ester (365 mg, 1.75 mmol) in benzene (11 mL) and a drop of dimethylformamide at room temperature under argon gas over a 5 minute period. Stir the reaction mixture for 2 hours at room temperature. Concentrate the reaction mixture to an oil. Redissolve the oil in dimethylformamide (10 mL) and N-hydroxy-2-(4-methoxyphenoxy)-acetamidine (380 mg, 1.9 mmol) is added. Stir the reaction mixture at room temperature for 3 hours. Heat the reaction mixture to 120° C. and stir for 7 hours. After cooling to room temperature, quench the reaction mixture with water and extract with ethyl acetate (3×). Combine the organic layers, wash with brine, dry over sodium sulfate, and concentrate. Purify the residue by flash column chromatography using 20% ethyl acetate/hexane to give the title compound (201 mg, 31%). LC-MS (m/e): 369 (M+1).

Preparation 170

Synthesis of 4-(3-hydroxymethyl-[1,2,4]oxadiazol-5-ylmethyl)-benzoic acid ethyl ester Add half of the ammonium cerium(IV) nitrate (285 mg, 0.52 mmol) to a solution of 4-[3-(4-methoxy-phenoxymethyl)-[1,2,4]oxadiazol-5-ylmethyl]-benzoic acid ethyl ester (193 mg, 0.52 mmol) in acetonitrile (9 mL) and water (2.3 mL) at room temperature. Stir the reaction mixture at room temperature for one hour and add the second half of the ammonium cerium(IV) nitrate (285 mg, 0.52 mmol). Stir at room temperature for an additional hour, dilute the reaction is with saturated aqueous sodium hydrideCO$_3$, stir for 5 minutes, dilute with water, and extracte with ethyl acetate (3×). Wash the combined organic layers with brine, dry over MgSO$_4$, and concentrate. Purify the residue by flash column chromatography using 50% ethyl acetate/hexane to give the title compound (720 mg, 81%). LC-MS (m/e): 263 (M+1).

Preparation 171

Synthesis of 4-[3-(4-acetyl-2-chloro-3-hydroxy-phenoxymethyl)-[1,2,4]oxadiazol-5-ylmethyl]-benzoic acid ethyl ester Add polymer support PPh$_3$ (287 mg, 0.86 mmol to a solution of 4-(3-hydroxymethyl-[1,2,4]oxadiazol-5-ylmethyl)-benzoic acid ethyl ester (80 mg, 0.41 mmol) in anhydrous CH$_2$Cl$_2$ (8 mL) under argon gas at room temperature. Add 1-(3-chloro-2,4-dihydroxy-phenyl)-ethanone (115 mg, 0.62 mmol) to the mixture, followed by diisopropyl azodicarboxylate (194 µL, 0.86 mmol). After 1.5 hours at room temperature, remove the polymer by filtration and concentrate the filtrate. Purify the residue by flash column chromatography using 30% ethyl acetate/hexane to give the title compound (60 mg, 34%). LC-MS (m/e): 429 (M−1).

Example 142

Synthesis of 4-[3-(4-acetyl-2-chloro-3-hydroxy-phenoxymethyl)-[1,2,4]oxadiazol-5-ylmethyl]-benzoic acid

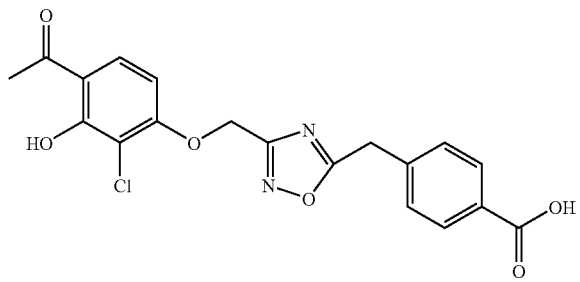

Add 1 N hydrochloric acid (3.6 mL) to a solution of 4-[3-(4-acetyl-2-chloro-3-hydroxy-phenoxymethyl)-[1,2,4]oxadiazol-5-ylmethyl]-benzoic acid ethyl ester (55 mg, 0.13 mmol) in EtOH (1.2 mL) in a microwave tube. Seal the tube and heat in a microwave reactor at 150° C. for 30 min. Purify the reaction mixture by reverse phase HPLC using a gradient of 90:10 to 20:80 ($H_2O$/0.1% TFA):$CH_3CN$ as eluent to give the title compound (17 mg, 33%). $^1$H NMR (DMSO-$d_6$) δ 13.07 (s, 1H), 12.92 (s, 1H), 7.86-7.94 (m, 3H), 7.44 (d, 2H), 6.89 (d, 1H), 5.49 (s, 2H), 4.49 (s, 2H), 2.59 (s, 3H). LC-MS (m/e): 401 (M−1).

Preparation 172

Synthesis of 3-[3-(4-methoxy-phenoxymethyl)-[1,2,4]oxadiazol-5-ylmethyl]-benzoic acid ethyl ester The title compound is prepared essentially as described for 4-[3-(4-methoxy-phenoxymethyl)-[1,2,4]oxadiazol-5-ylmethyl]-benzoic acid ethyl ester, employing 3-carboxymethyl-benzoic acid ethyl ester (45%). LC-MS (m/e): 369 (M+1).

Preparation 173

Synthesis of 3-(3-hydroxymethyl-[1,2,4]oxadiazol-5-ylmethyl)-benzoic acid ethyl ester The title compound is prepared essentially as described for 4-(3-hydroxymethyl-[1,2,4]oxadiazol-5-ylmethyl)-benzoic acid ethyl ester, employing 3-[3-(4-methoxy-phenoxymethyl)-[1,2,4]oxadiazol-5-ylmethyl]-benzoic acid ethyl ester (81%). LC-MS (m/e): 263 (M+1).

Preparation 174

Synthesis of 3-[3-(4-acetyl-2-chloro-3-hydroxy-phenoxymethyl)-[1,2,4]oxadiazol-5-ylmethyl]-benzoic acid ethyl ester The title compound is prepared essentially as described for 4-[3-(4-acetyl-2-chloro-3-hydroxy-phenoxymethyl)-[1,2,4]oxadiazol-5-ylmethyl]-benzoic acid ethyl ester, employing 3-(3-hydroxymethyl-[1,2,4]oxadiazol-5-ylmethyl)-benzoic acid ethyl ester (71%). LC-MS (m/e): 429 (M−1).

Example 143

Synthesis of 3-[3-(4-acetyl-2-chloro-3-hydroxy-phenoxymethyl)-[1,2,4]oxadiazol-5-ylmethyl]-benzoic acid

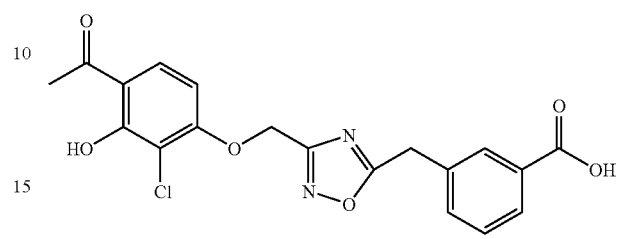

The title compound is prepared essentially as described for 4-[3-(4-acetyl-2-chloro-3-hydroxy-phenoxymethyl)-[1,2,4]oxadiazol-5-ylmethyl]-benzoic acid, employing 3-[3-(4-acetyl-2-chloro-3-hydroxy-phenoxymethyl)-[1,2,4]oxadiazol-5-ylmethyl]-benzoic acid ethyl ester. $^1$H NMR (DMSO-$d_6$) δ 13.06 (s, 1H), 12.99 (s, 1H), 7.91 (m, 2H), 7.83 (m, 1H), 7.58 (m, 1H), 7.46 (dd, 1H), 6.89 (d, 1H), 5.49 (s, 2H), 4.48 (s, 2H), 2.59 (s, 3H). LC-MS (m/e): 401 (M−1).

Preparation 175

Synthesis of N-hydroxy-2-(3-iodo-phenyl)-acetamidine

Add sodium carbonate (2.0 g, 18.5 mmol) to a mixture of 3-iodophenylacetonitrile (4.5 g, 18.5 mmol) and hydroxylamine hydrochloride (1.3 g, 18.5 mmol) in 10:1 EtOH:$H_2O$ (11 mL). Heat the reaction mixture to 50° C. for 2 days. Cool to RT, then filter to remove the solids. Concentrate the filtrate to afford the title compound (4.94 g). LC-MS (m/e): 277 (M+1).

Preparation 176

Synthesis of 5-chloromethyl-3-(3-iodo-benzyl)-[1,2,4]oxadiazole

Add a solution of chloroacetic anhydride (1.5 g, 9 mmol) in toluene (20 mL) to N-hydroxy-2-(3-iodo-phenyl)-acetamidine (2.5 g, 9 mmol) in anhydrous toluene (20 mL). Fit the flask with a Dean-Stark trap and heat to reflux for 7 h. Concentrate the mixture and purify the residue by flash chromatography using 15% tetrahydrofuran/hexane to give the title compound (1.45 g, 48%). $^1$H NMR ($CDCl_3$) δ 7.65 (s, 1H), 7.59 (d, 1H), 7.26 (d, 1H), 7.04 (dd, 1H), 4.62 (s, 2H), 4.01 (s, 2H).

Preparation 177

Synthesis of 1-{2-hydroxy-4-[3-(3-iodo-benzyl)-[1,2,4]oxadiazol-5-ylmethoxy]-3-methyl-phenyl}-ethanone Add lithium carbonate (49 mg, 0.66 mmol) and 5-chloromethyl-3-(3-iodo-benzyl)-[1,2,4]oxadiazole (200 mg, 0.60 mmol) to a solution of 1-(2,4-dihydroxy-3-methyl-phenyl)-ethanone (110 mg, 0.66 mmol) in anhydrous dimethylformamide (20 mL) 4]oxadiazole (200 mg, 0.60 mmol). Heat the reaction mixture at 60° C. overnight. Cool the reaction mixture to RT, pour into H₂O, and extract with diethyl ether (3×). Combine the organic layers, wash with brine, dry over sodium sulfate, and concentrate to provide the title compound (150 mg). LC-MS (m/e): 463 (M−1).

Example 144

Synthesis of 3-[5-(4-acetyl-3-hydroxy-2-methyl-phenoxymethyl)-[1,2,4]oxadiazol-3-ylmethyl]-benzoic acid

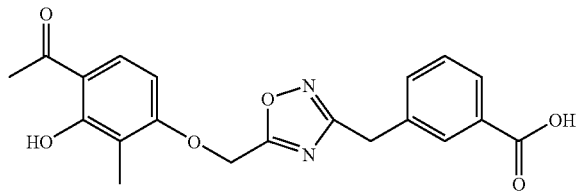

Combine 1-{2-hydroxy-4-[3-(3-iodo-benzyl)-[1,2,4]oxadiazol-5-ylmethoxy]-3-methyl-phenyl}-ethanone (150 mg, 0.32 mmol), sodium dodecyl sulfate (300 mg, 1.0 mmol), K₂CO₃ (45 mg, 0.32 mmol), 1-butanol (200 μL), and 1 drop of toluene in H₂O (4 mL) in a pressure vessel, then degas with Ar for 5 min. Add PdCl₂(MeCN)₂ (18 mg, 0.07 mmol) to the reaction mixture. Exchange the atmosphere with carbon monoxide and heat the mixture to 70° C. under 20 psi of carbon monoxide. The reaction is heated until complete. Filter the black mixture through filter cel. Acidify the filtrate with 5 N hydrochloric acid to pH=1. A milky white mixture forms. Add a small amount of methanol to induce crystallization Collect the crystals by filtration to give the title compound (79 mg, 65%). ¹H NMR (DMSO-d₆) δ 12.99 (s, 1H), 12.79 (s, 1H), 7.86 (m, 1H), 7.79 (m, 2H), 7.52 (m, 1H), 7.42 (dd, 1H), 6.67 (d, 1H), 5.60 (s, 2H), 4.19 (s, 2H), 2.55 (s, 3H), 1.99 (s, 3H). LC-MS (m/e): 381 (M−1).

Preparation 178

Synthesis of 1-{3-chloro-2-hydroxy-4-[3-(3-iodo-benzyl)-[1,2,4]oxadiazol-5-ylmethoxy]-phenyl}-ethanone The title compound is prepared essentially as described for 1-{2-hydroxy-4-[3-(3-iodo-benzyl)-[1,2,4]oxadiazol-5-ylmethoxy]-3-methyl-phenyl}-ethanone, employing 1-(3-chloro-2,4-dihydroxy-phenyl)-ethanone (57%). LC-MS (m/e): 483 (M−1).

Example 145

Synthesis of 3-[5-(4-acetyl-2-chloro-3-hydroxy-phenoxymethyl)-[1,2,4]oxadiazol-3-ylmethyl]-benzoic acid

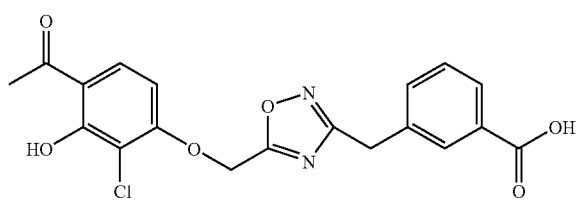

The title compound is prepared essentially as described for 3-[5-(4-acetyl-3-hydroxy-2-methyl-phenoxymethyl)-[1,2,4] oxadiazol-3-ylmethyl]-benzoic acid of Example 140 employing 1-{3-chloro-2-hydroxy-4-[3-(3-iodo-benzyl)-[1,2,4]oxadiazol-5-ylmethoxy]-phenyl}-ethanone. ¹H NMR (DMSO-d₆) δ 13.06 (s, 1H), 12.94 (s, 1H), 7.92 (d, 1H), 7.85 (s, 1H), 7.80 (m, 1H), 7.52 (m, 1H), 7.42 (dd, 1H), 6.84 (d, 1H), 5.71 (s, 2H), 4.20 (s, 2H), 2.60 (s, 3H). LC-MS (m/e): 401 (M−1).

Preparation 179

Synthesis of N-hydroxy-2-(4-iodo-phenyl)-acetamidine

The title compound is prepared essentially as described for N-hydroxy-2-(3-iodo-phenyl)-acetamidine, employing (4-iodo-phenyl)-acetonitrile. LC-MS (m/e): 277 (M+1).

Preparation 180

Synthesis of 5-chloromethyl-3-(4-iodo-benzyl)-[1,2,4]oxadiazole

The title compound is prepared essentially as described for 5-chloromethyl-3-(3-iodo-benzyl)-[1,2,4]oxadiazole, employing N-hydroxy-2-(4-iodo-phenyl)-acetamidine. LC-MS (m/e): 335 (M+1).

Preparation 181

Synthesis of 1-{3-chloro-2-hydroxy-4-[3-(4-iodo-benzyl)-[1,2,4]oxadiazol-5-ylmethoxy]-phenyl}-ethanone The title compound is prepared essentially as described for 1-{2-hydroxy-4-[3-(3-iodo-benzyl)-[1,2,4]oxadiazol-5-ylmethoxy]-3-methyl-phenyl}-ethanone, employing 1-(3-chloro-2,4-dihydroxy-phenyl)-ethanone and 5-Chlormethyl-3-(4-iodo-benzyl)-[1,2,4]oxadiazole. LC-MS (m/e): 485 (M+1).

Example 146

Synthesis of 4-[5-(4-acetyl-2-chloro-3-hydroxy-phenoxymethyl)-[1,2,4]oxadiazol-3-ylmethyl]-benzoic acid

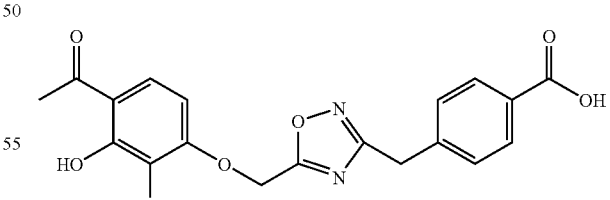

The title compound is prepared essentially as described for 3-[5-(4-acetyl-3-hydroxy-2-methyl-phenoxymethyl)-[1,2,4] oxadiazol-3-ylmethyl]-benzoic acid of Example 140, employing 1-{3-chloro-2-hydroxy-4-[3-(4-iodo-benzyl)-[1,2,4]oxadiazol-5-ylmethoxy]-phenyl}-ethanone. ¹H NMR (DMSO-d₆) δ 13.05 (s, 1H), 12.86 (s, 1H), 7.92 (d, 1H), 7.85 (m, 2H), 7.38 (d, 2H), 6.84 (d, 1H), 5.72 (s, 2H), 4.18 (s, 2H), 2.59 (s, 3H). LC-MS (m/e): 401 (M−1).

Preparation 182

Synthesis of 1-{2-Hydroxy-4-[3-(4-iodo-benzyl)-[1,2,4]oxadiazol-5-ylmethoxy]-3-methyl-phenyl}-ethanone The title compound is prepared essentially as described for 1-{2-hydroxy-4-[3-(3-iodo-benzyl)-[1,2,4]oxadiazol-5-ylmethoxy]-3-methyl-phenyl}-ethanone, employing 5-chloromethyl-3-(4-iodo-benzyl)-[1,2,4]oxadiazole and 1-(2,4-Dihydroxy-3-methyl-phenyl)-ethanone. LC-MS (m/e): 463 (M−1).

Example 147

Synthesis of 4-[5-(4-acetyl-3-hydroxy-2-methyl-phenoxymethyl)-[1,2,4]oxadiazol-3-ylmethyl]-benzoic acid

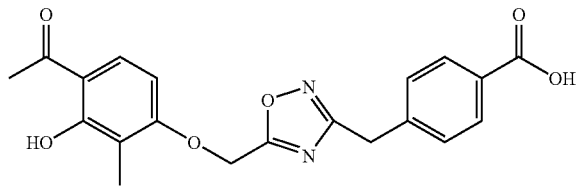

The title compound is prepared essentially as described for 3-[5-(4-acetyl-3-hydroxy-2-methyl-phenoxymethyl)-[1,2,4]oxadiazol-3-ylmethyl]-benzoic acid, employing 1-{2-hydroxy-4-[3-(4-iodo-benzyl)-[1,2,4]oxadiazol-5-ylmethoxy]-3-methyl-phenyl}-ethanone. $^1$H NMR (DMSO-$d_6$) δ 12.84 (s, 1H), 12.80 (s, 1H), 7.86 (m. 2H), 7.78 (d, 1H), 7.38 (d, 2H), 6.67 (d, 1H), 5.60 (s, 2H), 4.19 (s, 2H), 2.55 (s, 3H), 1.99 (s, 3H). LC-MS (m/e): 381 (M−1).

Preparation 183

Synthesis of N-hydroxy-2-(4-methoxy-phenoxy)-acetamidine

Add sodium acetate (5.1 g, 62 mmol) to 4-methoxyphenoxyacetonitrile (5.0 g, 31 mmol) and hydroxylamine hydrochloride (4.3 g, 62 mmol) in methanol (100 mL). Stir the resulting mixture at room temperature for 20 hours. Filter the resulting mixture through Celite, concentrate, stir in chloroform for 18 hours and filter. Concentrate the resulting solution to the title compound (5.1 g). LC-MS (m/e): 197 (M+1).

Preparation 184

Synthesis of 4-[3-(4-methoxy-phenoxymethyl)-[1,2,4]oxadiazol-5-ylmethyl]-benzoic acid ethyl ester Add oxaxyl chloride (1.25 mL, 14 mmol) to 4-carboxymethyl-benzoic acid ethyl ester (365 mg, 1.75 mmol) in benzene (11 mL) and a drop of dimethylformamide at room temperature under argon gas over a 5 minute period. Stir the reaction mixture for 2 hours at room temperature. Concentrate the reaction mixture to an oil. Redissolve the oil in dimethylformamide (10 mL) and N-hydroxy-2-(4-methoxy-phenoxy)-acetamidine (380 mg, 1.9 mmol) is added. Stir the reaction mixture at room temperature for 3 hours. Heat the reaction mixture to 120° C. and stir for 7 hours. After cooling to room temperature, quench the reaction mixture with water and extract with ethyl acetate (3×). Combine the organic layers, wash with brine, dry over sodium sulfate, and concentrate. Purify the residue by flash column chromatography using 20% ethyl acetate/hexane to give the title compound (201 mg, 31%). LC-MS (m/e): 369 (M+1).

Preparation 185

Synthesis of 4-(3-hydroxymethyl-[1,2,4]oxadiazol-5-ylmethyl)-benzoic acid ethyl ester Add half of the ammonium cerium(IV) nitrate (285 mg, 0.52 mmol) to a solution of 4-[3-(4-methoxy-phenoxymethyl)-[1,2,4]oxadiazol-5-ylmethyl]-benzoic acid ethyl ester (193 mg, 0.52 mmol) in acetonitrile (9 mL) and water (2.3 mL) at room temperature. Stir the reaction mixture at room temperature for one hour and add the second half of the ammonium cerium(IV) nitrate (285 mg, 0.52 mmol). Stir at room temperature for an additional hour, dilute the reaction is with saturated aqueous sodium hydrideCO$_3$, stir for 5 minutes, dilute with water, and extracte with ethyl acetate (3×). Wash the combined organic layers with brine, dry over MgSO$_4$, and concentrate. Purify the residue by flash column chromatography using 50% ethyl acetate/hexane to give the title compound (720 mg, 81%). LC-MS (m/e): 263 (M+1).

Preparation 186

Synthesis of 4-[3-(4-acetyl-2-chloro-3-hydroxy-phenoxymethyl)-[1,2,4]oxadiazol-5-ylmethyl]-benzoic acid ethyl ester Add polymer support PPh$_3$ (287 mg, 0.86 mmol to a solution of 4-(3-hydroxymethyl-[1,2,4]oxadiazol-5-ylmethyl)-benzoic acid ethyl ester (80 mg, 0.41 mmol) in anhydrous CH$_2$Cl$_2$ (8 mL) under argon gas at room temperature. Add 1-(3-chloro-2,4-dihydroxy-phenyl)-ethanone (115 mg, 0.62 mmol) to the mixture, followed by diisopropyl azodicarboxylate (194 μL, 0.86 mmol). After 1.5 hours at room temperature, remove the polymer by filtration and concentrate the filtrate. Purify the residue by flash column chromatography using 30% ethyl acetate/hexane to give the title compound (60 mg, 34%). LC-MS (m/e): 429 (M−1).

Example 148

Synthesis of 4-[3-(4-acetyl-2-chloro-3-hydroxy-phenoxymethyl)-[1,2,4]oxadiazol-5-ylmethyl]-benzoic acid

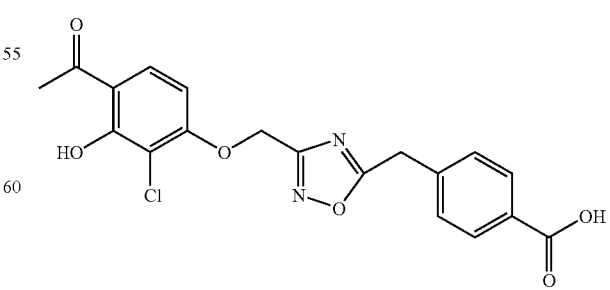

Add 1 N hydrochloric acid (3.6 mL) to a solution of 4-[3-(4-acetyl-2-chloro-3-hydroxy-phenoxymethyl)-[1,2,4]oxadiazol-5-ylmethyl]-benzoic acid ethyl ester (55 mg, 0.13 mmol) in EtOH (1.2 mL) in a microwave tube. Seal the tube and heat in a microwave reactor at 150° C. for 30 min. Purify the reaction mixture by reverse phase HPLC using a gradient of 90:10 to 20:80 (H$_2$O/0.1% TFA):CCH$_3$CN as eluent to give the title compound (17 mg, 33%). $^1$H NMR (DMSO-d$_6$) δ 13.07 (s, 1H), 12.92 (s, 1H), 7.86-7.94 (m, 3H), 7.44 (d, 2H), 6.89 (d, 1H), 5.49 (s, 2H), 4.49 (s, 2H), 2.59 (s, 3H). LC-MS (m/e): 401 (M−1).

Preparation 187

Synthesis of 3-[3-(4-methoxy-phenoxymethyl)-[1,2,4]oxadiazol-5-ylmethyl]-benzoic acid ethyl ester The title compound is prepared essentially as described for 4-[3-(4-methoxy-phenoxymethyl)-[1,2,4]oxadiazol-5-ylmethyl]-benzoic acid ethyl ester, employing 3-carboxymethyl-benzoic acid ethyl ester (45%). LC-MS (m/e): 369 (M+1).

Preparation 188

Synthesis of 3-(3-hydroxymethyl-[1,2,4]oxadiazol-5-ylmethyl)-benzoic acid ethyl ester The title compound is prepared essentially as described for 4-(3-hydroxymethyl-[1,2,4]oxadiazol-5-ylmethyl)-benzoic acid ethyl ester, employing 3-[3-(4-methoxy-phenoxymethyl)-[1,2,4]oxadiazol-5-ylmethyl]-benzoic acid ethyl ester (81%). LC-MS (m/e): 263 (M+1).

Preparation 189

Synthesis of 3-[3-(4-acetyl-2-chloro-3-hydroxy-phenoxymethyl)-[1,2,4]oxadiazol-5-ylmethyl]-benzoic acid ethyl ester The title compound is prepared essentially as described for 4-[3-(4-acetyl-2-chloro-3-hydroxy-phenoxymethyl)-[1,2,4]oxadiazol-5-ylmethyl]-benzoic acid ethyl ester, employing 3-(3-Hydroxymethyl-[1,2,4]oxadiazol-5-ylmethyl)-benzoic acid ethyl ester (71%). LC-MS (m/e): 429 (M−1).

Example 149

Synthesis of 3-[3-(4-acetyl-2-chloro-3-hydroxy-phenoxymethyl)-[1,2,4]oxadiazol-5-ylmethyl]-benzoic acid

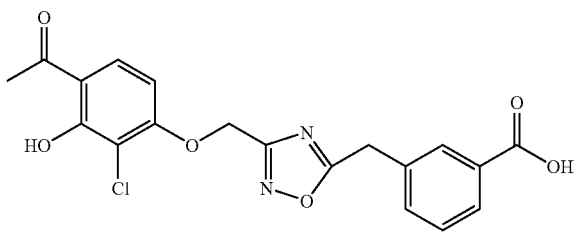

The title compound is prepared essentially as described for 4-[3-(4-acetyl-2-chloro-3-hydroxy-phenoxymethyl)-[1,2,4]oxadiazol-5-ylmethyl]-benzoic acid, employing 3-[3-(4-acetyl-2-chloro-3-hydroxy-phenoxymethyl)-[1,2,4]oxadiazol-5-ylmethyl]-benzoic acid ethyl ester. $^1$H NMR (DMSO-d$_6$) δ 13.06 (s, 1H), 12.99 (s, 1H), 7.91 (m, 2H), 7.83 (m, 1H), 7.58 (m, 1H), 7.46 (dd, 1H), 6.89 (d, 1H), 5.49 (s, 2H), 4.48 (s, 2H), 2.59 (s, 3H). LC-MS (m/e): 401 (M−1).

Preparation 190

Synthesis of N-hydroxy-2-(3-iodo-phenyl)-acetamidine

Add sodium carbonate (2.0 g, 18.5 mmol) to a mixture of 3-iodophenylacetonitrile (4.5 g, 18.5 mmol) and hydroxylamine hydrochloride (1.3 g, 18.5 mmol) in 10:1 EtOH:H$_2$O (11 mL) Heat the reaction mixture to 50° C. for 2 days. Cool to RT, then filter to remove the solids. Concentrate the filtrate to afford the title compound (4.94 g). LC-MS (m/e): 277 (M+1).

Preparation 191

Synthesis of 5-chloromethyl-3-(3-iodo-benzyl)-[1,2,4]oxadiazole

Add a solution of chloroacetic anhydride (1.5 g, 9 mmol) in toluene (20 mL) to N-hydroxy-2-(3-iodo-phenyl)-acetamidine (2.5 g, 9 mmol) in anhydrous toluene (20 mL). Fit the flask with a Dean-Stark trap and heat to reflux for 7 h. Concentrate the mixture and purify the residue by flash chromatography using 15% tetrahydrofuran/hexane to give the title compound (1.45 g, 48%). $^1$H NMR (CDCl$_3$) δ 7.65 (s, 1H), 7.59 (d, 1H), 7.26 (d, 1H), 7.04 (dd, 1H), 4.62 (s, 2H), 4.01 (s, 2H).

Preparation 192

Synthesis of 1-{2-hydroxy-4-[3-(3-iodo-benzyl)-[1,2,4]oxadiazol-5-ylmethoxy]-3-methyl-phenyl}-ethanone Add lithium carbonate (49 mg, 0.66 mmol) and 5-chloromethyl-3-(3-iodo-benzyl)-[1,2,4]oxadiazole (200 mg, 0.60 mmol) to a solution of 1-(2,4-dihydroxy-3-methyl-phenyl)-ethanone (110 mg, 0.66 mmol) in anhydrous dimethylformamide (20 mL) 4]oxadiazole (200 mg, 0.60 mmol). Heat the reaction mixture at 60° C. overnight. Cool the reaction mixture to RT, pour into H$_2$O, and extract with diethyl ether (3×). Combine the organic layers, wash with brine, dry over sodium sulfate, and concentrate to provide the title compound (150 mg). LC-MS (m/e): 463 (M−1).

Example 150

Synthesis of 3-[5-(4-acetyl-3-hydroxy-2-methyl-phenoxymethyl)-[1,2,4]oxadiazol-3-ylmethyl]-benzoic acid

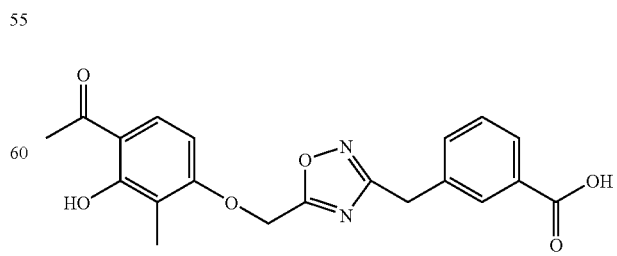

Combine 1-{2-hydroxy-4-[3-(3-iodo-benzyl)-[1,2,4]oxadiazol-5-ylmethoxy]-3-methyl-phenyl}-ethanone (150 mg, 0.32 mmol), sodium dodecyl sulfate (300 mg, 1.0 mmol), K₂CO₃ (45 mg, 0.32 mmol), 1-butanol (200 μL), and 1 drop of toluene in H₂O (4 mL) in a pressure vessel, then degas with Ar for 5 min. Add PdCl₂(MeCN)₂ (18 mg, 0.07 mmol) to the reaction mixture. Exchange the atmosphere with carbon monoxide and heat the mixture to 70° C. under 20 psig of carbon monoxide. The reaction is heated until complete. Filter the black mixture through celite. Acidify the filtrate with 5 N hydrochloric acid to pH=1. A milky white mixture forms. Add a small amount of methanol to induce crystallization Collect the crystals by filtration to give the title compound (79 mg, 65%). $^1$H NMR (DMSO-d₆) δ 12.99 (s, 1H), 12.79 (s, 1H), 7.86 (m, 1H), 7.79 (m, 2H), 7.52 (m, 1H), 7.42 (dd, 1H), 6.67 (d, 1H), 5.60 (s, 2H), 4.19 (s, 2H), 2.55 (s, 3H), 1.99 (s, 3H). LC-MS (m/e): 381 (M−1).

Preparation 193

Synthesis of 1-{3-chloro-2-hydroxy-4-[3-(3-iodo-benzyl)-[1,2,4]oxadiazol-5-ylmethoxy]-phenyl}-ethanone The title compound is prepared essentially as described for 1-{2-hydroxy-4-[3-(3-iodo-benzyl)-[1,2,4]oxadiazol-5-ylmethoxy]-3-methyl-phenyl}-ethanone, employing 1-(3-chloro-2,4-dihydroxy-phenyl)-ethanone (57%). LC-MS (m/e): 483 (M−1).

Example 151

Synthesis of 3-[5-(4-acetyl-2-chloro-3-hydroxy-phenoxymethyl)-[1,2,4]oxadiazol-3-ylmethyl]-benzoic acid

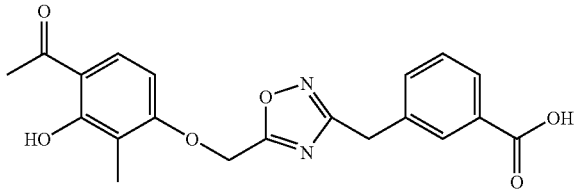

The title compound is prepared essentially as described for 3-[5-(4-acetyl-3-hydroxy-2-methyl-phenoxymethyl)-[1,2,4]oxadiazol-3-ylmethyl]-benzoic acid of Example 146 employing 1-{3-chloro-2-hydroxy-4-[3-(3-iodo-benzyl)-[1,2,4]oxadiazol-5-ylmethoxy]-phenyl}-ethanone. $^1$H NMR (DMSO-d₆) δ 13.06 (s, 1H), 12.94 (s, 1H), 7.92 (d, 1H), 7.85 (s, 1H), 7.80 (m, 1H), 7.52 (m, 1H), 7.42 (dd, 1H), 6.84 (d, 1H), 5.71 (s, 2H), 4.20 (s, 2H), 2.60 (s, 3H). LC-MS (m/e): 401 (M−1).

Preparation 194

Synthesis of N-hydroxy-2-(4-iodo-phenyl)-acetamidine

The title compound is prepared essentially as described for N-hydroxy-2-(3-iodo-phenyl)-acetamidine, employing (4-iodo-phenyl)-acetonitrile. LC-MS (m/e): 277 (M+1).

Preparation 195

Synthesis of 5-chloromethyl-3-(4-iodo-benzyl)-[1,2,4]oxadiazole

The title compound is prepared essentially as described for 5-chloromethyl-3-(3-iodo-benzyl)-[1,2,4]oxadiazole, employing N-hydroxy-2-(4-iodo-phenyl)-acetamidine. LC-MS (m/e): 335 (M+1).

Preparation 196

Synthesis of 1-{3-chloro-2-hydroxy-4-[3-(4-iodo-benzyl)-[1,2,4]oxadiazol-5-ylmethoxy]-phenyl}-ethanone The title compound is prepared essentially as described for 1-{2-hydroxy-4-[3-(3-iodo-benzyl)-[1,2,4]oxadiazol-5-ylmethoxy]-3-methyl-phenyl}-ethanone, employing 1-(3-chloro-2,4-dihydroxy-phenyl)-ethanone and 5-Chlormethyl-3-(4-iodo-benzyl)-[1,2,4]oxadiazole. LC-MS (m/e): 485 (M+1).

Example 152

Synthesis of 4-[5-(4-acetyl-2-chloro-3-hydroxy-phenoxymethyl)-[1,2,4]oxadiazol-3-ylmethyl]-benzoic acid

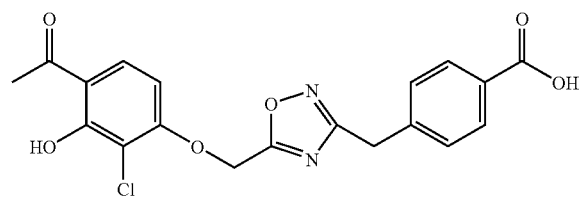

The title compound is prepared essentially as described for 3-[5-(4-acetyl-3-hydroxy-2-methyl-phenoxymethyl)-[1,2,4]oxadiazol-3-ylmethyl]-benzoic acid of Example 146, employing 1-{3-chloro-2-hydroxy-4-[3-(4-iodo-benzyl)-[1,2,4]oxadiazol-5-ylmethoxy]-phenyl}-ethanone. $^1$H NMR (DMSO-d₆) δ 13.05 (s, 1H), 12.86 (s, 1H), 7.92 (d, 1H), 7.85 (m, 2H), 7.38 (d, 2H), 6.84 (d, 1H), 5.72 (s, 2H), 4.18 (s, 2H), 2.59 (s, 3H). LC-MS (m/e): 401 (M−1).

Preparation 197

Synthesis of 1-{2-hydroxy-4-[3-(4-iodo-benzyl)-[1,2,4]oxadiazol-5-ylmethoxy]-3-methyl-phenyl}-ethanone The title compound is prepared essentially as described for 1-{2-hydroxy-4-[3-(3-iodo-benzyl)-[1,2,4]oxadiazol-5-ylmethoxy]-3-methyl-phenyl}-ethanone, employing 5-chloromethyl-3-(4-iodo-benzyl)-[1,2,4]oxadiazole and 1-(2,4-Dihydroxy-3-methyl-phenyl)-ethanone. LC-MS (m/e): 463 (M−1).

Example 153

Synthesis of 4-[5-(4-acetyl-3-hydroxy-2-methyl-phenoxymethyl)-[1,2,4]oxadiazol-3-ylmethyl]-benzoic acid

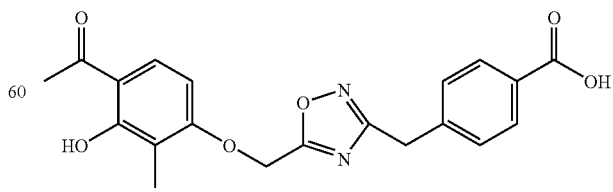

The title compound is prepared essentially as described for 3-[5-(4-acetyl-3-hydroxy-2-methyl-phenoxymethyl)-[1,2,4]oxadiazol-3-ylmethyl]-benzoic acid of Example 146, employing 1-{2-hydroxy-4-[3-(4-iodo-benzyl)-[1,2,4]oxadiazol-5-ylmethoxy]-3-methyl-phenyl}-ethanone. $^1$H NMR (DMSO-d$_6$) δ 12.84 (s, 1H), 12.80 (s, 1H), 7.86 (m. 2H), 7.78 (d, 1H), 7.38 (d, 2H), 6.67 (d, 1H), 5.60 (s, 2H), 4.19 (s, 2H), 2.55 (s, 3H), 1.99 (s, 3H). LC-MS (m/e): 381 (M−1).

Preparation 198

Synthesis of 5-(3-bromophenyl)isoxazol-3-ol

Add a solution of hydroxyamine (50% in water, 0.50 mL, 16.3 mmol) in water and NaOH (197 mg, 4.92 mmol) to a solution of methyl 3-(3-bromophenyl)propiolate (980 mg, 4.10 mmol) in a mixture of MeOH and THF (6.0 mL/12.0 mL). Remove the solvents after 2 d. Dissolve the residue in water. Adjust the pH of the aqueous phase to 2 and extract with EtOAc. Dry, filter and concentrate. Purify the residue by flash chromatography eluting with a mixture of EtOAc and hexanes (50:50) to afford the title compound (856 mg, 87%): $^1$H NMR (d$_6$-DMSO) δ 11.54 (s, 1H), 8.08 (dd, 1H, J=2.0, 1.6 Hz), 7.87 (ddd, 1H, J=8.6, 1.6, 0.8 Hz), 7.75 (ddd, 1H, J=8.2, 2.0, 0.8 Hz), 7.54 (t, 1H, J=7.8 Hz), 6.75 (s, 1H).

Preparation 199

Synthesis of 3-(3-hydroxyisoxazol-5-yl)phenylboronic acid

Add a 2.5 M solution of n-butyllithium in hexane (0.60 mL, 1.10 mmol) to a solution of 5-(3-bromophenyl)isoxazol-3-ol (120 mg, 0.50 mmol) and triisopropyl borate (113 mg, 0.60 mmol) in a mixture of toluene (2.5 mL) and THF (2.5 mL) at −78° C. After 1.5 h, warm the mixture to −20° C. and add a 2.0 N aqueous HCl solution (1 mL). Extract the mixture with EtOAc after warm to room temperature. Dry, filter and concentrate the organic layer to a white solid.

Preparation 200

Synthesis of 1-(4-(4-(bromomethyl)benzyloxy)-3-chloro-2-hydroxyphenyl)ethanone

Add K$_2$CO$_3$ (1.48 g, 10.7 mmol) to a solution of 1-(3-chloro-2,4-dihydroxy-phenyl)ethanone (2.00 g, 10.7 mmol) and 1,4-bis(bromomethyl)benzene (2.83 g, 10.7 mmol) in acetone (100 mL). Cool and work up with a 10% HCl solution and EtOAc. Triturate in acetone to remove insoluble material. Dry, filter, and concentrate. Purify the residue by flash chromatography on silica gel (731 mg, 18%): MS (esi negative) m/z 368.9 (rel intensity) (M−H, 55%), 367.0 (45%).

Example 154

Synthesis of 1-(4-(4-(3-(3-Hydroxyisoxazol-5-yl) benzyl)benzyloxy)-3-chloro-2-hydroxyphenyl)ethanone

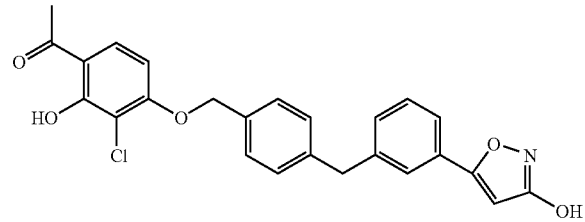

Add 1-(4-(4-(bromomethyl)benzyloxy)-3-chloro-2-hydroxyphenyl)ethanone (180 mg, 0.487 mmol) and 3-(3-hydroxyisoxazol-5-yl)phenylboronic acid (218 mg, 1.06 mmol) to a 2.0 M solution of Na$_2$CO$_3$ in water (2.36 mL), dimethoxyethane (4.72 mL), and n-PrOH (4.72 mL). Degas the solution. Add tetrakis(triphenylphosphine)palladium (0) (123 mg, 0.106 mmol) and degas the mixture. Heat the mixture at 70° C. for 12 h. Quench the reaction with water. Extract with EtOAc. Dry, filter and concentrate. Purify the residue by flash chromatography on silica gel afforded the title compound (12 mg, 5%): $^1$H NMR (d$_6$-DMSO) δ 2.61 (s, 3H), 4.02 (s, 2H), 5.31 (s, 2H), 6.51 (s, 1H), 6.89 (d, J=9.0 Hz, 1H), 7.31-7.36 (m, 3H), 7.39-7.44 (m, 3H), 7.62 (d, J=7.8 Hz, 1H), 7.70 (s, 1H), 7.93 (d, J=9.4 Hz, 1H), 11.34 (s, 1H), 13.13 (s, 1H); MS (APCI-neg mode) m/z (rel intensity): 448 (M−H, 100%).

Preparation 201

Synthesis of 2,4,6-Tris-[4-(tert-butyldimethylsilanyloxymethyl)-phenyl]-cyclotriboroxane

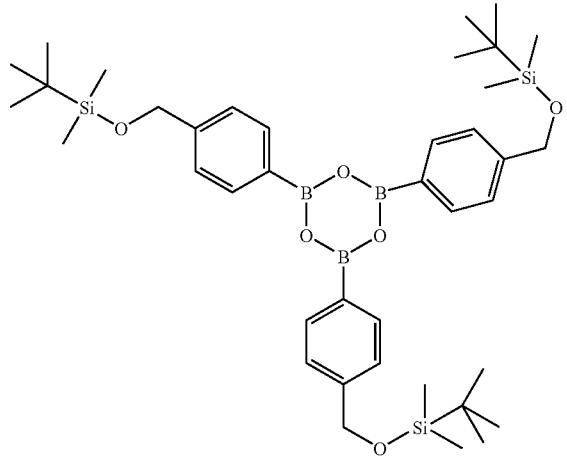

Combine (4-bromobenzyloxy)-tert-butyldimethylsilane (390.0 g, 1.29 mol), THF (3.90 L), toluene (827 mL) and triisopropyl borate (353.0 g, 1.88 mol) in a 12 L round-bottom flask at RT. Stir for 30 min. Cool the solution to −78° C. Add n-hexyllithium while maintaining the solution temperature <−68° C. Warm to −20° C. Add the reaction mixture to 2 N HCl (1325 mL). Warm the mixture to 0° C., and stir for 30 min. Add ethyl acetate (2.1 L) and stir the resulting mixture at 0° C. for 30 min. Separate the layers and wash the organic layer with 2 L of 5% aqueous NaHCO$_3$ containing NaCl (90 g). Concentrate the organic layer in vacuo to approximately 3 L total volume. Add acetonitrile (3 L) and concentrate in vacuo to 3 L total volumes. Repeat this process three times. Add acetonitrile (3 L) and stir overnight at RT. Cool the slurry to 0° C., stir for 30 min and filter. Wash the filter cake with acetonitrile (500 mL). Dry the resulting off-white solid under vacuum at 45° C. to afford the title compound: $^1$H NMR (500 MHz, CDCl$_3$) δ 8.22 (d, J=8.2 Hz, 6H), 7.47 (d, J=8.2 Hz, 6H), 4.85 (s, 6H), 0.98 (s, 27H), 0.14 (s, 18H).

Preparation 202

Synthesis of 3-{[4-(tert-butyldimethylsilanyloxymethyl)phenyl]-(S)-hydroxymethyl}-benzonitrile

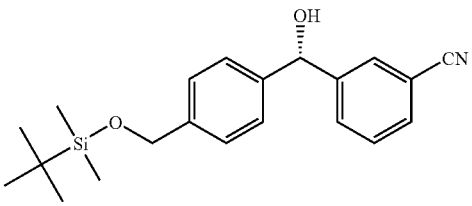

Under a nitrogen purge, add 1.1M diethyl zinc in toluene (312.3 mL, 343.5 mmol) to 2,4,6-Tris-[4-(tert-butyl-dimethyl-silanyloxymethyl)-phenyl]-cylcotriboroxane (30.1 g, 40.4 mmol) at ambient temperature and stir. After 5 minutes, heat to 60° C. and stir overnight. Cool to −10° C. and add via syringe, a mixture of (R)-(−)-2-Piperidino-1,1,2-triphenyle-thanol (6.7 g, 18.7 mmol) in toluene (70 mL) and stir 30 minutes. Via syringe, add a mixture of 3-cyanobenzaldehyde (12.2 g, 93.3 mmol) in toluene (40 mL) and continue stirring at −10 to −5° C. After 4 hours, add a mixture of acetic acid (59.0 mL, 1030 mmol) and deionized water (14 mL) to the mixture over 20 minutes. Filter off the resulting solids and rinse with toluene (50 mL). Wash the filtrate sequentially with 0.5 N HCl (2×200 mL), water (2×100 mL), 0.5N NaOH (200 mL), and water (100 mL). Dry the organic layer over sodium sulfate, filter, and concentrate under reduced pressure to give a crude residue. Purify the residue by dissolving in acetonitrile (330 mL) and performing heptane extractions (1×66 mL, 5×33 mL). Concentrate the acetonitrile portion under reduced pressure to give the title compound as a clear, thick oil: $^1$H NMR (500 MHz, CDCl$_3$) δ 0.04 (s, 6H), 0.87 (s, 9H), 4.64 (s, 2H), 5.74 (d, 1H), 6.08 (d, 1H), 7.22 (d, 2H, J=8.3 Hz), 7.33 (d, 2H, J=8.3 Hz), 7.49 (t, 1H), 7.64-7.68 (m, 2H), 7.78 (s, 1H). HPLC retention time: 6.3 minutes; Zorbax SB-C8 Rapid Resolution 4.6×75 mm 3.5-micron column. 220 nm wavelength, column temperature 30° C., 2 mL/min flow rate, A=0.1% H$_3$PO$_4$/milli-q water, B=Acetonitrile, Time=0 minute, 80% A, Time=0.5 minutes, 80% A, Time=7 minutes, 10% A, Time=8 minutes 10% A, Time=8.5 minutes 80% A, Time=9 minutes 80% A. Chiral assay retention time: desired isomer 7.1 minutes; 95.5% ee; ChiralCell AD-H 46×150 mm column, 240 nm wavelength, ambient column temperature, 0.8 mL/min flow rate. Eluent=1% 3A-Ethanol, 4% Methanol, 95% Heptane (v/v), isocratic run time=15 minutes.

Preparation 203

Synthesis of 3-[4-(hydroxymethylphenyl)-(S)-acetoxymethyl]-benzonitrile

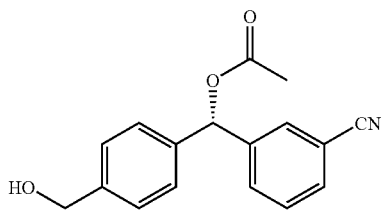

To a flask add acetic acid acetic acid anhydride (10.64 g, 104.20 mmol), triethylamine (11.37 g, 112.35 mmol), and N,N-dimethyl-4-pyridinamine (226.00 mg, 1.85 mmol) to 3-{[4-(tert-butyldimethylsilanyloxymethyl)phenyl]-(S)-hydroxymethyl}-benzonitrile (28.35 g, 80.19 mmol) in a solution of acetonitrile and heptane (280 mL) under nitrogen atmosphere and stir for 1 hour at ambient temperature to afford acetic acid 3-[4-(tert-butyl-dimethyl-silanyloxymethylphenyl)-(S)-acetoxymethyl]-benzonitrile. To this reaction solution add 5 N HCl (28 mL, 140 mmol) and stir for 2.75 hours at ambient temperature. Wash the reaction solution with heptane (3×320 mL) and transfer to a separatory funnel. Add toluene (476 mL) and deionized water (320 mL), agitate and separate the layers. Extract the aqueous layer with toluene (320 mL) and combine the organic layers. Wash the combined organics with saturated NaHCO$_3$ solution (320 mL), water (320 mL), concentrate to 40 mL total volume by vacuum distillation. Add toluene (286 mL) to afford a solution of the title compound. This solution may be taken into the proceeding step without purification. HPLC retention time: 3.69 minutes; Zorbax SB-C8 Rapid Resolution 4.6×75 mm 3.5-micron column. 220 nm wavelength, column temperature 30° C., 2 mL/min flow rate, A=0.1% H$_3$PO$_4$/milli-q water, B=Acetonitrile, Time=0 minute, 80% A, Time=0.5 minutes, 80% A, Time=7 minutes, 10% A, Time 8 minutes 10% A, Time=8.5 minutes 80% A, Time=9 minutes 80% A.

Preparation 204

Synthesis of 3-[4-(methanesulfonyloxymethylphenyl)-(S)-acetoxymethyl]-benzonitrile Add triethylamine (8.94 g, 88.39 mmol) to a solution of 3-[4-(hydroxymethylphenyl)-(S)-acetoxymethyl]-benzonitrile (20.70 g, 73.58 mmol) in toluene (~310 mL) at −2° C. under nitrogen atmosphere. Add methanesulfonyl chloride (9.69 g, 84.63 mmol) over a period of 30 minutes and stir for 1 hour at 0° C. Wash the reaction solution with water (2×210 mL), concentrate in vacuo to 75 mL total to afford a solution of the title compound, and take directly into the proceeding step: HPLC retention time: 4.52 minutes; Zorbax SB-C8 Rapid Resolution 4.6×75 mm 3.5-micron column. 220 nm wavelength, column temperature 30° C., 2 mL/min flow rate, A=0.1% H$_3$PO$_4$/milli-q water, B=Acetonitrile, Time=0 minute, 80% A, Time=0.5 minutes, 80% A, Time=7 minutes, 10% A, Time=8 minutes 10% A, Time=8.5 minutes 80% A, Time=9 minutes 80% A.

Preparation 205

Synthesis of 3-{[4-(4-acetyl-3-hydroxy-2-propylphenoxymethyl)-phenyl]-(S)-acetoxymethyl}-benzonitrile Add 3-[4-(methanesulfonyloxymethylphenyl)-(S)-acetoxymethyl]-benzonitrile (26.45 g, 73.59 mmol) in toluene (~53 mL) to a flask containing acetone (344 mL), 2',4'-dihydroxy-3'-propyl-acetophenone (12.91 g, 66.47 mmol), and K$_2$CO$_3$ (10.21 g, 73.88 mmol) and stir under a nitrogen atmosphere. Heat to 60° C. for 6.5 hours. Add 2',4'-dihydroxy-3'-propyl-acetophenone (670 mg, 3.44 mmol) and stir the suspension for 5.5 h. Cool the reaction to ambient temperature and filter. Wash the filter cake with toluene (3 vol) and concentrate in vacuo to 132 mL. Wash the concentrate with deionized water (2×132 mL) and further concentrate in vacuo to 60 mL. Add hot absolute EtOH (240 mL) and concentrate in vacuo to 234 mL. Add hot EtOH (66 mL) to the solution and concentrate to 100 mL. To the hot solution, add absolute EtOH (190 mL), stir, and slowly cool to ambient temperature. Stir the suspension for 15 hours and filter. Wash the filter cake with absolute EtOH (34 mL) and dry the resulting solid in a vacuum oven at 45° C. Add dry, crystalline 3-{[4-(4-acetyl-3-hydroxy-2-propylphenoxymethyl)-phenyl]-(S)-acetoxymethyl}-benzonitrile (24.54 g) and MTBE (123 mL) to a flask and heat to reflux for 10 minutes. Cool the resulting solution to 27° C. before adding heptane (50 mL) dropwise over 20 minutes. Stir the mixture at ambient temperature for two hours and filter. Wash the filter cake and flask with 50/50 MTBE/heptane and dry in a vacuum oven at 45° C. to afford the title compound: mass spectrum (m/e): 456.5 (M−); $^1$H NMR (500 MHz, DMSO) 612.82 (s, 1H), 7.91 (s, 1H), 7.55 (t, 1H, 7 Hz), 7.45 (d, 2H, J=8 Hz), 7.42 (d, 2H, J=8 Hz), 6.83 (s, 1H), 6.68 (d, 1H, J=8 Hz), 5.21 (s, 2H), 2.55-2.58 (m, 2H), 2.54 (s, 3H), 2.15 (s, 3H), 1.42-1.49 (m, 2H), 0.84 (t, 3H, J=7 Hz), ppm.

Example 155

Synthesis of 3-{[4-(4-acetyl-3-hydroxy-2-propyl-phenoxymethyl)-phenyl]-(S)-hydroxymethyl}-benzoic acid

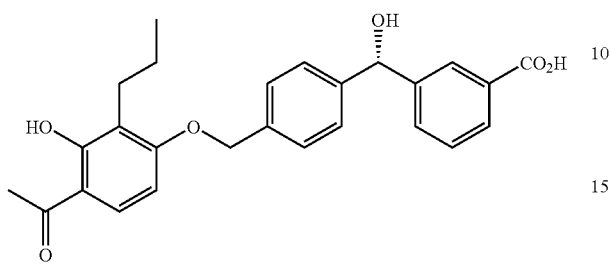

To a flask under nitrogen atmosphere add 3-{[4-(4-acetyl-3-hydroxy-2-propylphenoxy-methyl)-phenyl]-(S)-acetoxymethyl}-benzonitrile (19.40 g, 42.40 mmol) and DI water (390 mL). Heat the suspension to 60° C. and stir for 30 minutes. Add KOH (16.86 g, 255.32 mmol) and heat the flask to 101° C. for 22.5 hours. Cool the solution to 36° C. and acidify with 5N HCl (59.4 mL, 296.8 mmol) over 30. Cool the mixture to 25° C. over 1 hour and filter. Wash the cake and flask with deionized water (3×100 mL). Place the filter cake in a vacuum oven at 45° C. for 24 hours. Add the dry solid to a flask with absolute EtOH (278 mL) and stir at reflux for 30 min. Cool the suspension to room temperature and add deionized water (278 mL) dropwise over 25 minutes. Stir the suspension for 1 hour at room temperature and filter. Wash the flask and cake with 50% aqueous EtOH (20 mL) and dry in a vacuum oven at 45° C. overnight to afford the title compound. mass spectrum (m/e): 433.5 (M−); $^1$H NMR (500 MHz, DMSO) δ 0.84 (t, 3H, J=7 Hz), 1.45 (q, 2H, J=7 Hz), 2.54 (s, 3H), 2.49-2.57 (m, 2H), 5.19 (s, 2H), 5.77 (d, 1H), 6.02 (d, 1H), 6.67 (d, 1H), 7.36-7.43 (m, 5H), 7.61 (d, 1H), 7.77 (dd, 2H), 7.95 (s, 1H), 12.82 (s, 1H), 12.90 (s, 1H) ppm; melting point (DSC onset)= 198.35° C.

We claim:

1. A compound of formula I

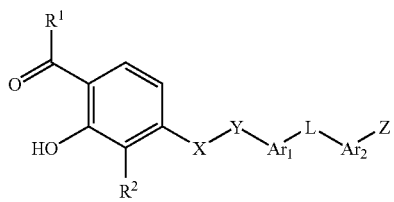

wherein $R^1$ is selected from the group consisting of C1-C5 alkyl, C3-C7 cycloalkyl, C4-C8 cycloalkylalkyl, phenyl and substituted phenyl;

$R^2$ is selected from the group consisting of hydrogen, C1-C5 alkyl, substituted C1-C5 alkyl, halo, phenyl, substituted phenyl, C1-C3 fluoroalkyl, CN, $CO_2R^3$, thiophenyl, substituted thiophenyl, thiazolyl, substituted thiazoyl, furanyl, substituted furanyl, pyridinyl, substituted pyridinyl, oxazolyl, substituted oxazloyl, isothiazolyl, substituted isothiazoyl, isoxazolyl, substituted isoxazolyl, 1,2,4-oxadiazolyl, substituted 1,2,4-oxadiazolyl, pyrimidinyl, substituted pyrimidinyl, pyridazinyl, and substituted pyridazinyl;

X is selected from the group consisting of O, $S(O)_m$, and $NR^3$;

Y is selected from the group consisting of C1-C3 alkanediyl and substituted C1-C3 alkanediyl;

$Ar_1$ and $Ar_2$ are independently selected from the group consisting of phenylene and substituted phenylene;

L is selected from the group consisting of C1-C5 alkanediyl, substituted C1-C5 alkanediyl, and —G—C (=W)—J—;

W is $CR^3R^3$, O or $NR^3$;

G and J are independently selected from the group consisting of a bond and C1-C3 alkanediyl;

$R^3$ is independently hydrogen or C1-C5 alkyl;

Z is selected from the group consisting of $(CH_2)_nCOOH$,

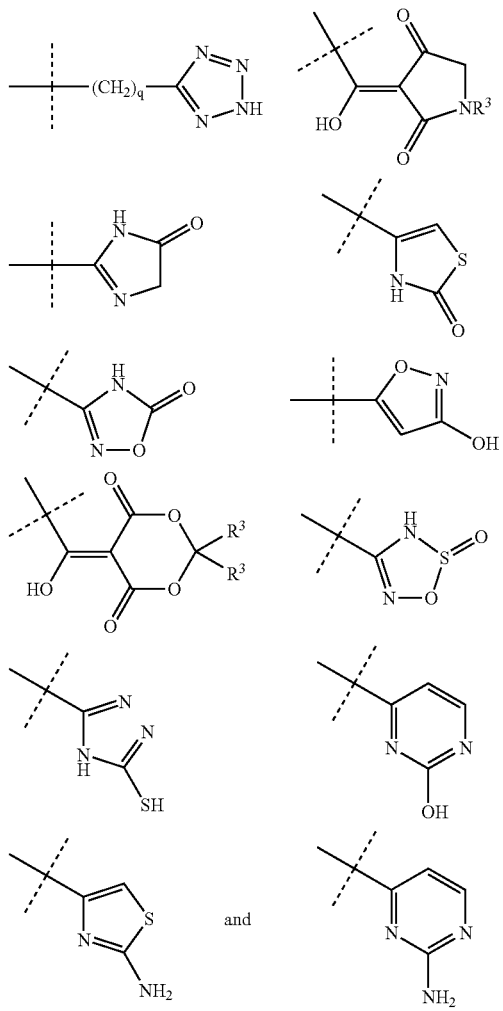

m is 0, 1, or 2;

n and q are independently 0, 1, 2 or 3; and pharmaceutically acceptable salts thereof.

2. A compound according to claim 1 wherein Z is selected from the group consisting of $(CH_2)_nCOOH$,

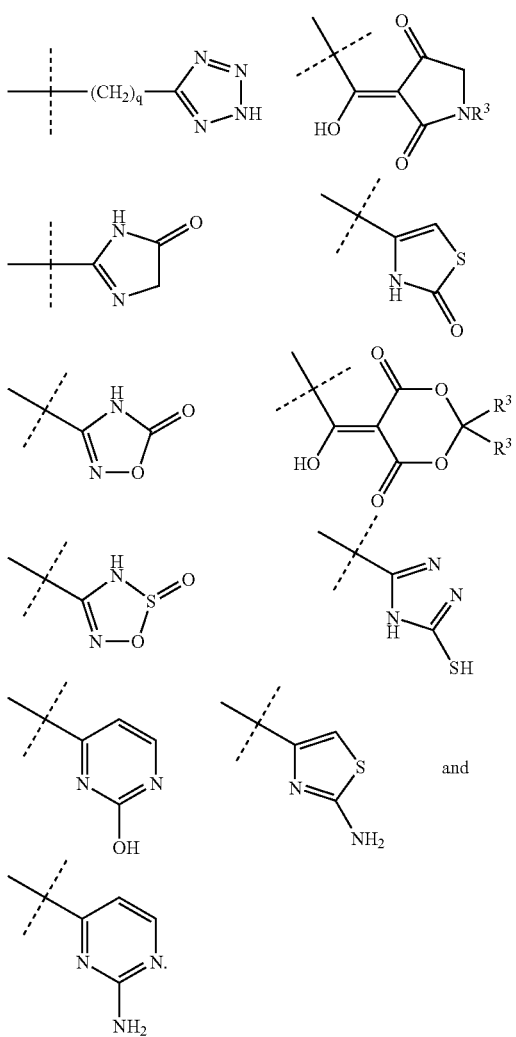

3. A compound according to claim 2 wherein X is O.

4. A compound according to claim 3 wherein Y is C1-C3 alkanediyl.

5. A compound according to claim 4 wherein $Ar_1$ and $Ar_2$ are phenylene.

6. A compound according to claim 5 wherein $R^2$ is selected from the group consisting of C1-C5 alkyl, halo and C1-C3 fluoroalkyl.

7. A compound according to claim 6 wherein L is selected from the group consisting of —(CH$_2$)—, —CH(OH)—, and C(=O).

8. A compound according to claim 1 wherein
X is O;
Y is C1-C3 alkanediyl;
$Ar_1$ and $Ar_2$ are phenylene
$R^2$ is selected from the group consisting of C1-C5 alkyl, halo and C1-C3 fluoroalkyl;
L is selected from the group consisting of —(CH$_2$)—, —CH(OH)—, and C(=O);
Z is selected from the group consisting of (CH$_2$)$_n$COOH and

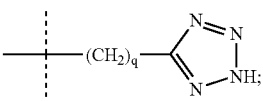

and n and q are 0.

9. A compound according to claim 1 wherein $Ar_1$ is phenylene.

10. A compound according to claim 1 wherein $Ar_2$ is attached at the 1-4 position.

11. A compound according to claim 1 wherein $Ar_2$ is attached at the 1-3 position.

12. A compound according to claim 10 or claim 11 wherein $Ar_1$ is attached at the 1-3 position or 1-4 position.

13. A compound according to claim 8 wherein $R^1$ is methyl.

14. A compound according to claim 1 wherein $R^1$ methyl or ethyl;

$R^2$ is selected from the group consisting of methyl, ethyl, n-propyl, iso-propyl, fluoro, chloro, iodo, phenyl, 4-fluorophenyl, trifluoromethyl, CN, 2-thiophenyl, 3-thiophenyl, 2-thiazolyl, 2-pyridinyl, 3-pyridinyl, and 4-pyridinyl;

X is selected from the group consisting of O, S, SO$_2$, NH and NCH$_3$;

Y is methylene;

$Ar_1$ is phenylene;

$Ar_2$ is selected from the group consisting of phenylene, fluorophenylene, and methoxyphenylene;

L is selected from the group consisting of CH$_2$, CHCH$_3$, CH(OH), CH(F), CHN$_3$, CH(OCH$_3$), CHNH$_2$, CHNH(C=O)CH$_3$, CHNH(SO$_2$)CH$_3$, C=O, and CH=CH$_2$;

Z is selected from the group consisting of (CH$_2$)$_n$COOH,

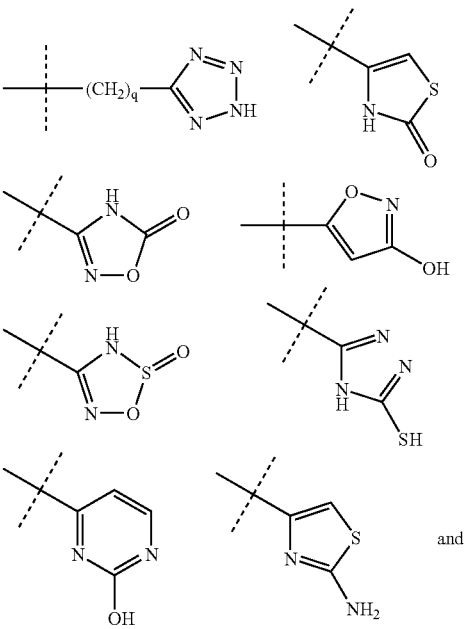

-continued

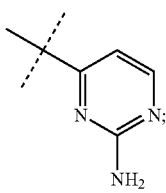

n is 0; and q is 0.

15. A compound according to claim 1 selected from the group consisting of (+)-3-{[4-(4-acetyl-3-hydroxy-2-propyl-phenoxymethyl)-phenyl]-hydroxy-methyl}benzoic acid (isomer 1) and (−)-3-{[4-(4-acetyl-3-hydroxy-2-propyl-phenoxymethyl)phenyl]-hydroxy-methyl}-benzoic acid (isomer 2).

16. A compound according to claim 1 which is 3-{[4-(4-acetyl-3-hydroxy-2-propylphenoxymethyl)-phenyl]-(S)-hydroxymethyl}-benzoic acid.

17. A pharmaceutical composition comprising a compound of claim 1 and a pharmaceutically acceptable carrier, diluent or excipient.

18. A method of treating migraine, comprising administering to a patient in need thereof an effective amount of a compound of claim 1.

19. A process for preparing the compound of formula I, or a pharmaceutically acceptable salt thereof, wherein $R^1$, $R^2$, X, Y, $Ar_1$, L and $Ar_2$ are defined as in claim 1 comprising the step selected from (A) for a compound of formula I where Z is tetrazolyl,

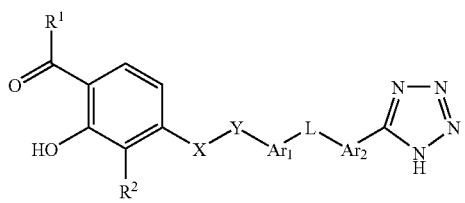

I, Z is tetrazolyl cycloaddition of a compound of formula II where $R^{10}$ is cyano with an azide reagent;

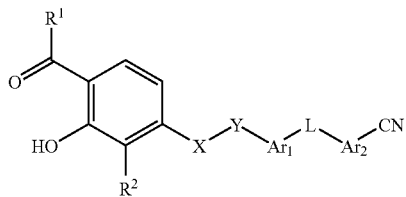

II, $R^{10}$ is cyano (B) for a compound of formula I where Z is COOH,

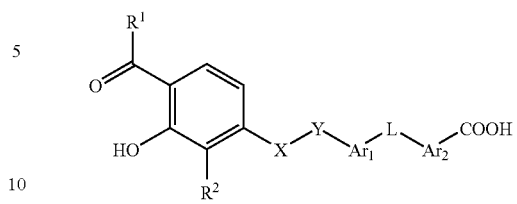

I, Z is COOH hydrolysis of a compound of formula II wherein $R^{10}$ is $COOR^{14}$ and $R^{14}$ is selected from the group consisting of C1-C5 alkyl, phenyl and benzyl;

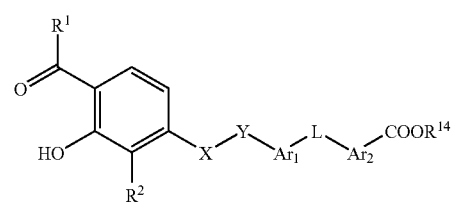

(C) for a compound of formula I where Z is COOH,

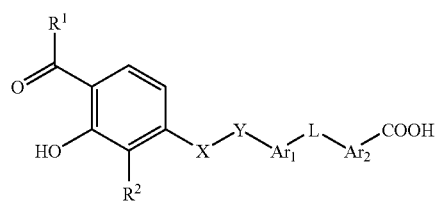

I, Z is COOH hydrolysis of a compound of formula II where $R^{10}$ is cyano; and

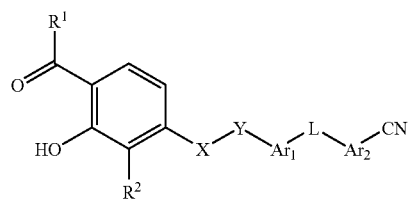

II, $R^{10}$ is cyano (D) for a compound of formula I

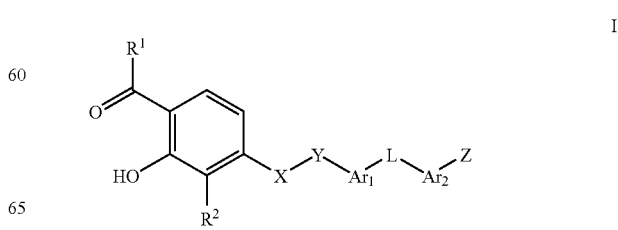

where Z is

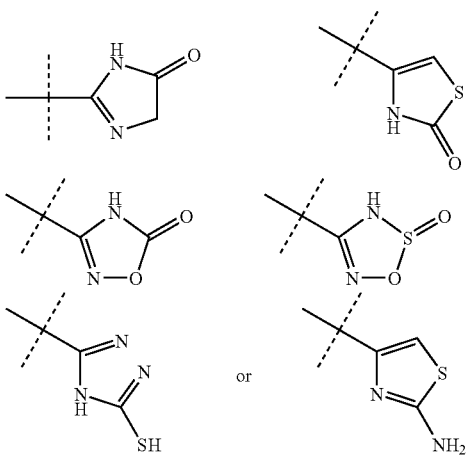

cyclocondensating a compound of formula II where $R^{10}$ is an acyl halide such as the acyl chloride;

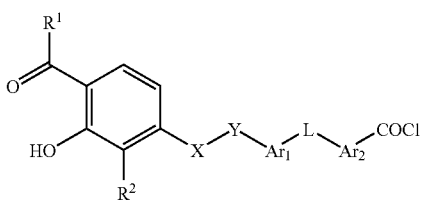

II, $R^{10}$ is acyl chloride whereafter, when a pharmaceutically acceptable salt of the compound of formula I is required, it is obtained by reacting the acid of formula I with a physiologically acceptable base or by reacting a basic compound of formula I with a physiologically acceptable acid.

20. A compound of formula II

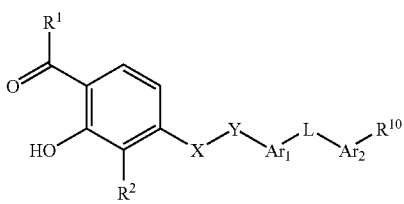

wherein
$R^1$, $R^2$, X, Y, $Ar_1$, $Ar_2$ and L are defined as in claim 1; and
$R^{10}$ is CN or $COOR^{14}$ in which $R^{14}$ is selected from the group consisting of C1-C5 alkyl, phenyl and benzyl.

21. The compound according to claim 20 wherein $R^{14}$ is C1-C5 alkyl.

22. The process of claim 19 for preparing 3-{[4-(4-acetyl-3-hydroxy-2-propyl-phenoxymethyl)-phenyl]-(S)-hydroxymethyl}-benzoic acid or a pharmaceutically acceptable salt thereof,
comprising
(i) alkylating 2,4-dihydroxy-3-propyl-acetophenone with 3-[4-(methane-sulfonyloxymethylphenyl)-(S)-acetoxymethyl]-benzonitrile in the presence of potassium carbonate to afford 3-{[4-(4-acetyl-3-hydroxy-2-propylphenoxymethyl)-phenyl]-(S)-acetoxymethyl}-benzonitrile; and
(ii) hydrolyzing 3-{[4-(4-acetyl-3-hydroxy-2-propylphenoxymethyl)-phenyl]-(S)-acetoxymethyl}-benzonitrile in the presence of potassium hydroxide wherein the hydrolysis reaction is followed by acidification with hydrochloric acid to afford 3-{[4-(4-acetyl-3-hydroxy-2-propyl-phenoxymethyl)-phenyl]-(S)-hydroxymethyl}benzoic acid; whereafter, when a pharmaceutically acceptable salt of 3-{[4-(4-acetyl-3-hydroxy-2-propyl-phenoxymethyl)-phenyl]-(S)-hydroxymethyl}-benzoic acid is required, it is obtained by reacting 3-{[4-(4-acetyl-3-hydroxy-2-propyl-phenoxymethyl)-phenyl]-(S)-hydroxymethyl}-benzoic acid with a physiologically acceptable base.

23. The process of claim 22 wherein the starting 3-[4-(methanesulfonyloxymethylphenyl)-(S)-acetoxymethyl]-benzonitrile is prepared using a process comprising
(i) arylating enantioselectively 3-cyanobenzaldehyde with 2,4,6-tris-[4-(tert-butyl-dimethyl-silanyloxymethyl)-phenyl]-cyclotriboroxane in the presence of a dialkyl zinc and chiral catalyst wherein the dialkyl zinc is diethyl zinc; and the chiral catalyst is (R)-(−)-2-piperidino-1,1,2-triphenyl ethanol to afford 3-{[4-(tert-butyldimethylsilanyloxymethyl)phenyl]-(S)-hydroxymethyl}-benzonitrile;
(ii) acylating 3-{[4-(tert-butyldimethylsilanyloxymethyl)phenyl]-(S)-hydroxymethyl}-benzonitrile with acetic anhydride whereafter hydrolyzing the 4-(tert-butyldimethylsilanyl group with hydrochloric acid to afford 3-[4-(hydroxymethylphenyl)-(S)-acetoxymethyl]-benzonitrile; and
(iii) sulfonating 3-[4-(hydroxymethylphenyl)-(S)-acetoxymethyl]-benzonitrile with methane sulfonyl chloride to afford 3-[4-(methanesulfonyloxymethylphenyl)-(S)-acetoxymethyl]-benzonitrile.

* * * * *

UNITED STATES PATENT AND TRADEMARK OFFICE
CERTIFICATE OF CORRECTION

| | | |
|---|---|---|
| PATENT NO. | : 7,598,423 B2 | Page 1 of 1 |
| APPLICATION NO. | : 11/718753 | |
| DATED | : October 6, 2009 | |
| INVENTOR(S) | : Thomas Daniel Aicher | |

It is certified that error appears in the above-identified patent and that said Letters Patent is hereby corrected as shown below:

First (cover) page, under item (56) References Cited, Other Publications, Pinkerton et al reference, "mteabotropic" should be -- metabotropic --.

Column 4, line 24, in the Specification, "thiazoyl," should be -- thiazolyl, --.

Column 4, line 27, in the Specification, "isothiazoyl," should be -- isothiazolyl, --.

Column 171, line 64, in Claim 1, "thiazoyl," should be -- thiazolyl, --.

Column 171, line 65, in Claim 1, "oxazloyl," should be -- oxazolyl, --.

Column 171, line 66, in Claim 1, "isothiazoyl," should be -- isothiazolyl, --.

Signed and Sealed this

Sixteenth Day of February, 2010

David J. Kappos
*Director of the United States Patent and Trademark Office*